(12) United States Patent
Nilsson et al.

(10) Patent No.: US 10,858,422 B2
(45) Date of Patent: *Dec. 8, 2020

(54) METHODS FOR TREATING SYSTEMIC LUPUS ERYTHEMATOSUS WITH AN ANTI-APOLIPOPROTEIN B ANTIBODY

(71) Applicant: Abcentra, LLC, Los Angeles, CA (US)

(72) Inventors: Jan Nilsson, Genarp (SE); Ryan Benjamin Abbott, Tallahassee, FL (US); Bertrand C. Liang, San Diego, CA (US); Christopher John Farina, Los Angeles, CA (US); Stacey Ruiz, Beverly Hills, CA (US)

(73) Assignee: Abcentra, LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/428,631

(22) Filed: May 31, 2019

(65) Prior Publication Data

US 2019/0284268 A1 Sep. 19, 2019

Related U.S. Application Data

(63) Continuation-in-part of application No. 15/610,527, filed on May 31, 2017, now Pat. No. 10,434,141.

(60) Provisional application No. 62/343,601, filed on May 31, 2016, provisional application No. 62/678,940, filed on May 31, 2018.

(51) Int. Cl.
| | |
|---|---|
| *A61P 37/06* | (2006.01) |
| *A61P 9/10* | (2006.01) |
| *A61K 39/395* | (2006.01) |
| *C07K 16/18* | (2006.01) |
| *A61K 9/00* | (2006.01) |
| *A61K 45/06* | (2006.01) |
| *C07K 14/435* | (2006.01) |
| *C07K 14/775* | (2006.01) |
| *A61K 39/00* | (2006.01) |

(52) U.S. Cl.
CPC ............ *C07K 16/18* (2013.01); *A61K 9/0019* (2013.01); *A61K 39/3955* (2013.01); *A61K 45/06* (2013.01); *A61P 9/10* (2018.01); *A61P 37/06* (2018.01); *A61K 2039/505* (2013.01); *A61K 2039/54* (2013.01); *A61K 2039/545* (2013.01); *C07K 2317/21* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,330,910 A | 7/1994 | Young et al. |
| 5,460,947 A | 10/1995 | Young et al. |
| 5,753,227 A | 5/1998 | Strahilevitz |
| 5,827,516 A | 10/1998 | Urban et al. |
| 6,039,946 A | 3/2000 | Strahilevitz |
| 6,096,516 A | 8/2000 | Kwak et al. |
| 6,264,623 B1 | 7/2001 | Strahilevitz |
| 6,375,925 B1 | 4/2002 | Tsimikas et al. |
| 6,379,699 B1 | 4/2002 | Virtanen et al. |
| 6,727,102 B1 | 4/2004 | Holvoet et al. |
| 6,825,318 B2 | 11/2004 | Kim |
| 6,887,712 B1 | 5/2005 | Medford et al. |
| 7,166,469 B2 | 1/2007 | Holvoet et al. |
| 7,229,775 B2 | 6/2007 | Holvoet et al. |
| 7,229,776 B2 | 6/2007 | Holvoet et al. |
| 7,288,374 B2 | 10/2007 | Pincemail et al. |
| 7,378,250 B2 | 5/2008 | Holvoet et al. |
| 7,390,627 B2 | 6/2008 | Holvoet et al. |
| 7,468,183 B2 | 12/2008 | Nilsson et al. |
| 7,556,927 B2 | 7/2009 | Witztum et al. |
| 7,575,873 B2 | 8/2009 | Witztum et al. |
| 7,579,159 B2 | 8/2009 | Holvoet et al. |
| 7,731,648 B2 | 6/2010 | Ivkov |
| 7,785,589 B2 | 8/2010 | Nilsson et al. |
| 7,829,667 B2 | 11/2010 | Kim |
| 7,993,643 B2 | 8/2011 | Kobayashi et al. |
| 8,097,283 B2 | 1/2012 | Fisher et al. |
| 8,114,966 B2 | 2/2012 | Nilsson et al. |
| 8,318,161 B2 | 11/2012 | Esue |
| 8,470,768 B2 | 6/2013 | Nilsson et al. |
| 8,575,314 B2 | 11/2013 | Matsuura et al. |
| 8,647,628 B2 | 2/2014 | Nilsson et al. |
| 8,729,240 B2 | 5/2014 | Chiba et al. |
| 9,322,833 B2 | 4/2016 | Krauss et al. |
| 9,393,303 B2 | 7/2016 | Sverdlov et al. |

(Continued)

FOREIGN PATENT DOCUMENTS

| | | |
|---|---|---|
| EP | 1186299 A1 | 3/2002 |
| WO | 2002080954 A1 | 10/2002 |

(Continued)

OTHER PUBLICATIONS

Rudikoff et al (Proc Natl Acad Sci USA 1982 vol. 79 pp. 1979-1983).*
International Search Report and Written Opinion of PCT/US2019/34423, dated Oct. 16, 2019, 15 Pages.
International Search Report and Written Opinion of PCT/US2019/34439, dated Oct. 18, 2019, 18 Pages.
Armstrong et al., A tale of two plaques: convergent mechanisms of T-cell-mediated inflammation in psoriasis and atherosclerosis, 2011, Exp. Dermato., vol. 20, pp. 544-549.
Fotiadou et al., Management of psoriasis in adolescence, 2014, Adolescent Health, Medicine and Therapeutics, vol. 5, pp. 25-34.
Szekanecz et al., Accelerated Atherosclerpsis in Rheumatoid Arthritis, Ann. N.Y. Acad. Sci., 2007, vol. 1108, pp. 349-358.

(Continued)

*Primary Examiner* — Zachary C Howard
(74) *Attorney, Agent, or Firm* — Nixon Peabody LLP

(57) ABSTRACT

Described herein are peptides and antibodies for prevention and/or therapeutic treatment of mammals, including humans, against systemic lupus erythematosus, as well as diagnosing the presence or absence of antibodies related to increased or decreased risk of developing SLE and/or to disease grading, staging, and/or prognosis.

20 Claims, 58 Drawing Sheets

Specification includes a Sequence Listing.

(56) References Cited

U.S. PATENT DOCUMENTS

| | | |
|---|---|---|
| 9,512,222 B2 | 12/2016 | Heldwein et al. |
| 9,562,101 B2 | 2/2017 | Heldwein et al. |
| 9,738,722 B2 | 8/2017 | Moore et al. |
| 9,913,886 B2 | 3/2018 | Kyutoku et al. |
| 9,982,046 B2 | 5/2018 | Heldwein et al. |
| 9,987,375 B2 | 6/2018 | Sahebkar |
| 9,988,455 B2 | 6/2018 | Heldwein et al. |
| 10,434,141 B2 | 10/2019 | Nilsson et al. |
| 2003/0143226 A1 | 7/2003 | Kobayashi et al. |
| 2004/0202653 A1 | 10/2004 | Nilsson et al. |
| 2005/0112572 A1 | 5/2005 | Pincemail |
| 2005/0271653 A1 | 12/2005 | Strahilevitz |
| 2006/0039857 A1 | 2/2006 | Adcock |
| 2006/0099644 A1 | 5/2006 | Matsuura |
| 2007/0003548 A1 | 1/2007 | Heavner et al. |
| 2007/0020682 A1 | 1/2007 | Soto-Jara et al. |
| 2007/0112339 A9 | 5/2007 | Ivkov |
| 2007/0243136 A1 | 10/2007 | Fisher et al. |
| 2008/0241134 A1 | 10/2008 | Kobayashi et al. |
| 2008/0261234 A1 | 10/2008 | Narvanen |
| 2008/0268029 A1 | 10/2008 | Nilsson et al. |
| 2009/0098145 A1 | 4/2009 | Mata et al. |
| 2009/0155258 A1 | 6/2009 | Nilsson et al. |
| 2009/0169544 A1 | 7/2009 | Nilsson et al. |
| 2009/0208503 A1 | 8/2009 | Carlsson et al. |
| 2010/0028363 A1 | 2/2010 | Valdes et al. |
| 2010/0081149 A1 | 4/2010 | Matsuura |
| 2010/0239567 A1 | 9/2010 | Esue et al. |
| 2010/0273671 A1 | 10/2010 | Lauwerys et al. |
| 2010/0286025 A1 | 11/2010 | Anantharamaiah et al. |
| 2011/0002955 A1 | 1/2011 | Kim et al. |
| 2011/0014189 A1 | 1/2011 | Soula et al. |
| 2011/0014203 A1 | 1/2011 | Nilsson |
| 2011/0182816 A1 | 7/2011 | Matsuura et al. |
| 2011/0182851 A1 | 7/2011 | Nilsson |
| 2011/0207917 A1 | 8/2011 | Ilag et al. |
| 2011/0256134 A1 | 10/2011 | Bunting |
| 2012/0093922 A1 | 4/2012 | Manku et al. |
| 2012/0121698 A1 | 5/2012 | Manku et al. |
| 2013/0243784 A1 | 9/2013 | Swergold |
| 2013/0253174 A1 | 9/2013 | Chiba et al. |
| 2014/0037672 A1 | 2/2014 | Nilsson et al. |
| 2014/0044734 A1 | 2/2014 | Sverdlov |
| 2014/0093517 A1 | 4/2014 | Cipolla |
| 2014/0127227 A1 | 5/2014 | Chang |
| 2014/0154705 A1 | 6/2014 | Manneh |
| 2014/0308306 A1 | 10/2014 | Chyu et al. |
| 2015/0056209 A1 | 2/2015 | Witztum et al. |
| 2015/0064195 A1 | 3/2015 | Kupper et al. |
| 2015/0125443 A1 | 5/2015 | Crispin et al. |
| 2015/0204866 A1 | 7/2015 | McAndrew et al. |
| 2016/0060360 A1 | 3/2016 | Moore et al. |
| 2016/0116493 A1 | 4/2016 | Guadagno et al. |
| 2017/0056504 A1 | 3/2017 | Kohn |
| 2017/0121407 A1 | 5/2017 | Cipolla |
| 2017/0209550 A1 | 7/2017 | Kjellman et al. |
| 2017/0305999 A1 | 10/2017 | Leber et al. |
| 2017/0340702 A1 | 11/2017 | Carvlin et al. |
| 2017/0342493 A1 | 11/2017 | Barril et al. |
| 2018/0036285 A1 | 2/2018 | Tunac et al. |
| 2018/0201686 A1 | 7/2018 | Moore et al. |
| 2018/0208636 A1 | 7/2018 | Lim et al. |
| 2018/0256747 A1 | 9/2018 | Hawthorne et al. |
| 2018/0318387 A1 | 11/2018 | Farina et al. |

FOREIGN PATENT DOCUMENTS

| | | |
|---|---|---|
| WO | 2004030607 A2 | 4/2004 |
| WO | 2004030698 A1 | 4/2004 |
| WO | 2008070861 A2 | 6/2008 |
| WO | 2008/104194 A1 | 9/2008 |
| WO | 2009083225 A2 | 7/2009 |
| WO | 2015175968 A1 | 11/2015 |
| WO | 2017021631 A1 | 2/2017 |
| WO | 2017123556 A1 | 7/2017 |
| WO | 2017186928 A1 | 11/2017 |
| WO | 2017210360 A1 | 12/2017 |
| WO | 2018063796 A1 | 4/2018 |
| WO | 2018067987 A1 | 4/2018 |
| WO | 2018129188 A1 | 7/2018 |
| WO | 2018129207 A1 | 7/2018 |
| WO | 2019/232070 A1 | 12/2019 |
| WO | 2019/232081 A1 | 12/2019 |
| WO | 2020/010024 A1 | 1/2020 |

OTHER PUBLICATIONS

International Search Report and Written Opinion of PCT/US2019/34423, dated Oct. 16, 2019, 14 Pages.

International Search Report and Written Opinion of PCT/US2019/34439, dated Oct. 18, 2019, 19 Pages.

International Search Report and Written Opinion of PCT/US2019/040196, dated Nov. 15, 2019, 13 Pages.

Torzewski et al., Lipoprotein(a)-Associated Molecules are Prominent Components in Plasma and Valve Leaflets in Calcific Aortic Valve Stenosis, 2017, JACC: Basic to Translational Science, vol. 2(3), pp. 229-240.

Mattisson et al., Passive Immunization with BI-204 Reduces Atherosclerosis in SLE Mice, presentation in Atheroma Club Meeting 2015 in Marstrand, Sweden, Sep. 10, 2015, 16 Pages.

Mattisson et al., Passive Immunization with Recombinant Human IgG1 against an ApoB100 Peptide Decreases Atherosclerosis Development in a Mouse Model of SLE; 1-page abstract for Atheroma Club Meeting 2015, abstract submission deadline Jun. 12, 2015 for meeting held between Sep. 9, 2015 and Sep. 11, 2015.

Shih et al., Oxidized Low-Density Lipoprotein-Deteriorated Psoriasis is Associated with the Upregulation of Lox-1 Receptor and I1-23 Expression In Vivo and In Vitro, 2018, International Journal of Molecular Sciences, vol. 19(2610), 14 Pages.

Bjorkbacka et al, Low Levels of Apolipoprotein B-100 Autoantibodies are Associated with Increased Risk of Coronary Events, 2016, Arterioscler Thromb Vasc. Biol., Feb. 25, 2016, 17 pages.

Svenungsson et al, Decreased Levels of Autoantibodies Against Apolipoprotein B-100 Antigens are Associated with Cardiovascular Disease in Systemic Lupus Erythemotosus, Jun. 22, 2015, Clinical & Experimental Immunology, 10 Pages.

International Search Report and Written Opinion of PCT/US2017/035308, dated Oct. 19, 2017, 21 Pages.

Benjamini et al., Immunology: A Short Course, 2nd Edition, 1991, p. 40.

Ferrara et al., Recombinant Renewable Polyclonal Antibodies, 2015, mAbs, vol. 7(1), pp. 32-41.

Presentation of European Atherosclerosis Society (EAS) Advanced Course in Regulatory Immunity in Atherosclerosis, Sep. 11, 2013, Landskrona, Sweden, 17 Pages.

Anton Gistera, T-Cell Specificity and Regulation in Atherosclerosis, Dec. 14, 2015, Thesis for Doctoral Degree, Karolinska Institutet, Stockholm, 74 Pages.

Ketelhuth et al, Evaluation of T Cell Response Against Apolipoprotein B100 (ApoB100) Peptides in Atherosclerosis (Abstract) at 13th International Congress on Immunology (ICI) in Rio de Janeiro, 2007, Experimental Cardiovascular Research Unit, Center for Molecular Medicine, Karolinska University Hospital, Stockholm, Sweden, 1 Page.

Ketelhuth et al, Evaluation of T Cell Response Against Apolipoprotein B100 (ApoB100) Peptides in Atherosclerosis (Poster), 2008, Experimental Cardiovascular Research Unit, Center for Molecular Medicine, Karolinska University Hospital, Stockholm, Sweden, 1 Page.

Ketelhuth et al, Evaluation of T Cell Response Against Apolipoprotein B100 (ApoB100) Peptides in Atherosclerosis, Presentation at 13th International Congress on Immunology (ICI) in Rio de Janeiro, 2007, Experimental Cardiovascular Research Unit, Center for Molecular Medicine, Karolinska University Hospital, Stockholm, Sweden, 12 Pages.

Ketelhuth et al, Evaluation of T Cell Response Against Apolipoprotein B100 (ApoB100): A New Opportunity for Immunotherapy Against Atherosclerosis (Abstract), 2008, Department of Medicine, Karolinska University Hospital, Stockholm, Sweden, 1 Page.

(56) References Cited

OTHER PUBLICATIONS

The American College of Cardiology Foundation, FDG-PET Imaging for Oxidized LDL in Stable Atherosclerotic Disease: A Phase II Study of Safety, Tolerability, and Anti-Inflammatory Activity, 2015, JACC: Cadiovascular Imaging, vol. 8(4), pp. 493-498.

clinicaltrials.gov, Bioavailability Study of MLDL1278A After Subcutaneous and Intravenous Administration in Healthy Subjects, 2011, NCT01486823, Downloaded from https://clinicaltrials.gov/ct2/show/study/NCT01486823 on Feb. 7, 2019, 4 Pages.

clinicaltrials.gov, A Study to Evaluate the Safety, Tolerability, and Activity of Intravenous MLDL1278A in Patients on Standard-of-Care Therapy for Stable Atherosclerotic Cardiovascular Disease (GLACIER), 2010, NCT01258907, Downloaded from https://clinicaltrials.gov/ct2/show/NCT01258907 on Feb. 7, 2019, 5 Pages.

* cited by examiner

FIG. 3
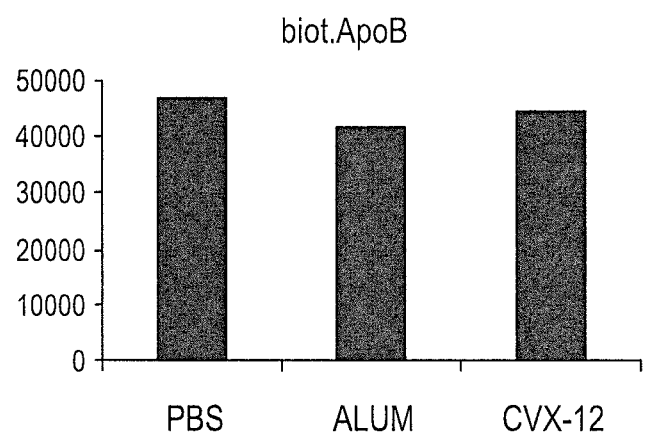
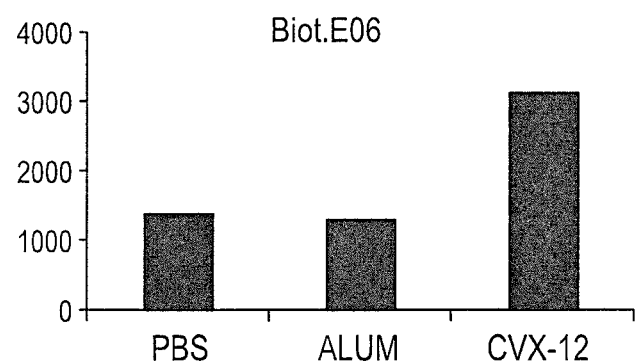
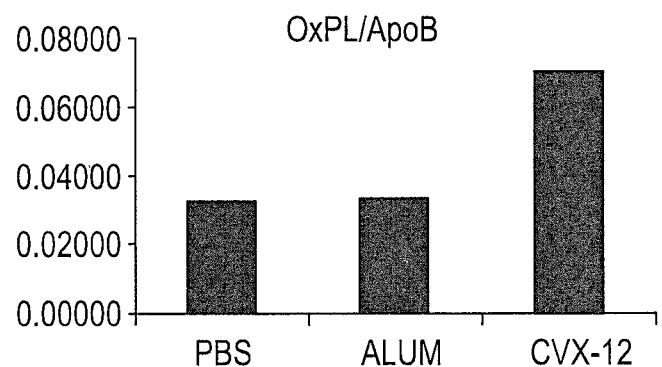

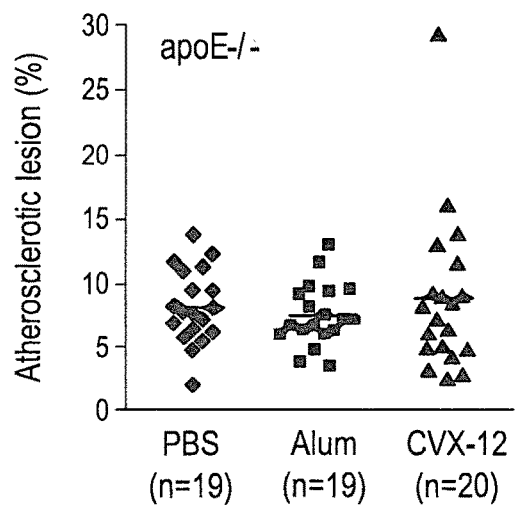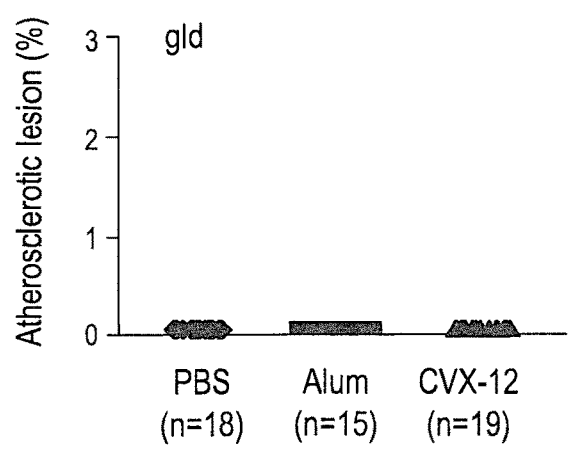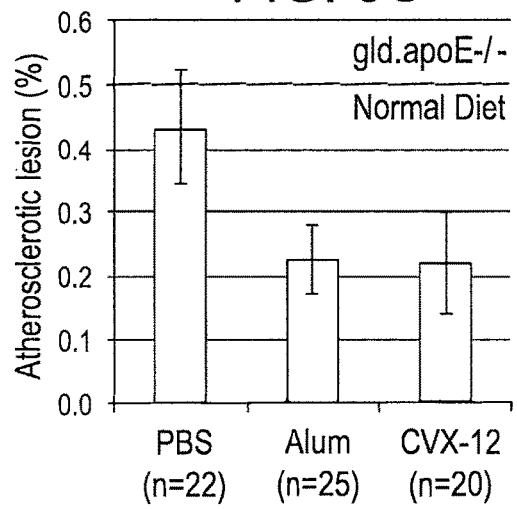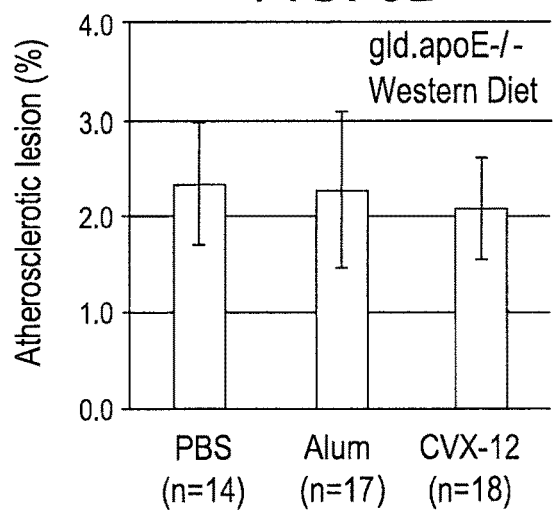

FIG. 9
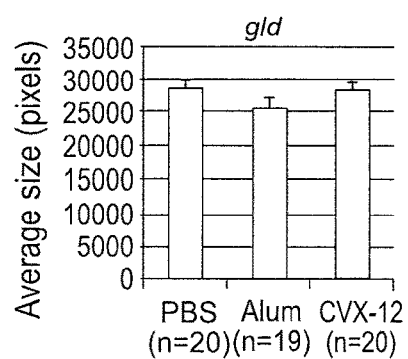
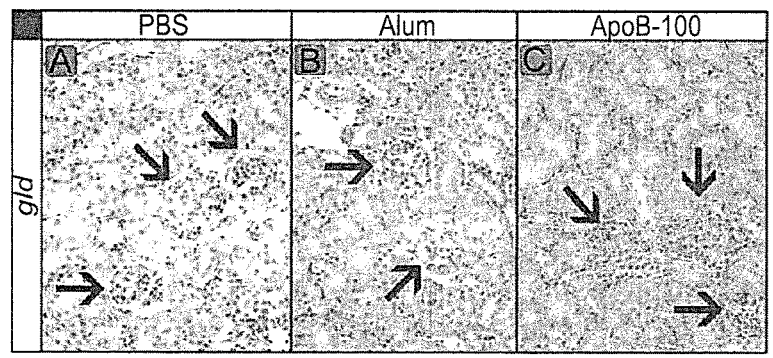
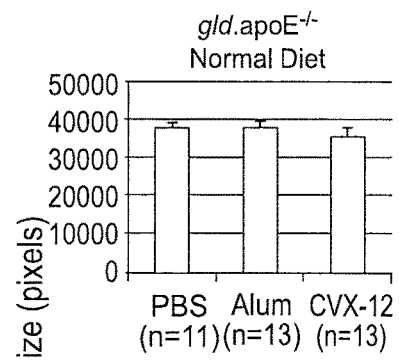
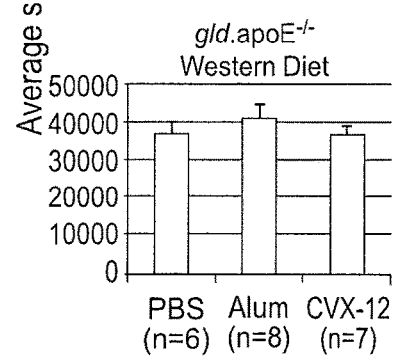
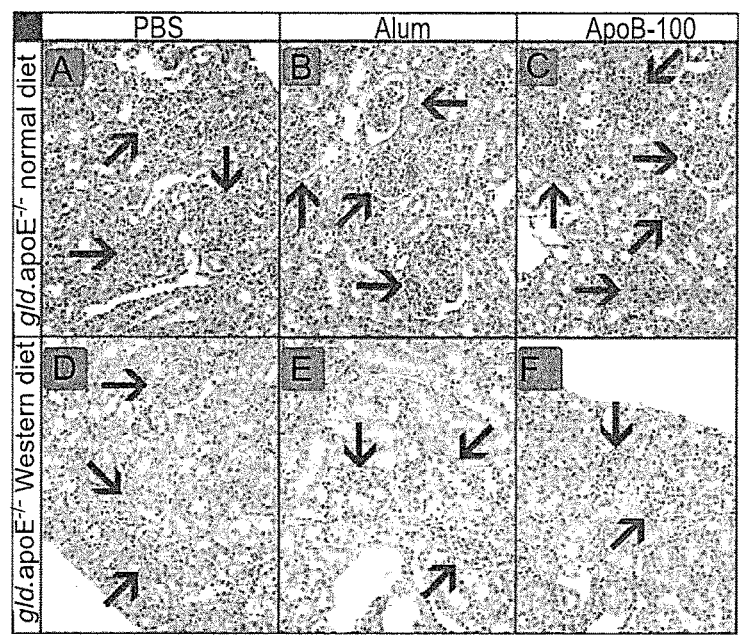

Aortic arch

T helper

T cytolytic

CD4+ Tcem

CD4+ Teff

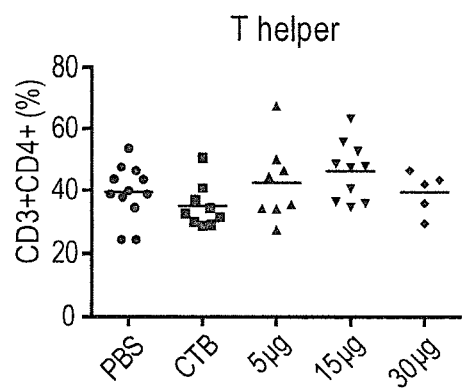
FIG. 19A T helper
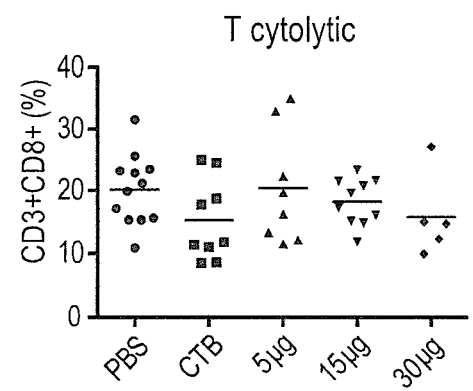
FIG. 19B T cytolytic
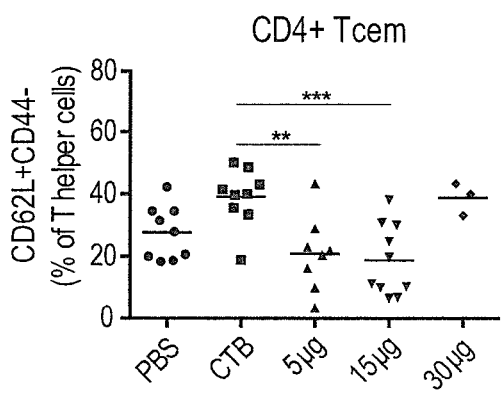
FIG. 19C CD4+ Tcem
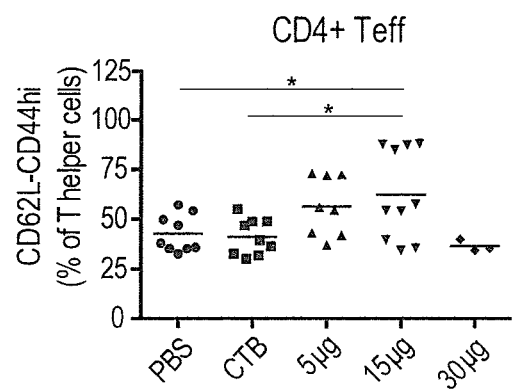
FIG. 19D CD4+ Teff
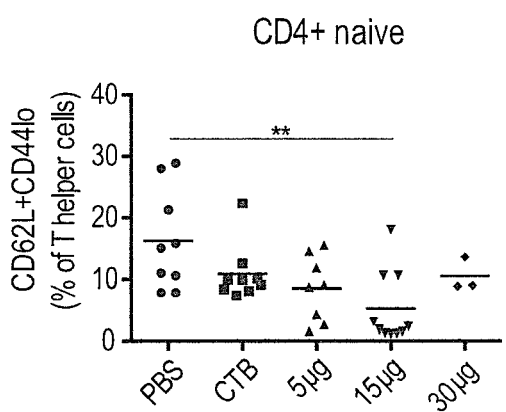
FIG. 19E CD4+ naive
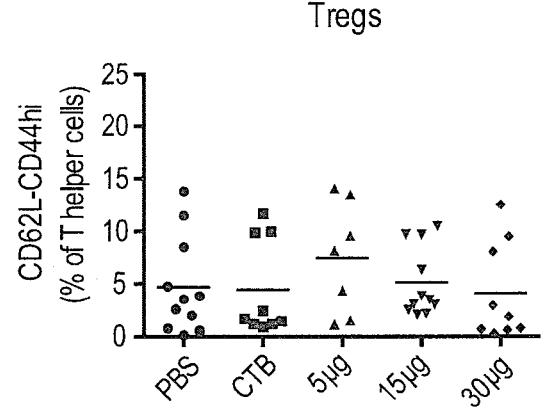
FIG. 19F Tregs

FIG. 21A

Polynucleotide sequence encoding heavy chain SEQ ID NO: 303

GAGGTGCAGCTGTTGGAGTCTGGGGGAGGCTTGGTACAGCCTGGGGGGTCCCTGAGACTCTCCTGTGCAGCCTCT
GGATTCACCTTCAGTAACGCCTGGATGAGCTGGGTCCGCCAGGCTCCAGGGAAGGGGCTGGAGTGGGTCTCAAGT
ATTAGTGTTGGTGGACATAGGACATATTATGCAGATTCCGTGAAGGGCCGGTCCACCATCTCCAGAGACAATTCC
AAGAACACGCTGTATCTGCAAATGAACAGCCTGAGAGCCGAGGACACTGCCGTGTATTACTGTGCACGGATACGG
GTGGGTCCGTCCGGCGGGGCCTTTGACTACTGGGGCCAGGGTACACTGGTCACCGTGAGCTCAGCCTCCACCAAG
GGCCCATCGGTCTTCCCCCTGGCACCCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCTGACCAGCGGCGTGCACACCTTCCCG
GCTGTCCTACAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAAAGTTGAGCCCAAATCTTGTGAC
AAAACTCACACATGCCCACCGTGCCCAGCACCTGAACTCCTGGGGGGACCGTCAGTCTTCCTCTTCCCCCCAAAA
CCCAAGGACACCCTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGAGTACAAGTGC
AAGGTCTCCAACAAAGCCCTCCCAGCCCCCATCGAGAAAACCATCTCCAAAGCCAAAGGGCAGCCCCGAGAACCA
CAGGTGTACACCCTGCCCCCATCCCGGGATGAGCTGACCAAGAACCAGGTCAGCCTGACCTGCCTGGTCAAAGGC
TTCTATCCCAGCGACATCGCCGTGGAGTGGGAGAGCAATGGGCAGCCGGAGAACAACTACAAGACCACGCCTCCC
GTGCTGGACTCCGACGGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTCTCCCTGTCTCCGGGT
AAA

Polynucleotide sequence encoding light chain SEQ ID NO: 304

CAGTCTGTGCTGACTCAGCCACCCTCAGCGTCTGGGACCCCCGGGCAGAGGGTCACCATCTCCTGCTCTGGAAGC
AACACCAACATTGGGAAGAACTATGTATCTTGGTATCAGCAGCTCCCAGGAACGGCCCCCAAACTCCTCATCTAT
GCTAATAGCAATCGGCCCTCAGGGGTCCCTGACCGATTCTCTGGCTCCAAGTCTGGCACCTCAGCCTCCCTGGCC
ATCAGTGGGCTCCGGTCCGAGGATGAGGCTGATTATTACTGTGCGTCATGGGATGCCAGCCTGAATGGTTGGGTA
TTCGGCGGAGGAACCAAGCTGACGGTCCTAGGTCAGCCCAAGGCTGCCCCCTCGGTCACTCTGTTCCCGCCCTCC
TCTGAGGAGCTTCAAGCCAACAAGGCCACACTGGTGTGTCTCATAAGTGACTTCTACCCGGGAGCCGTGACAGTG
GCCTGGAAGGCAGATAGCAGCCCCGTCAAGGCGGGAGTGGAGACCACCACACCCTCCAAACAAAGCAACAACAAG
TACGCGGCCAGCAGCTATCTGAGCCTGACGCCTGAGCAGTGGAAGTCCCACAGAAGCTACAGCTGCCAGGTCACG
CATGAAGGGAGCACCGTGGAGAAGACAGTGGCCCCTACAGAATGTTCA

FIG. 21B

Translated heavy chain sequence SEQ ID NO: 316

```
  5  gaggtgcagctgttggagtctggggaggcttggtacagcctggggggtccctgagactc
     E  V  Q  L  L  E  S  G  G  G  L  V  Q  P  G  G  S  L  R  L tcctgtgcagcctctggattcaccttcagtaacgcctggatgagctgggtccgccaggct
     S  C  A  A  S  G  F  T  F  S  N  A  W  M  S  W  V  R  Q  A
 10
     ccagggaaggggctggagtgggtctcaagtattagtgttggtggacataggacatattat
     P  G  K  G  L  E  W  V  S  S  I  S  V  G  G  H  R  T  Y  Y gcagattccgtgaagggccggtccaccatctccagagacaattccaagaacacgctgtat
 15  A  D  S  V  K  G  R  S  T  I  S  R  D  N  S  K  N  T  L  Y ctgcaaatgaacagcctgagagccgaggacactgccgtgtattactgtgcacggatacgg
     L  Q  M  N  S  L  R  A  E  D  T  A  V  Y  Y  C  A  R  I  R 20  gtgggtccgtccggcggggcctttgactactggggccagggtacactggtcaccgtgagc
     V  G  P  S  G  G  A  F  D  Y  W  G  Q  G  T  L  V  T  V  S tcagcctccaccaagggcccatcggtcttccccctggcaccctcctccaagagcacctct
     S  A  S  T  K  G  P  S  V  F  P  L  A  P  S  S  K  S  T  S
 25
     gggggcacagcggccctgggctgcctggtcaaggactacttccccgaaccggtgacggtg
     G  G  T  A  A  L  G  C  L  V  K  D  Y  F  P  E  P  V  T  V tcgtggaactcaggcgccctgaccagcggcgtgcacaccttcccggctgtcctacagtcc
 30  S  W  N  S  G  A  L  T  S  G  V  H  T  F  P  A  V  L  Q  S tcaggactctactccctcagcagcgtggtgaccgtgccctccagcagcttgggcacccag
     S  G  L  Y  S  L  S  S  V  V  T  V  P  S  S  S  L  G  T  Q 35  acctacatctgcaacgtgaatcacaagcccagcaacaccaaggtggacaagaaagttgag
     T  Y  I  C  N  V  N  H  K  P  S  N  T  K  V  D  K  K  V  E cccaaatcttgtgacaaaactcacacatgcccaccgtgcccagcacctgaactcctgggg
     P  K  S  C  D  K  T  H  T  C  P  P  C  P  A  P  E  L  L  G
 40
     ggaccgtcagtcttcctcttccccccaaaacccaaggacaccctcatgatctcccggacc
     G  P  S  V  F  L  F  P  P  K  P  K  D  T  L  M  I  S  R  T cctgaggtcacatgcgtggtggtggacgtgagccacgaagaccctgaggtcaagttcaac
 45  P  E  V  T  C  V  V  V  D  V  S  H  E  D  P  E  V  K  F  N tggtacgtggacggcgtggaggtgcataatgccaagacaaagccgcgggaggagcagtac
     W  Y  V  D  G  V  E  V  H  N  A  K  T  K  P  R  E  E  Q  Y 50  aacagcacgtaccgtgtggtcagcgtcctcaccgtcctgcaccaggactggctgaatggc
     N  S  T  Y  R  V  V  S  V  L  T  V  L  H  Q  D  W  L  N  G aaggagtacaagtgcaaggtctccaacaaagcccteccagcccccatcgagaaaaccatc
     K  E  Y  K  C  K  V  S  N  K  A  L  P  A  P  I  E  K  T  I
 55
     tccaaagccaaagggcagccccgagaaccacaggtgtacaccctgcccccatcccgggat
     S  K  A  K  G  Q  P  R  E  P  Q  V  Y  T  L  P  P  S  R  D 60  gagctgaccaagaaccaggtcagcctgacctgcctggtcaaaggcttctatcccagcgac
     E  L  T  K  N  Q  V  S  L  T  C  L  V  K  G  F  Y  P  S  D atcgccgtggagtgggagagcaatgggcagccggagaacaactacaagaccacgcctccc
```

FIG. 21C

```
      I  A  V  E  W  E  S  N  G  Q  P  E  N  N  Y  K  T  T  P  P
    gtgctggactccgacggctccttcttcctctacagcaagctcaccgtggacaagagcagg
      V  L  D  S  D  G  S  F  F  L  Y  S  K  L  T  V  D  K  S  R tggcagcaggggaacgtcttctcatgctccgtgatgcatgaggctctgcacaaccactac
      W  Q  Q  G  N  V  F  S  C  S  V  M  H  E  A  L  H  N  H  Y acgcagaagagcctctccctgtctccgggtaaa
      T  Q  K  S  L  S  L  S  P  G  K
```

Translated light chain sequence SEQ ID NO: 317

```
    cagtctgtgctgactcagccaccctcagcgtctgggaccccgggcagagggtcaccatc
     Q  S  V  L  T  Q  P  P  S  A  S  G  T  P  G  Q  R  V  T  I tcctgctctggaagcaacaccaacattgggaagaactatgtatcttggtatcagcagctc
     S  C  S  G  S  N  T  N  I  G  K  N  Y  V  S  W  Y  Q  Q  L ccaggaacggccccaaactcctcatctatgctaatagcaatcggccctcaggggtccct
     P  G  T  A  P  K  L  L  I  Y  A  N  S  N  R  P  S  G  V  P gaccgattctctggctccaagtctggcacctcagcctccctggccatcagtgggctccgg
     D  R  F  S  G  S  K  S  G  T  S  A  S  L  A  I  S  G  L  R tccgaggatgaggctgattattactgtgcgtcatgggatgccagcctgaatggttgggta
     S  E  D  E  A  D  Y  Y  C  A  S  W  D  A  S  L  N  G  W  V ttcggcggaggaaccaagctgacggtcctaggtcagcccaaggctgccccctcggtcact
     F  G  G  G  T  K  L  T  V  L  G  Q  P  K  A  A  P  S  V  T ctgttcccgccctcctctgaggagcttcaagccaacaaggccacactggtgtgtctcata
     L  F  P  P  S  S  E  E  L  Q  A  N  K  A  T  L  V  C  L  I agtgacttctacccgggagccgtgacagtggcctggaaggcagatagcagccccgtcaag
     S  D  F  Y  P  G  A  V  T  V  A  W  K  A  D  S  S  P  V  K gcgggagtggagaccaccacaccctccaaacaaagcaacaacaagtacgcggccagcagc
     A  G  V  E  T  T  T  P  S  K  Q  S  N  N  K  Y  A  A  S  S tatctgagcctgacgcctgagcagtggaagtcccacagaagctacagctgccaggtcacg
     Y  L  S  L  T  P  E  Q  W  K  S  H  R  S  Y  S  C  Q  V  T catgaagggagcaccgtggagaagacagtggcccctacagaatgttca
     H  E  G  S  T  V  E  K  T  V  A  P  T  E  C  S
```

FIG. 26
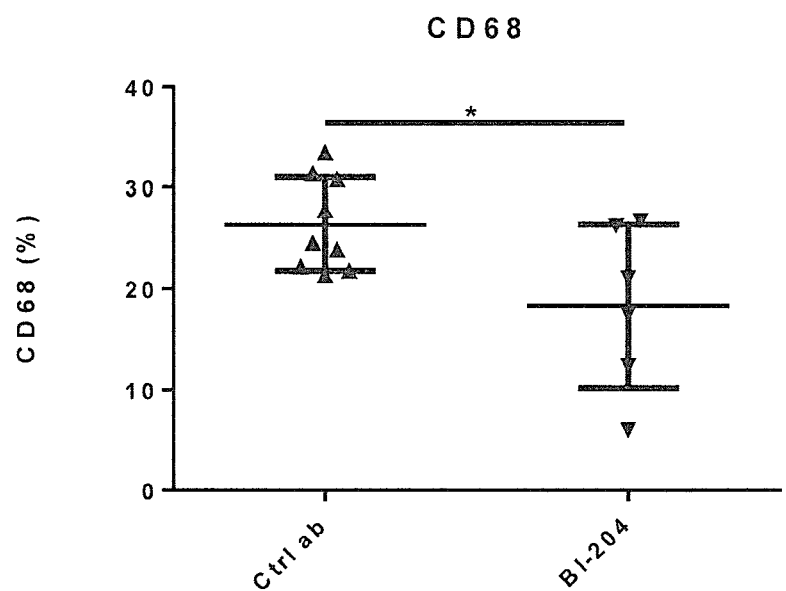
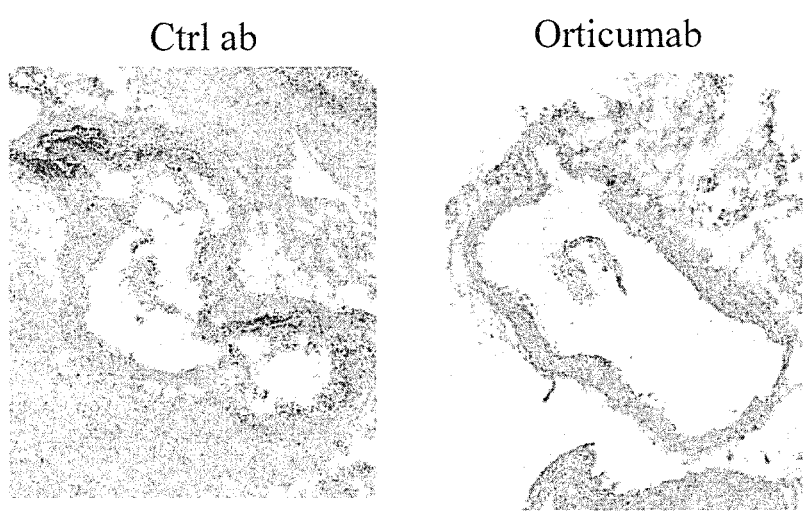
Ctrl ab          Orticumab

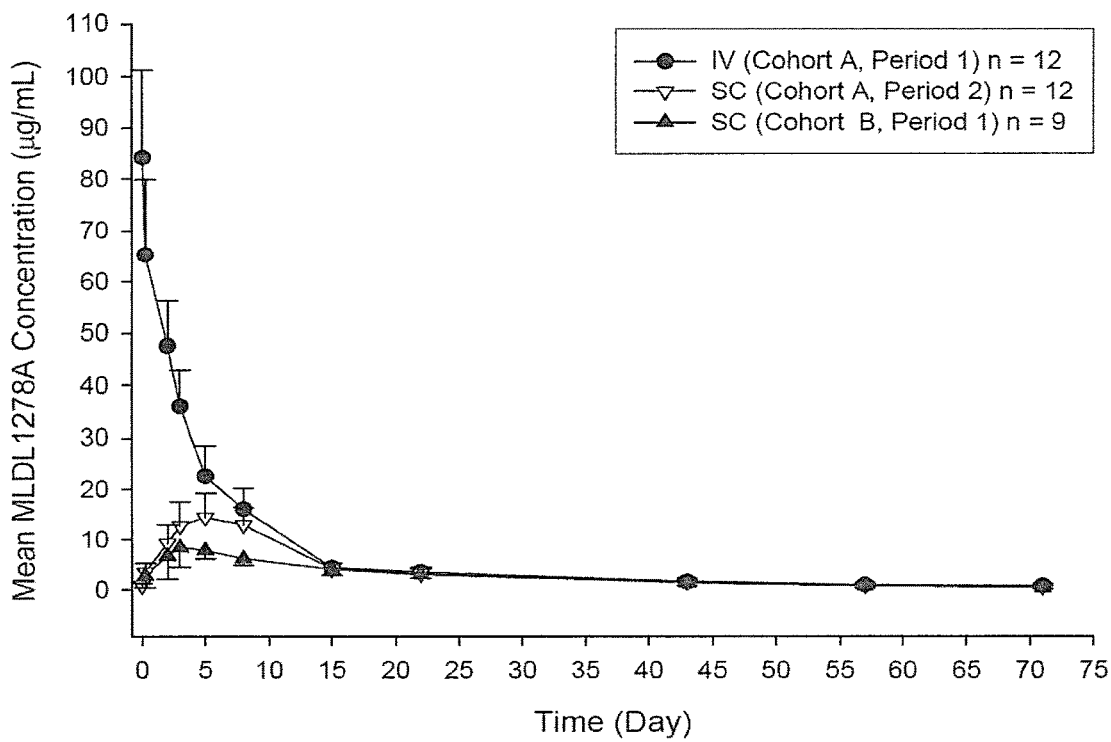
FIG. 30
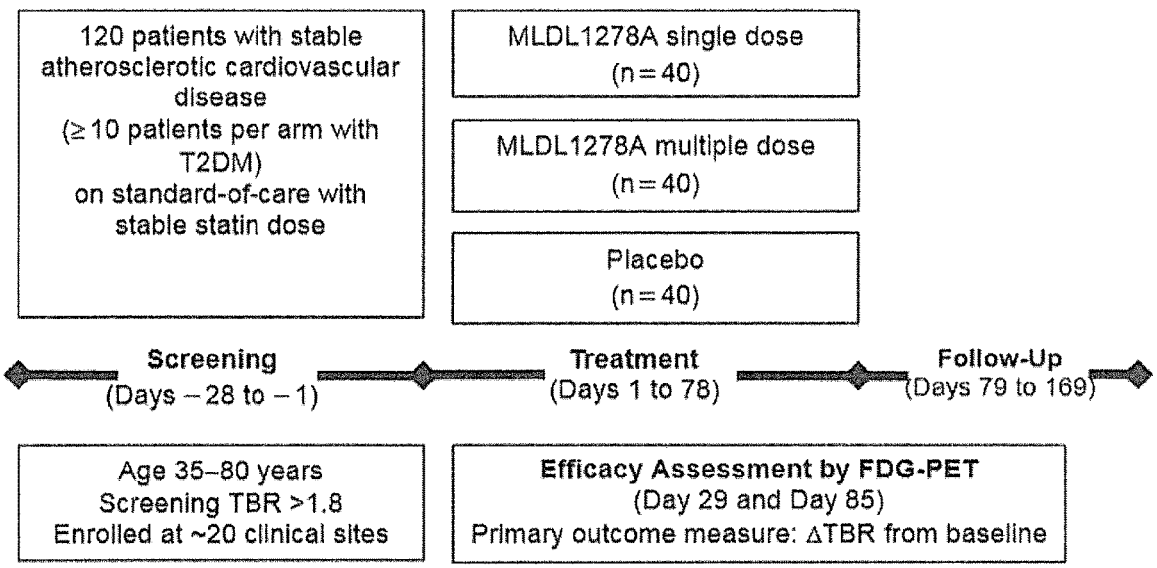
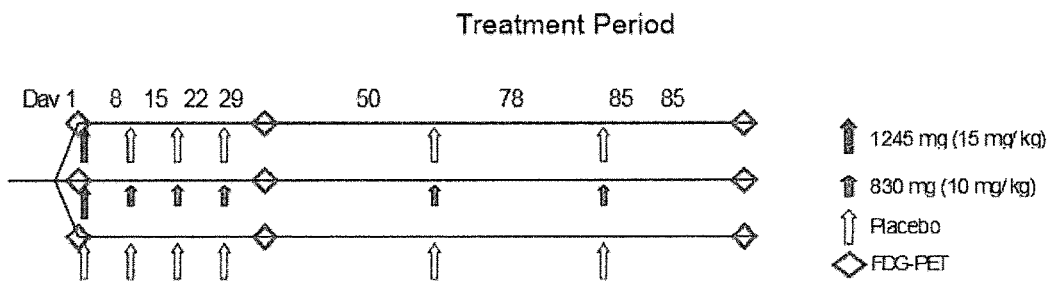
FIG. 31

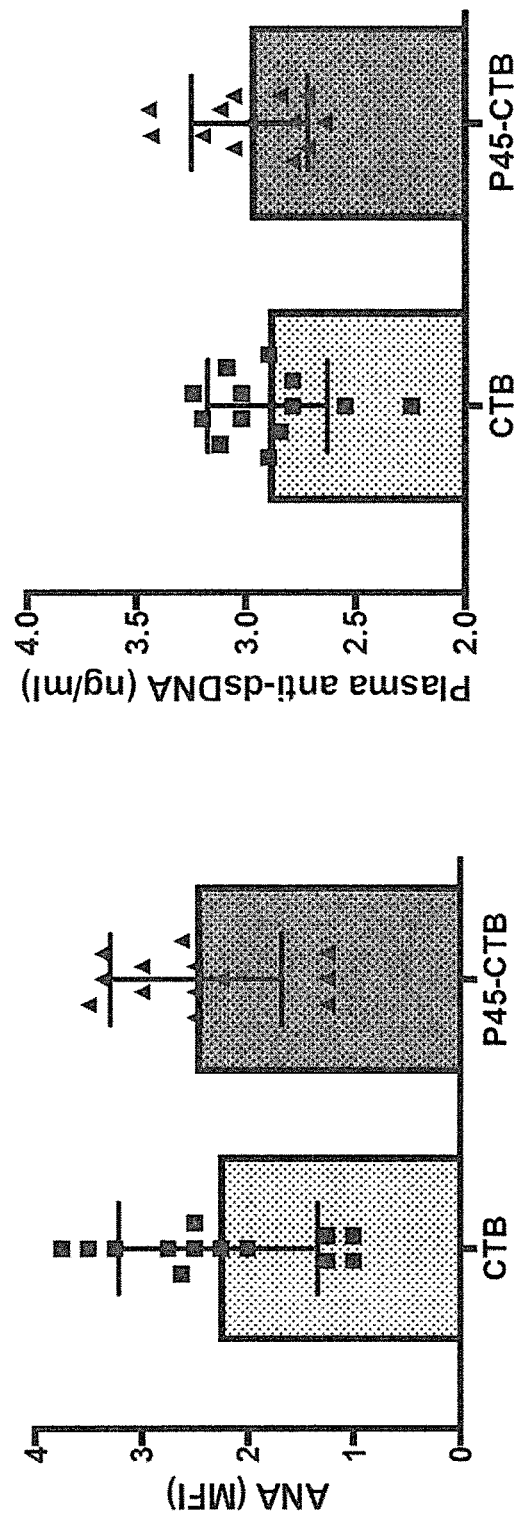
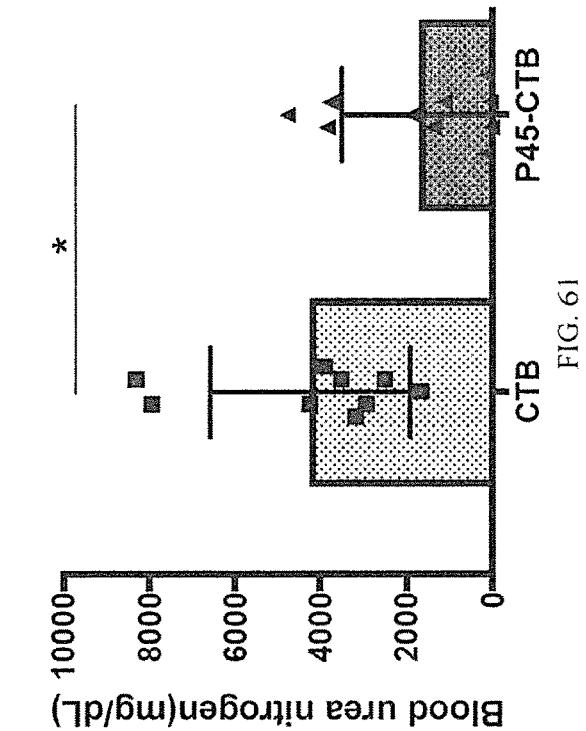
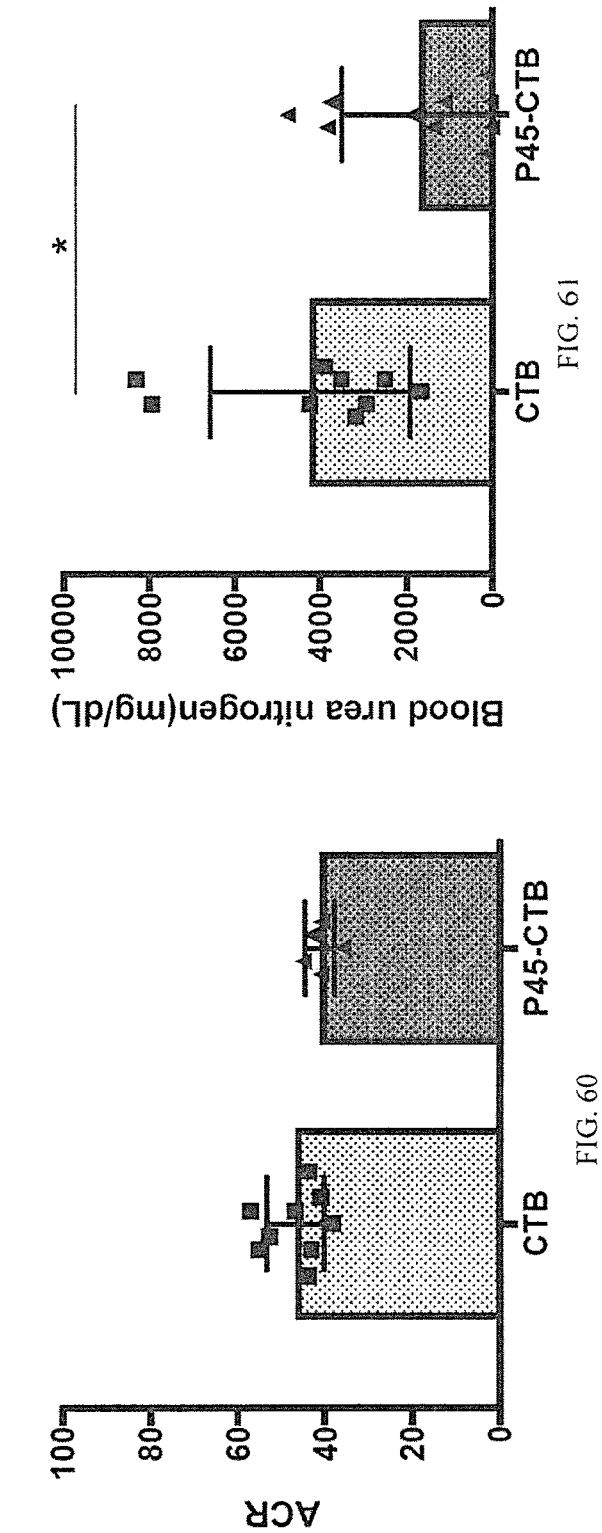
FIG. 58
FIG. 59
FIG. 60
FIG. 61

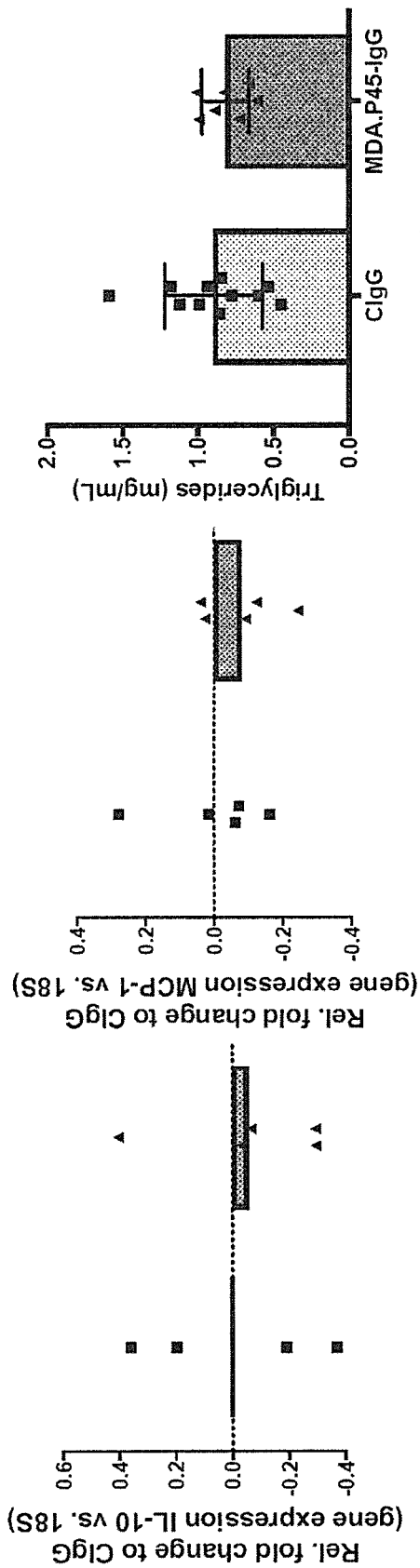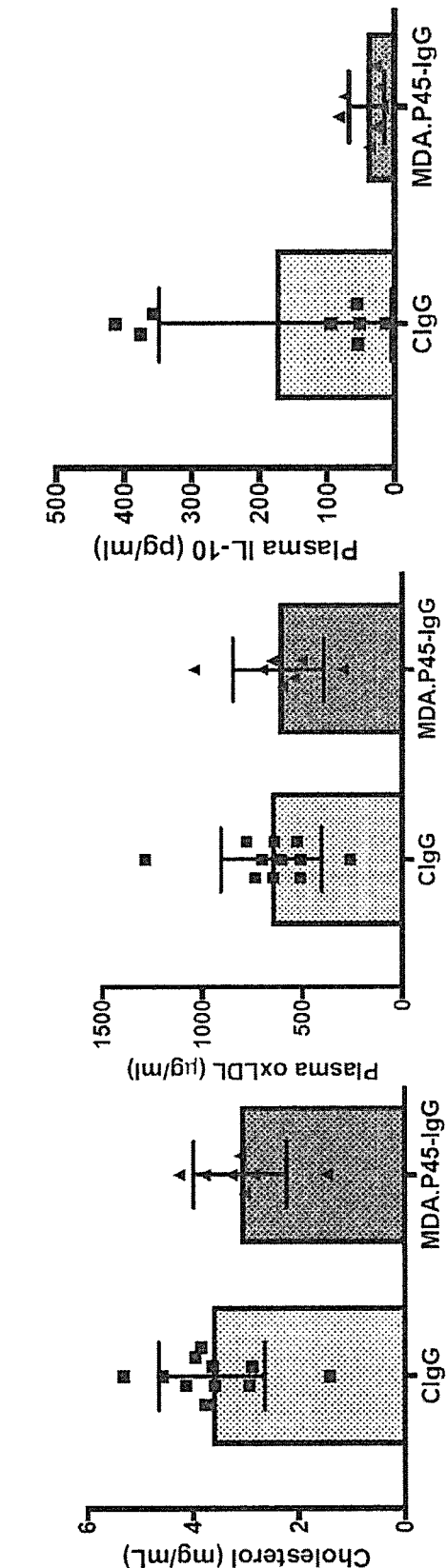

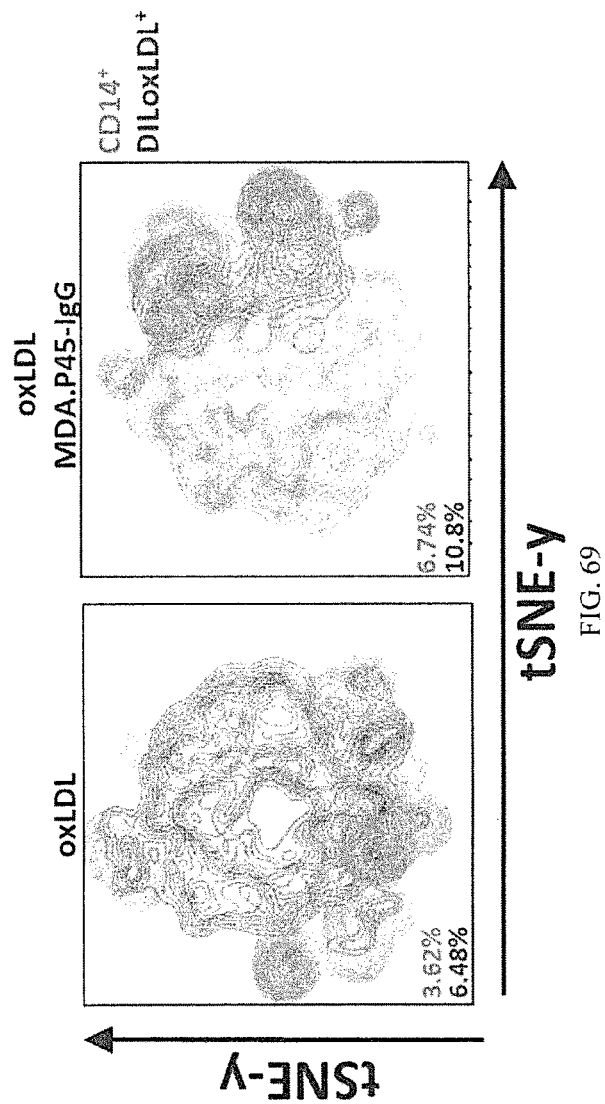
FIG. 69
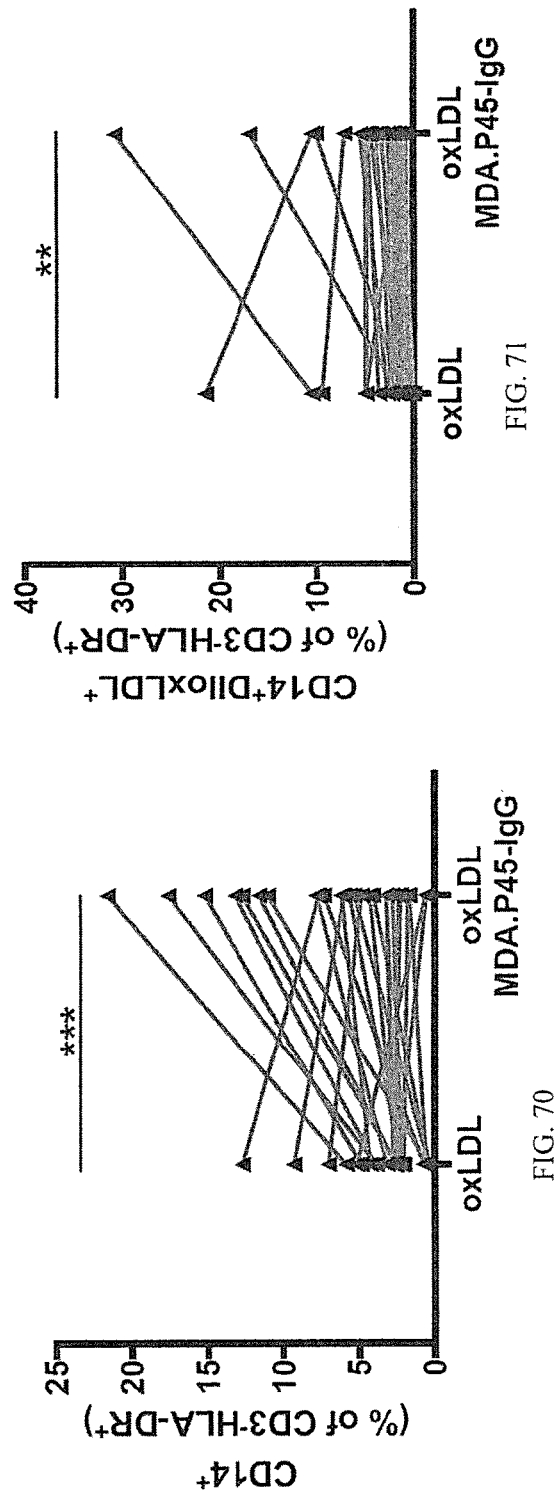
FIG. 70
FIG. 71

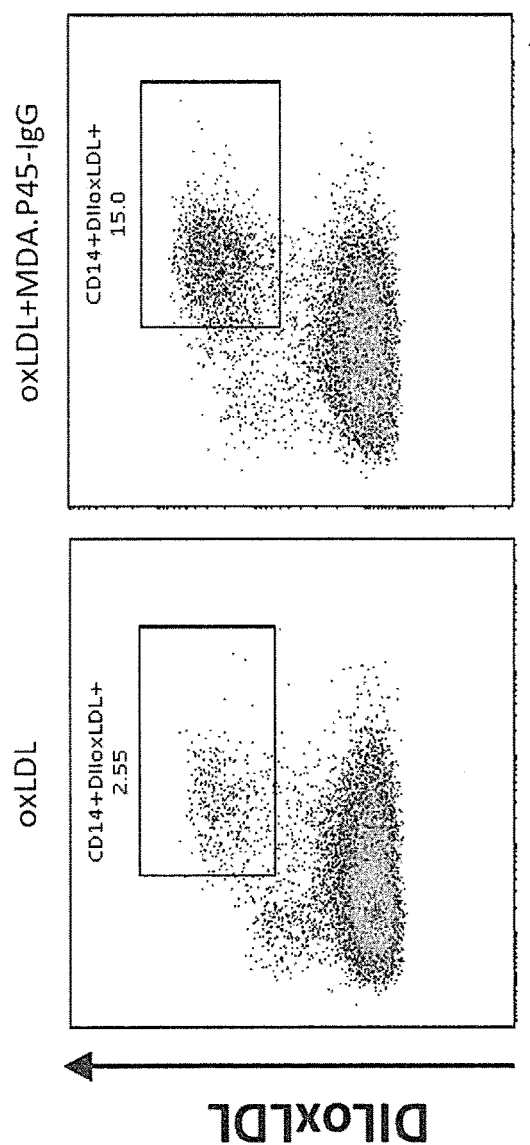
FIG. 72
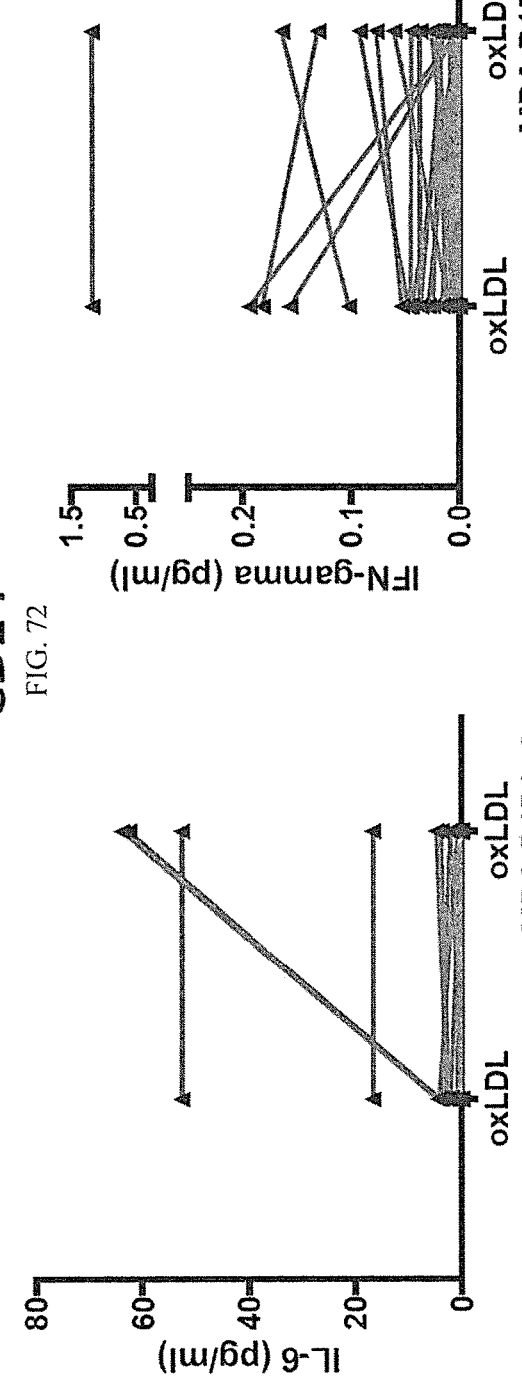
FIG. 73A
FIG. 73B

SEQUENCE LISTING

<160> NUMBER OF SEQ ID NOS: 325

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Glu Glu Glu Met Leu Glu Asn Val Ser Leu Val Cys Pro Lys Asp Ala
1               5                   10                  15

Thr Arg Phe Lys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Ala Thr Arg Phe Lys His Leu Arg Lys Tyr Thr Tyr Asn Tyr Glu Ala
1               5                   10                  15

Glu Ser Ser Ser
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Ala Glu Ser Ser Ser Gly Val Pro Gly Thr Ala Asp Ser Arg Ser Ala
1               5                   10                  15

Thr Arg Ile Asn
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Ala Thr Arg Ile Asn Cys Lys Val Glu Leu Glu Val Pro Gln Leu Cys
1               5                   10                  15

Ser Phe Ile Leu
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 5

Cys Ser Phe Ile Leu Lys Thr Ser Gln Cys Thr Leu Lys Glu Val Tyr
1               5                   10                  15

Gly Phe Asn Pro
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Tyr Gly Phe Asn Pro Glu Gly Lys Ala Leu Leu Lys Lys Thr Lys Asn
1               5                   10                  15

Ser Glu Glu Phe
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Asn Ser Glu Glu Phe Ala Ala Ala Met Ser Arg Tyr Glu Leu Lys Leu
1               5                   10                  15

Ala Ile Pro Glu
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Leu Ala Ile Pro Glu Gly Lys Gln Val Phe Leu Tyr Pro Glu Lys Asp
1               5                   10                  15

Glu Pro Thr Tyr
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Asp Glu Pro Thr Tyr Ile Leu Asn Ile Lys Arg Gly Ile Ile Ser Ala
1               5                   10                  15

Leu Leu Val Pro
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 10

Ala Leu Leu Val Pro Pro Glu Thr Glu Glu Ala Lys Gln Val Leu Phe
1               5                   10                  15

Leu Asp Thr Val
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Phe Leu Asp Thr Val Tyr Gly Asn Cys Ser Thr His Phe Thr Val Lys
1               5                   10                  15

Thr Arg Lys Gly
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Lys Thr Arg Lys Gly Asn Val Ala Thr Glu Ile Ser Thr Glu Arg Asp
1               5                   10                  15

Leu Gly Gln Cys
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

Asp Leu Gly Gln Cys Asp Arg Phe Lys Pro Ile Arg Thr Gly Ile Ser
1               5                   10                  15

Pro Leu Ala Leu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide

<400> SEQUENCE: 14

Ser Pro Leu Ala Leu Ile Lys Gly Met Thr Arg Pro Leu Ser Thr Leu
1               5                   10                  15

Ile Ser Ser Ser
            20

<210> SEQ ID NO 15
<211> LENGTH: 20
<212> TYPE: PRT
<213> ORGANISM: Artificial Sequence
<220> FEATURE:
```

<223> OTHER INFORMATION: Synthetic peptide

<400> SEQUENCE: 15

Leu Ile Ser Ser Ser Gln Ser Cys Gln Tyr Thr Leu Asp Ala Lys Arg
1               5                   10                  15

Lys His Val Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Arg Lys His Val Ala Glu Ala Ile Cys Lys Glu Gln His Leu Phe Leu
1               5                   10                  15

Pro Phe Ser Tyr
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

Leu Pro Phe Ser Tyr Asn Asn Lys Tyr Gly Met Val Ala Gln Val Thr
1               5                   10                  15

Gln Thr Leu Lys
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide

<400> SEQUENCE: 18

Thr Gln Thr Leu Lys Leu Glu Asp Thr Pro Lys Ile Asn Ser Arg Phe
1               5                   10                  15

Phe Gly Glu Gly
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide

<400> SEQUENCE: 19

Phe Phe Gly Glu Gly Thr Lys Lys Met Gly Leu Ala Phe Glu Ser Thr
1               5                   10                  15

Lys Ser Thr Ser
            20

<210> SEQ ID NO 20
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 20

Thr Lys Ser Thr Ser Pro Pro Lys Gln Ala Glu Ala Val Leu Lys Thr
1               5                   10                  15

Leu Gln Glu Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

Thr Leu Gln Glu Leu Lys Lys Leu Thr Ile Ser Glu Gln Asn Ile Gln
1               5                   10                  15

Arg Ala Asn Leu
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Gln Arg Ala Asn Leu Phe Asn Lys Leu Val Thr Glu Leu Arg Gly Leu
1               5                   10                  15

Ser Asp Glu Ala
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Leu Ser Asp Glu Ala Val Thr Ser Leu Leu Pro Gln Leu Ile Glu Val
1               5                   10                  15

Ser Ser Pro Ile
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

Val Ser Ser Pro Ile Thr Leu Gln Ala Leu Val Gln Cys Gly Gln Pro
1               5                   10                  15

Gln Cys Ser Thr
            20

<210> SEQ ID NO 25
<211> LENGTH: 20
<212> TYPE: PRT
```

```
<213> ORGANISM: Artificial Sequence
<220> FEATURE:
<223> OTHER INFORMATION: Synthetic peptide

<400> SEQUENCE: 25

Pro Gln Cys Ser Thr His Ile Leu Gln Trp Leu Lys Arg Val His Ala
1               5                   10                  15

Asn Pro Leu Leu
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Ala Asn Pro Leu Leu Ile Asp Val Val Thr Tyr Leu Val Ala Leu Ile
1               5                   10                  15

Pro Glu Pro Ser
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Ile Pro Glu Pro Ser Ala Gln Gln Leu Arg Glu Ile Phe Asn Met Ala
1               5                   10                  15

Arg Asp Gln Arg
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide

<400> SEQUENCE: 28

Ala Arg Asp Gln Arg Ser Arg Ala Thr Leu Tyr Ala Leu Ser His Ala
1               5                   10                  15

Val Asn Asn Tyr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Ala Val Asn Asn Tyr His Lys Thr Asn Pro Thr Gly Thr Gln Glu Leu
1               5                   10                  15

Leu Asp Ile Ala
            20

<210> SEQ ID NO 30
<211> LENGTH: 20
```

```
<212> TYPE: PRT
<213> ORGANISM: Artificial Sequence
<220> FEATURE:
<223> OTHER INFORMATION: Synthetic peptide

<400> SEQUENCE: 30

Leu Leu Asp Ile Ala Asn Tyr Leu Met Glu Gln Ile Gln Asp Cys
1               5                   10                  15

Thr Gly Asp Glu
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide

<400> SEQUENCE: 31

Cys Thr Gly Asp Glu Asp Tyr Thr Tyr Leu Ile Leu Arg Val Ile Gly
1               5                   10                  15

Asn Met Gly Gln
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic peptide

<400> SEQUENCE: 32

Gly Asn Met Gly Gln Thr Met Glu Gln Leu Thr Pro Glu Leu Lys Ser
1               5                   10                  15

Ser Ile Leu Lys
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

Ser Ser Ile Leu Lys Cys Val Gln Ser Thr Lys Pro Ser Leu Met Ile
1               5                   10                  15

Gln Lys Ala Ala
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Ile Gln Lys Ala Ala Ile Gln Ala Leu Arg Lys Met Glu Pro Lys Asp
1               5                   10                  15

Lys Asp Gln Glu
            20

<210> SEQ ID NO 35
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Asp Lys Asp Gln Glu Val Leu Leu Gln Thr Phe Leu Asp Asp Ala Ser
1               5                   10                  15

Pro Gly Asp Lys
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Ser Pro Gly Asp Lys Arg Leu Ala Ala Tyr Leu Met Leu Met Arg Ser
1               5                   10                  15

Pro Ser Gln Ala
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide

<400> SEQUENCE: 37

Ser Pro Ser Gln Ala Asp Ile Asn Lys Ile Val Gln Ile Leu Pro Trp
1               5                   10                  15

Glu Gln Asn Glu
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide

<400> SEQUENCE: 38

Trp Glu Gln Asn Glu Gln Val Lys Asn Phe Val Ala Ser His Ile Ala
1               5                   10                  15

Asn Ile Leu Asn
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic peptide

<400> SEQUENCE: 39

Ala Asn Ile Leu Asn Ser Glu Glu Leu Asp Ile Gln Asp Leu Lys Lys
1               5                   10                  15

Leu Val Lys Glu
            20
```

<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40

Lys Leu Val Lys Glu Ala Leu Lys Glu Ser Gln Leu Pro Thr Val Met
1               5                   10                  15

Asp Phe Arg Lys
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide

<400> SEQUENCE: 41

Met Asp Phe Arg Lys Phe Ser Arg Asn Tyr Gln Leu Tyr Lys Ser Val
1               5                   10                  15

Ser Leu Pro Ser
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide

<400> SEQUENCE: 42

Val Ser Leu Pro Ser Leu Asp Pro Ala Ser Ala Lys Ile Glu Gly Asn
1               5                   10                  15

Leu Ile Phe Asp
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic peptide

<400> SEQUENCE: 43

Asn Leu Ile Phe Asp Pro Asn Asn Tyr Leu Pro Lys Glu Ser Met Leu
1               5                   10                  15

Lys Thr Thr Leu
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic peptide

<400> SEQUENCE: 44

Leu Lys Thr Thr Leu Thr Ala Phe Gly Phe Ala Ser Ala Asp Leu Ile
1               5                   10                  15

Glu Ile Gly Leu
            20

```
<210> SEQ ID NO 45
<211> LENGTH: 20
<212> TYPE: PRT
<213> ORGANISM: Artificial Sequence
<220> FEATURE:
<223> OTHER INFORMATION: Synthetic peptide

<400> SEQUENCE: 45

Ile Glu Ile Gly Leu Glu Gly Lys Gly Phe Glu Pro Thr Leu Glu Ala
1               5                   10                  15

Leu Phe Gly Lys
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Ala Leu Phe Gly Lys Gln Gly Phe Phe Pro Asp Ser Val Asn Lys Ala
1               5                   10                  15

Leu Tyr Trp Val
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic peptide

<400> SEQUENCE: 47

Ala Leu Tyr Trp Val Asn Gly Gln Val Pro Asp Gly Val Ser Lys Val
1               5                   10                  15

Leu Val Asp His
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

Val Leu Val Asp His Phe Gly Tyr Thr Lys Asp Lys His Glu Gln
1               5                   10                  15

Asp Met Val Asn
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic peptide

<400> SEQUENCE: 49

Gln Asp Met Val Asn Gly Ile Met Leu Ser Val Glu Lys Leu Ile Lys
1               5                   10                  15

Asp Leu Lys Ser
            20
```

```
<210> SEQ ID NO 50
<211> LENGTH: 20
<212> TYPE: PRT
<213> ORGANISM: Artificial Sequence
<220> FEATURE:
<223> OTHER INFORMATION: Synthetic peptide

<400> SEQUENCE: 50

Lys Asp Leu Lys Ser Lys Glu Val Pro Glu Ala Arg Ala Tyr Leu Arg
1               5                   10                  15

Ile Leu Gly Glu
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic peptide

<400> SEQUENCE: 51

Arg Ile Leu Gly Glu Glu Leu Gly Phe Ala Ser Leu His Asp Leu Gln
1               5                   10                  15

Leu Leu Gly Lys
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Gln Leu Leu Gly Lys Leu Leu Leu Met Gly Ala Arg Thr Leu Gln Gly
1               5                   10                  15

Ile Pro Gln Met
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic peptide

<400> SEQUENCE: 53

Gly Ile Pro Gln Met Ile Gly Glu Val Ile Arg Lys Gly Ser Lys Asn
1               5                   10                  15

Asp Phe Phe Leu
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic peptide

<400> SEQUENCE: 54

Asn Asp Phe Phe Leu His Tyr Ile Phe Met Glu Asn Ala Phe Glu Leu
1               5                   10                  15

Pro Thr Gly Ala
```

```
                          20

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Leu Pro Thr Gly Ala Gly Leu Gln Leu Gln Ile Ser Ser Ser Gly Val
1               5                   10                  15

Ile Ala Pro Gly
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Val Ile Ala Pro Gly Ala Lys Ala Gly Val Lys Leu Glu Val Ala Asn
1               5                   10                  15

Met Gln Ala Glu
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic peptide

<400> SEQUENCE: 57

Asn Met Gln Ala Glu Leu Val Ala Lys Pro Ser Val Ser Val Glu Phe
1               5                   10                  15

Val Thr Asn Met
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic peptide

<400> SEQUENCE: 58

Phe Val Thr Asn Met Gly Ile Ile Ile Pro Asp Phe Ala Arg Ser Gly
1               5                   10                  15

Val Gln Met Asn
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide

<400> SEQUENCE: 59

Gly Val Gln Met Asn Thr Asn Phe Phe His Glu Ser Gly Leu Glu Ala
1               5                   10                  15
```

```
His Val Ala Leu
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic peptide

<400> SEQUENCE: 60

Ala His Val Ala Leu Lys Ala Gly Lys Leu Lys Phe Ile Ile Pro Ser
1               5                   10                  15

Pro Lys Arg Pro
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic peptide

<400> SEQUENCE: 61

Ser Pro Lys Arg Pro Val Lys Leu Leu Ser Gly Gly Asn Thr Leu His
1               5                   10                  15

Leu Val Ser Thr
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic peptide

<400> SEQUENCE: 62

His Leu Val Ser Thr Thr Lys Thr Glu Val Ile Pro Pro Leu Ile Glu
1               5                   10                  15

Asn Arg Gln Ser
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic peptide

<400> SEQUENCE: 63

Glu Asn Arg Gln Ser Trp Ser Val Cys Lys Gln Val Phe Pro Gly Leu
1               5                   10                  15

Asn Tyr Cys Thr
            20

<210> SEQ ID NO 64
<211> LENGTH: 20
<212> TYPE: PRT
<213> ORGANISM: Artificial Sequence
<220> FEATURE:
<223> OTHER INFORMATION: Synthetic peptide

<400> SEQUENCE: 64

Leu Asn Tyr Cys Thr Ser Gly Ala Tyr Ser Asn Ala Ser Ser Thr Asp
1               5                   10                  15
```

```
Ser Ala Ser Tyr
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic peptide

<400> SEQUENCE: 65

Asp Ser Ala Ser Tyr Tyr Pro Leu Thr Gly Asp Thr Arg Leu Glu Leu
1               5                   10                  15

Glu Leu Arg Pro
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide

<400> SEQUENCE: 66

Leu Glu Leu Arg Pro Thr Gly Glu Ile Glu Gln Tyr Ser Val Ser Ala
1               5                   10                  15

Thr Tyr Glu Leu
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic peptide

<400> SEQUENCE: 67

Ala Thr Tyr Glu Leu Gln Arg Glu Asp Arg Ala Leu Val Asp Thr Leu
1               5                   10                  15

Lys Phe Val Thr
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic peptide

<400> SEQUENCE: 68

Leu Lys Phe Val Thr Gln Ala Glu Gly Ala Lys Gln Thr Glu Ala Thr
1               5                   10                  15

Met Thr Phe Lys
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide

<400> SEQUENCE: 69

Thr Met Thr Phe Lys Tyr Asn Arg Gln Ser Met Thr Leu Ser Ser Glu
```

```
                1               5                  10                 15
Val Gln Ile Pro
           20

<210> SEQ ID NO 70
<211> LENGTH: 20
<212> TYPE: PRT
<213> ORGANISM: Artificial Sequence
<220> FEATURE:
<223> OTHER INFORMATION: Synthetic peptide

<400> SEQUENCE: 70

Glu Val Gln Ile Pro Asp Phe Asp Val Asp Leu Gly Thr Ile Leu Arg
1               5                  10                 15

Val Asn Asp Glu
           20

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide

<400> SEQUENCE: 71

Arg Val Asn Asp Glu Ser Thr Glu Gly Lys Thr Ser Tyr Arg Leu Thr
1               5                  10                 15

Leu Asp Ile Gln
           20

<210> SEQ ID NO 72
<211> LENGTH: 20
<212> TYPE: PRT
<213> ORGANISM: Artificial Sequence
<220> FEATURE:
<223> OTHER INFORMATION: Synthetic peptide

<400> SEQUENCE: 72

Thr Leu Asp Ile Gln Asn Lys Lys Ile Thr Glu Val Ala Leu Met Gly
1               5                  10                 15

His Leu Ser Cys
           20

<210> SEQ ID NO 73
<211> LENGTH: 20
<212> TYPE: PRT
<213> ORGANISM: Artificial Sequence
<220> FEATURE:
<223> OTHER INFORMATION: Synthetic peptide

<400> SEQUENCE: 73

Gly His Leu Ser Cys Asp Thr Lys Glu Glu Arg Lys Ile Lys Gly Val
1               5                  10                 15

Ile Ser Ile Pro
           20

<210> SEQ ID NO 74
<211> LENGTH: 20
<212> TYPE: PRT
<213> ORGANISM: Artificial Sequence
<220> FEATURE:
<223> OTHER INFORMATION: Synthetic peptide

<400> SEQUENCE: 74
```

```
Val Ile Ser Ile Pro Arg Leu Gln Ala Glu Ala Arg Ser Glu Ile Leu
1               5                   10                  15

Ala His Trp Ser
            20

<210> SEQ ID NO 75
<211> LENGTH: 20
<212> TYPE: PRT
<213> ORGANISM: Artificial Sequence
<220> FEATURE:
<223> OTHER INFORMATION: Synthetic peptide

<400> SEQUENCE: 75

Leu Ala His Trp Ser Pro Ala Lys Leu Leu Leu Gln Met Asp Ser Ser
1               5                   10                  15

Ala Thr Ala Tyr
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic peptide

<400> SEQUENCE: 76

Ser Ala Thr Ala Tyr Gly Ser Thr Val Ser Lys Arg Val Ala Trp His
1               5                   10                  15

Tyr Asp Glu Glu
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic peptide

<400> SEQUENCE: 77

His Tyr Asp Glu Glu Lys Ile Glu Phe Glu Trp Asn Thr Gly Thr Asn
1               5                   10                  15

Val Asp Thr Lys
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic peptide

<400> SEQUENCE: 78

Asn Val Asp Thr Lys Lys Met Thr Ser Asn Phe Pro Val Asp Leu Ser
1               5                   10                  15

Asp Tyr Pro Lys
            20

<210> SEQ ID NO 79
<211> LENGTH: 20
<212> TYPE: PRT
<213> ORGANISM: Artificial Sequence
<220> FEATURE:
<223> OTHER INFORMATION: Synthetic peptide

<400> SEQUENCE: 79
```

```
Ser Asp Tyr Pro Lys Ser Leu His Met Tyr Ala Asn Arg Leu Leu Asp
1               5                   10                  15

His Arg Val Pro
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic peptide

<400> SEQUENCE: 80

Asp His Arg Val Pro Glu Thr Asp Met Thr Phe Arg His Val Gly Ser
1               5                   10                  15

Lys Leu Ile Val
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic peptide

<400> SEQUENCE: 81

Ser Lys Leu Ile Val Ala Met Ser Ser Trp Leu Gln Lys Ala Ser Gly
1               5                   10                  15

Ser Leu Pro Tyr
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic peptide

<400> SEQUENCE: 82

Gly Ser Leu Pro Tyr Thr Gln Thr Leu Gln Asp His Leu Asn Ser Leu
1               5                   10                  15

Lys Glu Phe Asn
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic peptide

<400> SEQUENCE: 83

Leu Lys Glu Phe Asn Leu Gln Asn Met Gly Leu Pro Asp Phe His Ile
1               5                   10                  15

Pro Glu Asn Leu
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 84

Ile Pro Glu Asn Leu Phe Leu Lys Ser Asp Gly Arg Val Lys Tyr Thr
1               5                   10                  15

Leu Asn Lys Asn
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic peptide

<400> SEQUENCE: 85

Thr Leu Asn Lys Asn Ser Leu Lys Ile Glu Ile Pro Leu Pro Phe Gly
1               5                   10                  15

Gly Lys Ser Ser
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic peptide

<400> SEQUENCE: 86

Gly Gly Lys Ser Ser Arg Asp Leu Lys Met Leu Glu Thr Val Arg Thr
1               5                   10                  15

Pro Ala Leu His
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic peptide

<400> SEQUENCE: 87

Thr Pro Ala Leu His Phe Lys Ser Val Gly Phe His Leu Pro Ser Arg
1               5                   10                  15

Glu Phe Gln Val
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic peptide

<400> SEQUENCE: 88

Arg Glu Phe Gln Val Pro Thr Phe Thr Ile Pro Lys Leu Tyr Gln Leu
1               5                   10                  15

Gln Val Pro Leu
            20

<210> SEQ ID NO 89
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 89

Leu Gln Val Pro Leu Leu Gly Val Leu Asp Leu Ser Thr Asn Val Tyr
1               5                   10                  15

Ser Asn Leu Tyr
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic peptide

<400> SEQUENCE: 90

Tyr Ser Asn Leu Tyr Asn Trp Ser Ala Ser Tyr Ser Gly Gly Asn Thr
1               5                   10                  15

Ser Thr Asp His
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic peptide

<400> SEQUENCE: 91

Thr Ser Thr Asp His Phe Ser Leu Arg Ala Arg Tyr His Met Lys Ala
1               5                   10                  15

Asp Ser Val Val
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic peptide

<400> SEQUENCE: 92

Ala Asp Ser Val Val Asp Leu Leu Ser Tyr Asn Val Gln Gly Ser Gly
1               5                   10                  15

Glu Thr Thr Tyr
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic peptide

<400> SEQUENCE: 93

Gly Glu Thr Thr Tyr Asp His Lys Asn Thr Phe Thr Leu Ser Cys Asp
1               5                   10                  15

Gly Ser Leu Arg
            20

<210> SEQ ID NO 94
<211> LENGTH: 20
<212> TYPE: PRT
<213> ORGANISM: Artificial Sequence
<220> FEATURE:

<223> OTHER INFORMATION: Synthetic peptide

<400> SEQUENCE: 94

Asp Gly Ser Leu Arg His Lys Phe Leu Asp Ser Asn Ile Lys Phe Ser
1               5                   10                  15

His Val Glu Lys
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic peptide

<400> SEQUENCE: 95

Ser His Val Glu Lys Leu Gly Asn Asn Pro Val Ser Lys Gly Leu Leu
1               5                   10                  15

Ile Phe Asp Ala
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic peptide

<400> SEQUENCE: 96

Leu Ile Phe Asp Ala Ser Ser Ser Trp Gly Pro Gln Met Ser Ala Ser
1               5                   10                  15

Val His Leu Asp
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic peptide

<400> SEQUENCE: 97

Ser Val His Leu Asp Ser Lys Lys Lys Gln His Leu Phe Val Lys Glu
1               5                   10                  15

Val Lys Ile Asp
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic peptide

<400> SEQUENCE: 98

Glu Val Lys Ile Asp Gly Gln Phe Arg Val Ser Ser Phe Tyr Ala Lys
1               5                   10                  15

Gly Thr Tyr Gly
            20

<210> SEQ ID NO 99
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 99

Lys Gly Thr Tyr Gly Leu Ser Cys Gln Arg Asp Pro Asn Thr Gly Arg
1               5                   10                  15

Leu Asn Gly Glu
            20

<210> SEQ ID NO 100
<211> LENGTH: 20
<212> TYPE: PRT
<213> ORGANISM: Artificial Sequence
<220> FEATURE:
<223> OTHER INFORMATION: Synthetic peptide

<400> SEQUENCE: 100

Arg Leu Asn Gly Glu Ser Asn Leu Arg Phe Asn Ser Ser Tyr Leu Gln
1               5                   10                  15

Gly Thr Asn Gln
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic peptide

<400> SEQUENCE: 101

Gln Gly Thr Asn Gln Ile Thr Gly Arg Tyr Glu Asp Gly Thr Leu Ser
1               5                   10                  15

Leu Thr Ser Thr
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic peptide

<400> SEQUENCE: 102

Ser Leu Thr Ser Thr Ser Asp Leu Gln Ser Gly Ile Ile Lys Asn Thr
1               5                   10                  15

Ala Ser Leu Lys
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic peptide

<400> SEQUENCE: 103

Thr Ala Ser Leu Lys Tyr Glu Asn Tyr Glu Leu Thr Leu Lys Ser Asp
1               5                   10                  15

Thr Asn Gly Lys
            20

<210> SEQ ID NO 104
<211> LENGTH: 20
<212> TYPE: PRT
```

```
<213> ORGANISM: Artificial Sequence
<220> FEATURE:
<223> OTHER INFORMATION: Synthetic peptide

<400> SEQUENCE: 104

Asp Thr Asn Gly Lys Tyr Lys Asn Phe Ala Thr Ser Asn Lys Met Asp
1               5                   10                  15

Met Thr Phe Ser
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic peptide

<400> SEQUENCE: 105

Asp Met Thr Phe Ser Lys Gln Asn Ala Leu Leu Arg Ser Glu Tyr Gln
1               5                   10                  15

Ala Asp Tyr Glu
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic peptide

<400> SEQUENCE: 106

Gln Ala Asp Tyr Glu Ser Leu Arg Phe Phe Ser Leu Leu Ser Gly Ser
1               5                   10                  15

Leu Asn Ser His
            20

<210> SEQ ID NO 107
<211> LENGTH: 20
<212> TYPE: PRT
<213> ORGANISM: Artificial Sequence
<220> FEATURE:
<223> OTHER INFORMATION: Synthetic peptide

<400> SEQUENCE: 107

Ser Leu Asn Ser His Gly Leu Glu Leu Asn Ala Asp Ile Leu Gly Thr
1               5                   10                  15

Asp Lys Ile Asn
            20

<210> SEQ ID NO 108
<211> LENGTH: 20
<212> TYPE: PRT
<213> ORGANISM: Artificial Sequence
<220> FEATURE:
<223> OTHER INFORMATION: Synthetic peptide

<400> SEQUENCE: 108

Thr Asp Lys Ile Asn Ser Gly Ala His Lys Ala Thr Leu Arg Ile Gly
1               5                   10                  15

Gln Asp Gly Ile
            20

<210> SEQ ID NO 109
<211> LENGTH: 20
```

<212> TYPE: PRT
<213> ORGANISM: Artificial Sequence
<220> FEATURE:
<223> OTHER INFORMATION: Synthetic peptide

<400> SEQUENCE: 109

Gly Gln Asp Gly Ile Ser Thr Ser Ala Thr Thr Asn Leu Lys Cys Ser
1               5                   10                  15

Leu Leu Val Leu
            20

<210> SEQ ID NO 110
<211> LENGTH: 20
<212> TYPE: PRT
<213> ORGANISM: Artificial Sequence
<220> FEATURE:
<223> OTHER INFORMATION: Synthetic peptide

<400> SEQUENCE: 110

Ser Leu Leu Val Leu Glu Asn Glu Leu Asn Ala Glu Leu Gly Leu Ser
1               5                   10                  15

Gly Ala Ser Met
            20

<210> SEQ ID NO 111
<211> LENGTH: 20
<212> TYPE: PRT
<213> ORGANISM: Artificial Sequence
<220> FEATURE:
<223> OTHER INFORMATION: Synthetic peptide

<400> SEQUENCE: 111

Ser Gly Ala Ser Met Lys Leu Thr Thr Asn Gly Arg Phe Arg Glu His
1               5                   10                  15

Asn Ala Lys Phe
            20

<210> SEQ ID NO 112
<211> LENGTH: 20
<212> TYPE: PRT
<213> ORGANISM: Artificial Sequence
<220> FEATURE:
<223> OTHER INFORMATION: Synthetic peptide

<400> SEQUENCE: 112

His Asn Ala Lys Phe Ser Leu Asp Gly Lys Ala Ala Leu Thr Glu Leu
1               5                   10                  15

Ser Leu Gly Ser
            20

<210> SEQ ID NO 113
<211> LENGTH: 20
<212> TYPE: PRT
<213> ORGANISM: Artificial Sequence
<220> FEATURE:
<223> OTHER INFORMATION: Synthetic peptide

<400> SEQUENCE: 113

Leu Ser Leu Gly Ser Ala Tyr Gln Ala Met Ile Leu Gly Val Asp Ser
1               5                   10                  15

Lys Asn Ile Phe
            20

<210> SEQ ID NO 114

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 114

Ser Lys Asn Ile Phe Asn Phe Lys Val Ser Gln Glu Gly Leu Lys Leu
1               5                   10                  15

Ser Asn Asp Met
            20

<210> SEQ ID NO 115
<211> LENGTH: 20
<212> TYPE: PRT
<213> ORGANISM: Artificial Sequence
<220> FEATURE:
<223> OTHER INFORMATION: Synthetic peptide

<400> SEQUENCE: 115

Leu Ser Asn Asp Met Met Gly Ser Tyr Ala Glu Met Lys Phe Asp His
1               5                   10                  15

Thr Asn Ser Leu
            20

<210> SEQ ID NO 116
<211> LENGTH: 20
<212> TYPE: PRT
<213> ORGANISM: Artificial Sequence
<220> FEATURE:
<223> OTHER INFORMATION: Synthetic peptide

<400> SEQUENCE: 116

His Thr Asn Ser Leu Asn Ile Ala Gly Leu Ser Leu Asp Phe Ser Ser
1               5                   10                  15

Lys Leu Asp Asn
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic peptide

<400> SEQUENCE: 117

Ser Lys Leu Asp Asn Ile Tyr Ser Ser Asp Lys Phe Tyr Lys Gln Thr
1               5                   10                  15

Val Asn Leu Gln
            20

<210> SEQ ID NO 118
<211> LENGTH: 20
<212> TYPE: PRT
<213> ORGANISM: Artificial Sequence
<220> FEATURE:
<223> OTHER INFORMATION: Synthetic peptide

<400> SEQUENCE: 118

Thr Val Asn Leu Gln Leu Gln Pro Tyr Ser Leu Val Thr Thr Leu Asn
1               5                   10                  15

Ser Asp Leu Lys
            20
```

<210> SEQ ID NO 119
<211> LENGTH: 20
<212> TYPE: PRT
<213> ORGANISM: Artificial Sequence
<220> FEATURE:
<223> OTHER INFORMATION: Synthetic peptide

<400> SEQUENCE: 119

Asn Ser Asp Leu Lys Tyr Asn Ala Leu Asp Leu Thr Asn Asn Gly Lys
1               5                   10                  15

Leu Arg Leu Glu
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic peptide

<400> SEQUENCE: 120

Lys Leu Arg Leu Glu Pro Leu Lys Leu His Val Ala Gly Asn Leu Lys
1               5                   10                  15

Gly Ala Tyr Gln
            20

<210> SEQ ID NO 121
<211> LENGTH: 20
<212> TYPE: PRT
<213> ORGANISM: Artificial Sequence
<220> FEATURE:
<223> OTHER INFORMATION: Synthetic peptide

<400> SEQUENCE: 121

Lys Gly Ala Tyr Gln Asn Asn Glu Ile Lys His Ile Tyr Ala Ile Ser
1               5                   10                  15

Ser Ala Ala Leu
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic peptide

<400> SEQUENCE: 122

Ser Ser Ala Ala Leu Ser Ala Ser Tyr Lys Ala Asp Thr Val Ala Lys
1               5                   10                  15

Val Gln Gly Val
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic peptide

<400> SEQUENCE: 123

Lys Val Gln Gly Val Glu Phe Ser His Arg Leu Asn Thr Asp Ile Ala
1               5                   10                  15

Gly Leu Ala Ser
            20

```
<210> SEQ ID NO 124
<211> LENGTH: 20
<212> TYPE: PRT
<213> ORGANISM: Artificial Sequence
<220> FEATURE:
<223> OTHER INFORMATION: Synthetic peptide

<400> SEQUENCE: 124

Ala Gly Leu Ala Ser Ala Ile Asp Met Ser Thr Asn Tyr Asn Ser Asp
1               5                   10                  15

Ser Leu His Phe
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic peptide

<400> SEQUENCE: 125

Asp Ser Leu His Phe Ser Asn Val Phe Arg Ser Val Met Ala Pro Phe
1               5                   10                  15

Thr Met Thr Ile
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic peptide

<400> SEQUENCE: 126

Phe Thr Met Thr Ile Asp Ala His Thr Asn Gly Asn Gly Lys Leu Ala
1               5                   10                  15

Leu Trp Gly Glu
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic peptide

<400> SEQUENCE: 127

Ala Leu Trp Gly Glu His Thr Gly Gln Leu Tyr Ser Lys Phe Leu Leu
1               5                   10                  15

Lys Ala Glu Pro
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic peptide

<400> SEQUENCE: 128

Leu Lys Ala Glu Pro Leu Ala Phe Thr Phe Ser His Asp Tyr Lys Gly
1               5                   10                  15

Ser Thr Ser His
            20
```

<210> SEQ ID NO 129
<211> LENGTH: 20
<212> TYPE: PRT
<213> ORGANISM: Artificial Sequence
<220> FEATURE:
<223> OTHER INFORMATION: Synthetic peptide

<400> SEQUENCE: 129

Gly Ser Thr Ser His His Leu Val Ser Arg Lys Ser Ile Ser Ala Ala
1               5                   10                  15

Leu Glu His Lys
            20

<210> SEQ ID NO 130
<211> LENGTH: 20
<212> TYPE: PRT
<213> ORGANISM: Artificial Sequence
<220> FEATURE:
<223> OTHER INFORMATION: Synthetic peptide

<400> SEQUENCE: 130

Ala Leu Glu His Lys Val Ser Ala Leu Leu Thr Pro Ala Glu Gln Thr
1               5                   10                  15

Gly Thr Trp Lys
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic peptide

<400> SEQUENCE: 131

Thr Gly Thr Trp Lys Leu Lys Thr Gln Phe Asn Asn Asn Glu Tyr Ser
1               5                   10                  15

Gln Asp Leu Asp
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide

<400> SEQUENCE: 132

Ser Gln Asp Leu Asp Ala Tyr Asn Thr Lys Asp Lys Ile Gly Val Glu
1               5                   10                  15

Leu Thr Gly Arg
            20

<210> SEQ ID NO 133
<211> LENGTH: 20
<212> TYPE: PRT
<213> ORGANISM: Artificial Sequence
<220> FEATURE:
<223> OTHER INFORMATION: Synthetic peptide

<400> SEQUENCE: 133

Glu Leu Thr Gly Arg Thr Leu Ala Asp Leu Thr Leu Leu Asp Ser Pro
1               5                   10                  15

Ile Lys Val Pro

-continued

20

<210> SEQ ID NO 134
<211> LENGTH: 20
<212> TYPE: PRT
<213> ORGANISM: Artificial Sequence
<220> FEATURE:
<223> OTHER INFORMATION: Synthetic peptide

<400> SEQUENCE: 134

Pro Ile Lys Val Pro Leu Leu Leu Ser Glu Pro Ile Asn Ile Ile Asp
1               5                   10                  15

Ala Leu Glu Met
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic peptide

<400> SEQUENCE: 135

Asp Ala Leu Glu Met Arg Asp Ala Val Glu Lys Pro Gln Glu Phe Thr
1               5                   10                  15

Ile Val Ala Phe
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic peptide

<400> SEQUENCE: 136

Thr Ile Val Ala Phe Val Lys Tyr Asp Lys Asn Gln Asp Val His Ser
1               5                   10                  15

Ile Asn Leu Pro
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic peptide

<400> SEQUENCE: 137

Ser Ile Asn Leu Pro Phe Phe Glu Thr Leu Gln Glu Tyr Phe Glu Arg
1               5                   10                  15

Asn Arg Gln Thr
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic peptide

<400> SEQUENCE: 138

Arg Asn Arg Gln Thr Ile Ile Val Val Val Glu Asn Val Gln Arg Asn
1               5                   10                  15

-continued

Leu Lys His Ile
            20

<210> SEQ ID NO 139
<211> LENGTH: 20
<212> TYPE: PRT
<213> ORGANISM: Artificial Sequence
<220> FEATURE:
<223> OTHER INFORMATION: Synthetic peptide

<400> SEQUENCE: 139

Asn Leu Lys His Ile Asn Ile Asp Gln Phe Val Arg Lys Tyr Arg Ala
1               5                   10                  15

Ala Leu Gly Lys
            20

<210> SEQ ID NO 140
<211> LENGTH: 20
<212> TYPE: PRT
<213> ORGANISM: Artificial Sequence
<220> FEATURE:
<223> OTHER INFORMATION: Synthetic peptide

<400> SEQUENCE: 140

Ala Ala Leu Gly Lys Leu Pro Gln Gln Ala Asn Asp Tyr Leu Asn Ser
1               5                   10                  15

Phe Asn Trp Glu
            20

<210> SEQ ID NO 141
<211> LENGTH: 20
<212> TYPE: PRT
<213> ORGANISM: Artificial Sequence
<220> FEATURE:
<223> OTHER INFORMATION: Synthetic peptide

<400> SEQUENCE: 141

Ser Phe Asn Trp Glu Arg Gln Val Ser His Ala Lys Glu Lys Leu Thr
1               5                   10                  15

Ala Leu Thr Lys
            20

<210> SEQ ID NO 142
<211> LENGTH: 20
<212> TYPE: PRT
<213> ORGANISM: Artificial Sequence
<220> FEATURE:
<223> OTHER INFORMATION: Synthetic peptide

<400> SEQUENCE: 142

Thr Ala Leu Thr Lys Lys Tyr Arg Ile Thr Glu Asn Asp Ile Gln Ile
1               5                   10                  15

Ala Leu Asp Asp
            20

<210> SEQ ID NO 143
<211> LENGTH: 20
<212> TYPE: PRT
<213> ORGANISM: Artificial Sequence
<220> FEATURE:
<223> OTHER INFORMATION: Synthetic peptide

<400> SEQUENCE: 143

Ile Ala Leu Asp Asp Ala Lys Ile Asn Phe Asn Glu Lys Leu Ser Gln
1               5                   10                  15

```
Leu Gln Thr Tyr
            20

<210> SEQ ID NO 144
<211> LENGTH: 20
<212> TYPE: PRT
<213> ORGANISM: Artificial Sequence
<220> FEATURE:
<223> OTHER INFORMATION: Synthetic peptide

<400> SEQUENCE: 144

Gln Leu Gln Thr Tyr Met Ile Gln Phe Asp Gln Tyr Ile Lys Asp Ser
1               5                   10                  15

Tyr Asp Leu His
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic peptide

<400> SEQUENCE: 145

Ser Tyr Asp Leu His Asp Leu Lys Ile Ala Ile Ala Asn Ile Ile Asp
1               5                   10                  15

Glu Ile Ile Glu
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic peptide

<400> SEQUENCE: 146

Asp Glu Ile Ile Glu Lys Leu Lys Ser Leu Asp Glu His Tyr His Ile
1               5                   10                  15

Arg Val Asn Leu
            20

<210> SEQ ID NO 147
<211> LENGTH: 20
<212> TYPE: PRT
<213> ORGANISM: Artificial Sequence
<220> FEATURE:
<223> OTHER INFORMATION: Synthetic peptide

<400> SEQUENCE: 147

Ile Arg Val Asn Leu Val Lys Thr Ile His Asp Leu His Leu Phe Ile
1               5                   10                  15

Glu Asn Ile Asp
            20

<210> SEQ ID NO 148
<211> LENGTH: 20
<212> TYPE: PRT
<213> ORGANISM: Artificial Sequence
<220> FEATURE:
<223> OTHER INFORMATION: Synthetic peptide

<400> SEQUENCE: 148

Ile Glu Asn Ile Asp Phe Asn Lys Ser Gly Ser Ser Thr Ala Ser Trp
```

```
1               5                   10                  15

Ile Gln Asn Val
            20

<210> SEQ ID NO 149
<211> LENGTH: 20
<212> TYPE: PRT
<213> ORGANISM: Artificial Sequence
<220> FEATURE:
<223> OTHER INFORMATION: Synthetic peptide

<400> SEQUENCE: 149

Trp Ile Gln Asn Val Asp Thr Lys Tyr Gln Ile Arg Ile Gln Ile Gln
1               5                   10                  15

Glu Lys Leu Gln
            20

<210> SEQ ID NO 150
<211> LENGTH: 20
<212> TYPE: PRT
<213> ORGANISM: Artificial Sequence
<220> FEATURE:
<223> OTHER INFORMATION: Synthetic peptide

<400> SEQUENCE: 150

Gln Glu Lys Leu Gln Gln Leu Lys Arg His Ile Gln Asn Ile Asp Ile
1               5                   10                  15

Gln His Leu Ala
            20

<210> SEQ ID NO 151
<211> LENGTH: 20
<212> TYPE: PRT
<213> ORGANISM: Artificial Sequence
<220> FEATURE:
<223> OTHER INFORMATION: Synthetic peptide

<400> SEQUENCE: 151

Ile Gln His Leu Ala Gly Lys Leu Lys Gln His Ile Glu Ala Ile Asp
1               5                   10                  15

Val Arg Val Leu
            20

<210> SEQ ID NO 152
<211> LENGTH: 20
<212> TYPE: PRT
<213> ORGANISM: Artificial Sequence
<220> FEATURE:
<223> OTHER INFORMATION: Synthetic peptide

<400> SEQUENCE: 152

Asp Val Arg Val Leu Leu Asp Gln Leu Gly Thr Thr Ile Ser Phe Glu
1               5                   10                  15

Arg Ile Asn Asp
            20

<210> SEQ ID NO 153
<211> LENGTH: 20
<212> TYPE: PRT
<213> ORGANISM: Artificial Sequence
<220> FEATURE:
<223> OTHER INFORMATION: Synthetic peptide

<400> SEQUENCE: 153
```

```
Glu Arg Ile Asn Asp Val Leu Glu His Val Lys His Phe Val Ile Asn
1               5                   10                  15

Leu Ile Gly Asp
            20

<210> SEQ ID NO 154
<211> LENGTH: 20
<212> TYPE: PRT
<213> ORGANISM: Artificial Sequence
<220> FEATURE:
<223> OTHER INFORMATION: Synthetic peptide

<400> SEQUENCE: 154

Asn Leu Ile Gly Asp Phe Glu Val Ala Glu Lys Ile Asn Ala Phe Arg
1               5                   10                  15

Ala Lys Val His
            20

<210> SEQ ID NO 155
<211> LENGTH: 20
<212> TYPE: PRT
<213> ORGANISM: Artificial Sequence
<220> FEATURE:
<223> OTHER INFORMATION: Synthetic peptide

<400> SEQUENCE: 155

Arg Ala Lys Val His Glu Leu Ile Glu Arg Tyr Glu Val Asp Gln Gln
1               5                   10                  15

Ile Gln Val Leu
            20

<210> SEQ ID NO 156
<211> LENGTH: 20
<212> TYPE: PRT
<213> ORGANISM: Artificial Sequence
<220> FEATURE:
<223> OTHER INFORMATION: Synthetic peptide

<400> SEQUENCE: 156

Gln Ile Gln Val Leu Met Asp Lys Leu Val Glu Leu Thr His Gln Tyr
1               5                   10                  15

Lys Leu Lys Glu
            20

<210> SEQ ID NO 157
<211> LENGTH: 20
<212> TYPE: PRT
<213> ORGANISM: Artificial Sequence
<220> FEATURE:
<223> OTHER INFORMATION: Synthetic peptide

<400> SEQUENCE: 157

Tyr Lys Leu Lys Glu Thr Ile Gln Lys Leu Ser Asn Val Leu Gln Gln
1               5                   10                  15

Val Lys Ile Lys
            20

<210> SEQ ID NO 158
<211> LENGTH: 20
<212> TYPE: PRT
<213> ORGANISM: Artificial Sequence
<220> FEATURE:
<223> OTHER INFORMATION: Synthetic peptide

<400> SEQUENCE: 158
```

```
Gln Val Lys Ile Lys Asp Tyr Phe Glu Lys Leu Val Gly Phe Ile Asp
1               5                   10                  15

Asp Ala Val Lys
            20

<210> SEQ ID NO 159
<211> LENGTH: 20
<212> TYPE: PRT
<213> ORGANISM: Artificial Sequence
<220> FEATURE:
<223> OTHER INFORMATION: Synthetic peptide

<400> SEQUENCE: 159

Asp Asp Ala Val Lys Lys Leu Asn Glu Leu Ser Phe Lys Thr Phe Ile
1               5                   10                  15

Glu Asp Val Asn
            20

<210> SEQ ID NO 160
<211> LENGTH: 20
<212> TYPE: PRT
<213> ORGANISM: Artificial Sequence
<220> FEATURE:
<223> OTHER INFORMATION: Synthetic peptide

<400> SEQUENCE: 160

Ile Glu Asp Val Asn Lys Phe Leu Asp Met Leu Ile Lys Lys Leu Lys
1               5                   10                  15

Ser Phe Asp Tyr
            20

<210> SEQ ID NO 161
<211> LENGTH: 20
<212> TYPE: PRT
<213> ORGANISM: Artificial Sequence
<220> FEATURE:
<223> OTHER INFORMATION: Synthetic peptide

<400> SEQUENCE: 161

Lys Ser Phe Asp Tyr His Gln Phe Val Asp Glu Thr Asn Asp Lys Ile
1               5                   10                  15

Arg Glu Val Thr
            20

<210> SEQ ID NO 162
<211> LENGTH: 20
<212> TYPE: PRT
<213> ORGANISM: Artificial Sequence
<220> FEATURE:
<223> OTHER INFORMATION: Synthetic peptide

<400> SEQUENCE: 162

Ile Arg Glu Val Thr Gln Arg Leu Asn Gly Glu Ile Gln Ala Leu Glu
1               5                   10                  15

Leu Pro Gln Lys
            20

<210> SEQ ID NO 163
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 163

Glu Leu Pro Gln Lys Ala Glu Ala Leu Lys Leu Phe Leu Glu Glu Thr
1               5                   10                  15

Lys Ala Thr Val
            20

<210> SEQ ID NO 164
<211> LENGTH: 20
<212> TYPE: PRT
<213> ORGANISM: Artificial Sequence
<220> FEATURE:
<223> OTHER INFORMATION: Synthetic peptide

<400> SEQUENCE: 164

Thr Lys Ala Thr Val Ala Val Tyr Leu Glu Ser Leu Gln Asp Thr Lys
1               5                   10                  15

Ile Thr Leu Ile
            20

<210> SEQ ID NO 165
<211> LENGTH: 20
<212> TYPE: PRT
<213> ORGANISM: Artificial Sequence
<220> FEATURE:
<223> OTHER INFORMATION: Synthetic peptide

<400> SEQUENCE: 165

Lys Ile Thr Leu Ile Ile Asn Trp Leu Gln Glu Ala Leu Ser Ser Ala
1               5                   10                  15

Ser Leu Ala His
            20

<210> SEQ ID NO 166
<211> LENGTH: 20
<212> TYPE: PRT
<213> ORGANISM: Artificial Sequence
<220> FEATURE:
<223> OTHER INFORMATION: Synthetic peptide

<400> SEQUENCE: 166

Ala Ser Leu Ala His Met Lys Ala Lys Phe Arg Glu Thr Leu Glu Asp
1               5                   10                  15

Thr Arg Asp Arg
            20

<210> SEQ ID NO 167
<211> LENGTH: 20
<212> TYPE: PRT
<213> ORGANISM: Artificial Sequence
<220> FEATURE:
<223> OTHER INFORMATION: Synthetic peptide

<400> SEQUENCE: 167

Asp Thr Arg Asp Arg Met Tyr Gln Met Asp Ile Gln Gln Glu Leu Gln
1               5                   10                  15

Arg Tyr Leu Ser
            20

<210> SEQ ID NO 168
<211> LENGTH: 20
<212> TYPE: PRT
<213> ORGANISM: Artificial Sequence
<220> FEATURE:
<223> OTHER INFORMATION: Synthetic peptide

<400> SEQUENCE: 168

Gln Arg Tyr Leu Ser Leu Val Gly Gln Val Tyr Ser Thr Leu Val Thr
1               5                   10                  15

Tyr Ile Ser Asp
            20

<210> SEQ ID NO 169
<211> LENGTH: 20
<212> TYPE: PRT
<213> ORGANISM: Artificial Sequence
<220> FEATURE:
<223> OTHER INFORMATION: Synthetic peptide

<400> SEQUENCE: 169

Thr Tyr Ile Ser Asp Trp Trp Thr Leu Ala Ala Lys Asn Leu Thr Asp
1               5                   10                  15

Phe Ala Glu Gln
            20

<210> SEQ ID NO 170
<211> LENGTH: 20
<212> TYPE: PRT
<213> ORGANISM: Artificial Sequence
<220> FEATURE:
<223> OTHER INFORMATION: Synthetic peptide

<400> SEQUENCE: 170

Asp Phe Ala Glu Gln Tyr Ser Ile Gln Asp Trp Ala Lys Arg Met Lys
1               5                   10                  15

Ala Leu Val Glu
            20

<210> SEQ ID NO 171
<211> LENGTH: 20
<212> TYPE: PRT
<213> ORGANISM: Artificial Sequence
<220> FEATURE:
<223> OTHER INFORMATION: Synthetic peptide

<400> SEQUENCE: 171

Lys Ala Leu Val Glu Gln Gly Phe Thr Val Pro Glu Ile Lys Thr Ile
1               5                   10                  15

Leu Gly Thr Met
            20

<210> SEQ ID NO 172
<211> LENGTH: 20
<212> TYPE: PRT
<213> ORGANISM: Artificial Sequence
<220> FEATURE:
<223> OTHER INFORMATION: Synthetic peptide

<400> SEQUENCE: 172

Ile Leu Gly Thr Met Pro Ala Phe Glu Val Ser Leu Gln Ala Leu Gln
1               5                   10                  15

Lys Ala Thr Phe
            20

<210> SEQ ID NO 173
<211> LENGTH: 20
<212> TYPE: PRT
<213> ORGANISM: Artificial Sequence
<220> FEATURE:

<223> OTHER INFORMATION: Synthetic peptide

<400> SEQUENCE: 173

Gln Lys Ala Thr Phe Gln Thr Pro Asp Phe Ile Val Pro Leu Thr Asp
1               5                   10                  15

Leu Arg Ile Pro
            20

<210> SEQ ID NO 174
<211> LENGTH: 20
<212> TYPE: PRT
<213> ORGANISM: Artificial Sequence
<220> FEATURE:
<223> OTHER INFORMATION: Synthetic peptide

<400> SEQUENCE: 174

Asp Leu Arg Ile Pro Ser Val Gln Ile Asn Phe Lys Asp Leu Lys Asn
1               5                   10                  15

Ile Lys Ile Pro
            20

<210> SEQ ID NO 175
<211> LENGTH: 20
<212> TYPE: PRT
<213> ORGANISM: Artificial Sequence
<220> FEATURE:
<223> OTHER INFORMATION: Synthetic peptide

<400> SEQUENCE: 175

Asn Ile Lys Ile Pro Ser Arg Phe Ser Thr Pro Glu Phe Thr Ile Leu
1               5                   10                  15

Asn Thr Phe His
            20

<210> SEQ ID NO 176
<211> LENGTH: 20
<212> TYPE: PRT
<213> ORGANISM: Artificial Sequence
<220> FEATURE:
<223> OTHER INFORMATION: Synthetic peptide

<400> SEQUENCE: 176

Leu Asn Thr Phe His Ile Pro Ser Phe Thr Ile Asp Phe Val Glu Met
1               5                   10                  15

Lys Val Lys Ile
            20

<210> SEQ ID NO 177
<211> LENGTH: 20
<212> TYPE: PRT
<213> ORGANISM: Artificial Sequence
<220> FEATURE:
<223> OTHER INFORMATION: Synthetic peptide

<400> SEQUENCE: 177

Met Lys Val Lys Ile Ile Arg Thr Ile Asp Gln Met Gln Asn Ser Glu
1               5                   10                  15

Leu Gln Trp Pro
            20

<210> SEQ ID NO 178
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 178

Glu Leu Gln Trp Pro Val Pro Asp Ile Tyr Leu Arg Asp Leu Lys Val
1               5                   10                  15

Glu Asp Ile Pro
            20

<210> SEQ ID NO 179
<211> LENGTH: 20
<212> TYPE: PRT
<213> ORGANISM: Artificial Sequence
<220> FEATURE:
<223> OTHER INFORMATION: Synthetic peptide

<400> SEQUENCE: 179

Val Glu Asp Ile Pro Leu Ala Arg Ile Thr Leu Pro Asp Phe Arg Leu
1               5                   10                  15

Pro Glu Ile Ala
            20

<210> SEQ ID NO 180
<211> LENGTH: 20
<212> TYPE: PRT
<213> ORGANISM: Artificial Sequence
<220> FEATURE:
<223> OTHER INFORMATION: Synthetic peptide

<400> SEQUENCE: 180

Leu Pro Glu Ile Ala Ile Pro Glu Phe Ile Ile Pro Thr Leu Asn Leu
1               5                   10                  15

Asn Asp Phe Gln
            20

<210> SEQ ID NO 181
<211> LENGTH: 20
<212> TYPE: PRT
<213> ORGANISM: Artificial Sequence
<220> FEATURE:
<223> OTHER INFORMATION: Synthetic peptide

<400> SEQUENCE: 181

Leu Asn Asp Phe Gln Val Pro Asp Leu His Ile Pro Glu Phe Gln Leu
1               5                   10                  15

Pro His Ile Ser
            20

<210> SEQ ID NO 182
<211> LENGTH: 20
<212> TYPE: PRT
<213> ORGANISM: Artificial Sequence
<220> FEATURE:
<223> OTHER INFORMATION: Synthetic peptide

<400> SEQUENCE: 182

Leu Pro His Ile Ser His Thr Ile Glu Val Pro Thr Phe Gly Lys Leu
1               5                   10                  15

Tyr Ser Ile Leu
            20

<210> SEQ ID NO 183
<211> LENGTH: 20
<212> TYPE: PRT
```

```
<213> ORGANISM: Artificial Sequence
<220> FEATURE:
<223> OTHER INFORMATION: Synthetic peptide

<400> SEQUENCE: 183

Leu Tyr Ser Ile Leu Lys Ile Gln Ser Pro Leu Phe Thr Leu Asp Ala
1               5                   10                  15

Asn Ala Asp Ile
            20

<210> SEQ ID NO 184
<211> LENGTH: 20
<212> TYPE: PRT
<213> ORGANISM: Artificial Sequence
<220> FEATURE:
<223> OTHER INFORMATION: Synthetic peptide

<400> SEQUENCE: 184

Ala Asn Ala Asp Ile Gly Asn Gly Thr Thr Ser Ala Asn Glu Ala Gly
1               5                   10                  15

Ile Ala Ala Ser
            20

<210> SEQ ID NO 185
<211> LENGTH: 20
<212> TYPE: PRT
<213> ORGANISM: Artificial Sequence
<220> FEATURE:
<223> OTHER INFORMATION: Synthetic peptide

<400> SEQUENCE: 185

Gly Ile Ala Ala Ser Ile Thr Ala Lys Gly Glu Ser Lys Leu Glu Val
1               5                   10                  15

Leu Asn Phe Asp
            20

<210> SEQ ID NO 186
<211> LENGTH: 20
<212> TYPE: PRT
<213> ORGANISM: Artificial Sequence
<220> FEATURE:
<223> OTHER INFORMATION: Synthetic peptide

<400> SEQUENCE: 186

Val Leu Asn Phe Asp Phe Gln Ala Asn Ala Gln Leu Ser Asn Pro Lys
1               5                   10                  15

Ile Asn Pro Leu
            20

<210> SEQ ID NO 187
<211> LENGTH: 20
<212> TYPE: PRT
<213> ORGANISM: Artificial Sequence
<220> FEATURE:
<223> OTHER INFORMATION: Synthetic peptide

<400> SEQUENCE: 187

Lys Ile Asn Pro Leu Ala Leu Lys Glu Ser Val Lys Phe Ser Ser Lys
1               5                   10                  15

Tyr Leu Arg Thr
            20

<210> SEQ ID NO 188
<211> LENGTH: 20
```

<212> TYPE: PRT
<213> ORGANISM: Artificial Sequence
<220> FEATURE:
<223> OTHER INFORMATION: Synthetic peptide

<400> SEQUENCE: 188

Lys Tyr Leu Arg Thr Glu His Gly Ser Glu Met Leu Phe Phe Gly Asn
1               5                   10                  15

Ala Ile Glu Gly
            20

<210> SEQ ID NO 189
<211> LENGTH: 20
<212> TYPE: PRT
<213> ORGANISM: Artificial Sequence
<220> FEATURE:
<223> OTHER INFORMATION: Synthetic peptide

<400> SEQUENCE: 189

Asn Ala Ile Glu Gly Lys Ser Asn Thr Val Ala Ser Leu His Thr Glu
1               5                   10                  15

Lys Asn Thr Leu
            20

<210> SEQ ID NO 190
<211> LENGTH: 20
<212> TYPE: PRT
<213> ORGANISM: Artificial Sequence
<220> FEATURE:
<223> OTHER INFORMATION: Synthetic peptide

<400> SEQUENCE: 190

Glu Lys Asn Thr Leu Glu Leu Ser Asn Gly Val Ile Val Lys Ile Asn
1               5                   10                  15

Asn Gln Leu Thr
            20

<210> SEQ ID NO 191
<211> LENGTH: 20
<212> TYPE: PRT
<213> ORGANISM: Artificial Sequence
<220> FEATURE:
<223> OTHER INFORMATION: Synthetic peptide

<400> SEQUENCE: 191

Asn Asn Gln Leu Thr Leu Asp Ser Asn Thr Lys Tyr Phe His Lys Leu
1               5                   10                  15

Asn Ile Pro Lys
            20

<210> SEQ ID NO 192
<211> LENGTH: 20
<212> TYPE: PRT
<213> ORGANISM: Artificial Sequence
<220> FEATURE:
<223> OTHER INFORMATION: Synthetic peptide

<400> SEQUENCE: 192

Leu Asn Ile Pro Lys Leu Asp Phe Ser Ser Gln Ala Asp Leu Arg Asn
1               5                   10                  15

Glu Ile Lys Thr
            20

<210> SEQ ID NO 193

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 193

Asn Glu Ile Lys Thr Leu Leu Lys Ala Gly His Ile Ala Trp Thr Ser
1               5                   10                  15

Ser Gly Lys Gly
            20

<210> SEQ ID NO 194
<211> LENGTH: 20
<212> TYPE: PRT
<213> ORGANISM: Artificial Sequence
<220> FEATURE:
<223> OTHER INFORMATION: Synthetic peptide

<400> SEQUENCE: 194

Ser Ser Gly Lys Gly Ser Trp Lys Trp Ala Cys Pro Arg Phe Ser Asp
1               5                   10                  15

Glu Gly Thr His
            20

<210> SEQ ID NO 195
<211> LENGTH: 20
<212> TYPE: PRT
<213> ORGANISM: Artificial Sequence
<220> FEATURE:
<223> OTHER INFORMATION: Synthetic peptide

<400> SEQUENCE: 195

Asp Glu Gly Thr His Glu Ser Gln Ile Ser Phe Thr Ile Glu Gly Pro
1               5                   10                  15

Leu Thr Ser Phe
            20

<210> SEQ ID NO 196
<211> LENGTH: 20
<212> TYPE: PRT
<213> ORGANISM: Artificial Sequence
<220> FEATURE:
<223> OTHER INFORMATION: Synthetic peptide

<400> SEQUENCE: 196

Pro Leu Thr Ser Phe Gly Leu Ser Asn Lys Ile Asn Ser Lys His Leu
1               5                   10                  15

Arg Val Asn Gln
            20

<210> SEQ ID NO 197
<211> LENGTH: 20
<212> TYPE: PRT
<213> ORGANISM: Artificial Sequence
<220> FEATURE:
<223> OTHER INFORMATION: Synthetic peptide

<400> SEQUENCE: 197

Leu Arg Val Asn Gln Asn Leu Val Tyr Glu Ser Gly Ser Leu Asn Phe
1               5                   10                  15

Ser Lys Leu Glu
            20
```

<210> SEQ ID NO 198
<211> LENGTH: 20
<212> TYPE: PRT
<213> ORGANISM: Artificial Sequence
<220> FEATURE:
<223> OTHER INFORMATION: Synthetic peptide

<400> SEQUENCE: 198

Phe Ser Lys Leu Glu Ile Gln Ser Gln Val Asp Ser Gln His Val Gly
1               5                   10                  15
His Ser Val Leu
            20

<210> SEQ ID NO 199
<211> LENGTH: 20
<212> TYPE: PRT
<213> ORGANISM: Artificial Sequence
<220> FEATURE:
<223> OTHER INFORMATION: Synthetic peptide

<400> SEQUENCE: 199

Gly His Ser Val Leu Thr Ala Lys Gly Met Ala Leu Phe Gly Glu Gly
1               5                   10                  15
Lys Ala Glu Phe
            20

<210> SEQ ID NO 200
<211> LENGTH: 20
<212> TYPE: PRT
<213> ORGANISM: Artificial Sequence
<220> FEATURE:
<223> OTHER INFORMATION: Synthetic peptide

<400> SEQUENCE: 200

Gly Lys Ala Glu Phe Thr Gly Arg His Asp Ala His Leu Asn Gly Lys
1               5                   10                  15
Val Ile Gly Thr
            20

<210> SEQ ID NO 201
<211> LENGTH: 20
<212> TYPE: PRT
<213> ORGANISM: Artificial Sequence
<220> FEATURE:
<223> OTHER INFORMATION: Synthetic peptide

<400> SEQUENCE: 201

Lys Val Ile Gly Thr Leu Lys Asn Ser Leu Phe Phe Ser Ala Gln Pro
1               5                   10                  15
Phe Glu Ile Thr
            20

<210> SEQ ID NO 202
<211> LENGTH: 20
<212> TYPE: PRT
<213> ORGANISM: Artificial Sequence
<220> FEATURE:
<223> OTHER INFORMATION: Synthetic peptide

<400> SEQUENCE: 202

Pro Phe Glu Ile Thr Ala Ser Thr Asn Asn Glu Gly Asn Leu Lys Val
1               5                   10                  15
Arg Phe Pro Leu
            20

<210> SEQ ID NO 203
<211> LENGTH: 20
<212> TYPE: PRT
<213> ORGANISM: Artificial Sequence
<220> FEATURE:
<223> OTHER INFORMATION: Synthetic peptide

<400> SEQUENCE: 203

Val Arg Phe Pro Leu Arg Leu Thr Gly Lys Ile Asp Phe Leu Asn Asn
1               5                   10                  15

Tyr Ala Leu Phe
            20

<210> SEQ ID NO 204
<211> LENGTH: 20
<212> TYPE: PRT
<213> ORGANISM: Artificial Sequence
<220> FEATURE:
<223> OTHER INFORMATION: Synthetic peptide

<400> SEQUENCE: 204

Asn Tyr Ala Leu Phe Leu Ser Pro Ser Ala Gln Gln Ala Ser Trp Gln
1               5                   10                  15

Val Ser Ala Arg
            20

<210> SEQ ID NO 205
<211> LENGTH: 20
<212> TYPE: PRT
<213> ORGANISM: Artificial Sequence
<220> FEATURE:
<223> OTHER INFORMATION: Synthetic peptide

<400> SEQUENCE: 205

Gln Val Ser Ala Arg Phe Asn Gln Tyr Lys Tyr Asn Gln Asn Phe Ser
1               5                   10                  15

Ala Gly Asn Asn
            20

<210> SEQ ID NO 206
<211> LENGTH: 20
<212> TYPE: PRT
<213> ORGANISM: Artificial Sequence
<220> FEATURE:
<223> OTHER INFORMATION: Synthetic peptide

<400> SEQUENCE: 206

Ser Ala Gly Asn Asn Glu Asn Ile Met Glu Ala His Val Gly Ile Asn
1               5                   10                  15

Gly Glu Ala Asn
            20

<210> SEQ ID NO 207
<211> LENGTH: 20
<212> TYPE: PRT
<213> ORGANISM: Artificial Sequence
<220> FEATURE:
<223> OTHER INFORMATION: Synthetic peptide

<400> SEQUENCE: 207

Asn Gly Glu Ala Asn Leu Asp Phe Leu Asn Ile Pro Leu Thr Ile Pro
1               5                   10                  15

Glu Met Arg Leu
            20

<210> SEQ ID NO 208
<211> LENGTH: 20
<212> TYPE: PRT
<213> ORGANISM: Artificial Sequence
<220> FEATURE:
<223> OTHER INFORMATION: Synthetic peptide

<400> SEQUENCE: 208

Pro Glu Met Arg Leu Pro Tyr Thr Ile Ile Thr Thr Pro Pro Leu Lys
1               5                   10                  15

Asp Phe Ser Leu
            20

<210> SEQ ID NO 209
<211> LENGTH: 20
<212> TYPE: PRT
<213> ORGANISM: Artificial Sequence
<220> FEATURE:
<223> OTHER INFORMATION: Synthetic peptide

<400> SEQUENCE: 209

Lys Asp Phe Ser Leu Trp Glu Lys Thr Gly Leu Lys Glu Phe Leu Lys
1               5                   10                  15

Thr Thr Lys Gln
            20

<210> SEQ ID NO 210
<211> LENGTH: 20
<212> TYPE: PRT
<213> ORGANISM: Artificial Sequence
<220> FEATURE:
<223> OTHER INFORMATION: Synthetic peptide

<400> SEQUENCE: 210

Lys Thr Thr Lys Gln Ser Phe Asp Leu Ser Val Lys Ala Gln Tyr Lys
1               5                   10                  15

Lys Asn Lys His
            20

<210> SEQ ID NO 211
<211> LENGTH: 20
<212> TYPE: PRT
<213> ORGANISM: Artificial Sequence
<220> FEATURE:
<223> OTHER INFORMATION: Synthetic peptide

<400> SEQUENCE: 211

Lys Lys Asn Lys His Arg His Ser Ile Thr Asn Pro Leu Ala Val Leu
1               5                   10                  15

Cys Glu Phe Ile
            20

<210> SEQ ID NO 212
<211> LENGTH: 20
<212> TYPE: PRT
<213> ORGANISM: Artificial Sequence
<220> FEATURE:
<223> OTHER INFORMATION: Synthetic peptide

<400> SEQUENCE: 212

Leu Cys Glu Phe Ile Ser Gln Ser Ile Lys Ser Phe Asp Arg His Phe
1               5                   10                  15

Glu Lys Asn Arg

20

<210> SEQ ID NO 213
<211> LENGTH: 20
<212> TYPE: PRT
<213> ORGANISM: Artificial Sequence
<220> FEATURE:
<223> OTHER INFORMATION: Synthetic peptide

<400> SEQUENCE: 213

Phe Glu Lys Asn Arg Asn Asn Ala Leu Asp Phe Val Thr Lys Ser Tyr
1               5                   10                  15

Asn Glu Thr Lys
            20

<210> SEQ ID NO 214
<211> LENGTH: 20
<212> TYPE: PRT
<213> ORGANISM: Artificial Sequence
<220> FEATURE:
<223> OTHER INFORMATION: Synthetic peptide

<400> SEQUENCE: 214

Tyr Asn Glu Thr Lys Ile Lys Phe Asp Lys Tyr Lys Ala Glu Lys Ser
1               5                   10                  15

His Asp Glu Leu
            20

<210> SEQ ID NO 215
<211> LENGTH: 20
<212> TYPE: PRT
<213> ORGANISM: Artificial Sequence
<220> FEATURE:
<223> OTHER INFORMATION: Synthetic peptide

<400> SEQUENCE: 215

Ser His Asp Glu Leu Pro Arg Thr Phe Gln Ile Pro Gly Tyr Thr Val
1               5                   10                  15

Pro Val Val Asn
            20

<210> SEQ ID NO 216
<211> LENGTH: 20
<212> TYPE: PRT
<213> ORGANISM: Artificial Sequence
<220> FEATURE:
<223> OTHER INFORMATION: Synthetic peptide

<400> SEQUENCE: 216

Val Pro Val Val Asn Val Glu Val Ser Pro Phe Thr Ile Glu Met Ser
1               5                   10                  15

Ala Phe Gly Tyr
            20

<210> SEQ ID NO 217
<211> LENGTH: 20
<212> TYPE: PRT
<213> ORGANISM: Artificial Sequence
<220> FEATURE:
<223> OTHER INFORMATION: Synthetic peptide

<400> SEQUENCE: 217

Ser Ala Phe Gly Tyr Val Phe Pro Lys Ala Val Ser Met Pro Ser Phe
1               5                   10                  15

Ser Ile Leu Gly
            20

<210> SEQ ID NO 218
<211> LENGTH: 20
<212> TYPE: PRT
<213> ORGANISM: Artificial Sequence
<220> FEATURE:
<223> OTHER INFORMATION: Synthetic peptide

<400> SEQUENCE: 218

Phe Ser Ile Leu Gly Ser Asp Val Arg Val Pro Ser Tyr Thr Leu Ile
1               5                   10                  15

Leu Pro Ser Leu
            20

<210> SEQ ID NO 219
<211> LENGTH: 20
<212> TYPE: PRT
<213> ORGANISM: Artificial Sequence
<220> FEATURE:
<223> OTHER INFORMATION: Synthetic peptide

<400> SEQUENCE: 219

Ile Leu Pro Ser Leu Glu Leu Pro Val Leu His Val Pro Arg Asn Leu
1               5                   10                  15

Lys Leu Ser Leu
            20

<210> SEQ ID NO 220
<211> LENGTH: 20
<212> TYPE: PRT
<213> ORGANISM: Artificial Sequence
<220> FEATURE:
<223> OTHER INFORMATION: Synthetic peptide

<400> SEQUENCE: 220

Leu Lys Leu Ser Leu Pro His Phe Lys Glu Leu Cys Thr Ile Ser His
1               5                   10                  15

Ile Phe Ile Pro
            20

<210> SEQ ID NO 221
<211> LENGTH: 20
<212> TYPE: PRT
<213> ORGANISM: Artificial Sequence
<220> FEATURE:
<223> OTHER INFORMATION: Synthetic peptide

<400> SEQUENCE: 221

His Ile Phe Ile Pro Ala Met Gly Asn Ile Thr Tyr Asp Phe Ser Phe
1               5                   10                  15

Lys Ser Ser Val
            20

<210> SEQ ID NO 222
<211> LENGTH: 20
<212> TYPE: PRT
<213> ORGANISM: Artificial Sequence
<220> FEATURE:
<223> OTHER INFORMATION: Synthetic peptide

<400> SEQUENCE: 222

Phe Lys Ser Ser Val Ile Thr Leu Asn Thr Asn Ala Glu Leu Phe Asn
1               5                   10                  15

Gln Ser Asp Ile
            20

<210> SEQ ID NO 223
<211> LENGTH: 20
<212> TYPE: PRT
<213> ORGANISM: Artificial Sequence
<220> FEATURE:
<223> OTHER INFORMATION: Synthetic peptide

<400> SEQUENCE: 223

Asn Gln Ser Asp Ile Val Ala His Leu Leu Ser Ser Ser Ser Ser Val
1               5                   10                  15

Ile Asp Ala Leu
            20

<210> SEQ ID NO 224
<211> LENGTH: 20
<212> TYPE: PRT
<213> ORGANISM: Artificial Sequence
<220> FEATURE:
<223> OTHER INFORMATION: Synthetic peptide

<400> SEQUENCE: 224

Val Ile Asp Ala Leu Gln Tyr Lys Leu Glu Gly Thr Thr Arg Leu Thr
1               5                   10                  15

Arg Lys Arg Gly
            20

<210> SEQ ID NO 225
<211> LENGTH: 20
<212> TYPE: PRT
<213> ORGANISM: Artificial Sequence
<220> FEATURE:
<223> OTHER INFORMATION: Synthetic peptide

<400> SEQUENCE: 225

Thr Arg Lys Arg Gly Leu Lys Leu Ala Thr Ala Leu Ser Leu Ser Asn
1               5                   10                  15

Lys Phe Val Glu
            20

<210> SEQ ID NO 226
<211> LENGTH: 20
<212> TYPE: PRT
<213> ORGANISM: Artificial Sequence
<220> FEATURE:
<223> OTHER INFORMATION: Synthetic peptide

<400> SEQUENCE: 226

Asn Lys Phe Val Glu Gly Ser His Asn Ser Thr Val Ser Leu Thr Thr
1               5                   10                  15

Lys Asn Met Glu
            20

<210> SEQ ID NO 227
<211> LENGTH: 20
<212> TYPE: PRT
<213> ORGANISM: Artificial Sequence
<220> FEATURE:
<223> OTHER INFORMATION: Synthetic peptide

<400> SEQUENCE: 227

Thr Lys Asn Met Glu Val Ser Val Ala Lys Thr Thr Lys Ala Glu Ile

```
                1               5                  10                  15
Pro Ile Leu Arg
            20

<210> SEQ ID NO 228
<211> LENGTH: 20
<212> TYPE: PRT
<213> ORGANISM: Artificial Sequence
<220> FEATURE:
<223> OTHER INFORMATION: Synthetic peptide

<400> SEQUENCE: 228

Ile Pro Ile Leu Arg Met Asn Phe Lys Gln Glu Leu Asn Gly Asn Thr
1               5                  10                  15

Lys Ser Lys Pro
            20

<210> SEQ ID NO 229
<211> LENGTH: 20
<212> TYPE: PRT
<213> ORGANISM: Artificial Sequence
<220> FEATURE:
<223> OTHER INFORMATION: Synthetic peptide

<400> SEQUENCE: 229

Thr Lys Ser Lys Pro Thr Val Ser Ser Met Glu Phe Lys Tyr Asp
1               5                  10                  15

Phe Asn Ser Ser
            20

<210> SEQ ID NO 230
<211> LENGTH: 20
<212> TYPE: PRT
<213> ORGANISM: Artificial Sequence
<220> FEATURE:
<223> OTHER INFORMATION: Synthetic peptide

<400> SEQUENCE: 230

Asp Phe Asn Ser Ser Met Leu Tyr Ser Thr Ala Lys Gly Ala Val Asp
1               5                  10                  15

His Lys Leu Ser
            20

<210> SEQ ID NO 231
<211> LENGTH: 20
<212> TYPE: PRT
<213> ORGANISM: Artificial Sequence
<220> FEATURE:
<223> OTHER INFORMATION: Synthetic peptide

<400> SEQUENCE: 231

Asp His Lys Leu Ser Leu Glu Ser Leu Thr Ser Tyr Phe Ser Ile Glu
1               5                  10                  15

Ser Ser Thr Lys
            20

<210> SEQ ID NO 232
<211> LENGTH: 20
<212> TYPE: PRT
<213> ORGANISM: Artificial Sequence
<220> FEATURE:
<223> OTHER INFORMATION: Synthetic peptide

<400> SEQUENCE: 232
```

```
Glu Ser Ser Thr Lys Gly Asp Val Lys Gly Ser Val Leu Ser Arg Glu
1               5                   10                  15

Tyr Ser Gly Thr
            20

<210> SEQ ID NO 233
<211> LENGTH: 20
<212> TYPE: PRT
<213> ORGANISM: Artificial Sequence
<220> FEATURE:
<223> OTHER INFORMATION: Synthetic peptide

<400> SEQUENCE: 233

Glu Tyr Ser Gly Thr Ile Ala Ser Glu Ala Asn Thr Tyr Leu Asn Ser
1               5                   10                  15

Lys Ser Thr Arg
            20

<210> SEQ ID NO 234
<211> LENGTH: 20
<212> TYPE: PRT
<213> ORGANISM: Artificial Sequence
<220> FEATURE:
<223> OTHER INFORMATION: Synthetic peptide

<400> SEQUENCE: 234

Ser Lys Ser Thr Arg Ser Ser Val Lys Leu Gln Gly Thr Ser Lys Ile
1               5                   10                  15

Asp Asp Ile Trp
            20

<210> SEQ ID NO 235
<211> LENGTH: 20
<212> TYPE: PRT
<213> ORGANISM: Artificial Sequence
<220> FEATURE:
<223> OTHER INFORMATION: Synthetic peptide

<400> SEQUENCE: 235

Ile Asp Asp Ile Trp Asn Leu Glu Val Lys Glu Asn Phe Ala Gly Glu
1               5                   10                  15

Ala Thr Leu Gln
            20

<210> SEQ ID NO 236
<211> LENGTH: 20
<212> TYPE: PRT
<213> ORGANISM: Artificial Sequence
<220> FEATURE:
<223> OTHER INFORMATION: Synthetic peptide

<400> SEQUENCE: 236

Glu Ala Thr Leu Gln Arg Ile Tyr Ser Leu Trp Glu His Ser Thr Lys
1               5                   10                  15

Asn His Leu Gln
            20

<210> SEQ ID NO 237
<211> LENGTH: 20
<212> TYPE: PRT
<213> ORGANISM: Artificial Sequence
<220> FEATURE:
<223> OTHER INFORMATION: Synthetic peptide

<400> SEQUENCE: 237
```

Lys Asn His Leu Gln Leu Glu Gly Leu Phe Phe Thr Asn Gly Glu His
1               5                   10                  15

Thr Ser Lys Ala
            20

<210> SEQ ID NO 238
<211> LENGTH: 20
<212> TYPE: PRT
<213> ORGANISM: Artificial Sequence
<220> FEATURE:
<223> OTHER INFORMATION: Synthetic peptide

<400> SEQUENCE: 238

His Thr Ser Lys Ala Thr Leu Glu Leu Ser Pro Trp Gln Met Ser Ala
1               5                   10                  15

Leu Val Gln Val
            20

<210> SEQ ID NO 239
<211> LENGTH: 20
<212> TYPE: PRT
<213> ORGANISM: Artificial Sequence
<220> FEATURE:
<223> OTHER INFORMATION: Synthetic peptide

<400> SEQUENCE: 239

Ala Leu Val Gln Val His Ala Ser Gln Pro Ser Ser Phe His Asp Phe
1               5                   10                  15

Pro Asp Leu Gly
            20

<210> SEQ ID NO 240
<211> LENGTH: 20
<212> TYPE: PRT
<213> ORGANISM: Artificial Sequence
<220> FEATURE:
<223> OTHER INFORMATION: Synthetic peptide

<400> SEQUENCE: 240

Phe Pro Asp Leu Gly Gln Glu Val Ala Leu Asn Ala Asn Thr Lys Asn
1               5                   10                  15

Gln Lys Ile Arg
            20

<210> SEQ ID NO 241
<211> LENGTH: 20
<212> TYPE: PRT
<213> ORGANISM: Artificial Sequence
<220> FEATURE:
<223> OTHER INFORMATION: Synthetic peptide

<400> SEQUENCE: 241

Asn Gln Lys Ile Arg Trp Lys Asn Glu Val Arg Ile His Ser Gly Ser
1               5                   10                  15

Phe Gln Ser Gln
            20

<210> SEQ ID NO 242
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 242

Ser Phe Gln Ser Gln Val Glu Leu Ser Asn Asp Gln Glu Lys Ala His
1               5                   10                  15

Leu Asp Ile Ala
            20

<210> SEQ ID NO 243
<211> LENGTH: 20
<212> TYPE: PRT
<213> ORGANISM: Artificial Sequence
<220> FEATURE:
<223> OTHER INFORMATION: Synthetic peptide

<400> SEQUENCE: 243

His Leu Asp Ile Ala Gly Ser Leu Glu Gly His Leu Arg Phe Leu Lys
1               5                   10                  15

Asn Ile Ile Leu
            20

<210> SEQ ID NO 244
<211> LENGTH: 20
<212> TYPE: PRT
<213> ORGANISM: Artificial Sequence
<220> FEATURE:
<223> OTHER INFORMATION: Synthetic peptide

<400> SEQUENCE: 244

Lys Asn Ile Ile Leu Pro Val Tyr Asp Lys Ser Leu Trp Asp Phe Leu
1               5                   10                  15

Lys Leu Asp Val
            20

<210> SEQ ID NO 245
<211> LENGTH: 20
<212> TYPE: PRT
<213> ORGANISM: Artificial Sequence
<220> FEATURE:
<223> OTHER INFORMATION: Synthetic peptide

<400> SEQUENCE: 245

Leu Lys Leu Asp Val Thr Thr Ser Ile Gly Arg Arg Gln His Leu Arg
1               5                   10                  15

Val Ser Thr Ala
            20

<210> SEQ ID NO 246
<211> LENGTH: 20
<212> TYPE: PRT
<213> ORGANISM: Artificial Sequence
<220> FEATURE:
<223> OTHER INFORMATION: Synthetic peptide

<400> SEQUENCE: 246

Arg Val Ser Thr Ala Phe Val Tyr Thr Lys Asn Pro Asn Gly Tyr Ser
1               5                   10                  15

Phe Ser Ile Pro
            20

<210> SEQ ID NO 247
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 247

Ser Phe Ser Ile Pro Val Lys Val Leu Ala Asp Lys Phe Ile Thr Pro
1               5                   10                  15

Gly Leu Lys Leu
            20

<210> SEQ ID NO 248
<211> LENGTH: 20
<212> TYPE: PRT
<213> ORGANISM: Artificial Sequence
<220> FEATURE:
<223> OTHER INFORMATION: Synthetic peptide

<400> SEQUENCE: 248

Pro Gly Leu Lys Leu Asn Asp Leu Asn Ser Val Leu Val Met Pro Thr
1               5                   10                  15

Phe His Val Pro
            20

<210> SEQ ID NO 249
<211> LENGTH: 20
<212> TYPE: PRT
<213> ORGANISM: Artificial Sequence
<220> FEATURE:
<223> OTHER INFORMATION: Synthetic peptide

<400> SEQUENCE: 249

Thr Phe His Val Pro Phe Thr Asp Leu Gln Val Pro Ser Cys Lys Leu
1               5                   10                  15

Asp Phe Arg Glu
            20

<210> SEQ ID NO 250
<211> LENGTH: 20
<212> TYPE: PRT
<213> ORGANISM: Artificial Sequence
<220> FEATURE:
<223> OTHER INFORMATION: Synthetic peptide

<400> SEQUENCE: 250

Leu Asp Phe Arg Glu Ile Gln Ile Tyr Lys Lys Leu Arg Thr Ser Ser
1               5                   10                  15

Phe Ala Leu Asn
            20

<210> SEQ ID NO 251
<211> LENGTH: 20
<212> TYPE: PRT
<213> ORGANISM: Artificial Sequence
<220> FEATURE:
<223> OTHER INFORMATION: Synthetic peptide

<400> SEQUENCE: 251

Ser Phe Ala Leu Asn Leu Pro Thr Leu Pro Glu Val Lys Phe Pro Glu
1               5                   10                  15

Val Asp Val Leu
            20

<210> SEQ ID NO 252
<211> LENGTH: 20
<212> TYPE: PRT
<213> ORGANISM: Artificial Sequence
<220> FEATURE:

<223> OTHER INFORMATION: Synthetic peptide

<400> SEQUENCE: 252

Glu Val Asp Val Leu Thr Lys Tyr Ser Gln Pro Glu Asp Ser Leu Ile
1               5                   10                  15

Pro Phe Phe Glu
            20

<210> SEQ ID NO 253
<211> LENGTH: 20
<212> TYPE: PRT
<213> ORGANISM: Artificial Sequence
<220> FEATURE:
<223> OTHER INFORMATION: Synthetic peptide

<400> SEQUENCE: 253

Ile Pro Phe Phe Glu Ile Thr Val Pro Glu Ser Gln Leu Thr Val Ser
1               5                   10                  15

Gln Phe Thr Leu
            20

<210> SEQ ID NO 254
<211> LENGTH: 20
<212> TYPE: PRT
<213> ORGANISM: Artificial Sequence
<220> FEATURE:
<223> OTHER INFORMATION: Synthetic peptide

<400> SEQUENCE: 254

Ser Gln Phe Thr Leu Pro Lys Ser Val Ser Asp Gly Ile Ala Ala Leu
1               5                   10                  15

Asp Leu Asn Ala
            20

<210> SEQ ID NO 255
<211> LENGTH: 20
<212> TYPE: PRT
<213> ORGANISM: Artificial Sequence
<220> FEATURE:
<223> OTHER INFORMATION: Synthetic peptide

<400> SEQUENCE: 255

Leu Asp Leu Asn Ala Val Ala Asn Lys Ile Ala Asp Phe Glu Leu Pro
1               5                   10                  15

Thr Ile Ile Val
            20

<210> SEQ ID NO 256
<211> LENGTH: 20
<212> TYPE: PRT
<213> ORGANISM: Artificial Sequence
<220> FEATURE:
<223> OTHER INFORMATION: Synthetic peptide

<400> SEQUENCE: 256

Pro Thr Ile Ile Val Pro Glu Gln Thr Ile Glu Ile Pro Ser Ile Lys
1               5                   10                  15

Phe Ser Val Pro
            20

<210> SEQ ID NO 257
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 257

Lys Phe Ser Val Pro Ala Gly Ile Val Ile Pro Ser Phe Gln Ala Leu
1               5                   10                  15
Thr Ala Arg Phe
            20

<210> SEQ ID NO 258
<211> LENGTH: 20
<212> TYPE: PRT
<213> ORGANISM: Artificial Sequence
<220> FEATURE:
<223> OTHER INFORMATION: Synthetic peptide

<400> SEQUENCE: 258

Leu Thr Ala Arg Phe Glu Val Asp Ser Pro Val Tyr Asn Ala Thr Trp
1               5                   10                  15
Ser Ala Ser Leu
            20

<210> SEQ ID NO 259
<211> LENGTH: 20
<212> TYPE: PRT
<213> ORGANISM: Artificial Sequence
<220> FEATURE:
<223> OTHER INFORMATION: Synthetic peptide

<400> SEQUENCE: 259

Trp Ser Ala Ser Leu Lys Asn Lys Ala Asp Tyr Val Glu Thr Val Leu
1               5                   10                  15
Asp Ser Thr Cys
            20

<210> SEQ ID NO 260
<211> LENGTH: 20
<212> TYPE: PRT
<213> ORGANISM: Artificial Sequence
<220> FEATURE:
<223> OTHER INFORMATION: Synthetic peptide

<400> SEQUENCE: 260

Leu Asp Ser Thr Cys Ser Ser Thr Val Gln Phe Leu Glu Tyr Glu Leu
1               5                   10                  15
Asn Val Leu Gly
            20

<210> SEQ ID NO 261
<211> LENGTH: 20
<212> TYPE: PRT
<213> ORGANISM: Artificial Sequence
<220> FEATURE:
<223> OTHER INFORMATION: Synthetic peptide

<400> SEQUENCE: 261

Leu Asn Val Leu Gly Thr His Lys Ile Glu Asp Gly Thr Leu Ala Ser
1               5                   10                  15
Lys Thr Lys Gly
            20

<210> SEQ ID NO 262
<211> LENGTH: 20
<212> TYPE: PRT
```

```
<213> ORGANISM: Artificial Sequence
<220> FEATURE:
<223> OTHER INFORMATION: Synthetic peptide

<400> SEQUENCE: 262

Ser Lys Thr Lys Gly Thr Leu Ala His Arg Asp Phe Ser Ala Glu Tyr
1               5                   10                  15

Glu Glu Asp Gly
            20

<210> SEQ ID NO 263
<211> LENGTH: 20
<212> TYPE: PRT
<213> ORGANISM: Artificial Sequence
<220> FEATURE:
<223> OTHER INFORMATION: Synthetic peptide

<400> SEQUENCE: 263

Tyr Glu Glu Asp Gly Lys Phe Glu Gly Leu Gln Glu Trp Glu Gly Lys
1               5                   10                  15

Ala His Leu Asn
            20

<210> SEQ ID NO 264
<211> LENGTH: 20
<212> TYPE: PRT
<213> ORGANISM: Artificial Sequence
<220> FEATURE:
<223> OTHER INFORMATION: Synthetic peptide

<400> SEQUENCE: 264

Lys Ala His Leu Asn Ile Lys Ser Pro Ala Phe Thr Asp Leu His Leu
1               5                   10                  15

Arg Tyr Gln Lys
            20

<210> SEQ ID NO 265
<211> LENGTH: 20
<212> TYPE: PRT
<213> ORGANISM: Artificial Sequence
<220> FEATURE:
<223> OTHER INFORMATION: Synthetic peptide

<400> SEQUENCE: 265

Leu Arg Tyr Gln Lys Asp Lys Lys Gly Ile Ser Thr Ser Ala Ala Ser
1               5                   10                  15

Pro Ala Val Gly
            20

<210> SEQ ID NO 266
<211> LENGTH: 20
<212> TYPE: PRT
<213> ORGANISM: Artificial Sequence
<220> FEATURE:
<223> OTHER INFORMATION: Synthetic peptide

<400> SEQUENCE: 266

Ser Pro Ala Val Gly Thr Val Gly Met Asp Met Asp Glu Asp Asp
1               5                   10                  15

Phe Ser Lys Trp
            20

<210> SEQ ID NO 267
<211> LENGTH: 20
```

```
<212> TYPE: PRT
<213> ORGANISM: Artificial Sequence
<220> FEATURE:
<223> OTHER INFORMATION: Synthetic peptide

<400> SEQUENCE: 267

Asp Phe Ser Lys Trp Asn Phe Tyr Tyr Ser Pro Gln Ser Ser Pro Asp
1               5                   10                  15

Lys Lys Leu Thr
            20

<210> SEQ ID NO 268
<211> LENGTH: 20
<212> TYPE: PRT
<213> ORGANISM: Artificial Sequence
<220> FEATURE:
<223> OTHER INFORMATION: Synthetic peptide

<400> SEQUENCE: 268

Asp Lys Lys Leu Thr Ile Phe Lys Thr Glu Leu Arg Val Arg Glu Ser
1               5                   10                  15

Asp Glu Glu Thr
            20

<210> SEQ ID NO 269
<211> LENGTH: 20
<212> TYPE: PRT
<213> ORGANISM: Artificial Sequence
<220> FEATURE:
<223> OTHER INFORMATION: Synthetic peptide

<400> SEQUENCE: 269

Ser Asp Glu Glu Thr Gln Ile Lys Val Asn Trp Glu Glu Ala Ala
1               5                   10                  15

Ser Gly Leu Leu
            20

<210> SEQ ID NO 270
<211> LENGTH: 20
<212> TYPE: PRT
<213> ORGANISM: Artificial Sequence
<220> FEATURE:
<223> OTHER INFORMATION: Synthetic peptide

<400> SEQUENCE: 270

Ala Ser Gly Leu Leu Thr Ser Leu Lys Asp Asn Val Pro Lys Ala Thr
1               5                   10                  15

Gly Val Leu Tyr
            20

<210> SEQ ID NO 271
<211> LENGTH: 20
<212> TYPE: PRT
<213> ORGANISM: Artificial Sequence
<220> FEATURE:
<223> OTHER INFORMATION: Synthetic peptide

<400> SEQUENCE: 271

Thr Gly Val Leu Tyr Asp Tyr Val Asn Lys Tyr His Trp Glu His Thr
1               5                   10                  15

Gly Leu Thr Leu
            20

<210> SEQ ID NO 272
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 272

Thr Gly Leu Thr Leu Arg Glu Val Ser Ser Lys Leu Arg Arg Asn Leu
1               5                   10                  15

Gln Asn Asn Ala
            20

<210> SEQ ID NO 273
<211> LENGTH: 20
<212> TYPE: PRT
<213> ORGANISM: Artificial Sequence
<220> FEATURE:
<223> OTHER INFORMATION: Synthetic peptide

<400> SEQUENCE: 273

Leu Gln Asn Asn Ala Glu Trp Val Tyr Gln Gly Ala Ile Arg Gln Ile
1               5                   10                  15

Asp Asp Ile Asp
            20

<210> SEQ ID NO 274
<211> LENGTH: 20
<212> TYPE: PRT
<213> ORGANISM: Artificial Sequence
<220> FEATURE:
<223> OTHER INFORMATION: Synthetic peptide

<400> SEQUENCE: 274

Ile Asp Asp Ile Asp Val Arg Phe Gln Lys Ala Ala Ser Gly Thr Thr
1               5                   10                  15

Gly Thr Tyr Gln
            20

<210> SEQ ID NO 275
<211> LENGTH: 20
<212> TYPE: PRT
<213> ORGANISM: Artificial Sequence
<220> FEATURE:
<223> OTHER INFORMATION: Synthetic peptide

<400> SEQUENCE: 275

Thr Gly Thr Tyr Gln Glu Trp Lys Asp Lys Ala Gln Asn Leu Tyr Gln
1               5                   10                  15

Glu Leu Leu Thr
            20

<210> SEQ ID NO 276
<211> LENGTH: 20
<212> TYPE: PRT
<213> ORGANISM: Artificial Sequence
<220> FEATURE:
<223> OTHER INFORMATION: Synthetic peptide

<400> SEQUENCE: 276

Gln Glu Leu Leu Thr Gln Glu Gly Gln Ala Ser Phe Gln Gly Leu Lys
1               5                   10                  15

Asp Asn Val Phe
            20
```

-continued

```
<210> SEQ ID NO 277
<211> LENGTH: 20
<212> TYPE: PRT
<213> ORGANISM: Artificial Sequence
<220> FEATURE:
<223> OTHER INFORMATION: Synthetic peptide

<400> SEQUENCE: 277

Lys Asp Asn Val Phe Asp Gly Leu Val Arg Val Thr Gln Lys Phe His
1               5                   10                  15

Met Lys Val Lys
            20

<210> SEQ ID NO 278
<211> LENGTH: 20
<212> TYPE: PRT
<213> ORGANISM: Artificial Sequence
<220> FEATURE:
<223> OTHER INFORMATION: Synthetic peptide

<400> SEQUENCE: 278

His Met Lys Val Lys His Leu Ile Asp Ser Leu Ile Asp Phe Leu Asn
1               5                   10                  15

Phe Pro Arg Phe
            20

<210> SEQ ID NO 279
<211> LENGTH: 20
<212> TYPE: PRT
<213> ORGANISM: Artificial Sequence
<220> FEATURE:
<223> OTHER INFORMATION: Synthetic peptide

<400> SEQUENCE: 279

Asn Phe Pro Arg Phe Gln Phe Pro Gly Lys Pro Gly Ile Tyr Thr Arg
1               5                   10                  15

Glu Glu Leu Cys
            20

<210> SEQ ID NO 280
<211> LENGTH: 20
<212> TYPE: PRT
<213> ORGANISM: Artificial Sequence
<220> FEATURE:
<223> OTHER INFORMATION: Synthetic peptide

<400> SEQUENCE: 280

Arg Glu Glu Leu Cys Thr Met Phe Ile Arg Glu Val Gly Thr Val Leu
1               5                   10                  15

Ser Gln Val Tyr
            20

<210> SEQ ID NO 281
<211> LENGTH: 20
<212> TYPE: PRT
<213> ORGANISM: Artificial Sequence
<220> FEATURE:
<223> OTHER INFORMATION: Synthetic peptide

<400> SEQUENCE: 281

Leu Ser Gln Val Tyr Ser Lys Val His Asn Gly Ser Glu Ile Leu Phe
1               5                   10                  15

Ser Tyr Phe Gln
            20
```

<210> SEQ ID NO 282
<211> LENGTH: 20
<212> TYPE: PRT
<213> ORGANISM: Artificial Sequence
<220> FEATURE:
<223> OTHER INFORMATION: Synthetic peptide

<400> SEQUENCE: 282

Phe Ser Tyr Phe Gln Asp Leu Val Ile Thr Leu Pro Phe Glu Leu Arg
1               5                   10                  15

Lys His Lys Leu
            20

<210> SEQ ID NO 283
<211> LENGTH: 20
<212> TYPE: PRT
<213> ORGANISM: Artificial Sequence
<220> FEATURE:
<223> OTHER INFORMATION: Synthetic peptide

<400> SEQUENCE: 283

Arg Lys His Lys Leu Ile Asp Val Ile Ser Met Tyr Arg Glu Leu Leu
1               5                   10                  15

Lys Asp Leu Ser
            20

<210> SEQ ID NO 284
<211> LENGTH: 20
<212> TYPE: PRT
<213> ORGANISM: Artificial Sequence
<220> FEATURE:
<223> OTHER INFORMATION: Synthetic peptide

<400> SEQUENCE: 284

Leu Lys Asp Leu Ser Lys Glu Ala Gln Glu Val Phe Lys Ala Ile Gln
1               5                   10                  15

Ser Leu Lys Thr
            20

<210> SEQ ID NO 285
<211> LENGTH: 20
<212> TYPE: PRT
<213> ORGANISM: Artificial Sequence
<220> FEATURE:
<223> OTHER INFORMATION: Synthetic peptide

<400> SEQUENCE: 285

Gln Ser Leu Lys Thr Thr Glu Val Leu Arg Asn Leu Gln Asp Leu Leu
1               5                   10                  15

Gln Phe Ile Phe
            20

<210> SEQ ID NO 286
<211> LENGTH: 20
<212> TYPE: PRT
<213> ORGANISM: Artificial Sequence
<220> FEATURE:
<223> OTHER INFORMATION: Synthetic peptide

<400> SEQUENCE: 286

Leu Gln Phe Ile Phe Gln Leu Ile Glu Asp Asn Ile Lys Gln Leu Lys
1               5                   10                  15

Glu Met Lys Phe
            20

<210> SEQ ID NO 287
<211> LENGTH: 20
<212> TYPE: PRT
<213> ORGANISM: Artificial Sequence
<220> FEATURE:
<223> OTHER INFORMATION: Synthetic peptide

<400> SEQUENCE: 287

Lys Glu Met Lys Phe Thr Tyr Leu Ile Asn Tyr Ile Gln Asp Glu Ile
1               5                   10                  15

Asn Thr Ile Phe
            20

<210> SEQ ID NO 288
<211> LENGTH: 20
<212> TYPE: PRT
<213> ORGANISM: Artificial Sequence
<220> FEATURE:
<223> OTHER INFORMATION: Synthetic peptide

<400> SEQUENCE: 288

Ile Asn Thr Ile Phe Asn Asp Tyr Ile Pro Tyr Val Phe Lys Leu Leu
1               5                   10                  15

Lys Glu Asn Leu
            20

<210> SEQ ID NO 289
<211> LENGTH: 20
<212> TYPE: PRT
<213> ORGANISM: Artificial Sequence
<220> FEATURE:
<223> OTHER INFORMATION: Synthetic peptide

<400> SEQUENCE: 289

Leu Lys Glu Asn Leu Cys Leu Asn Leu His Lys Phe Asn Glu Phe Ile
1               5                   10                  15

Gln Asn Glu Leu
            20

<210> SEQ ID NO 290
<211> LENGTH: 20
<212> TYPE: PRT
<213> ORGANISM: Artificial Sequence
<220> FEATURE:
<223> OTHER INFORMATION: Synthetic peptide

<400> SEQUENCE: 290

Ile Gln Asn Glu Leu Gln Glu Ala Ser Gln Glu Leu Gln Gln Ile His
1               5                   10                  15

Gln Tyr Ile Met
            20

<210> SEQ ID NO 291
<211> LENGTH: 20
<212> TYPE: PRT
<213> ORGANISM: Artificial Sequence
<220> FEATURE:
<223> OTHER INFORMATION: Synthetic peptide

<400> SEQUENCE: 291

His Gln Tyr Ile Met Ala Leu Arg Glu Glu Tyr Phe Asp Pro Ser Ile
1               5                   10                  15

Val Gly Trp Thr

```
<210> SEQ ID NO 292
<211> LENGTH: 20
<212> TYPE: PRT
<213> ORGANISM: Artificial Sequence
<220> FEATURE:
<223> OTHER INFORMATION: Synthetic peptide

<400> SEQUENCE: 292

Ile Val Gly Trp Thr Val Lys Tyr Tyr Glu Leu Glu Glu Lys Ile Val
1               5                   10                  15

Ser Leu Ile Lys
            20

<210> SEQ ID NO 293
<211> LENGTH: 20
<212> TYPE: PRT
<213> ORGANISM: Artificial Sequence
<220> FEATURE:
<223> OTHER INFORMATION: Synthetic peptide

<400> SEQUENCE: 293

Val Ser Leu Ile Lys Asn Leu Leu Val Ala Leu Lys Asp Phe His Ser
1               5                   10                  15

Glu Tyr Ile Val
            20

<210> SEQ ID NO 294
<211> LENGTH: 20
<212> TYPE: PRT
<213> ORGANISM: Artificial Sequence
<220> FEATURE:
<223> OTHER INFORMATION: Synthetic peptide

<400> SEQUENCE: 294

Ser Glu Tyr Ile Val Ser Ala Ser Asn Phe Thr Ser Gln Leu Ser Ser
1               5                   10                  15

Gln Val Glu Gln
            20

<210> SEQ ID NO 295
<211> LENGTH: 20
<212> TYPE: PRT
<213> ORGANISM: Artificial Sequence
<220> FEATURE:
<223> OTHER INFORMATION: Synthetic peptide

<400> SEQUENCE: 295

Ser Gln Val Glu Gln Phe Leu His Arg Asn Ile Gln Glu Tyr Leu Ser
1               5                   10                  15

Ile Leu Thr Asp
            20

<210> SEQ ID NO 296
<211> LENGTH: 20
<212> TYPE: PRT
<213> ORGANISM: Artificial Sequence
<220> FEATURE:
<223> OTHER INFORMATION: Synthetic peptide

<400> SEQUENCE: 296

Ser Ile Leu Thr Asp Pro Asp Gly Lys Gly Lys Glu Lys Ile Ala Glu
1               5                   10                  15
```

-continued

Leu Ser Ala Thr
        20

<210> SEQ ID NO 297
<211> LENGTH: 20
<212> TYPE: PRT
<213> ORGANISM: Artificial Sequence
<220> FEATURE:
<223> OTHER INFORMATION: Synthetic peptide

<400> SEQUENCE: 297

Glu Leu Ser Ala Thr Ala Gln Glu Ile Ile Lys Ser Gln Ala Ile Ala
1               5                   10                  15

Thr Lys Lys Ile
        20

<210> SEQ ID NO 298
<211> LENGTH: 20
<212> TYPE: PRT
<213> ORGANISM: Artificial Sequence
<220> FEATURE:
<223> OTHER INFORMATION: Synthetic peptide

<400> SEQUENCE: 298

Thr Lys Lys Ile Ile Ser Asp Tyr His Gln Gln Phe Arg Tyr Lys Leu
1               5                   10                  15

Gln Asp Phe Ser
        20

<210> SEQ ID NO 299
<211> LENGTH: 20
<212> TYPE: PRT
<213> ORGANISM: Artificial Sequence
<220> FEATURE:
<223> OTHER INFORMATION: Synthetic peptide

<400> SEQUENCE: 299

Leu Gln Asp Phe Ser Asp Gln Leu Ser Asp Tyr Tyr Glu Lys Phe Ile
1               5                   10                  15

Ala Glu Ser Lys
        20

<210> SEQ ID NO 300
<211> LENGTH: 20
<212> TYPE: PRT
<213> ORGANISM: Artificial Sequence
<220> FEATURE:
<223> OTHER INFORMATION: Synthetic peptide

<400> SEQUENCE: 300

Ile Ala Glu Ser Lys Arg Leu Ile Asp Leu Ser Ile Gln Asn Tyr His
1               5                   10                  15

Thr Phe Leu Ile
        20

<210> SEQ ID NO 301
<211> LENGTH: 20
<212> TYPE: PRT
<213> ORGANISM: Artificial Sequence
<220> FEATURE:
<223> OTHER INFORMATION: Synthetic peptide

<400> SEQUENCE: 301

His Thr Phe Leu Ile Tyr Ile Thr Glu Leu Leu Lys Lys Leu Gln Ser
1               5                   10                  15

Thr Thr Val Met
            20

<210> SEQ ID NO 302
<211> LENGTH: 20
<212> TYPE: PRT
<213> ORGANISM: Artificial Sequence
<220> FEATURE:
<223> OTHER INFORMATION: Synthetic peptide

<400> SEQUENCE: 302

Ser Thr Thr Val Met Asn Pro Tyr Met Lys Leu Ala Pro Gly Glu Leu
1               5                   10                  15

Thr Ile Ile Leu
            20

<210> SEQ ID NO 303
<211> LENGTH: 1353
<212> TYPE: DNA
<213> ORGANISM: Artificial Sequence
<220> FEATURE:
<223> OTHER INFORMATION: Polynucleotide sequence encoding heavy chain of
      P45 specific antibody

<400> SEQUENCE: 303

| | | | | | |
|---|---|---|---|---|---|
| gaggtgcagc | tgttggagtc | tggggggaggc | ttggtacagc | ctgggggggtc | cctgagactc | 60 |
| tcctgtgcag | cctctggatt | caccttcagt | aacgcctgga | tgagctgggt | ccgccaggct | 120 |
| ccagggaagg | ggctggagtg | ggtctcaagt | attagtgttg | gtggacatag | gacatattat | 180 |
| gcagattccg | tgaagggccg | gtccaccatc | tccagagaca | attccaagaa | cacgctgtat | 240 |
| ctgcaaatga | acagcctgag | agccgaggac | actgccgtgt | attactgtgc | acggatacgg | 300 |
| gtgggtccgt | ccggcggggc | ctttgactac | tggggccagg | gtacactggt | caccgtgagc | 360 |
| tcagcctcca | ccaagggccc | atcggtcttc | cccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gaaagttgag | 660 |
| cccaaatctt | gtgacaaaac | tcacacatgc | ccaccgtgcc | cagcacctga | actcctgggg | 720 |
| ggaccgtcag | tcttcctctt | ccccccaaaa | cccaaggaca | cctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgtgtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggat | 1080 |
| gagctgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tacagcaagc | tcaccgtgga | caagagcagg | 1260 |
| tggcagcagg | ggaacgtctt | ctcatgctcc | gtgatgcatg | aggctctgca | caaccactac | 1320 |
| acgcagaaga | gcctctccct | gtctccgggt | aaa | | | 1353 |

<210> SEQ ID NO 304

-continued

```
<211> LENGTH: 648
<212> TYPE: DNA
<213> ORGANISM: Artificial Sequence
<220> FEATURE:
<223> OTHER INFORMATION: Polynucleotide sequence encoding light chain of
      P45 specific antibody

<400> SEQUENCE: 304
cagtctgtgc tgactcagcc accctcagcg tctgggaccc ccgggcagag ggtcaccatc      60
tcctgctctg gaagcaacac caacattggg aagaactatg tatcttggta tcagcagctc     120
ccaggaacgg cccccaaact cctcatctat gctaatagca atcggccctc aggggtccct     180
gaccgattct ctggctccaa gtctggcacc tcagcctccc tggccatcag tgggctccgg     240
tccgaggatg aggctgatta ttactgtgcg tcatgggatg ccagcctgaa tggttgggta     300
ttcggcggag gaaccaagct gacggtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tatctgagcc tgacgcctga gcagtggaag tcccacagaa gctacagctg ccaggtcacg     600
catgaaggga gcaccgtgga agacagtg gcccctacag aatgttca                    648

<210> SEQ ID NO 305
<211> LENGTH: 7
<212> TYPE: PRT
<213> ORGANISM: Artificial Sequence
<220> FEATURE:
<223> OTHER INFORMATION: Synthetic peptide

<400> SEQUENCE: 305

Pro Lys Lys Lys Arg Lys Val
1               5

<210> SEQ ID NO 306
<211> LENGTH: 16
<212> TYPE: PRT
<213> ORGANISM: Artificial Sequence
<220> FEATURE:
<223> OTHER INFORMATION: Synthetic peptide

<400> SEQUENCE: 306

Lys Arg Pro Ala Ala Thr Lys Lys Ala Gly Gln Ala Lys Lys Lys Lys
1               5                   10                  15

<210> SEQ ID NO 307
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc
<222> LOCATION: (2)..(2)
<223> OTHER INFORMATION: X can be K or R
<220> FEATURE:
<221> NAME/KEY: misc
<222> LOCATION: (3)..(3)
<223> OTHER INFORMATION: X can be any amino acid
<220> FEATURE:
<221> NAME/KEY: misc
<222> LOCATION: (4)..(4)
<223> OTHER INFORMATION: X can be K or R

<400> SEQUENCE: 307
```

Lys Xaa Xaa Xaa
1

<210> SEQ ID NO 308
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 308

Lys Lys Xaa Arg
1

<210> SEQ ID NO 309
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 309

Lys Lys Xaa Lys
1

<210> SEQ ID NO 310
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 310

Lys Arg Xaa Lys
1

<210> SEQ ID NO 311
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 311

Lys Arg Xaa Arg
1

<210> SEQ ID NO 312
<211> LENGTH: 18
<212> TYPE: PRT
<213> ORGANISM: Artificial Sequence
<220> FEATURE:
<223> OTHER INFORMATION: Synthetic peptide -continued

<400> SEQUENCE: 312

Met Lys Trp Val Thr Phe Ile Ser Leu Leu Phe Leu Phe Ser Ser Ala
1               5                   10                  15

Tyr Ser

<210> SEQ ID NO 313
<211> LENGTH: 18
<212> TYPE: PRT
<213> ORGANISM: Artificial Sequence
<220> FEATURE:
<223> OTHER INFORMATION: Synthetic peptide

<400> SEQUENCE: 313

Met Ala Phe Leu Trp Leu Leu Ser Cys Trp Ala Leu Leu Gly Thr Thr
1               5                   10                  15

Gly Phe

<210> SEQ ID NO 314
<211> LENGTH: 14
<212> TYPE: PRT
<213> ORGANISM: Artificial Sequence
<220> FEATURE:
<223> OTHER INFORMATION: Synthetic peptide

<400> SEQUENCE: 314

Met Gln Leu Leu Ser Cys Ile Ala Leu Ile Leu Ala Leu Val
1               5                   10

<210> SEQ ID NO 315
<211> LENGTH: 15
<212> TYPE: PRT
<213> ORGANISM: Artificial Sequence
<220> FEATURE:
<223> OTHER INFORMATION: Synthetic peptide

<400> SEQUENCE: 315

Met Asn Leu Leu Leu Ile Leu Thr Phe Val Ala Ala Val Ala
1               5                   10                  15

<210> SEQ ID NO 316
<211> LENGTH: 451
<212> TYPE: PRT
<213> ORGANISM: Artificial Sequence
<220> FEATURE:
<223> OTHER INFORMATION: Heavy chain

<400> SEQUENCE: 316

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 317
<211> LENGTH: 216
<212> TYPE: PRT
<213> ORGANISM: Artificial Sequence
<220> FEATURE:
<223> OTHER INFORMATION: Light chain

<400> SEQUENCE: 317

Gln Ser Val Leu Thr Gln Pro Pro Ser Ala Ser Gly Thr Pro Gly Gln
1               5                   10                  15

```
Arg Val Thr Ile Ser Cys Ser Gly Ser Asn Thr Asn Ile Gly Lys Asn
             20                  25                  30

Tyr Val Ser Trp Tyr Gln Gln Leu Pro Gly Thr Ala Pro Lys Leu Leu
         35                  40                  45

Ile Tyr Ala Asn Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ser Trp Asp Ala Ser Leu
                 85                  90                  95

Asn Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 318
<211> LENGTH: 14
<212> TYPE: PRT
<213> ORGANISM: Artificial Sequence
<220> FEATURE:
<223> OTHER INFORMATION: HCDR1

<400> SEQUENCE: 318

Phe Ser Asn Ala Trp Met Ser Trp Val Arg Gln Ala Pro Gly
 1               5                  10

<210> SEQ ID NO 319
<211> LENGTH: 19
<212> TYPE: PRT
<213> ORGANISM: Artificial Sequence
<220> FEATURE:
<223> OTHER INFORMATION: HCDR2

<400> SEQUENCE: 319

Ser Ser Ile Ser Val Gly Gly His Arg Thr Tyr Tyr Ala Asp Ser Val
 1               5                  10                  15

Lys Gly Arg

<210> SEQ ID NO 320
<211> LENGTH: 14
<212> TYPE: PRT
<213> ORGANISM: Artificial Sequence
<220> FEATURE:
<223> OTHER INFORMATION: HCDR3

<400> SEQUENCE: 320

Ala Arg Ile Arg Val Gly Pro Ser Gly Gly Ala Phe Asp Tyr
 1               5                  10
```

<210> SEQ ID NO 321
<211> LENGTH: 14
<212> TYPE: PRT
<213> ORGANISM: Artificial Sequence
<220> FEATURE:
<223> OTHER INFORMATION: LCDR1

<400> SEQUENCE: 321

Cys Ser Gly Ser Asn Thr Asn Ile Gly Lys Asn Tyr Val Ser
1               5                   10

<210> SEQ ID NO 322
<211> LENGTH: 7
<212> TYPE: PRT
<213> ORGANISM: Artificial Sequence
<220> FEATURE:
<223> OTHER INFORMATION: LCDR2

<400> SEQUENCE: 322

Ala Asn Ser Asn Arg Pro Ser
1               5

<210> SEQ ID NO 323
<211> LENGTH: 12
<212> TYPE: PRT
<213> ORGANISM: Artificial Sequence
<220> FEATURE:
<223> OTHER INFORMATION: LCDR3

<400> SEQUENCE: 323

Cys Ala Ser Trp Asp Ala Ser Leu Asn Gly Trp Val
1               5                   10

<210> SEQ ID NO 324
<211> LENGTH: 120
<212> TYPE: PRT
<213> ORGANISM: Artificial Sequence
<220> FEATURE:
<223> OTHER INFORMATION: Variable heavy region

<400> SEQUENCE: 324

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Ser Ile Ser Val Gly Gly His Arg Thr Tyr Tyr Ala Asp Ser Val
    50                  55                  60

Lys Gly Arg Ser Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Val Gly Pro Ser Gly Gly Ala Phe Asp Tyr Trp Gly
            100                 105                 110

Gln Gly Thr Leu Val Thr Val Ser
        115                 120

<210> SEQ ID NO 325
<211> LENGTH: 110
<212> TYPE: PRT
<213> ORGANISM: Artificial Sequence

```
<220> FEATURE:
<223> OTHER INFORMATION: Variable light region

<400> SEQUENCE: 325

Gln Ser Val Leu Thr Gln Pro Pro Ser Ala Ser Gly Thr Pro Gly Gln
1               5                   10                  15

Arg Val Thr Ile Ser Cys Ser Gly Ser Asn Thr Asn Ile Gly Lys Asn
                20                  25                  30

Tyr Val Ser Trp Tyr Gln Gln Leu Pro Gly Thr Ala Pro Lys Leu Leu
            35                  40                  45

Ile Tyr Ala Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Ala Ser Leu
                85                  90                  95

Asn Gly Trp Val Phe Gly Gly Gly Thr Lys Leu Thr Val Leu
            100                 105                 110
```

METHODS FOR TREATING SYSTEMIC LUPUS ERYTHEMATOSUS WITH AN ANTI-APOLIPOPROTEIN B ANTIBODY

CROSS-REFERENCE TO RELATED APPLICATIONS

This application claims the benefit under 35 U.S.C. § 120 as a continuation-in-part of U.S. application Ser. No. 15/610,527, filed May 31, 2017, now U.S. Pat. No. 10,434,141, which claims priority under 35 U.S.C. § 119(e) to U.S. provisional patent application No. 62/343,601, filed May 31, 2016, the entireties of both of which are hereby incorporated by reference. This application also includes a claim of priority under 35 U.S.C. § 119(e) to U.S. provisional patent application No. 62/678,940, filed May 31, 2018, the entirety of which is hereby incorporated by reference.

REFERENCE TO SEQUENCE LISTING

The Sequence Listing submitted May 31, 2019, as a text file named "SequenceListing-070017-000023US02_ST25" created on May 31, 2019 and having a size of 106,496 bytes, is hereby incorporated by reference.

TECHNICAL FIELD

The invention provides methods for treating systemic lupus erythematosus (SLE) and diagnosing SLE and cardiovascular disease in subject with SLE.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Accelerated atherosclerosis is a severe and life threatening complication of systemic lupus erythematosus (SLE). SLE is more prevalent in women of childbearing age and African-Americans. Current treatment is non-specific immunosuppression with substantial serious side effects. Even with these agents, patients remain at risk for cardiovascular complications. The incomplete response to treatment indicates the need for more specific and less toxic therapies. It is now understood that the initiation and progression of atherosclerosis in SLE patients is modulated by the balance between opposing immune responses, atheroprotective and proatherogenic. Provided herein are methods for treating SLE and diagnosing the likelihood of cardiovascular diseases in subject with SLE.

SUMMARY

The following embodiments and aspects thereof are described and illustrated in conjunction with systems, compositions and methods which are meant to be exemplary and illustrative, not limiting in scope.

Provided herein are methods for treating, inhibiting, preventing, reducing the severity of, slowing progression of, and/or promoting prophylaxis of a disease-state in a subject in need thereof. The methods include providing a composition comprising one or more peptides of ApoB100 or derivatives, pharmaceutical equivalents, peptidomimetics or analogs thereof; and administering an effective amount of the composition to the subject, so as to treat, inhibit, reduce the severity of, slow progression of and/or promote prophylaxis of the disease-state in the subject. In one embodiment, the disease-state is systemic lupus erythematosus (SLE). In another embodiment, the disease-state is cardiovascular disease. In a further embodiment, the disease-state is cardiovascular disease in the subject with SLE.

Also provided herein are methods for treating, inhibiting, preventing, reducing the severity of, slowing progression of, and/or promoting prophylaxis of a disease-state in a subject in need thereof. The methods include providing a composition comprising CD8+ T cells activated with one or more peptides of ApoB100 or derivatives, pharmaceutical equivalents, peptidomimetics or analogs thereof and (b) administering an effective amount of the composition to the subject, so as to treat, inhibit, reduce the severity of, slow progression of and/or promote prophylaxis of the disease-state in the subject. In one embodiment, the disease-state is systemic lupus erythematosus (SLE). In another embodiment, the disease-state is cardiovascular disease. In a further embodiment, the disease-state is cardiovascular disease in the subject with SLE.

In various embodiments of the methods described herein, the peptides of ApoB100 are any one or more of peptides 1 to 302 of ApoB100 as set forth in SEQ ID NO: 1 to SEQ ID NO: 302. In one embodiment, the peptide of ApoB100 is P210 (SEQ ID NO: 210). In another embodiment, the peptide of ApoB100 is P45 (SEQ ID NO: 45). In some embodiments, the peptides of ApoB100 are fused to cholera toxin B (CTB). In one embodiment, P210 is fused to CTB. In another embodiment, P45 is fused to CTB.

Also provided herein are methods for diagnosing disease-states in a subject in need thereof. The methods include obtaining a sample from the subject; assaying the sample to determine the level of autoantibodies against ApoB100; and determining that the subject has increased likelihood of having the disease if the level of the autoantibodies is decreased relative to a reference value, or determining that the subject has decreased likelihood of having the disease if the level of autoantibodies is increased relative to a reference value. In one embodiment, the disease-state is SLE. In another embodiment, the disease-state is cardiovascular disease. In a further embodiment, the disease-state is cardiovascular disease in subject with SLE.

Further provided herein are assays for determining the efficacy of treatment for a disease in a subject in need thereof. The assays comprise obtaining a sample from the subject; assaying the sample to determine the level of autoantibodies against ApoB100; and determining that the treatment is effective if the level of the autoantibodies is increased relative to a reference value, or determining that the treatment is ineffective if the level of autoantibodies is decreases relative to a reference value. In one embodiment, the disease is cardiovascular disease in subject with SLE. In another embodiment, the disease is SLE. In a further embodiment, the disease is cardiovascular disease.

Also provided are methods for treating, reducing the severity or likelihood of, slowing progression of or inhibiting systemic lupus erythematosus (SLE) in a subject, or atherosclerosis in a subject exhibiting symptoms or having been diagnosed with SLE, which includes administering to the subject an effective amount of an antibody or antibody fragment capable of binding to a fragment (comprising or consisting of P45, SEQ ID NO: 45) of apolipoprotein B100

(ApoB100), wherein the antibody contains one, two or three heavy chain complementarity determining regions (HCDRs) selected from the group consisting of HCDR 1 (HCDR1), HCDR 2 (HCDR2) and HCDR 3 (HCDR3) sequences of SEQ ID Nos: 318, 319 and 320, respectively, and one, two or three light chain complementarity determining regions (LCDRs) selected from the group consisting of LCDR 1 (LCDR1), LCDR 2 (LCDR2) and LCDR 3 (LCDR3) sequences of SEQ ID Nos: 321, 322 and 323, respectively.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 3 depicts in accordance with various embodiments of the invention, significant increase in oxPL with CVX-12 administration in gld.apoE$^{-/-}$ mice on normal diet. Biotinylated ApoB (biot.ApoB), biotinylated antibody to oxidized phospholipids (biot.E06) and oxidized phospholipid/apoB100 (OxPL/ApoB) in Example 1 for PBS, Alum, and CVX-12 groups.

FIG. 6A-FIG. 6D depict in accordance with various embodiments of the invention, atherosclerotic plaque coverage of en face aorta. Atherosclerotic lesion coverage is represented as a percentage of total en face aortic area (plaque covered area/total area). Aorta plaque measurements are apoE−/− (FIG. 6A), gld (FIG. 6B), gld.apoE−/− on normal diet (FIG. 6C), and gld.apoE−/− on western diet (FIG. 6D).

FIG. 9 depicts in accordance with various embodiments of the invention described in example 1, glomerular tuft size in lupus mouse models. Arrows designate glomerular tufts. Size of tuft area is measured by pixel count. SEM is shown.

(FIG. 11D) Peripheral blood mononuclear cells gated in the forward and site scatter lymphocyte gate shown as (FIG. 11E) early apoptotic lymphocytic cells (Annexin$^+$/7-AAD$^-$) and (FIG. 11F) late apoptotic lymphocytic cells (Annexin$^+$/7-AAD$^+$) after treatment with soluble Fas ligand (2.5 μg/ml).

FIG. 19A-FIG. 19I depicts, in accordance with an embodiment of the invention, lymph node cell phenotype assessment with flow cytometry after treatment of MRL/lpr/Apoe$^{-/-}$ mice with PBS, CTB 30 μg/ml, P45-CTB 5, 15 and 30 μg/ml. Splenocyte percentage of (FIG. 19A) T helper cells (CD3$^+$CD4$^+$), (FIG. 19B) cytolytic T cells (CD3$^+$CD8$^+$), (FIG. 19C) T helper central memory cells (CD4$^+$CD62L$^+$CD44$^{int-hi}$), (FIG. 19D) T helper effector cells (CD4$^+$CD62$^-$CD44$^{hi}$), (FIG. 19E) naïve T helper cells (CD4$^+$CD62L$^+$CD44$^{lo}$), (FIG. 19F) regulatory T cells (CD3$^+$CD4$^+$CD25$^+$FoxP3$^+$), (FIG. 19G) central memory cytolytic T cells (CD8$^+$CD62L$^+$CD44$^{int-hi}$), (FIG. 19H) cytolytic effector T cells (CD8$^+$CD62$^-$CD44$^{hi}$) and (FIG. 19I) naïve cytolytic T cells (CD8$^+$CD62L$^+$CD44$^{lo}$). Statistical analysis was performed using One-way ANOVA with Sidak's multiple comparison test, comparing to PBS and CTB where *p<0.05, p<0.01 and *p<0.001. Each point represents one mouse.

FIG. 21A depicts the polynucleotide sequences encoding heavy chain (SEQ ID NO:303) and encoding light chain (SEQ ID NO: 304) of an exemplary antibody (orticumab) for use with the methods described herein. FIG. 21B and the first ten lines of FIG. 21C depict the amino acid sequence of the heavy chain (SEQ ID NO: 316) of orticumab in upper case letters, which is translated from the adjacent lowercase letters showing the polynucleotide sequence. Starting from line 15 of FIG. 21C, the amino acid sequence of the light chain (SEQ ID NO: 317) of orticumab is depicted in upper case letters, which is translated from the adjacent lowercase letters showing the polynucleotide sequence.

FIG. 26 depicts the quantification and the staining micrographs of CD68(%) in SLExApoE$^{-/-}$ mice injected with a control antibody or with orticumab (BI-204).

FIG. 30 depicts the arithmetic mean serum concentration (linear scale) of orticumab over time (day) following a single dose of 360 mg orticumab in the second Phase I study.

FIG. 31 shows a schematic of the trial design of a Phase IIa study in Example 10.

In FIG. 33A, the highest solid line between 0 and 96 hours indicates dosing at a weekly frequency at 2 mg/kg; generally the middle solid line between 24 and 96 hours indicates dosing at a bi-weekly frequency at 2 mg/kg; and generally the lowest solid line indicates dosing at a monthly frequency at 2 mg/kg. In FIG. 33B, the solid line indicates a loading dose at 5 mg/kg and subsequent doses at 2 mg/kg every two weeks. Generally lower dashed line indicates a desired threshold of 4 μg/mL of the serum concentration of orticumab. Generally higher dashed line indicates a desired threshold of 12 μg/mL of the serum concentration of orticumab.

FIG. 39C as a comparison.

FIG. 40 as a comparison.

FIG. 41C as a comparison. FIG. 42C as a comparison. FIG. 43C as a comparison. FIG. 44C as a comparison. Concentrations are normalized to the number of seeded cells. Each dot represents one individual patient in FIGS. 37A-37C and one sample replicate. Cell population frequencies from each individual are presented as percent and individual percent change. Wilcoxon paired samples rank test of same individual data in unstimulated vs oxLDL stimulated samples and Mann-Whitney rank test of individual plasma level values and individual percent change were used, $*p \le 0.05$, $p \le 0.01$ and $*p \le 0.001$.

FIG. 58-FIG. 61 demonstrate p45-CTB did not aggravate SLE phenotype. FIG. 58 depicts the score of plasma anti-nuclear antibody (ANA), which is expressed as mean of four individual persons scoring independently according to a scoring matrix. FIG. 59 depicts the plasma anti-dsDNA. FIG. 60 depicts urine albumin:creatinine ratio (ACR). FIG. 61 depicts blood urea nitrogen concentrations. Four mice in CTB group were excluded in all urine analyses for technical reasons. Eight and three mice in P45-CTB were excluded from the albumin:creatinine ratio and blood urea nitrogen analyses respectively. Each dot represents one mouse and data is shown as mean±standard deviation, $*p \le 0.05$ with Students t-test on normally distributed data or Mann-Whitney rank test on not normally distributed data.

FIG. 62, FIG. 63A, FIG. 63B, FIG. 64, FIG. 65A, FIG. 65B, FIG. 66A-FIG. 66D, FIG. 67A and FIG. 67B demonstrate passive immunization with an ApoB100 peptide antibody reduced atherosclerotic plaques development. FIG. 62 is a diagram depicting that male B6.lpr.ApoE$^{-/-}$ mice were fed high-fat diet (HFD) at 6 weeks of age until termination of the study at 22 weeks of age. Mice were given intra-peritoneal injections of control IgG1 (CIgG, 1 mg, n=11) or MDA.p45-IgG1 (1 mg, n=7) at 18, 19 and 20 weeks of age. FIG. 63A and FIG. 63B show Oil Red O lipid stained area of en face aortic arch and subvalvular plaque area, respectively. FIG. 64 depicts CD68 positive subvalvular plaque area including representative pictures of sections. FIG. 65A and FIG. 65B depict carotid artery mRNA expression of IL-10 and MCP-1, respectively, at termination of the study expressed as log transformed relative fold change to CTB, normalized to 18S housekeeping gene. Gene expression data was log transformed before analysis. FIG. 66A-FIG. 66D depict the plasma concentrations of plasma triglyceride (66A), plasma cholesterol (66B), plasma oxLDL (66C) and plasma IL-10 (66D) at termination of the study. Seven and six mice in CIgG group were excluded from gene expression analysis of IL-10 and MCP-1 respectively, two mice were excluded in MDA.P45-IgG group. FIG. 67A and FIG. 67B depict glomerular area (67A) and cell count (67B) from kidney. Five mice and one mouse in CIgG and MDA.p45-IgG respectively were excluded. Each dot represents one mouse and data is shown as mean±standard deviation, *p≤0.05 with Students t-test on normally distributed data or Mann-Whitney rank test on not normally distributed data.

FIG. 68A, FIG. 68B, FIG. 69-FIG. 72 and FIG. 73A-FIG. 73D demonstrate MDA.p45-IgG enhance uptake of oxLDL in $CD14^+$ monocytes. OxLDL conjugated to DiI-fluorochrome difference in mean MFI (68A) and in individual MFI (68B) from total SLE PBMC's (n=26). FIG. 69 depicts manually gated CD14+ and DILoxLDL+ populations in concatenated data of all samples and visualized in t-SNE plot of 24 h in vitro cultured PBMCs after oxLDL and oxLDL with MDA.P45-IgG respectively. Percent of $CD14^+$ (FIG. 70) and $CD14^+$ DiI-OxLDL$^+$ double positive cells (FIG. 71) including representative plot from one individual from PBMCs exposed to oxLDL or oxLDL with MDA.P45-IgG (FIG. 72). Each dot represents one individual and in vitro stimulation. Cell population frequencies from each individual are presented as percent. Wilcoxon paired samples rank test of same individual data in oxLDL vs oxLDL with MDA.Pp45-IgG stimulated samples were used, *p≤0.05, p≤0.01 and *p≤0.001. FIG. 73A-FIG. 73D depict the addition of the antibody (MDA.P45-IgG) had small effects on the cytokine release (IL-6, IFNγ and IL-10 in FIGS. 73A, 73B and 73C, respective) from SLE PBMC, except only a modest increase in the anti-inflammatory cytokine IL-1RA reaching statistical significance (FIG. 73D).

DETAILED DESCRIPTION

Figure 1:
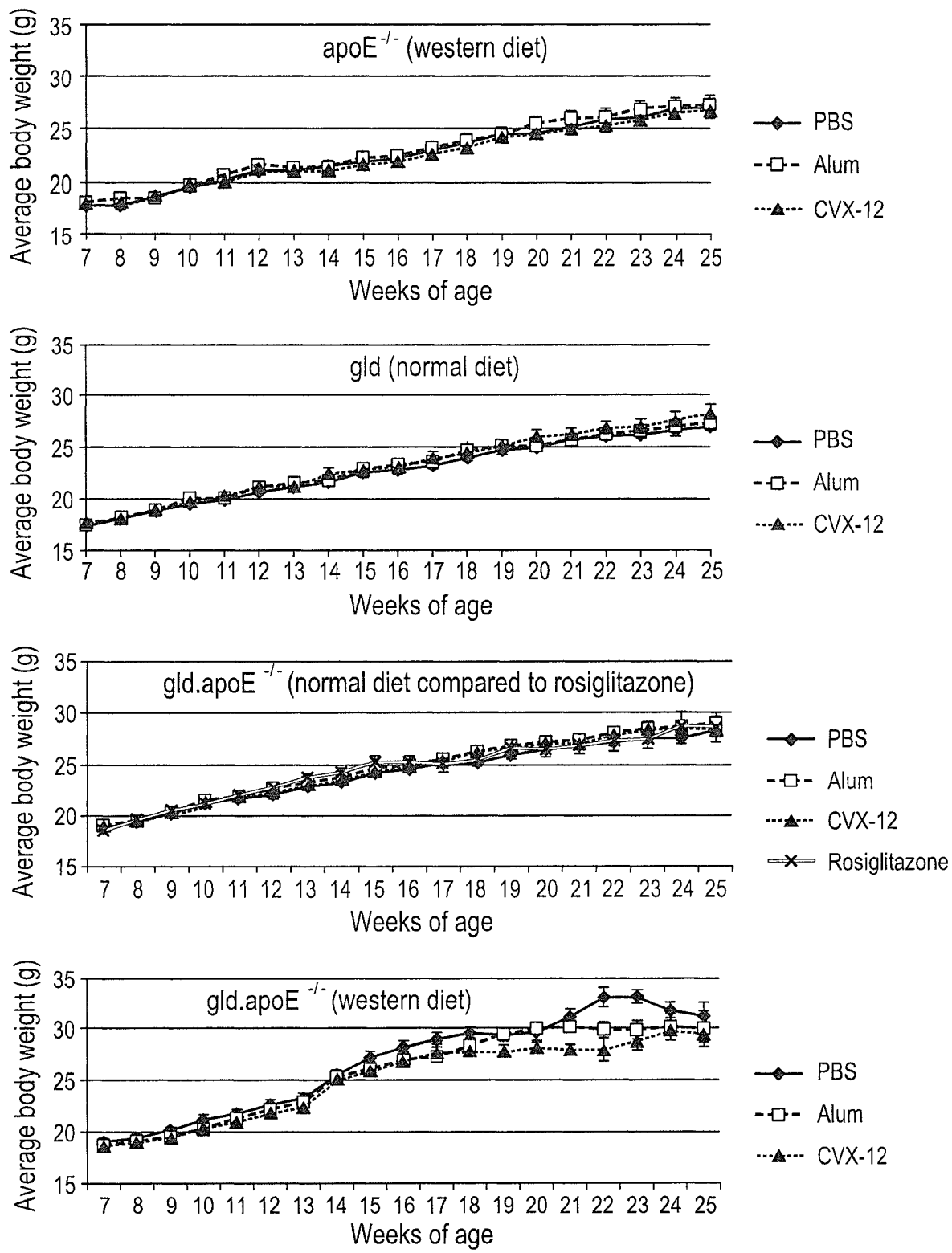
FIG. 1 depicts in accordance with various embodiments of the invention, body weight measurements for the duration of the study described in Example 1. Values=averages+/−SEM.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 Jul. 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and/or prolonging a patient's life or life expectancy. In some embodiments, the disease condition is SLE.

The term "effective amount" as used herein refers to the amount of a pharmaceutical composition comprising one or more peptides as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the peptides described herein. Measured or measurable parameters include clinically detectable markers of disease, for example, elevated or depressed levels of a biological marker, as well as parameters related to a clinically accepted scale of symptoms or markers for atherosclerosis. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

"Subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Patient outcome" refers to whether a patient survives or dies as a result of treatment. A more accurate prognosis for patients as provided in this invention increases the chances of patient survival.

"Poor Prognosis" means that the prospect of survival and recovery of disease is unlikely despite the standard of care for the treatment of the cancer (for example, lung cancer), that is, surgery, radiation, chemotherapy. Poor prognosis is the category of patients whose survival is less than that of the median survival.

"Good Prognosis" means that the prospect of survival and recovery of disease is likely with the standard of care for the treatment of the disease, for example, surgery, radiation, chemotherapy. Good prognosis is the category of patients whose survival is not less than that of the median survival.

"Pharmaceutically acceptable carriers" as used herein refer to conventional pharmaceutically acceptable carriers useful in this invention.

The term "fusion protein" as used herein indicates a protein created through the attaching of two or more polypeptides which originated from separate proteins. In particular fusion proteins can be created by recombinant DNA technology and are typically used in biological research or therapeutics. Fusion proteins can also be created through chemical covalent conjugation with or without a linker between the polypeptides portion of the fusion proteins.

The term "attach" or "attached" as used herein, refers to connecting or uniting by a bond, link, force or tie in order to keep two or more components together, which encompasses either direct or indirect attachment such that for example where a first polypeptide is directly bound to a second polypeptide or material, and the embodiments wherein one or more intermediate compounds, and in particular polypeptides, are disposed between the first polypeptide and the second polypeptide or material.

The term "protein" or "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog "Peptidomimetic" as used herein is a small protein-like chain designed to mimic a protein function. They may be modifications of an existing peptide or newly designed to mimic known peptides. They may be, for example peptoids and/or β-peptides and/or D-peptides.

"Recombinant virus" refers to a virus that has been genetically altered (e.g., by the addition or insertion of a heterologous nucleic acid construct into the particle).

A "gene" or "coding sequence" or a sequence which "encodes" a particular protein or peptide is a nucleic acid molecule that is transcribed (in the case of DNA) and translated (in the case of mRNA) into a polypeptide in vitro or in vivo when placed under the control of appropriate regulatory sequences. The boundaries of the gene are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346. Examples of well-known vehicles for gene transfer include adenovirus and recombinant adenovirus (RAd), adeno-associated virus (AAV), herpes simplex virus type 1 (HSV-1), and lentivirus (LV).

"Genetically modified cells", "genetically engineered cells", or "modified cells" as used herein refer to cells that express the polynucleotide having the sequence of any one or more SEQ ID Nos: 1-302 or combinations thereof or variants, derivatives, pharmaceutical equivalents, peptidomimetics or analogs thereof. In one embodiment, the cell express the polynucleotide having the sequence of SEQ ID NO: 210 or a variant, derivative, pharmaceutical equivalent, peptidomimetic or an analog thereof.

"Naked DNA" as used herein refers to DNA encoding a polypeptide having the sequence of any one or more of SEQ ID Nos: 1-302 or a combination thereof, or a variant, derivative, pharmaceutical equivalent, peptidomimetic or an analog thereof, cloned in a suitable expression vector in proper orientation for expression. Viral vectors which may be used include but are not limited SIN lentiviral vectors, retroviral vectors, foamy virus vectors, adeno-associated virus (AAV) vectors, hybrid vectors and/or plasmid transposons (for example sleeping beauty transposon system) or integrase based vector systems. Other vectors that may be used in connection with alternate embodiments of the invention will be apparent to those of skill in the art.

"Polynucleotide" as used herein includes but is not limited to DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. Virology, 52:456 (1973); Sambrook et al. Molecular Cloning, a laboratory manual, Cold Spring Harbor Laboratories, New York (1989); Davis et al., Basic Methods in Molecular Biology, Elsevier (1986), and Chu et al. Gene 13:197 (1981). Such techniques can be used to introduce one or more exogenous DNA moieties, such as a plasmid vector and other nucleic acid molecules, into suitable host cells. The term refers to both stable and transient uptake of the genetic material.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Vectors include plasmids, phages, viruses, etc.

Therapeutic Methods

Provided herein are methods for treating, inhibiting, preventing, reducing the severity of, slowing progression of and/or promoting prophylaxis of SLE in a subject in need thereof. The methods include providing one or more peptides of ApoB100 or derivatives, pharmaceutical equivalents, peptidomimetics or analogs thereof and administering a therapeutically or prophylactically effective amount of the one or more peptides to the subject so as to treat, inhibit, reduce the severity of and/or promote prophylaxis of SLE in the subject. In some embodiments, the subject with SLE is diagnosed with or is suspected of having cardiovascular disease. In some embodiments, the one or more peptides of ApoB100 are peptides having sequences set forth in SEQ ID Nos: 1-302 or as described in Table 1. In some embodiments, the one or more peptides of ApoB100 are immunogenic fragments of the peptides set forth in SEQ ID Nos 1-302 or as described in Table 1. In some embodiments, the ApoB100 peptides for uses in the therapeutic methods described herein are administered sequentially or simultaneously with antibodies specific to ApoB100. In exemplary embodiments, the antibodies comprise, consist of or consist essentially of the sequence set forth in SEQ ID NOs: 303 and/or 304. In some embodiments, the peptides described herein are administered sequentially or simultaneously with existing treatments for SLE. In some embodiments, the antibodies described herein are administered sequentially or simultaneously with existing treatments for SLE. In some embodiments, the peptides and antibodies described herein are administered sequentially or simultaneously with existing treatments for SLE. In some embodiments, the one or more peptides of ApoB100 are administrated to the subject 1-3 times per day or 1-7 times per week. In some embodiments, the one or more peptides of ApoB100 are administrated to the subject for 1-5 days, 1-5 weeks, 1-5 months, or 1-5 years. In one embodiment, the ApoB100 peptide for use in the therapeutic methods described herein is the peptide P210 having the sequence set forth in SEQ ID NO: 210, or a derivative, pharmaceutical equivalent, peptidomimetic or analog thereof. In one embodiment, the ApoB100 peptide for use in the therapeutic methods described herein is the peptide P45 having the sequence set forth in SEQ ID NO: 45, or a derivative, pharmaceutical equivalent, peptidomimetic or analog thereof. In some embodiments, the ApoB100 peptide for use in the therapeutic methods described herein are fused to CTB. In one embodiment, the ApoB100 peptide for use in the therapeutic methods described herein is the peptide P210 having the sequence set forth in SEQ ID NO: 210, or a derivative, pharmaceutical equivalent, peptidomimetic or analog thereof and is fused to CTB (P210-CTB). In one embodiment, the ApoB100 peptide for use in the therapeutic methods described herein is the peptide P45 having the sequence set forth in SEQ ID NO: 45, or a derivative, pharmaceutical equivalent, peptidomimetic or analog thereof and is fused to CTB (P45-CTB).

Also provided herein are methods for treating, inhibiting, preventing, reducing the severity of, slowing progression of and/or promoting prophylaxis of cardiovascular diseases in a subject in need thereof. The methods include providing one or more peptides of ApoB100 or derivatives, pharmaceutical equivalents, peptidomimetics or analogs thereof and administering a therapeutically or prophylactically effective amount of the one or more peptides to the subject so as to treat, inhibit, reduce the severity of and/or promote prophylaxis of cardiovascular disease in the subject. In some embodiments, the subject with cardiovascular disease is diagnosed with or is suspected of having SLE. In some embodiments, the one or more peptides of ApoB100 are peptides having sequences set forth in SEQ ID Nos: 1-302 or as described in Table 1. In some embodiments, the one or more peptides of ApoB100 are immunogenic fragments of the peptides set forth in SEQ ID Nos 1-302 or as described in Table 1. In some embodiments, the ApoB100 peptides for uses in the therapeutic methods described herein are administered sequentially or simultaneously with antibodies specific to ApoB100. In exemplary embodiments, the antibodies comprise the sequence set forth in SEQ ID NOs: 303 and/or 304. In some embodiments, the peptides described herein are administered sequentially or simultaneously with treatments for SLE. In some embodiments, the antibodies described herein are administered sequentially or simultaneously with treatments for SLE. In some embodiments, the peptides and antibodies described herein are administered sequentially or simultaneously with treatments for SLE. In various embodiments, the ApoB100 peptides described herein or derivatives, pharmaceutical equivalents, peptidomimetics or analogs thereof are administrated to the subject before, during, or after the subject having or suspected of having SLE develops the cardiovascular disease. In some embodiments, the one or more peptides of ApoB100 are administrated to the subject 1-3 times per day or 1-7 times per week. In some embodiments, the one or more peptides of ApoB100 are administrated to the subject for 1-5 days, 1-5 weeks, 1-5 months, or 1-5 years. In one embodiment, the ApoB100 peptide for use in the therapeutic methods described herein is the peptide P210 having the sequence set forth in SEQ ID NO: 210, or a derivative, pharmaceutical equivalent, peptidomimetic or analog thereof. In some embodiments, the methods described herein further comprise co-administering, either simultaneously or sequentially, existing therapies for atherosclerosis with the peptides described herein. In one embodiment, the ApoB100 peptide for use in the therapeutic methods described herein is the peptide P45 having the sequence set forth in SEQ ID NO: 45, or a derivative, pharmaceutical equivalent, peptidomimetic or analog thereof. In some embodiments, the ApoB100 peptide for use in the therapeutic methods described herein are fused to CTB. In one embodiment, the ApoB100 peptide for use in the therapeutic methods described herein is the peptide P210 having the sequence set forth in SEQ ID NO: 210, or a derivative, pharmaceutical equivalent, peptidomimetic or analog thereof and is fused to CTB (P210-CTB). In one embodiment, the ApoB100 peptide for use in the therapeutic methods described herein is the peptide P45 having the sequence set forth in SEQ ID NO: 45, or a derivative, pharmaceutical equivalent, peptidomimetic or analog thereof and is fused to CTB (P45-CTB).

Also provided herein are methods for treating, inhibiting, preventing, reducing the severity of, slowing progression of and/or promoting prophylaxis of cardiovascular diseases in subjects having SLE or suspected of having SLE. The methods include providing one or more peptides of ApoB100 or derivatives, pharmaceutical equivalents, peptidomimetics or analogs thereof and administering a therapeutically or prophylactically effective amount of the one or more peptides to the subject so as to treat, inhibit, reduce the severity of and/or promote prophylaxis of SLE in the subject. In some embodiments, the one or more peptides of ApoB100 are peptides having sequences set forth in SEQ ID Nos: 1-302 or as described in Table 1. In some embodiments, the one or more peptides of ApoB100 are immunogenic fragments of the peptides set forth in SEQ ID Nos 1-302 or as described in Table 1. In some embodiments, the ApoB100 peptides for uses in the therapeutic methods described herein are administered sequentially or simultaneously with antibodies specific to ApoB100. In exemplary embodiments, the antibodies comprise the sequence set forth in SEQ ID NOs: 303 and/or 304. In some embodiments, the peptides described herein are administered sequentially or simultaneously with existing treatments for SLE. In some embodiments, the antibodies described herein are administered sequentially or simultaneously with existing treatments for SLE. In some embodiments, the peptides and antibodies described herein are administered sequentially or simultaneously with existing treatments for SLE. In some embodiments, the one or more peptides of ApoB100 are administrated to the subject 1-3 times per day or 1-7 times per week. In some embodiments, the one or more peptides of ApoB100 are administrated to the subject for 1-5 days, 1-5 weeks, 1-5 months, or 1-5 years. In one embodiment, the ApoB100 peptide for use in the therapeutic methods described herein is the peptide P210 having the sequence set forth in SEQ ID NO: 210, or a derivative, pharmaceutical equivalent, peptidomimetic or analog thereof. In one embodiment, the ApoB100 peptide for use in the therapeutic methods described herein is the peptide P45 having the sequence set forth in SEQ ID NO: 45, or a derivative, pharmaceutical equivalent, peptidomimetic or analog thereof. In some embodiments, the ApoB100 peptide for use in the therapeutic methods described herein are fused to CTB. In one embodiment, the ApoB100 peptide for use in the therapeutic methods described herein is the peptide P210 having the sequence set forth in SEQ ID NO: 210, or a derivative, pharmaceutical equivalent, peptidomimetic or analog thereof and is fused to CTB (P210-CTB). In one embodiment, the ApoB100 peptide for use in the therapeutic methods described herein is the peptide P45 having the sequence set forth in SEQ ID NO: 45, or a derivative, pharmaceutical equivalent, peptidomimetic or analog thereof and is fused to CTB (P45-CTB).

Further provided herein are methods for treating, inhibiting, preventing, reducing the severity of, slowing progression of and/or promoting prophylaxis of SLE in a subject in need thereof. The methods include providing CD8+ T cells activated with one or more peptides of ApoB100 or derivatives, pharmaceutical equivalents, peptidomimetics or analogs thereof and administering a therapeutically or prophylactically effective amount of the one or more peptides to the subject so as to treat, inhibit, reduce the severity of and/or promote prophylaxis of SLE in the subject. In some embodiments, the subject with SLE has or is suspected of having cardiovascular disease. In some embodiments, the one or more peptides of ApoB100 are peptides having sequences set forth in SEQ ID Nos: 1-302 or as described in Table 1. In some embodiments, the one or more peptides of ApoB100 are immunogenic fragments of the peptides set forth in SEQ ID Nos 1-302 or as described in Table 1. In some embodiments, the CD8+ T cells activated with the ApoB100 peptides for uses in the therapeutic methods described herein are administered sequentially or simultaneously with antibodies specific to ApoB100. In exemplary embodiments, the antibodies comprise the sequence set forth in SEQ ID NOs: 303 and/or 304. In some embodiments, the CD8+ T cells activated with the ApoB100 peptides described herein are administered sequentially or simultaneously with existing treatments for SLE. In some embodiments, the antibodies described herein are administered sequentially or simultaneously with existing treatments for SLE. In some embodiments, the CD8+ T cells activated with the ApoB100 peptides and the antibodies described herein are administered sequentially or simultaneously with existing treatments for SLE. In some embodiments, the CD8+ T cells activated with the ApoB100 peptides or derivatives, pharmaceutical equivalents, peptidomimetics or analogs thereof are administrated to the subject 1-3 times per day or 1-7 times per week. In some embodiments, the CD8+ T cells activated with the ApoB100 peptides or derivatives, pharmaceutical equivalents, peptidomimetics or analogs thereof are administrated to the subject for 1-5 days, 1-5 weeks, 1-5 months, or 1-5 years. In one embodiment, the CD8+ T cells are activated with the peptide P210 having the sequence set forth in SEQ ID NO: 210, or a derivative, pharmaceutical equivalent, peptidomimetic or analog thereof. In one embodiment, the CD8+ T cells are activated with the peptide P45 having the sequence set forth in SEQ ID NO: 45, or a derivative, pharmaceutical equivalent, peptidomimetic or analog thereof. In one embodiment, the CD8+ T cells are activated with the peptide P45 having the sequence set forth in SEQ ID NO: 45, or a derivative, pharmaceutical equivalent, peptidomimetic or analog thereof. In some embodiments, the methods described herein further comprise co-administering, either simultaneously or sequentially, existing therapies for SLE with the CD8+ T cells activated with the ApoB100 peptides as described herein.

Also provided herein are methods for treating, inhibiting, preventing, reducing the severity of, slowing progression of and/or promoting prophylaxis of cardiovascular diseases in a subject in need thereof. The methods include providing CD8+ T cells activated with one or more peptides of ApoB100 or derivatives, pharmaceutical equivalents, peptidomimetics or analogs thereof and administering a therapeutically or prophylactically effective amount of the one or more peptides to the subject so as to treat, inhibit, reduce the severity of and/or promote prophylaxis of cardiovascular disease in the subject. In some embodiments, the subject with cardiovascular disease is diagnosed with or is suspected of having SLE. In some embodiments, the one or more peptides of ApoB100 are peptides having sequences set forth in SEQ ID Nos: 1-302 or as described in Table 1. In some embodiments, the one or more peptides of ApoB100 are immunogenic fragments of the peptides set forth in SEQ ID Nos 1-302 or as described in Table 1. In some embodiments, the CD8+ T cells activated with the ApoB100 peptides for uses in the therapeutic methods described herein are administered sequentially or simultaneously with antibodies specific to ApoB100. In exemplary embodiments, the antibodies comprise the sequence set forth in SEQ ID NOs: 303 and/or 304. In some embodiments, the CD8+ T cells activated with the ApoB100 peptides described herein are administered sequentially or simultaneously with treatments for SLE. In some embodiments, the antibodies described herein are administered sequentially or simultaneously with treatments for SLE. In some embodiments, the CD8+ T cells activated with the ApoB100 peptides and the antibodies described herein are administered sequentially or simultaneously with treatments for SLE. In various embodiments, the CD8+ T cells activated with the ApoB100 peptides or derivatives, pharmaceutical equivalents, peptidomimetics or analogs thereof, are administered to the subject before, during, or after the subject having or suspected of having SLE develops the cardiovascular disease. In some embodiments, the CD8+ T cells activated with the ApoB100 peptides or derivatives, pharmaceutical equivalents, peptidomimetics or analogs thereof are administered to the subject 1-3 times per day or 1-7 times per week. In some embodiments, the CD8+ T cells activated with the ApoB100 peptides or derivatives, pharmaceutical equivalents, peptidomimetics or analogs thereof are administered to the subject for 1-5 days, 1-5 weeks, 1-5 months, or 1-5 years. In one embodiment, the CD8+ T cells are activated with the peptide P210 having the sequence set forth in SEQ ID NO: 210, or a derivative, pharmaceutical equivalent, peptidomimetic or analog thereof. In some embodiments, the methods described herein further comprise co-administering, either simultaneously or sequentially, existing therapies for atherosclerosis with the peptides described herein. In one embodiment, the CD8+ T cells are activated with the peptide P45 having the sequence set forth in SEQ ID NO: 45, or a derivative, pharmaceutical equivalent, peptidomimetic or analog thereof.

As described herein, in some embodiments, the peptides and/or antibodies described herein are administered sequentially or simultaneously with treatments for SLE. In exemplary embodiments, existing treatments for SLE include but are not limited to systemic inflammation directed treatments (such as antimalarials-hydroxychloroquine, corticosteroids, cyclophosphamide, mycophenolate mofetil, azathioprine, methotrexate or combinations thereof), immune cell-targeted therapies (such as anti-CD20 (rituximab), anti-CD22 (epratuzumab), abetimus (LJP-394), belimumab, atacicept), agents that target co-stimulatory pathways, anti-cytokine therapies, memantine, intravenous immunoglobulin (IVIG), DNA vaccinations, or combinations thereof. In exemplary embodiments, existing treatments for atherosclerosis include but are not limited to statins, anti-platelet agents, beta blockers, angiotensin-converting enzyme (ACE) inhibitors, calcium channel blockers, surgery (such as angioplasty and stent placement, fibrinolytic therapy, percutaneous coronary intervention (PCI), coronary artery bypass grafting (CABG), carotid endarterectomy), or combinations thereof.

In various embodiments, the therapeutically or prophylactically effective amount of any one or more of the ApoB100 peptides and/or a combinations thereof, or analogs, pharmaceutical equivalents or a peptidomimetics thereof for use with the methods described herein is any one or more of about 0.01 to 0.05 µg/kg/day, 0.05-0.1 µg/kg/day, 0.1 to 0.5 µg/kg/day, 0.5 to 5 µg/kg/day, 0.5 to 1 µg/kg/day, 1 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Typical dosages of the any one or more of the ApoB100 peptides and/or a combinations thereof, or analogs, pharmaceutical equivalents or a peptidomimetics thereof can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, the any one or more of the ApoB100 peptides and/or a combinations thereof, or analogs, pharmaceutical equivalents or a peptidomimetics thereof may be administered once a day (SID/QD), twice a day (BID), three times a day (TID), four times a day (QID), or more, so as to administer an effective amount to the subject, where the effective amount is any one or more of the doses described herein.

In various embodiments, the therapeutically or prophylactically effective amount of the antibodies or fragments thereof specific to ApoB100, for use with the methods described herein is any one or more of about 0.01 to 0.05 µg/kg/day, 0.05-0.1 µg/kg/day, 0.1 to 0.5 µg/kg/day, 0.5 to 5 µg/kg/day, 0.5 to 1 µg/kg/day, 1 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Typical dosages of the antibodies can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, the antibodies may be administered once a day (SID/QD), twice a day (BID), three times a day (TID), four times a day (QID), or more, so as to administer an effective amount to the subject, where the effective amount is any one or more of the doses described herein.

In various embodiments, the subject is selected from the group consisting of human, non-human primate, monkey, ape, dog, cat, cow, horse, rabbit, mouse and rat.

Diagnostic Methods

Further provided herein are assays for diagnosing SLE in a subject in need thereof. The assays include obtaining a sample from the subject; assaying the sample to determine the level of autoantibodies against ApoB100; and determining that the subject has increased likelihood of SLE if the level of the autoantibodies is decreased relative to a reference value, or determining that the subject has decreased likelihood of SLE if the level of autoantibodies is increased relative to a reference value. In some embodiments, the method may further comprise selecting or prescribing a therapy for SLE.

Also provided herein are assays for determining likelihood of cardiovascular disease in a subject having or suspected of having SLE. The assays include obtaining a sample from the subject; assaying the sample to determine the level of autoantibodies against ApoB100; and determining that the subject has increased likelihood of cardiovascular disease if the level of the autoantibodies is decreased relative to a reference value, or determining that the subject has decreased likelihood of cardiovascular disease if the level of autoantibodies is increased relative to a reference value. In some embodiments, the method may further comprise selecting or prescribing a therapy for cardiovascular disease.

Also provided herein are assays for determining the efficacy of treatment for SLE in a subject in need thereof. The assays include obtaining a sample from the subject undergoing treatment for SLE; assaying the sample to determine the level of autoantibodies against ApoB100; and determining that the treatment is effective if the level of the autoantibodies is increased relative to a reference value, or determining that the treatment is ineffective if the level of autoantibodies is decreased or unchanged relative to a reference value.

Also provided herein are assays for determining the efficacy of treatment for cardiovascular diseases in subject with SLE. The assays include obtaining a sample from the subject undergoing treatment for cardiovascular diseases; assaying the sample to determine the level of autoantibodies against ApoB100; and determining that the treatment is effective if the level of the autoantibodies is increased relative to a reference value, or determining that the treatment is ineffective if the level of autoantibodies is decreased or unchanged relative to a reference value.

Further provided herein is an assay for diagnosing SLE in a subject in need thereof. The assay includes obtaining a sample from the subject; assaying the sample to determine the level of soluble forms of the apoptosis-signaling receptors Fas, TNF-R1, and/or TRAIL-R2; and determining that the subject has increased likelihood of having SLE if the level of the said apoptosis-signaling receptors is increased relative to a reference value, or determining that the subject has decreased likelihood of having SLE if the level of said apoptosis-signaling receptors is decreased relative to a reference value.

Further provided herein is an assay for determining the efficacy of treatment for SLE in a subject in need thereof. The assay includes obtaining a sample from the subject; assaying the sample to determine the level of soluble forms of the apoptosis-signaling receptors Fas, TNF-R1, and/or TRAIL-R2; and determining that the treatment is effective if the level of the said apoptosis-signaling receptors is decreased relative to a reference value, or determining that the treatment is less effective or not effective if the level of said apoptosis-signaling receptors is increased relative to a reference value Also provided herein is an assay for determining likelihood of cardiovascular disease in a subject having or suspected of having SLE. The assay includes obtaining a sample from the subject; assaying the sample to determine the level of soluble forms of the apoptosis-signaling receptors Fas, TNF-R1, and/or TRAIL-R2; and determining that the subject has increased likelihood of cardiovascular disease if the level of said apoptosis-signaling receptors is increased relative to a reference value, or determining that the subject has decreased likelihood of cardiovascular disease if the level of said apoptosis-signaling receptors is decreased relative to a reference value.

In various embodiments, assaying comprises using is immunoassays. Exemplary embodiments of immunoassays include but are not limited to any one or more of ELISA, RIA, Western blotting, Southern blotting, or combinations thereof.

In some embodiments of the assays described herein, the sample is any one or more of blood, plasma, urine, tissue or combinations thereof. In some embodiments of the assays described herein, the sample is obtained before, during or after treatment for SLE.

In one embodiment of the assays described herein, the subject is human.

In one embodiment of the assays described herein, cardiovascular disease is atherosclerosis. In an exemplary embodiment, the atherosclerosis is accelerated atherosclerosis. In some embodiments, the sample is obtained before, during and/or after treatment for cardiovascular diseases in subject having or suspected of having SLE.

Any suitable immunoassay method may be utilized, including those which are commercially available, to determine the level ApoB100 specific autoantibodies measured according to the invention. Extensive discussion of the known immunoassay techniques is not required here since these are known to those of skill in the art. Typical suitable immunoassay techniques include sandwich enzyme-linked immunoassays (ELISA), radioimmunoassays (RIA), competitive binding assays, homogeneous assays, heterogeneous assays, etc. Various known immunoassay methods are reviewed, e.g., in Methods in Enzymology, 70, pp. 30-70 and 166-198 (1980).

In the assays of the invention, "sandwich-type" assay formats can be used. Some examples of such sandwich-type assays are described in by U.S. Pat. No. 4,168,146 to Grubb, et al. and U.S. Pat. No. 4,366,241 to Tom, et al. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al.

The antibodies can be labeled. In some embodiments, the detection antibody is labeled by covalently linking to an enzyme, label with a fluorescent compound or metal, label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease. For a detailed discussion of enzymes in immunoassays see Engvall, Enzyme Immunoassay ELISA and EMIT, Methods of Enzymology, 70, 419-439 (1980).

The antibody can be attached to a surface. Examples of useful surfaces on which the antibody can be attached for the purposes of detecting the desired antigen include nitrocellulose, PVDF, polystyrene, and nylon. The surface or support may also be a porous support (see, e.g., U.S. Pat. No. 7,939,342). The assays can be carried out in various assay device formats including those described in U.S. Pat. Nos. 4,906,439; 5,051,237 and 5,147,609 to PB Diagnostic Systems, Inc.

Reference Values

In various embodiments of the assays described herein, the reference value is based on the levels of ApoB100 specific autoantibodies. In one embodiment, the reference value is the mean or median level of autoantibodies against ApoB100 in a population of subjects that do not have SLE. In another embodiment, the reference value is the mean or median level of autoantibodies against ApoB100 in a sample obtained from the subject at a different time point (for example, prior to starting treatment). In a further embodiment, the reference value is the mean or median level of autoantibodies against ApoB100 in a population of subjects that have SLE and have undergone or are undergoing treatment for SLE. In an additional embodiment, the reference value is the mean or median level of autoantibodies against ApoB100 in a population of subjects that have SLE and have undergone or are undergoing treatment for SLE and have not undergone or are not undergoing treatment for cardiovascular diseases. In an additional embodiment, the reference value is the mean or median level of autoantibodies against ApoB100 in a population of subjects that have SLE and have undergone or are undergoing treatment for SLE and have undergone or are undergoing treatment for cardiovascular diseases.

In various embodiments, the levels of ApoB100 specific autoantibodies in the subject compared to the reference values is decreased by at least or about 10%, 20%, 30%, 40%, 50%, 60%, 70%, 80%, 90% or 100%. In various embodiments, the levels of ApoB100 specific autoantibodies in the subject compared to the reference values is decreased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold or 100-fold Peptides of ApoB100

Specific immunogenic epitopes of ApoB100 were characterized and a peptide library including 302 peptides, each about 20 amino acid residues in length, covering the complete 4563 amino acid sequence of human ApoB100 was produced. The peptides were produced with a 5 amino acid overlap to cover all sequences at break points. Peptides were numbered 1-302 starting at the N-terminal of ApoB100 as indicated in Table 1 below.

TABLE 1

| Peptide | Sequence | Apolipoprotein B | SEQ ID NO |
|---|---|---|---|
| P1: | EEEML ENVSL VCPKD ATRFK | aa 1-20 | SEQ ID NO: 1 |
| P2: | ATRFK HLRKY TYNYE AESSS | aa 16-35 | SEQ ID NO: 2 |
| P3: | AESSS GVPGT ADSRS ATRIN | aa 31-50 | SEQ ID NO: 3 |
| P4: | ATRIN CKVEL EVPQL CSFIL | aa 46-65 | SEQ ID NO: 4 |
| P5: | CSFIL KTSQC TLKEV YGFNP | aa 61-80 | SEQ ID NO: 5 |
| P6: | YGFNP EGKAL LKKTK NSEEF | aa 76-95 | SEQ ID NO: 6 |
| P7: | NSEEF AAAMS RYELK LAIPE | aa 91-110 | SEQ ID NO: 7 |
| P8: | LAIPE GKQVF LYPEK DEPTY | aa 106-125 | SEQ ID NO: 8 |
| P9: | DEPTY ILNIK RGIIS ALLVP | aa 121-140 | SEQ ID NO: 9 |
| P10: | ALLVP PETEE AKQVL FLDTV | aa 136-155 | SEQ ID NO: 10 |
| P11: | FLDTV YGNCS THFTV KTRKG | aa 151-170 | SEQ ID NO: 11 |
| P12: | KTRKG NVATE ISTER DLGQC | aa 166-185 | SEQ ID NO: 12 |
| P13: | DLGQC DRFKP IRTGI SPLAL | aa 181-200 | SEQ ID NO: 13 |
| P14: | SPLAL IKGMT RPLST LISSS | aa 196-215 | SEQ ID NO: 14 |
| P15: | LISSS QSCQY TLDAK RKHVA | aa 211-230 | SEQ ID NO: 15 |
| P16: | RKHVA EAICK EQHLF LPFSY | aa 226-245 | SEQ ID NO: 16 |
| P17: | LPFSY NNKYG MVAQV TQTLK | aa 241-260 | SEQ ID NO: 17 |
| P18: | TQTLK LEDTP KINSR FFGEG | aa 256-275 | SEQ ID NO: 18 |
| P19: | FFGEG TKKMG LAFES TKSTS | aa 271-290 | SEQ ID NO: 19 |
| P20: | TKSTS PPKQA EAVLK TLQEL | aa 286-305 | SEQ ID NO: 20 |
| P21: | TLQEL KKLTI SEQNI QRANL | aa 301-320 | SEQ ID NO: 21 |
| P22: | QRANL FNKLV TELRG LSDEA | aa 316-335 | SEQ ID NO: 22 |
| P23: | LSDEA VTSLL PQLIE VSSPI | aa 331-350 | SEQ ID NO: 23 |
| P24: | VSSPI TLQAL VQCGQ PQCST | aa 346-365 | SEQ ID NO: 24 |
| P25: | PQCST HILQW LKRVH ANPLL | aa 361-380 | SEQ ID NO: 25 |
| P26: | ANPLL IDVVT YLVAL IPEPS | aa 376-395 | SEQ ID NO: 26 |
| P27: | IPEPS AQQLR EIFNM ARDQR | aa 391-410 | SEQ ID NO: 27 |
| P28: | ARDQR SRATL YALS AVNNY | aa 406-425 | SEQ ID NO: 28 |
| P29: | AVNNY HKTNP TGTQE LLDIA | aa 421-440 | SEQ ID NO: 29 |
| P30: | LLDIA NYLME QIQDD CTGDE | aa 436-455 | SEQ ID NO: 30 |
| P31: | CTGDE DYTYL ILRVI GNMGQ | aa 451-470 | SEQ ID NO: 31 |
| P32: | GNMGQ TMEQL TPELK SSILK | aa 466-485 | SEQ ID NO: 32 |
| P33: | SSILK CVQST KPSLM IQKAA | aa 481-500 | SEQ ID NO: 33 |
| P34: | IQKAA IQALR KMEPK DKDQE | aa 496-515 | SEQ ID NO: 34 |
| P35: | DKDQE VLLQT FLDDA SPGDK | aa 511-530 | SEQ ID NO: 35 |
| P36: | SPGDK RLAAY LMLMRSPSQA | aa 526-545 | SEQ ID NO: 36 |
| P37: | SPSQA DINKIVQILP WEQNE | aa 541-560 | SEQ ID NO: 37 |
| P38: | WEQNE QVKNF VASHI ANILN | aa 556-575 | SEQ ID NO: 38 |
| P39: | ANILN SEELD IQDLK KLVKE | aa 571-590 | SEQ ID NO: 39 |

TABLE 1-continued

| Peptide | Sequence | Apolipoprotein B | SEQ ID NO |
|---|---|---|---|
| P40: | KLVKE ALKES QLPTV MDFRK | aa 586-605 | SEQ ID NO: 40 |
| P41: | MDFRK FSRNY QLYKS VSLPS | aa 601-620 | SEQ ID NO: 41 |
| P42: | VSLPS LDPAS AKIEG NLIFD | aa 616-635 | SEQ ID NO: 42 |
| P43: | NLIFD PNNYL PKESM LKTTL | aa 631-650 | SEQ ID NO: 43 |
| P44: | LKTTL TAFGF ASADL IEIGL | aa 646-665 | SEQ ID NO: 44 |
| P45: | IEIGL EGKGF EPTLE ALFGK | aa 661-680 | SEQ ID NO: 45 |
| P46: | ALFGK QGFFP DSVNK ALYWV | aa 676-695 | SEQ ID NO: 46 |
| P47: | ALYWV NGQVP DGVSK VLVDH | aa 691-710 | SEQ ID NO: 47 |
| P48: | VLVDH FGYTK DDKHE QDMVN | aa 706-725 | SEQ ID NO: 48 |
| P49: | QDMVN GIMLS VEKLI KDLKS | aa 721-740 | SEQ ID NO: 49 |
| P50: | KDLKS KEVPE ARAYL RILGE | aa 736-755 | SEQ ID NO: 50 |
| P51: | RILGE ELGFA SLHDL QLLGK | aa 751-770 | SEQ ID NO: 51 |
| P52: | QLLGK LLLMG ARTLQ GIPQM | aa 766-785 | SEQ ID NO: 52 |
| P53: | GIPQM IGEVI RKGSK NDFFL | aa 781-800 | SEQ ID NO: 53 |
| P54: | NDFFL HYIFM ENAFE LPTGA | aa 796-815 | SEQ ID NO: 54 |
| P55: | LPTGA GLQLQ ISSSG VIAPG | aa 811-830 | SEQ ID NO: 55 |
| P56: | VIAPG AKAGV KLEVA NMQAE | aa 826-845 | SEQ ID NO: 56 |
| P57: | NMQAE LVAKP SVSVE FVTNM | aa 841-860 | SEQ ID NO: 57 |
| P58: | FVTNM GIIIP DFARS GVQMN | aa 856-875 | SEQ ID NO: 58 |
| P59: | GVQMN TNFFH ESGLE AHVAL | aa 871-890 | SEQ ID NO: 59 |
| P60: | AHVAL KAGKL KFIIP SPKRP | aa 886-905 | SEQ ID NO: 60 |
| P61: | SPKRP VKLLS GGNTL HLVST | aa 901-920 | SEQ ID NO: 61 |
| P62: | HLVST TKTEV IPPLI ENRQS | aa 916-935 | SEQ ID NO: 62 |
| P63: | ENRQS WSVCKQVFPG LNYCT | aa 931-950 | SEQ ID NO: 63 |
| P64: | LNYCT SGAYS NASST DSASY | aa 946-965 | SEQ ID NO: 64 |
| P65: | DSASY YPLTG DTRLE LELRP | aa 961-980 | SEQ ID NO: 65 |
| P66: | LELRP TGEIE QYSVS ATYEL | aa 976-995 | SEQ ID NO: 66 |
| P67: | ATYEL QREDR ALVDT LKFVT | aa 991-1010 | SEQ ID NO: 67 |
| P68: | LKFVT QAEGA KQTEA TMTFK | aa 1006-1025 | SEQ ID NO: 68 |
| P69: | TMTFK YNRQS MTLSS EVQIP | aa 1021-1040 | SEQ ID NO: 69 |
| P70: | EVQIP DFDVD LGTIL RVNDE | aa 1036-1055 | SEQ ID NO: 70 |
| P71: | RVNDE STEGK TSYRL TLDIQ | aa 1051-1070 | SEQ ID NO: 71 |
| P72: | TLDIQ NKKIT EVALM GHLSC | aa 1066-1085 | SEQ ID NO: 72 |
| P73: | GHLSC DTKEE RKIKG VISIP | aa 1081-1100 | SEQ ID NO: 73 |
| P74: | VISIP RLQAE ARSEI LAHWS | aa 1096-1115 | SEQ ID NO: 74 |
| P75: | LAHWS PAKLL LQMDS SATAY | aa 1111-1130 | SEQ ID NO: 75 |
| P76: | SATAY GSTVS KRVAW HYDEE | aa 1126-1145 | SEQ ID NO: 76 |
| P77: | HYDEE KIEFE WNTGT NVDTK | aa 1141-1160 | SEQ ID NO: 77 |
| P78: | NVDTK KMTSN FPVDL SDYPK | aa 1156-1175 | SEQ ID NO: 78 |

TABLE 1-continued

| Peptide | Sequence | Apolipoprotein B | SEQ ID NO |
|---|---|---|---|
| P79: | SDYPK SLHMY ANRLL DHRVP | aa 1171-1190 | SEQ ID NO: 79 |
| P80: | DHRVP ETDMT FRHVG SKLIV | aa 1186-1205 | SEQ ID NO: 80 |
| P81: | SKLIV AMSSW LQKAS GSLPY | aa 1201-1220 | SEQ ID NO: 81 |
| P82: | GSLPY TQTLQ DHLNS LKEFN | aa 1216-1235 | SEQ ID NO: 82 |
| P83: | LKEFN LQNMG LPDFH IPENL | aa 1231-1250 | SEQ ID NO: 83 |
| P84: | IPENL FLKSD GRVKY TLNKN | aa 1246-1260 | SEQ ID NO: 84 |
| P85: | TLNKN SLKIE IPLPF GGKSS | aa 1261-1280 | SEQ ID NO: 85 |
| P86: | GGKSS RDLKM LETVR TPALH | aa 1276-1295 | SEQ ID NO: 86 |
| P87: | TPALH FKSVG FHLPS REFQV | aa 1291-1310 | SEQ ID NO: 87 |
| P88: | REFQV PTFTI PKLYQ LQVPL | aa 1306-1325 | SEQ ID NO: 88 |
| P89: | LQVPL LGVLD LSTNV YSNLY | aa 1321-1340 | SEQ ID NO: 89 |
| P90: | YSNLY NWSAS YSGGN TSTDH | aa 1336-1355 | SEQ ID NO: 90 |
| P91: | TSTDH FSLRA RYHMK ADSVV | aa 1351-1370 | SEQ ID NO: 91 |
| P92: | ADSVV DLLSY NVQGS GETTY | aa 1366-1385 | SEQ ID NO: 92 |
| P93: | GETTY DHKNT FTLSC DGSLR | aa 1381-1400 | SEQ ID NO: 93 |
| P94: | DGSLR HKFLD SNIKF SHVEK | aa 1396-1415 | SEQ ID NO: 94 |
| P95: | SHVEK LGNNP VSKGL LIFDA | aa 1411-1430 | SEQ ID NO: 95 |
| P96: | LIFDA SSSWG PQMSA SVHLD | aa 1426-1445 | SEQ ID NO: 96 |
| P97: | SVHLD SKKKQ HLFVK EVKID | aa 1441-1460 | SEQ ID NO: 97 |
| P98: | EVKID GQFRV SSFYA KGTYG | aa 1456-1475 | SEQ ID NO: 98 |
| P99: | KGTYG LSCQR DPNTG RLNGE | aa 1471-1490 | SEQ ID NO: 99 |
| P100: | RLNGE SNLRF NSSYL QGTNQ | aa 1486-1505 | SEQ ID NO: 100 |
| P101: | QGTNQ ITGRY EDGTL SLTST | aa 1501-1520 | SEQ ID NO: 101 |
| P102: | SLTST SDLQS GIIKN TASLK | aa 1516-1535 | SEQ ID NO: 102 |
| P103: | TASLK YENYE LTLKS DTNGK | aa 1531-1550 | SEQ ID NO: 103 |
| P104: | DTNGK YKNFA TSNKM DMTFS | aa 1546-1565 | SEQ ID NO: 104 |
| P105: | DMTFS KQNAL LRSEY QADYE | aa 1561-1580 | SEQ ID NO: 105 |
| P106: | QADYE SLRFF SLLSG SLNSH | aa 1576-1595 | SEQ ID NO: 106 |
| P107: | SLNSH GLELN ADILG TDKIN | aa 1591-1610 | SEQ ID NO: 107 |
| P108: | TDKIN SGAHK ATLRI GQDGI | aa 1606-1625 | SEQ ID NO: 108 |
| P109: | GQDGI STSAT TNLKCSLLVL | aa 1621-1640 | SEQ ID NO: 109 |
| P110: | SLLVL ENELN AELGL SGASM | aa 1636-1655 | SEQ ID NO: 110 |
| P111: | SGASM KLTTN GRFRE HNAKF | aa 1651-1670 | SEQ ID NO: 111 |
| P112: | HNAKF SLDGK AALTE LSLGS | aa 1666-1685 | SEQ ID NO: 112 |
| P113: | LSLGS AYQAM ILGVD SKNIF | aa 1681-1700 | SEQ ID NO: 113 |
| P114: | SKNIF NFKVS QEGLK LSNDM | aa 1696-1715 | SEQ ID NO: 114 |
| P115: | LSNDM MGSYA EMKFD HTNSL | aa 1711-1730 | SEQ ID NO: 115 |
| P116: | HTNSL NIAGL SLDFS SKLDN | aa 1726-1745 | SEQ ID NO: 116 |
| P117: | SKLDN IYSSD KFYKQ TVNLQ | aa 1741-1760 | SEQ ID NO: 117 |

TABLE 1-continued

| Peptide | Sequence | Apolipoprotein B | SEQ ID NO |
|---|---|---|---|
| P118: | TVNLQ LQPYS LVTTL NSDLK | aa 1756-1775 | SEQ ID NO: 118 |
| P119: | NSDLK YNALD LTNNG KLRLE | aa 1771-1790 | SEQ ID NO: 119 |
| P120: | KLRLE PLKLH VAGNL KGAYQ | aa 1786-1805 | SEQ ID NO: 120 |
| P121: | KGAYQ NNEIK HIYAI SSAAL | aa 1801-1820 | SEQ ID NO: 121 |
| P122: | SSAAL SASYK ADTVA KVQGV | aa 1816-1835 | SEQ ID NO: 122 |
| P123: | KVQGV EFSHR LNTDI AGLAS | aa 1831-1850 | SEQ ID NO: 123 |
| P124: | AGLAS AIDMS TNYNS DSLHF | aa 1846-1865 | SEQ ID NO: 124 |
| P125: | DSLHF SNVFR SVMAP FTMTI | aa 1861-1880 | SEQ ID NO: 125 |
| P126: | FTMTI DAHTN GNGKL ALWGE | aa 1876-1895 | SEQ ID NO: 126 |
| P127: | ALWGE HTGQL YSKFL LKAEP | aa 1891-1910 | SEQ ID NO: 127 |
| P128: | LKAEP LAFTF SHDYK GSTSH | aa 1906-1925 | SEQ ID NO: 128 |
| P129: | GSTSH HLVSR KSISA ALEHK | aa 1921-1940 | SEQ ID NO: 129 |
| P130: | ALEHK VSALL TPAEQ TGTWK | aa 1936-1955 | SEQ ID NO: 130 |
| P131: | TGTWK LKTQF NNNEY SQDLD | aa 1951-1970 | SEQ ID NO: 131 |
| P132: | SQDLD AYNTK DKIGV ELTGR | aa 1966-1985 | SEQ ID NO: 132 |
| P133: | ELTGR TLADL TLLDS PIKVP | aa 1981-2000 | SEQ ID NO: 133 |
| P134: | PIKVP LLLSE PINII DALEM | aa 1996-2015 | SEQ ID NO: 134 |
| P135: | DALEM RDAVE KPQEF TIVAF | aa 2011-2030 | SEQ ID NO: 135 |
| P136: | TIVAF VKYDK NQDVH SINLP | aa 2026-2045 | SEQ ID NO: 136 |
| P137: | SINLP FFETL QEYFE RNRQT | aa 2041-2060 | SEQ ID NO: 137 |
| P138: | RNRQT IIVVV ENVQR NLKHI | aa 2056-2075 | SEQ ID NO: 138 |
| P139: | NLKHI NIDQF VRKYR AALGK | aa 2071-2090 | SEQ ID NO: 139 |
| P140: | AALGK LPQQA NDYLN SFNWE | aa 2086-2105 | SEQ ID NO: 140 |
| P141: | SFNWE RQVSH AKEKL TALTK | aa 2101-2120 | SEQ ID NO: 141 |
| P142: | TALTK KYRIT ENDIQ IALDD | aa 2116-2135 | SEQ ID NO: 142 |
| P143: | IALDD AKINF NEKLS QLQTY | aa 2131-2150 | SEQ ID NO: 143 |
| P144: | QLQTY MIQFD QYIKD SYDLH | aa 2146-2165 | SEQ ID NO: 144 |
| P145: | SYDLH DLKIA IANII DEIIE | aa 2161-2180 | SEQ ID NO: 145 |
| P146: | DEIIE KLKSL DEHYH IRVNL | aa 2176-2195 | SEQ ID NO: 146 |
| P147: | IRVNL VKTIH DLHLF IENID | aa 2191-2210 | SEQ ID NO: 147 |
| P148: | IENID FNKSG SSTAS WIQNV | aa 2206-2225 | SEQ ID NO: 148 |
| P149: | WIQNV DTKYQ IRIQI QEKLQ | aa 2221-2240 | SEQ ID NO: 149 |
| P150: | QEKLQ QLKRH IQNID IQHLA | aa 2236-2255 | SEQ ID NO: 150 |
| P151: | IQHLA GKLKQ HIEAI DVRVL | aa 2251-2270 | SEQ ID NO: 151 |
| P152: | DVRVL LDQLG TTISF ERIND | aa 2266-2285 | SEQ ID NO: 152 |
| P153: | ERIND VLEHV KHFVI NLIGD | aa 2281-2300 | SEQ ID NO: 153 |
| P154: | NLIGD FEVAE KINAF RAKVH | aa 2296-2315 | SEQ ID NO: 154 |
| P155: | RAKVH ELIER YEVDQ QIQVL | aa 2311-2330 | SEQ ID NO: 155 |
| P156: | QIQVL MDKLV ELTHQ YKLKE | aa 2326-2345 | SEQ ID NO: 156 |

TABLE 1-continued

| Peptide | Sequence | Apolipoprotein B | SEQ ID NO |
|---|---|---|---|
| P157: | YKLKE TIQKL SNVLQ QVKIK | aa 2341-2360 | SEQ ID NO: 157 |
| P158: | QVKIK DYFEK LVGFI DDAVK | aa 2356-2375 | SEQ ID NO: 158 |
| P159: | DDAVK KLNEL SFKTF IEDVN | aa 2371-2390 | SEQ ID NO: 159 |
| P160: | IEDVN KFLDM LIKKL KSFDY | aa 2386-2405 | SEQ ID NO: 160 |
| P161: | KSFDY HQFVD ETNDK IREVT | aa 2401-2420 | SEQ ID NO: 161 |
| P162: | IREVT QRLNG EIQAL ELPQK | aa 2416-2435 | SEQ ID NO: 162 |
| P163: | ELPQK AEALK LFLEE TKATV | aa 2431-2450 | SEQ ID NO: 163 |
| P164: | TKATV AVYLE SLQDT KITLI | aa 2446-2465 | SEQ ID NO: 164 |
| P165: | KITLI INWLQ EALSS ASLAH | aa 2461-2480 | SEQ ID NO: 165 |
| P166: | ASLAH MKAKF RETLE DTRDR | aa 2476-2495 | SEQ ID NO: 166 |
| P167: | DTRDR MYQMD IQQEL QRYLS | aa 2491-2510 | SEQ ID NO: 167 |
| P168: | QRYLS LVGQV YSTLV TYISD | aa 2506-2515 | SEQ ID NO: 168 |
| P169: | TYISD WWTLA AKNLT DFAEQ | aa 2521-2540 | SEQ ID NO: 169 |
| P170: | DFAEQ YSIQD WAKRM KALVE | aa 2536-2555 | SEQ ID NO: 170 |
| P171: | KALVE QGFTV PEIKT ILGTM | aa 2551-2570 | SEQ ID NO: 171 |
| P172: | ILGTM PAFEV SLQAL QKATF | aa 2566-2585 | SEQ ID NO: 172 |
| P173: | QKATF QTPDF IVPLT DLRIP | aa 2581-2600 | SEQ ID NO: 173 |
| P174: | DLRIP SVQIN FKDLK NIKIP | aa 2596-2615 | SEQ ID NO: 174 |
| P175: | NIKIP SRFST PEFTI LNTFH | aa 2611-2630 | SEQ ID NO: 175 |
| P176: | LNTFH IPSFT IDFVE MKVKI | aa 2626-2645 | SEQ ID NO: 176 |
| P177: | MKVKI IRTID QMQNS ELQWP | aa 2641-2660 | SEQ ID NO: 177 |
| P178: | ELQWP VPDIY LRDLK VEDIP | aa 2656-2675 | SEQ ID NO: 178 |
| P179: | VEDIP LARIT LPDFR LPEIA | aa 2671-2690 | SEQ ID NO: 179 |
| P180: | LPEIA IPEFI IPTLN LNDFQ | aa 2686-2705 | SEQ ID NO: 180 |
| P181: | LNDFQ VPDLH IPEFQ LPHIS | aa 2701-2720 | SEQ ID NO: 181 |
| P182: | LPHIS HTIEV PTFGK LYSIL | aa 2716-2735 | SEQ ID NO: 182 |
| P183: | LYSIL KIQSP LFTLD ANADI | aa 2731-2750 | SEQ ID NO: 183 |
| P184: | ANADI GNGTT SANEA GIAAS | aa 2746-2765 | SEQ ID NO: 184 |
| P185: | GIAAS ITAKG ESKLE VLNFD | aa 2761-2780 | SEQ ID NO: 185 |
| P186: | VLNFD FQANA QLSNP KINPL | aa 2776-2795 | SEQ ID NO: 186 |
| P187: | KINPL ALKES VKFSS KYLRT | aa 2791-2810 | SEQ ID NO: 187 |
| P188: | KYLRT EHGSE MLFFG NAIEG | aa 2806-2825 | SEQ ID NO: 188 |
| P189: | NAIEG KSNTV ASLHT EKNTL | aa 2821-2840 | SEQ ID NO: 189 |
| P190: | EKNTL ELSNG VIVKI NNQLT | aa 2836-2855 | SEQ ID NO: 190 |
| P191: | NNQLT LDSNT KYFHK LNIPK | aa 2851-2870 | SEQ ID NO: 191 |
| P192: | LNIPK LDFSS QADLR NEIKT | aa 2866-2885 | SEQ ID NO: 192 |
| P193: | NEIKT LLKAG HIAWT SSGKG | aa 2881-2900 | SEQ ID NO: 193 |
| P194: | SSGKG SWKWA CPRFS DEGTH | aa 2896-2915 | SEQ ID NO: 194 |
| P195: | DEGTH ESQIS FTIEG PLTSF | aa 2911-2930 | SEQ ID NO: 195 |

TABLE 1-continued

| Peptide | Sequence | Apolipoprotein B | SEQ ID NO |
|---|---|---|---|
| P196: | PLTSF GLSNK INSKH LRVNQ | aa 2926-2945 | SEQ ID NO: 196 |
| P197: | LRVNQ NLVYE SGSLN FSKLE | aa 2941-2960 | SEQ ID NO: 197 |
| P198: | FSKLE IQSQV DSQHV GHSVL | aa 2956-2975 | SEQ ID NO: 198 |
| P199: | GHSVL TAKGM ALFGE GKAEF | aa 2971-2990 | SEQ ID NO: 199 |
| P200: | GKAEF TGRHD AHLNG KVIGT | aa 2986-3005 | SEQ ID NO: 200 |
| P201: | KVIGT LKNSL FFSAQ PFEIT | aa 3001-3020 | SEQ ID NO: 201 |
| P202: | PFEIT ASTNN EGNLK VRFPL | aa 3016-3035 | SEQ ID NO: 202 |
| P203: | VRFPL RLTGK IDFLN NYALF | aa 3031-3050 | SEQ ID NO: 203 |
| P204: | NYALF LSPSA QQASW QVSAR | aa 3046-3065 | SEQ ID NO: 204 |
| P205: | QVSAR FNQYK YNQNF SAGNN | aa 3061-3080 | SEQ ID NO: 205 |
| P206: | SAGNN ENIME AHVGI NGEAN | aa 3076-3095 | SEQ ID NO: 206 |
| P207: | NGEAN LDFLN IPLTI PEMRL | aa 3091-3110 | SEQ ID NO: 207 |
| P208: | PEMRL PYTII TTPPL KDFSL | aa 3106-3125 | SEQ ID NO: 208 |
| P209: | KDFSL WEKTG LKEFL KTTKQ | aa 3121-3140 | SEQ ID NO: 209 |
| P210: | KTTKQ SFDLS VKAQY KKNKH | aa 3136-3155 | SEQ ID NO: 210 |
| P211: | KKNKH RHSIT NPLAV LCEFI | aa 3151-3170 | SEQ ID NO: 211 |
| P212: | LCEFI SQSIK SFDRH FEKNR | aa 3166-3185 | SEQ ID NO: 212 |
| P213: | FEKNR NNALD FVTKS YNETK | aa 3181-3200 | SEQ ID NO: 213 |
| P214: | YNETK IKFDK YKAEK SHDEL | aa 3196-3215 | SEQ ID NO: 214 |
| P215: | SHDEL PRTFQ IPGYT VPVVN | aa 3211-3230 | SEQ ID NO: 215 |
| P216: | VPVVN VEVSP FTIEM SAFGY | aa 3226-3245 | SEQ ID NO: 216 |
| P217: | SAFGY VFPKA VSMPS FSILG | aa 3241-3260 | SEQ ID NO: 217 |
| P218: | FSILG SDVRV PSYTL ILPSL | aa 3256-3275 | SEQ ID NO: 218 |
| P219: | ILPSL ELPVL HVPRN LKLSL | aa 3271-3290 | SEQ ID NO: 219 |
| P220: | LKLSL PHFKE LCTIS HIFIP | aa 3286-3305 | SEQ ID NO: 220 |
| P221: | HIFIP AMGNI TYDFS FKSSV | aa 3301-3320 | SEQ ID NO: 221 |
| P222: | FKSSV ITLNT NAELF NQSDI | aa 3316-3335 | SEQ ID NO: 222 |
| P223: | NQSDI VAHLL SSSSS VIDAL | aa 3331-3350 | SEQ ID NO: 223 |
| P224: | VIDAL QYKLE GTTRL TRKRG | aa 3346-3365 | SEQ ID NO: 224 |
| P225: | TRKRG LKLAT ALSLS NKFVE | aa 3361-3380 | SEQ ID NO: 225 |
| P226: | NKFVE GSHNS TVSLT TKNME | aa 3376-3395 | SEQ ID NO: 226 |
| P227: | TKNME VSVAK TTKAE IPILR | aa 3391-3410 | SEQ ID NO: 227 |
| P228: | IPILR MNFKQ ELNGN TKSKP | aa 3406-3425 | SEQ ID NO: 228 |
| P229: | TKSKP TVSSS MEFKY DFNSS | aa 3421-3440 | SEQ ID NO: 229 |
| P230: | DFNSS MLYST AKGAV DHKLS | aa 3436-3455 | SEQ ID NO: 230 |
| P231: | DHKLS LESLT SYFSI ESSTK | aa 3451-3470 | SEQ ID NO: 231 |
| P232: | ESSTK GDVKG SVLSR EYSGT | aa 3466-3485 | SEQ ID NO: 232 |
| P233: | EYSGT IASEA NTYLN SKSTR | aa 3481-3500 | SEQ ID NO: 233 |
| P234: | SKSTR SSVKL QGTSK IDDIW | aa 3496-3515 | SEQ ID NO: 234 |

TABLE 1-continued

| Peptide | Sequence | Apolipoprotein B | SEQ ID NO |
| --- | --- | --- | --- |
| P235: | IDDIW NLEVK ENFAG EATLQ | aa 3511-3530 | SEQ ID NO: 235 |
| P236: | EATLQ RIYSL WEHST KNHLQ | aa 3526-3545 | SEQ ID NO: 236 |
| P237: | KNHLQ LEGLF FTNGE HTSKA | aa 3541-3560 | SEQ ID NO: 237 |
| P238: | HTSKA TLELS PWQMS ALVQV | aa 3556-3575 | SEQ ID NO: 238 |
| P239: | ALVQV HASQP SSFHD FPDLG | aa 3571-3590 | SEQ ID NO: 239 |
| P240: | FPDLG QEVAL NANTK NQKIR | aa 3586-3605 | SEQ ID NO: 240 |
| P241: | NQKIR WKNEV RIHSG SFQSQ | aa 3601-3620 | SEQ ID NO: 241 |
| P242: | SFQSQ VELSN DQEKA HLDIA | aa 3616-3635 | SEQ ID NO: 242 |
| P243: | HLDIA GSLEG HLRFL KNIIL | aa 3631-3650 | SEQ ID NO: 243 |
| P244: | KNIIL PVYDK SLWDF LKLDV | aa 3646-3665 | SEQ ID NO: 244 |
| P245: | LKLDV TTSIG RRQHL RVSTA | aa 3661-3680 | SEQ ID NO: 245 |
| P246: | RVSTA FVYTK NPNGY SFSIP | aa 3676-3695 | SEQ ID NO: 246 |
| P247: | SFSIP VKVLA DKFIT PGLKL | aa 3691-3710 | SEQ ID NO: 247 |
| P248: | PGLKL NDLNS VLVMP TFHVP | aa 3706-3725 | SEQ ID NO: 248 |
| P249: | TFHVP FTDLQ VPSCK LDFRE | aa 3721-3740 | SEQ ID NO: 249 |
| P250: | LDFRE IQIYK KLRTS SFALN | aa 3736-3755 | SEQ ID NO: 250 |
| P251: | SFALN LPTLP EVKFP EVDVL | aa 3751-3770 | SEQ ID NO: 251 |
| P252: | EVDVL TKYSQ PEDSL IPFFE | aa 3766-3785 | SEQ ID NO: 252 |
| P253: | IPFFEITVPE SQLTV SQFTL | aa 3781-3800 | SEQ ID NO: 253 |
| P254: | SQFTL PKSVS DGIAA LDLNA | aa 3796-3815 | SEQ ID NO: 254 |
| P255: | LDLNA VANKI ADFEL PTIIV | aa 3811-3830 | SEQ ID NO: 255 |
| P256: | PTIIV PEQTI EIPSI KFSVP | aa 3826-3845 | SEQ ID NO: 256 |
| P257: | KFSVP AGIVI PSFQA LTARF | aa 3841-3860 | SEQ ID NO: 257 |
| P258: | LTARF EVDSP VYNAT WSASL | aa 3856-3875 | SEQ ID NO: 258 |
| P259: | WSASL KNKAD YVETV LDSTC | aa 3871-3890 | SEQ ID NO: 259 |
| P260: | LDSTC SSTVQ FLEYE LNVLG | aa 3886-3905 | SEQ ID NO: 260 |
| P261: | LNVLG THKIE DGTLA SKTKG | aa 3901-3920 | SEQ ID NO: 261 |
| P262: | SKTKG TLAHR DFSAE YEEDG | aa 3916-3935 | SEQ ID NO: 262 |
| P263: | YEEDG KFEGL QEWEG KAHLN | aa 3931-3950 | SEQ ID NO: 263 |
| P264: | KAHLN IKSPA FTDLH LRYQK | aa 3946-3965 | SEQ ID NO: 264 |
| P265: | LRYQK DKKGI STSAA SPAVG | aa 3961-3980 | SEQ ID NO: 265 |
| P266: | SPAVG TVGMD MDEDD DFSKW | aa 3976-3995 | SEQ ID NO: 266 |
| P267: | DFSKW NFYYS PQSSP DKKLT | aa 3991-4010 | SEQ ID NO: 267 |
| P268: | DKKLT IFKTE LRVRE SDEET | aa 4006-4025 | SEQ ID NO: 268 |
| P269: | SDEET QIKVN WEEEA ASGLL | aa 4021-4040 | SEQ ID NO: 269 |
| P270: | ASGLL TSLKD NVPKA TGVLY | aa 4036-4055 | SEQ ID NO: 270 |
| P271: | TGVLY DYVNK YHWEH TGLTL | aa 4051-4070 | SEQ ID NO: 271 |
| P272: | TGLTL REVSS KLRRN LQNNA | aa 4066-4085 | SEQ ID NO: 272 |
| P273: | LQNNA EWVYQ GAIRQ IDDID | aa 4081-4100 | SEQ ID NO: 273 |

TABLE 1-continued

| Peptide | Sequence | Apolipoprotein B | SEQ ID NO |
|---|---|---|---|
| P274: | IDDID VRFQK AASGT TGTYQ | aa 4096-4115 | SEQ ID NO: 274 |
| P275: | TGTYQ EWKDK AQNLY QELLT | aa 4111-4130 | SEQ ID NO: 275 |
| P276: | QELLT QEGQA SFQGL KDNVF | aa 4126-4145 | SEQ ID NO: 276 |
| P277: | KDNVF DGLVR VTQKF HMKVK | aa 4141-4160 | SEQ ID NO: 277 |
| P278: | HMKVK HLIDS LIDFL NFPRF | aa 4156-4175 | SEQ ID NO: 278 |
| P279: | NFPRF QFPGK PGIYT REELC | aa 4171-4190 | SEQ ID NO: 279 |
| P280: | REELC TMFIR EVGTV LSQVY | aa 4186-4205 | SEQ ID NO: 280 |
| P281: | LSQVY SKVHN GSEIL FSYFQ | aa 4201-4220 | SEQ ID NO: 281 |
| P282: | FSYFQ DLVIT LPFEL RKHKL | aa 4216-4235 | SEQ ID NO: 282 |
| P283: | RKHKL IDVIS MYREL LKDLS | aa 4231-4250 | SEQ ID NO: 283 |
| P284: | LKDLS KEAQE VFKAI QSLKT | aa 4246-4265 | SEQ ID NO: 284 |
| P285: | QSLKT TEVLR NLQDL LQFIF | aa 4261-4280 | SEQ ID NO: 285 |
| P286: | LQFIF QLIED NIKQL KEMKF | aa 4276-4295 | SEQ ID NO: 286 |
| P287: | KEMKF TYLIN YIQDE INTIF | aa 4291-4310 | SEQ ID NO: 287 |
| P288: | INTIF NDYIP YVFKL LKENL | aa 4306-4325 | SEQ ID NO: 288 |
| P289: | LKENL CLNLH KFNEF IQNEL | aa 4321-4340 | SEQ ID NO: 289 |
| P290: | IQNEL QEASQ ELQQI HQYIM | aa 4336-4355 | SEQ ID NO: 290 |
| P291: | HQYIM ALREE YFDPS IVGWT | aa 4351-4370 | SEQ ID NO: 291 |
| P292: | IVGWT VKYYE LEEKI VSLIK | aa 4366-4385 | SEQ ID NO: 292 |
| P293: | VSLIK NLLVA LKDFH SEYIV | aa 4381-4400 | SEQ ID NO: 293 |
| P294: | SEYIV SASNF TSQLS SQVEQ | aa 4396-4415 | SEQ ID NO: 294 |
| P295: | SQVEQ FLHRN IQEYL SILTD | aa 4411-4430 | SEQ ID NO: 295 |
| P296: | SILTD PDGKG KEKIA ELSAT | aa 4426-4445 | SEQ ID NO: 296 |
| P297: | ELSAT AQEII KSQAI ATKKI | aa 4441-4460 | SEQ ID NO: 297 |
| P298: | TKKII SDYHQ QFRYK LQDFS | aa 4457-4476 | SEQ ID NO: 298 |
| P299: | LQDFS DQLSD YYEKF IAESK | aa 4472-4491 | SEQ ID NO: 299 |
| P300: | IAESK RLIDL SIQNY HTFLI | aa 4487-4506 | SEQ ID NO: 300 |
| P301: | HTFLI YITEL LKKLQ STTVM | aa 4502-4521 | SEQ ID NO: 301 |
| P302: | STTVM NPYMK LAPGE LTIIL | aa 4517-4536 | SEQ ID NO: 302 |

These peptide sequences were prepared and evaluated for immunogenic activity as previously described in Patent Publication WO2002080954, the contents of which is herein incorporated by reference in its entirety.

Antibodies against these peptide sequences were prepared and evaluated for immunogenic activity as previously described in WO 2007/025781 and WO 2009/083225, the contents of which are herein incorporated by reference in their entirety.

Figure 2:
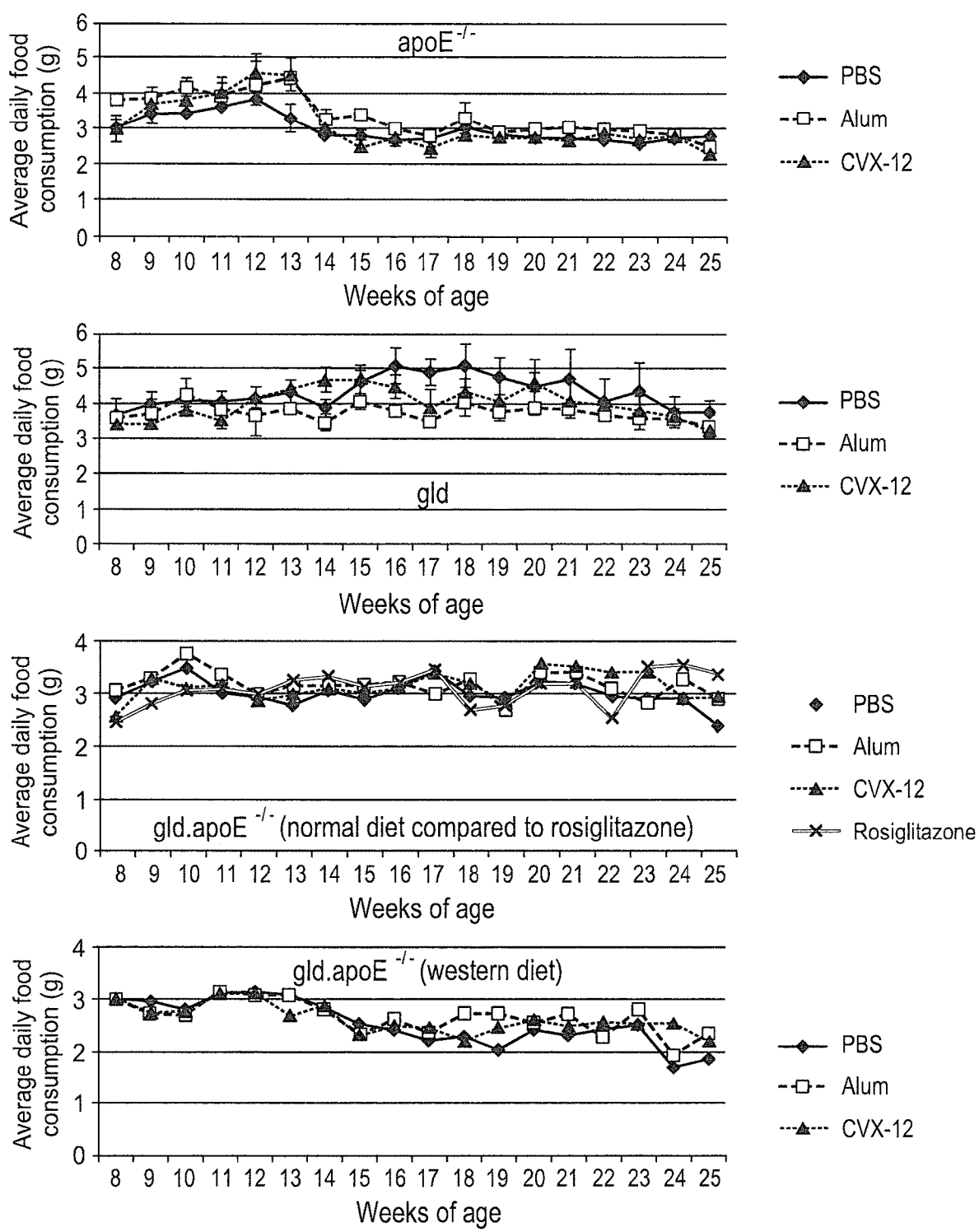
FIG. 2 depicts in accordance with various embodiments of the invention, food consumption measurements for the duration of the study. Values=averages+/−SEM.
Figure 17:
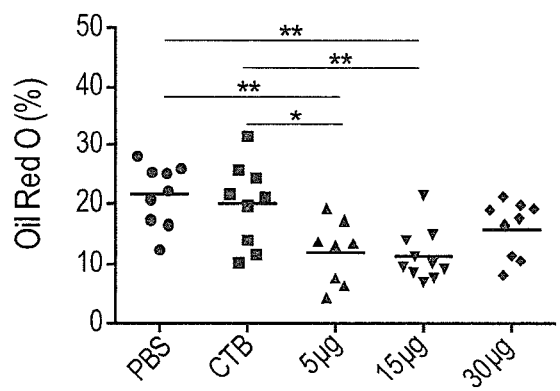
FIG. 17 depicts, in accordance with an embodiment of the invention, atherosclerotic plaque development in the aortic arch of MRL/lpr/Apoe$^{-/-}$ mice. Lipid staining with Oil Red O after weekly repeatedly administered oral immunizations for ten weeks. Treatment groups PBS n=11, CTB 30 μg/ml n=13, P45-CTB 5 μg/ml n=13, P45-CTB 15 μg/ml n=10 and P45-CTB 30 μg/ml n=12. Statistical analysis was performed using One-way ANOVA with Sidak's multiple comparison test, comparing to PBS and CTB where **p<0.01. Each point represents one mouse.
Figure 18A:
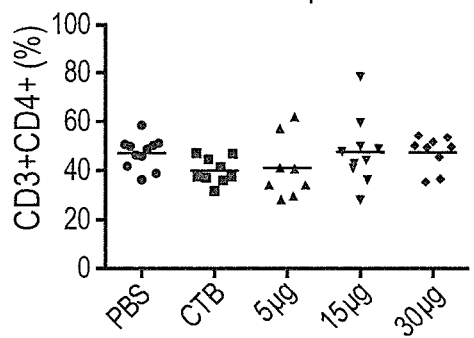
FIG. 18A-FIG. 18I depict, in accordance with an embodiment of the invention, splenocyte phenotype assessment with flow cytometry after treatment of MRL/lpr/Apoe$^{-/-}$ mice with PBS, CTB 30 μg/ml, P45-CTB 5, 15 and 30 μg/ml. Splenocyte percentage of (FIG. 18A) T helper cells (CD3$^+$CD4$^+$), (FIG. 18B) cytolytic T cells (CD3$^+$CD8$^+$), (FIG. 18C) T helper central memory cells (CD4$^+$CD62L$^+$CD44$^{int-hi}$), (FIG. 18D) T helper effector cells (CD4$^+$CD62$^-$CD44$^{hi}$), (FIG. 18E) naïve T helper cells (CD4$^+$CD62L$^+$CD44$^{lo}$), (FIG. 18F) regulatory T cells (CD3$^+$CD4$^+$CD25$^+$FoxP3$^+$), (FIG. 18G) central memory cytolytic T cells (CD8$^+$CD62L$^+$CD44$^{int-hi}$), (FIG. 18H) cytolytic effector T cells (CD8$^+$CD62$^-$CD44$^{hi}$) and (FIG. 18I) naïve cytolytic T cells)(CD8$^+$CD62L$^+$CD44$^{lo}$. Statistical analysis was performed using One-way ANOVA with Sidak's multiple comparison test, comparing to PBS and CTB where *p<0.05, p<0.01 and *p<0.001. Each point represents one mouse.
Figure 18B:
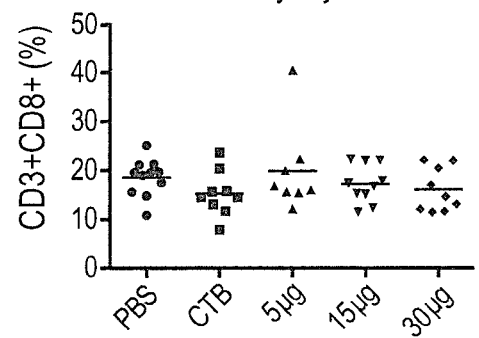
Figure 18C:
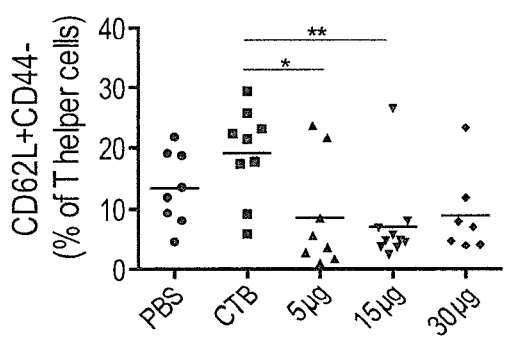
Figure 18D:
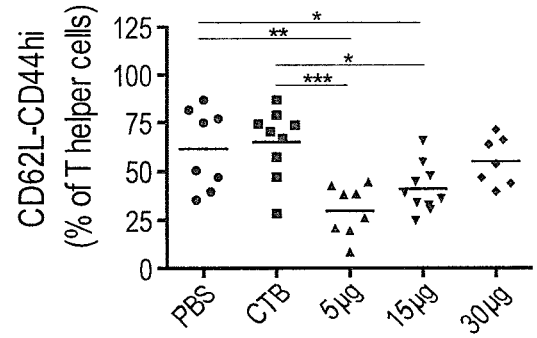
Figure 18E:
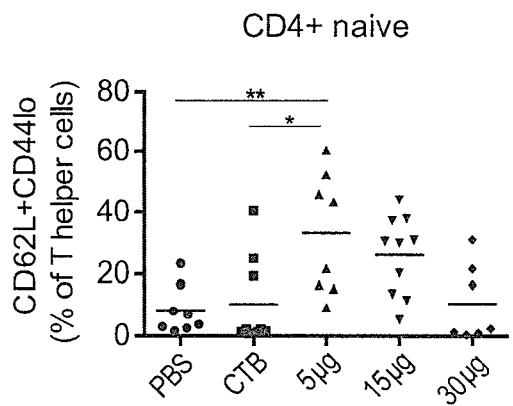
Figure 18F:
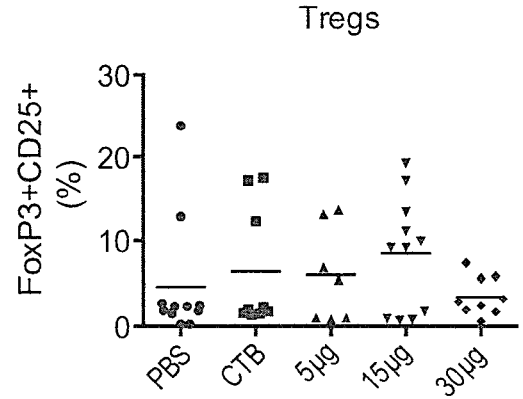
Figure 18G:
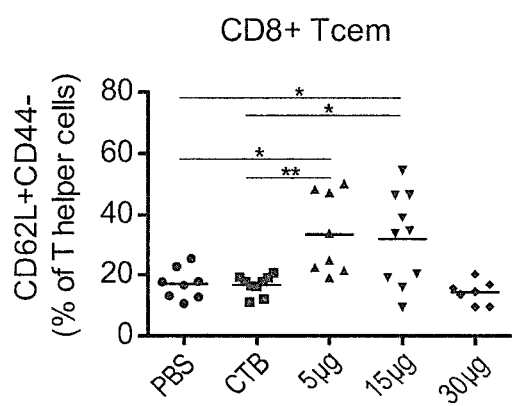
Figure 18H:
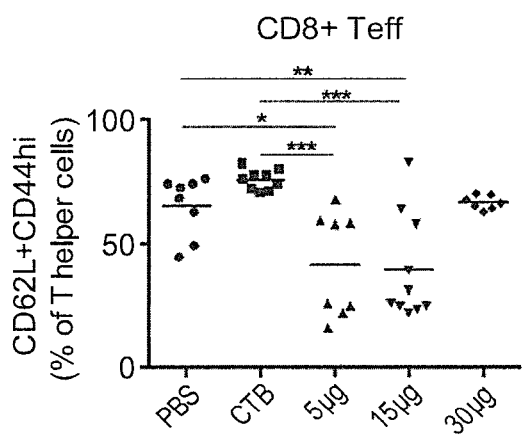
Figure 18I:
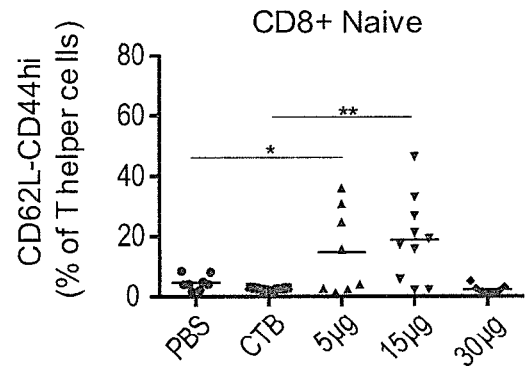
Figure 19G:
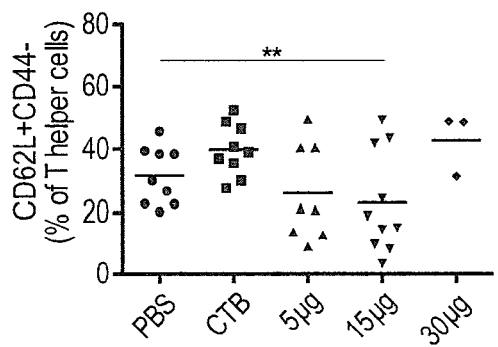
Figure 19H:
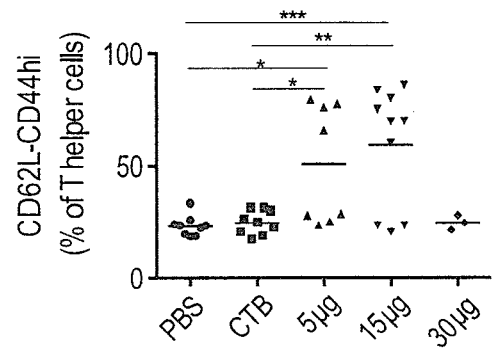
Figure 19I:
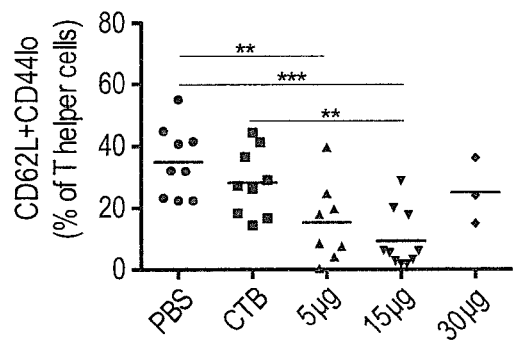
Figure 20:
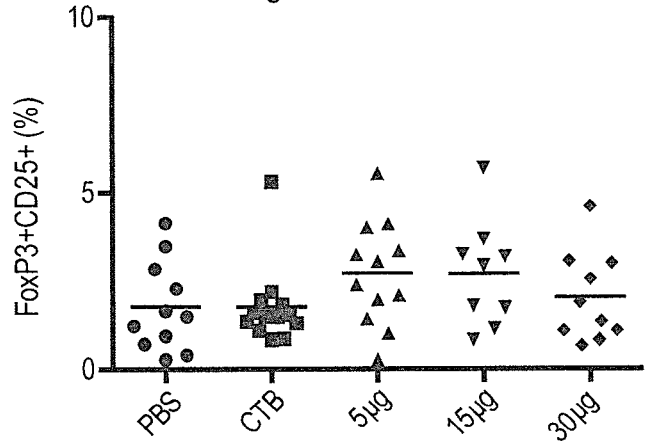
FIG. 20 depicts, in accordance with an embodiment of the invention, flow cytometry analysis of blood from MRL/lpr/Apoe$^{-/-}$ mice at treatment day 42 of 56. Blood regulatory T cell (CD3+CD4+CD25+FoxP3+) percentages during treatment. Treatment groups PBS n=11, CTB 30 μg/ml n=13, P45-CTB 5 μg/ml n=12, n=9 and P45-CTB 30 μg/ml n=11. Due to technical difficulties one mouse in P45-CTB 5 μg/ml, one mouse in P45-CTB 15 μg/ml and two mice in P45-CTB 30 μg/ml groups were excluded.

Specifically, FIG. 2 of WO 2009/083225 describes the amino acid sequence of the 2D03 heavy chain and the 2D03 light chain, underlining the complementarity determining regions (CDRs), which is shown in FIG. 21B and FIG. 21C of the present application. FIG. 21B and FIG. 21C of the present application are also seen in FIG. 17 of the present application's priority application, U.S. provisional application No. 62/343,601, filed May 31, 2016. Antibody 2D03 refers to orticumab.

Specifically, WO 2007/025781 describes in various locations such as pages 29, 30 and 16 that its invention also includes an antibody that selectively binds to the oxidised-LDL epitope that is selectively bound by antibody 2D03; a final aspect of the invention provides an antibody comprising at least one complementarity determining region (CDR) that has the amino acid sequence of the corresponding CDR of antibody 2D03; that more preferably, the antibody has two or three or four or five CDRs that have the sequence of the corresponding CDRs of antibody 2D03; that if the antibody has three or four CDRs that have the sequence of the corresponding CDRs of antibody 2D03, it is preferred if the antibody has all three heavy chain or all three light chain CDRs that have the sequence of the corresponding CDRs of antibody 2D03; that thus this aspect of the invention includes an antibody comprising three light chain CDRs that have the sequence of the corresponding three light chain CDRs of antibody 2D03, or three heavy chain CDRs that have the sequence of the corresponding three heavy chain CDRs of antibody 2D03; that yet more preferably, the antibody comprises three light chain CDRs and three heavy chain CDRs that have the sequence of the corresponding CDRs of antibody 2D03; that if the antibody does not comprise all six CDRs that have the sequence of the corresponding CDRs of antibody 2D03, it is preferred if some or all of the 1, 2, 3, 4 or 5 "non-identical" CDRs comprise a variant of the sequence of the corresponding CDRs of antibody 2D03, (by "a variant" WO 2007/025781 includes the meaning that the variant has at least 50% sequence identity with the sequence of the corresponding CDR, more preferably at least 70%, yet more preferably at least 80% or at least 90% or at least 95%; most preferably, the variant has 96% or 97% or 98% or 99% sequence identity with the sequence of the corresponding CDR of antibody 2D03; typically the "variant" CDR sequence has 5 or 4 or 3 or 2 or only 1 amino acid residue difference from the sequence of the corresponding CDR of antibody 2D03); and that this aspect of the invention includes antibody 2D03. The incorporation of WO 2007/025781 and WO 2009/083225 is also seen in paragraph [0081] (page 29) of the present application's priority application, U.S. provisional application No. 62/343,601, filed May 31, 2016. This description is further shown in paragraphs below, titled Further Methods and Systems in the present application.

Preparation of fusion proteins comprising peptides of ApoB100 (for example SEQ ID NO: 1-302) and Cholera toxin B (CTB) were prepared and evaluated as described in WO 2011/095628, the contents of which is herein incorporated by reference in its entirety.

In some embodiments, the ApoB100 peptides described herein or combinations thereof, or analogs, pharmaceutical equivalents and/or peptidomimetics thereof are modified peptides. "Modified peptide" may include the incorporation of lactam-bridge, head-to-tail cyclization, non-natural amino acids into the peptides of the invention, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. Therefore, in some embodiments the peptides as disclosed comprise L and D amino acids, wherein no more than 1, 2, 3, 4, 5, 6, 7, 8, 9, or 10 D-amino acids are included. In certain aspects, the peptides comprise more than 10 D-amino acids, and in certain aspects all the amino acids of the peptides are D-amino acids.

In some embodiments, the ApoB100 peptides described herein or combinations thereof, or analogs, pharmaceutical equivalents and/or peptidomimetics thereof are retro-inverso peptides the ApoB100 peptides described herein or combinations thereof, or analogs, pharmaceutical equivalents and/or peptidomimetics thereof. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous $\alpha$-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C, J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

Other variants of the peptides described herein (for example, the ApoB100 peptides described herein or combinations thereof, or analogs, pharmaceutical equivalents and/or peptidomimetics thereof) can comprise conservatively substituted sequences, meaning that one or more amino acid residues of an original peptide are replaced by different residues, and that the conservatively substituted peptide retains a desired biological activity, i.e., the ability to treat atherosclerosis that is essentially equivalent to that of the original peptide. Examples of conservative substitutions include substitution of amino acids that do not alter the secondary and/or tertiary structure of the ApoB100 peptides described herein or combinations thereof, or analogs, pharmaceutical equivalents and/or peptidomimetics thereof, substitutions that do not change the overall or local hydrophobic character, substitutions that do not change the overall or local charge, substitutions by residues of equivalent side chain size, or substitutions by side chains with similar reactive groups.

Other examples involve substitution of amino acids that have not been evolutionarily conserved in the parent sequence across species. Advantageously, in some embodiments, these conserved amino acids and structures are not altered when generating conservatively substituted sequences.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar side chain volume are well known. Isolated peptides comprising conservative amino acid substitutions can be tested in any one of the assays described herein to confirm that a desired activity, e.g. reducing atherosclerosis is retained, as determined by the assays described elsewhere herein.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

Particularly preferred conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

Any cysteine residue not involved in maintaining the proper conformation of the isolated peptide as described herein can also be substituted, generally with serine, to improve the oxidative stability of the molecule and prevent aberrant crosslinking. Conversely, cysteine bond(s) can be added to the isolated peptide as described herein to improve its stability or facilitate multimerization.

As used herein, a "functional fragment" is a fragment or segment of a peptide comprising at least 3, at least 4 or at least 5 amino acids and which can treat and/or atherosclerosis according to the assays described herein. A functional fragment can comprise conservative substitutions of the sequences disclosed herein so long as they preserve the function of treating and/or reducing atherosclerosis.

To enhance stability, bioavailability, and/or delivery of the peptides into the cells, the peptides can be modified. For example, in some embodiments, an isolated peptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof. In some embodiments, the ApoB100 peptides described herein or combinations thereof, or analogs, pharmaceutical equivalents and/or peptidomimetics thereof, are conjugated with agents that increase retention in the body. Examples of agents that increase retention include but are not limited to cellulose, fatty acids, polyethylene glycol (PEG) or combinations thereof.

In some embodiments, an isolated peptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, an isolated peptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, an isolated peptide can be modified, e.g. a moiety can be added to one or more of the amino acids comprising the peptide. In some embodiments, an isolated peptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, an isolated peptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties.

An isolated peptide as described herein can be coupled and or connected to a second functional molecule, peptide and/or polypeptide. In some embodiments, an isolated peptide as described herein is coupled to a targeting molecule. In some embodiments, an isolated peptide as described herein is coupled to a targeting molecule by expressing the peptide and the targeting molecule as a fusion peptide, optionally with a peptide linker sequence interposed between them. As used herein a "targeting molecule" can be any molecule, e.g. a peptide, antibody or fragment thereof, antigen, targeted liposome, or a small molecule that can bind to or be bound by a specific cell or tissue type. By way of non-limiting example, if it is desired to target an atherosclerotic region (e.g. to treat, inhibit, reduce the severity of and/or slow progression atherosclerosis in SLE subjects), an isolated peptide comprising the amino acid sequence of any of SEQ ID NO: 1-302 (for example, P210) could be coupled to an antibody or fragment thereof which is specific for the target region.

In some embodiments, an isolated peptide as described herein can be a fusion peptide or polypeptide. A fusion polypeptide can comprise a peptide linker domain interposed between the first domain of the peptide comprising an amino acid sequence of SEQ ID NOs: 1-302 or derivatives, variants, functional fragments, prodrug, or analog thereof as described herein and at least a second domain of the fusion peptide. The first peptide domain can be the N-terminal domain or the C-terminal domain or an internal sequence in the case where the partner domain forms after fragment complementation of constituent parts. Methods of synthesizing or producing a fusion protein are well known to those of ordinary skill in the art. The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. Fusion proteins can include an epitope tag or a half-life extender. Epitope tags include biotin, FLAG tag, c-myc, hemaglutinin, His6, digoxigenin, FITC, Cy3, Cy5, green fluorescent protein, V5 epitope tags, GST, β-galactosidase, AU1, AU5, and avidin. Half-life extenders include Fc domain and serum albumin.

In some embodiments, an isolated peptide as described herein can be a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Prodrug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), which are incorporated by reference herein in their entireties.

In some embodiments, an isolated peptide as described herein can be a pharmaceutically acceptable solvate. The term "solvate" refers to an isolated peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

In some embodiments, an isolated peptide as described herein can be in a non-crystalline, i.e. amorphous solid form.

In one aspect, described herein is a vector comprising a nucleic acid encoding a peptide as described herein. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. Many vectors useful for transferring exogenous genes into target mammalian cells are available. The vectors can be episomal, e.g., plasmids, virus derived vectors such cytomegalovirus, adenovirus, etc., or can be integrated into the target cell genome, through homologous recombination or random integration, e.g., retrovirus derived vectors such MMLV, HIV-1, ALV, etc. Many viral vectors are known in the art and can be used as carriers of a nucleic acid modulatory compound into the cell. For example, constructs containing the nucleic acid encoding a polypeptide can be integrated and packaged into non-replicating, defective viral genomes like Adenovirus, Adeno-associated virus (AAV), or Herpes simplex virus (HSV) or others, including retroviral and lentiviral vectors, for infection or transduction into cells. Alternatively, the construct can be incorporated into vectors capable of episomal replication, e.g. EPV and EBV vectors. The nucleic acid incorporated into the vector can be operatively linked to an expression control sequence such that the expression control sequence controls and regulates the transcription and translation of that polynucleotide sequence.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector can comprise additional elements, for example, the expression vector can have two replication systems, thus allowing it to be maintained in two organisms, for example in human cells for expression and in a prokaryotic host for cloning and amplification.

The term "transfection" as used herein to methods, such as chemical methods, to introduce exogenous nucleic acids, such as the nucleic acid sequences encoding a peptide as described herein into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to those that use cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

As used herein, the term "viral vector" refers to a nucleic acid vector construct that includes at least one element of viral origin and has the capacity to be packaged into a viral vector particle. The viral vector can contain the nucleic acid encoding a peptide as described herein in place of non-essential viral genes. The vector and/or particle can be utilized for the purpose of transferring any nucleic acids into cells either in vitro or in vivo. Numerous forms of viral vectors are known in the art. The term "replication incompetent" when used in reference to a viral vector means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins for packaging the virus) and viral particles cannot be formed in the patient's cells. The term "transduction" as used herein refers to the use of viral particles or viruses to introduce exogenous nucleic acids into a cell.

Retroviruses, such as lentiviruses, provide a convenient platform for delivery of nucleic acid sequences encoding an agent of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety.

In some embodiments, a nucleotide sequence of interest is inserted into an adenovirus-based expression vector. Unlike retroviruses, which integrate into the host genome, adenoviruses persist extrachromosomally thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76). Adenoviral vectors have several advantages in gene therapy. They infect a wide variety of cells, have a broad host-range, exhibit high efficiencies of infectivity, direct expression of heterologous sequences at high levels, and achieve long-term expression of those sequences in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. For all these reasons vectors derived from human adenoviruses, in which at least the E1 region has been deleted and replaced by a gene of interest, have been used extensively for gene therapy experiments in the pre-clinical and clinical phase. Adenoviral vectors for use with the compositions and methods described herein can be derived from any of the various adenoviral serotypes, including, without limitation, any of the over 40 serotype strains of adenovirus, such as serotypes 2, 5, 12, 40, and 41. The adenoviral vectors of used in the methods described herein are generally replication-deficient and contain the sequence of interest under the control of a suitable promoter. For example, U.S. Pat. No. 6,048,551, incorporated herein by reference in its entirety, describes replication-deficient adenoviral vectors that include a human gene under the control of the Rous Sarcoma Virus (RSV) promoter. Other recombinant adenoviruses of various serotypes, and comprising different promoter systems, can be created by those skilled in the art. See, e.g., U.S. Pat. No. 6,306,652, incorporated herein by reference in its entirety. Other useful adenovirus-based vectors for delivery of nucleic acid sequences include, but are not limited to: "minimal" adenovirus vectors as described in U.S. Pat. No. 6,306,652, which retain at least a portion of the viral genome required for encapsidation (the encapsidation signal), as well as at least one copy of at least a functional part or a derivative of the ITR; and the "gutless" (helper-dependent) adenovirus in which the vast majority of the viral genome has been removed and which produce essentially no viral proteins, such vectors can permit gene expression to persist for over a year after a single administration (Wu et al. (2001) Anesthes. 94:1119-32; Parks (2000) Clin. Genet. 58:1-11; Tsai et al. (2000) Curr. Opin. Mol. Ther. 2:515-23).

In some embodiments, a nucleotide sequence encoding a peptide as described herein is inserted into an adeno-associated virus-based expression vector. AAV is a parvovirus which belongs to the genus Dependovirus and has several features not found in other viruses. AAV can infect a wide range of host cells, including non-dividing cells. AAV can infect cells from different species. AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions, facilitating production, storage and transportation. AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus. Adeno-associated virus (AAV) has been used with success in gene therapy. AAV has been engineered to deliver genes of interest by deleting the internal nonrepeating portion of the AAV genome (i.e., the rep and cap genes) and inserting a heterologous sequence (in this case, the sequence encoding the agent) between the ITRs. The heterologous sequence is typically functionally linked to a heterologous promoter (constitutive, cell-specific, or inducible) capable of driving expression in the patient's target cells under appropriate conditions. Recombinant AAV virions comprising a nucleic acid sequence encoding an agent of interest can be produced using a variety of art-recognized techniques, as described in U.S. Pat. Nos. 5,139,941; 5,622,856; 5,139,941; 6,001,650; and 6,004,797, the contents of each of which are incorporated by reference herein in their entireties. Vectors and cell lines necessary for preparing helper virus-free rAAV stocks are commercially available as the AAV Helper-Free System (Catalog No. 240071) (Agilent Technologies, Santa Clara, Calif.).

Additional viral vectors useful for delivering nucleic acid molecules encoding a peptide as described herein include those derived from the pox family of viruses, including vaccinia virus and avian poxvirus. Alternatively, avipoxviruses, such as the fowlpox and canarypox viruses, can be used to deliver the genes. The use of avipox vectors in cells of human and other mammalian species is advantageous with regard to safety because members of the avipox genus can only productively replicate in susceptible avian species. Methods for producing recombinant avipoxviruses are known in the art and employ genetic recombination, see, e.g., WO 91/12882; WO 89/03429; and WO 92/03545.

Molecular conjugate vectors, such as the adenovirus chimeric vectors, can also be used for delivery of sequence encoding a peptide as described herein (Michael et al. (1993) J. Biol. Chem. 268:6866-69 and Wagner et al. (1992) Proc. Natl. Acad. Sci. USA 89:6099-6103). Members of the Alphavirus genus, for example the Sindbis and Semliki Forest viruses, can also be used as viral vectors for delivering a nucleic acid sequence (See, e.g., Dubensky et al. (1996) J. Virol. 70:508-19; WO 95/07995; WO 96/17072).

In some embodiments, the vector further comprises a signal peptide operably linked to the peptide. Signal peptides are terminally (usually N-terminally) located peptide sequences that provide for passage of the protein into or through a membrane. Different signal peptides can be of use in different applications. For example, as regards a cellular system for the production of isolated peptides as described herein, a secretory signal peptide can permit increased yields and ease of purification. As a further example, as regards cells which produce peptides as described herein and which are administered for therapeutic purposes to a subject, multiple signal peptides, e.g. a peptide signaling for secretion from the first cell, a peptide signaling for internalization by a second cell, and a final peptide signaling for nuclear localization can increase the amount of peptide reaching the target environment. As a further example, as regards, e.g. gene therapy applications, a peptide signaling for nuclear localization can increase the amount of peptide reaching the target environment. Signal peptides are known in the art. Non-limiting examples of nuclear localization signal (NLS) peptides for use in mammalian cells include; the SV40 large T-antigen NLS (PKKKRKV) (SEQ ID NO: 305); the nucleoplasmin NLS (KR[PAATKKAGQA]KKKK)(SEQ ID NO: 306); the K-K/R-X-K/R (SEQ ID NO: 307) consensus NLS (KKXR (SEQ ID NO: 308); KKXK (SEQ ID NO: 309); KRXK (SEQ ID NO: 310); KRXR (SEQ ID NO: 311); and PY-NLSs (see, e.g. Dingwall et al. J Cell Biol 188 107:841-9 and Makkerh et al. Curr Biol. 1996 6:1025-7; both of which are incorporated by reference herein in their entireties, for further discussion). Non-limiting examples of secretion signal peptides for use in mammalian cells include human albumin signal peptide (MKWVTFISLLFLF-SSAYS) (SEQ ID NO: 312); human chymotrypsin signal peptide (MAFLWLLSCWALLGTTGF) (SEQ ID NO: 313); human interleukin-2 signal peptide (MQLLSCIALILALV) (SEQ ID NO: 314); human trypsinogen-2 signal peptide (MNLLLILTFVAAAVA) (SEQ ID NO: 315); and sequences which include a coding region for a signal for precursor cleavage by signal peptidase, furin or other prohormone convertases (e.g., PC3). For example, a signal (peptide) sequence which is cleaved by furin (also known as PACE, see U.S. Pat. No. 5,460,950), other subtilisins (including PC2, PC1/PC3, PACE4, PC4, PC5/PC6, LPC/PC7IPC8/SPC7 and SKI-I; Nakayama, Biochem. J., 327:625-635 (1997)); enterokinase (see U.S. Pat. No. 5,270,181) or chymotrypsin can be introduced into the signal (peptide) sequence as defined herein. Additional signal peptides are known in the art and the choice of signal peptide can be influenced by the cell type, growth conditions, and the desired destination of the peptide.

In one aspect, described herein is a cell expressing a vector comprising a nucleic acid encoding a peptide as described herein. In some embodiments, the cell expressing a vector as described herein is a cell suitable for the production of polypeptides. A cell suitable for the production of polypeptides can be a prokaryotic or eukaryotic cell, e.g. bacteria, virus, yeast, fungi, mammalian cells, insect cells, plant cells, and the like. By way of non-limiting example, cells for the production of proteins are commercially available, e.g. bacterial cells (BL21 derived cells—Cat. No. 60401-1, Lucigen; Middleton, Wis. and mammalian cells (293 F cells—Cat. No. 11625-019, Invitrogen; Grand Island, N.Y.).

Recombinant molecules, e.g. vectors as described herein, can be introduced into cells via transformation, particularly transduction, conjugation, lipofection, protoplast fusion, mobilization, particle bombardment, electroporation (Neumann et al., "Gene Transfer into Mouse Lyoma Cells by Electroporation in High Electric Fields," *EMBO J.* 1(7):841-845 (1982); Wong et al., "Electric Field Mediated Gene Transfer," *Biochem Biophys Res Commun* 107(2):584-587 (1982); Potter et al., "Enhancer-dependent Expression of Human Kappa Immunoglobulin Genes Introduced into Mouse pre-B Lymphocytes by Electroporation," *Proc. Natl. Acad. Sci. USA* 81(22):7161-7165 (1984), which are hereby incorporated by reference in their entirety), polyethylene glycol-mediated DNA uptake (Joseph Sambrook & David W. Russell, Molecular Cloning: A Laboratory Manual cp. 16 (2d ed. 1989), which is hereby incorporated by reference in its entirety), or fusion of protoplasts with other entities (e.g., minicells, cells, lysosomes, or other fusible lipid-surfaced bodies that contain the chimeric gene) (Fraley et al., "Liposome-mediated Delivery of Tobacco Mosaic Virus RNA into Tobacco Protoplasts: A Sensitive Assay for Monitoring Liposome-protoplast Interactions," *Proc. Natl. Acad. Sci. USA,* 79(6):1859-1863 (1982), which is hereby incorporated by reference in its entirety). The host cell is then cultured in a suitable medium, and under conditions suitable for expression of the protein or polypeptide of interest. After cultivation, the cell is disrupted by physical or chemical means, and the protein or polypeptide purified from the resultant crude extract. Alternatively, cultivation may include conditions in which the protein or polypeptide is secreted into the growth medium of the recombinant host cell, and the protein or polypeptide is isolated from the growth medium. Alternative methods may be used as suitable.

The terms "enhancer" and "enhance" as it pertains to a molecule in connection with CD8 T cell refers to the ability of a molecule to modify the immune response by promoting the activation of cells of the immune system. The choice of appropriate enhancer can allow control of activation of the immune response. Exemplary enhancers include cytokines such as IL-2. The term "cytokine" as used herein refers cell signaling molecules that act as has immunomodulating agents, and comprise proteins such as interleukins and interferons as would be identifiable to a skilled person. Selection of a suitable cytokine can result under appropriate conditions in the preferential induction of a humoral or cellular immune response.

In an embodiment, the enhancer can be Interleukin 2 (IL2), Interleukin 15 (IL-15), TGF-beta (TGF-β), IL2-antiIL-2 antibody complex and/or additional enhancer identifiable by a skilled person upon reading of the present disclosure. Reference is made to the references Mitchell et al 2010 (38), Perret et al 2008 (39) and Kamimura et al 2007 (40), each incorporated by reference in its entirety, which describe exemplary use of enhancer in connection with T cell activation.

In particular in some embodiments, the enhancing is performed by reducing CD86 expression and/or IL12 secretion by dendritic cells in the individual.

The peptides can also be attached to adjuvants. The term "adjuvant" refers to a compound or mixture that enhances the immune response and/or promotes the proper rate of absorption following inoculation, and, as used herein, encompasses any uptake-facilitating agent. Non-limiting examples of adjuvants include, chemokines (e.g., defensins, HCC-1, HCC4, MCP-1, MCP-3, MCP4, MIP-1α, MIP-1β, MIP-1β, MIP-3α, RANTES); other ligands of chemokine receptors (e.g., CCR1, CCR-2, CCR-5, CCR6, CXCR-1); cytokines (e.g., IL-1β, IL-2, IL-4, IL-5, IL-6, IL-7, IL-8, IL-10, IL-12, IL-13, IL-15, IL-17 (A-F), IL-18; IFNα, IFN-γ; TNF-α; GM-CSF); TGF)-β; FLT-3 ligand; CD40 ligand; other ligands of receptors for those cytokines; Th1 cytokines including, without limitation, IFN-γ, IL-12, IL-18, and TNF; Th2 cytokines including, without limitation, IL-4, IL-5, IL-10, and IL-13; and Th17 cytokines including, without limitation, IL-17 (A through F), IL-23, TGF-β and IL-6; immunostimulatory CpG motifs in bacterial DNA or oligonucleotides; derivatives of lipopolysaccharides such as monophosphoryl lipid A (MPL); muramyl dipeptide (MDP) and derivatives thereof (e.g., murabutide, threonyl-MDP, muramyl tripeptide, N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alani-ne-2-(1'-2'-dipalmitoyl-sn-glycero-3hydroxyphosphoryloxy)-ethylamine (CGP 19835A, referred to as MTP-PE)); MF59 (see Int'l Publication No. WO 90/14837); poly[di(carboxylato-phenoxy)phosphazene] (PCPP polymer; Virus Research Institute, USA); RIBI (GSK), which contains three components extracted from bacteria, monophosphoryl lipid A, trehalose dimycolate and cell wall skeleton (MPL+TDM+CWS) in a 2% squalene/Tween 80 emulsion; OM-174 (a glucosamine disaccharide related to lipid A; OM Pharma SA, Meyrin, Switzerland); heat shock proteins and derivatives thereof; Leishmania homologs of elF4a and derivatives thereof; bacterial ADP-ribosylating exotoxins and derivatives thereof (e.g., genetic mutants, A and/or B subunit-containing fragments, chemically toxoided versions); chemical conjugates or genetic recombinants containing bacterial ADP-ribosylating exotoxins or derivatives thereof; C3d tandem array; lipid A and derivatives thereof (e.g., monophosphoryl or diphosphoryl lipid A, lipid A analogs, AGP, AS02, AS04, DC-Chol, Detox, OM-174); ISCOMS and saponins (e.g., Quil A, QS-21, STIMULON® (Cambridge Bioscience, Worcester, Mass.)); squalene; superantigens; or salts (e.g., aluminum hydroxide or phosphate, calcium phosphate). See also Nohria et al. *Biotherapy*, 7:261-269, 1994; Richards et al., in *Vaccine Design*, Eds. Powell et al., Plenum Press, 1995; and Pashine et al., *Nature Medicine*, 11:S63-S68, 4/2005) for other useful adjuvants. Further examples of adjuvants can include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co-polymer (CytRx, Atlanta Ga.), QS-21 (Cambridge Biotech Inc., Cambridge Mass.), and SAF-M (Chiron, Emeryville Calif.), AMPHIGEN® adjuvant, saponin, Quil A or other saponin fraction, monophosphoryl lipid A, and Avridine lipid-amine adjuvant, and METASTIM®. Other suitable adjuvants can include, for example, surface active substances such as lysolecithin, pluronic polyols, polyanions, peptides, oil or hydrocarbon emulsions, keyhole limpet hemocyanins, dinitrophenol, and others.

In some embodiment, cell may be genetically engineered to express the peptides described herein and the genetically engineered cells may be used for cell therapy. Examples of cells that may be used include but are not limited to, dendritic cells, T-lymphocytes (T-cells), naïve T cells ($T_N$), memory T cells (for example, central memory T cells ($T_{CM}$), effector memory cells ($T_{EM}$)), natural killer cells, hematopoietic stem cells and/or pluripotent embryonic/induced stem cells capable of giving rise to therapeutically relevant progeny. In an embodiment, the genetically engineered cells are autologous cells. By way of example, individual T-cells of the invention may be CD4+/CD8−, CD4−/CD8+, CD4−/CD8− or CD4+/CD8+. The T-cells may be a mixed population of CD4+/CD8− and CD4−/CD8+ cells or a population of a single clone. CD4+ T-cells may produce IL-2, IFNγ, TNFα and other T-cell effector cytokines when co-cultured in vitro with cells expressing the peptides (for example CD20+ and/or CD19+ tumor cells). $CD8^+$ T-cells may lyse antigen-specific target cells when co-cultured in vitro with the target cells. In some embodiments, T cells may be any one or more of $CD45RA^+CD62L^+$ naïve cells, $CD45RO^+CD62L^+$ central memory cells, $CD62L^-$ effector memory cells or a combination thereof (Berger et al., Adoptive transfer of virus-specific and tumor-specific T cell immunity. *Curr Opin Immunol* 2009 21(2) 224-232).

In some embodiments, tolerized antigen presenting cells may be used in cell therapy. Examples include B cells, dendritic cells, macrophages and the like. The cells may be of any origin, including from humans. The cells may be tolerized using the peptides described herein. In some embodiments, the cells are tolerized in the presence of cytokines.

In some embodiments, the cell producing the peptide as described herein can be administered to a subject, e.g. for treating, inhibiting, reducing the severity of and/or slow progression of atherosclerosis (such as accelerated atherosclerosis) in subjects with SLE.

In some embodiments, nanoparticles containing the peptide as described herein can be administered to a subject. In some embodiments, the nanoparticles for use with the peptides described herein may be as described in Levine et al., Polymersomes: A new multi-functional tool for cancer diagnosis and therapy. Methods 2008 Vol 46 pg 25-32 or as described in S Jain, et al., Gold nanoparticles as novel agents for cancer therapy. Br J Radiol. 2012 February; 85(1010): 101-113.

In some embodiments, the cell expressing a vector encoding a peptide as described herein can be a cell of a subject, e.g. a subject administered gene therapy for the treatment, inhibition, reduction of severity and/or slow progression of atherosclerosis (such as accelerated atherosclerosis) in subjects with SLE. Vectors for gene therapy can comprise viral or non-viral vectors as described elsewhere herein.

Some embodiments of the present invention can be defined as any of the following numbered paragraphs:

1. A method of treating, inhibiting, preventing, reducing the severity of slow progression of and/or promoting prophylaxis of cardiovascular diseases in subjects with SLE comprising: (a) providing a composition comprising one or more peptides of ApoB or derivatives, pharmaceutical equivalents, peptidomimetics or analogs thereof; and (b) administering an effective amount of the composition to the subject, so as to treat, inhibit, prevent, reduce the severity of, slow progression of and/or promote prophylaxis of cardiovascular diseases in subjects with (SLE).

2. A method of treating, inhibiting, preventing, reducing the severity of, slowing progression of, and/or promoting prophylaxis of systemic lupus erythematosus (SLE) in subjects in need thereof comprising: (a) providing a composition comprising one or more peptides of ApoB100 ("ApoB") or derivatives, pharmaceutical equivalents, peptidomimetics or analogs thereof; and (b) administering an effective amount of the composition to the subject, so as to treat, inhibit, prevent, reduce the severity, slow the progression, and/or promote prophylaxis of SLE in the subject.

3. The method of paragraphs 1 or 2, wherein the peptide of ApoB is any one or more of peptides 1 to 302 of ApoB100 as set forth in SEQ ID NO: 1 to SEQ ID NO: 302.

4. The method of paragraph 3, wherein the peptide of ApoB100 is P210 (SEQ ID NO: 210).

5. The method of paragraph 3, wherein the peptide of ApoB100 is P45 (SEQ ID NO: 45).

6. The method of paragraph 3, wherein the peptide is fused to cholera toxin B (CTB).

7. A method of treating, inhibiting, preventing, reducing the severity of, slowing progression of and/or promoting prophylaxis of SLE in a subject in need thereof comprising: (a) providing a composition comprising CD8+ T cells activated with one or more peptides of ApoB or derivatives, pharmaceutical equivalents, peptidomimetics or analogs thereof; and (b) administering an effective amount of the composition to the subject so as to treat, inhibit, prevent, reduce the severity of, slow progression of and/or promote prophylaxis of SLE in the subject.

8. A method of treating, inhibiting, preventing, reducing the severity of, slowing progression of and/or promoting prophylaxis of cardiovascular diseases in subjects with SLE comprising: (a) providing a composition comprising CD8+ T cells activated with one or more peptides of ApoB or derivatives, pharmaceutical equivalents, peptidomimetics or analogs thereof; and (b) administering an effective amount of the composition to the subject, so as to treat, inhibit, prevent, reduce the severity of, slow progression of and/or promote prophylaxis of cardiovascular diseases in subjects with (SLE).

9. The method of paragraphs 7 or 8, wherein the peptide of ApoB is any one or more of peptides 1 to 302 of ApoB as set forth in SEQ ID NO: 1 to SEQ ID NO: 302.

10. The method of paragraph 9, wherein the peptide of ApoB is P210 (SEQ ID NO: 210).

11. The method of paragraph 9, wherein the peptide of ApoB is P45 (SEQ ID NO: 45).

12. The method of paragraphs 7 or 8, wherein the peptide is fused to cholera toxin B (CTB).
13. The method of paragraphs 7 or 8, wherein the method further comprises administering an effective amount of one or more enhancers.
14. The method of paragraph 13, wherein the enhancers are any one or more of IL-2, IL-10, IL-15. TGF-β, IL2/Anti-IL-2 antibody complex, or combinations thereof.
15. A method for treating SLE in a subject in need thereof by passive immunization, comprising providing an antibody that binds at least one oxidized fragment of ApoB and administering a therapeutically or prophylactically effective amount of the antibody, so as to treat SLE.
16. The method of paragraph 15, wherein the antibody is a human antibody.
17. The method of paragraph 16, wherein the antibody comprises a variable heavy region ($V_H$) and a variable light region ($V_L$), wherein the $V_H$ region consists of the sequence set forth in SEQ ID NO 303 and the variable light region ($V_L$) No. 304.
18. The method of paragraph 1, 2, 5 or 6, further comprising administering an effective amount of an antibody that binds at least one oxidized fragment of ApoB.
19. The method of paragraph 18, wherein the antibody is a human antibody.
20. The method of paragraph 19, wherein the antibody comprises a variable heavy region ($V_H$) and a variable light region ($V_L$), wherein the $V_H$ region consists of the sequence set forth in SEQ ID NO 303 and the variable light region ($V_L$) No. 304.
21. The method of paragraph 1 or 8, wherein the cardiovascular disease is atherosclerosis.
22. The method of paragraph 21, wherein atherosclerosis is accelerated atherosclerosis.
23. An assay for diagnosing SLE in a subject in need thereof comprising:
  Obtaining a sample from the subject;
  Assaying the sample to determine the level of autoantibodies against ApoB100; and
  Determining that the subject has increased likelihood of having SLE if the level of the autoantibodies is decreased relative to a reference value, or determining that the subject has decreased likelihood of having SLE if the level of autoantibodies is increased relative to a reference value.
24. An assay for determining likelihood of cardiovascular disease in a subject having or suspected of having SLE comprising:
  Obtaining a sample from the subject;
  Assaying the sample to determine the level of autoantibodies against ApoB100; and
  Determining that the subject has increased likelihood of cardiovascular disease if the level of the autoantibodies is decreased relative to a reference value, or determining that the subject has decreased likelihood of cardiovascular disease if the level of autoantibodies is increased relative to a reference value.
25. The assay of paragraphs 23 or 24, wherein the assay comprises using is an immunoassays.
26. The assay of paragraph 25, wherein the immunoassay is any one or more of ELISA, RIA, Western blotting, Southern blotting, or combinations thereof.
27. The assay of paragraphs 23 or 24, wherein the sample is blood, plasma, urine, tissue or combinations thereof.
28. The assay of paragraph 27, wherein the sample is obtained before, during or after treatment for SLE.
29. The assay of paragraphs 23 or 24, wherein the subject is human.
30. The assay of paragraphs 23 or 24, wherein the reference value is the mean or median level of autoantibodies against ApoB100 in a population of subjects that do not have SLE.
31. The assay of paragraphs 23 or 24, wherein the reference value is the mean or median level of autoantibodies against ApoB100 in a sample obtained from the subject at a different time point.
32. The assay of paragraphs 23 or 24, wherein the reference value is the mean or median level of autoantibodies against ApoB100 in a population of subjects that have SLE and have undergone or are undergoing treatment for SLE.
33. The assay of paragraphs 23 or 24, wherein the reference value is the mean or median level of autoantibodies against ApoB100 in a population of subjects that have SLE and have undergone or are undergoing treatment for SLE and have not undergone or are not undergoing treatment for cardiovascular diseases.
34. The assay of paragraph 24, wherein the cardiovascular disease is atherosclerosis.
35. The assay of paragraph 34, wherein atherosclerosis is accelerated atherosclerosis.
36. The assay of paragraph 23, further comprising determine the level of soluble forms of the apoptosis-signaling receptors Fas, TNF-R1, and/or TRAIL-R2; and determining that the subject has increased likelihood of having SLE if the level of the said apoptosis-signaling receptors is increased relative to a reference value, or determining that the subject has decreased likelihood of having SLE if the level of said apoptosis-signaling receptors is decreased relative to a reference value.
37. An assay for determining the efficacy of treatment for SLE in a subject in need thereof comprising:
  Obtaining a sample from the subject;
  Assaying the sample to determine the level of autoantibodies against ApoB100; and
  Determining that the treatment is effective if the level of the autoantibodies is increased relative to a reference value, or determining that the treatment is ineffective if the level of autoantibodies is decreases relative to a reference value.
38. An assay for determining the efficacy of treatment for cardiovascular diseases in subject with SLE comprising:
  Obtaining a sample from the subject;
  Assaying the sample to determine the level of autoantibodies against ApoB100; and
  Determining that the treatment is effective if the level of the autoantibodies is increased relative to a reference value, or determining that the treatment is ineffective if the level of autoantibodies is decreases relative to a reference value.
39. An assay for diagnosing SLE in a subject in need thereof comprising:
  Obtaining a sample from the subject;
  Assaying the sample to determine the level of soluble forms of the apoptosis-signaling receptors Fas, TNF-R1, and/or TRAIL-R2; and
  Determining that the subject has increased likelihood of having SLE if the level of the said apoptosis-signaling receptors is increased relative to a reference value, or determining that the subject has decreased likelihood of having SLE if the level of said apoptosis-signaling receptors is decreased relative to a reference value.

40. The assay of paragraph 39, further comprising assaying the sample to determine the level of autoantibodies against ApoB100; and determining that the subject has increased likelihood of having SLE if the level of the autoantibodies is decreased relative to a reference value, or determining that the subject has decreased likelihood of having SLE if the level of autoantibodies is increased relative to a reference value.

41. An assay for determining likelihood of cardiovascular disease in a subject having or suspected of having SLE comprising:
Obtaining a sample from the subject;
Assaying the sample to determine the level of soluble forms of the apoptosis-signaling receptors Fas, TNF-R1, and/or TRAIL-R2; and
Determining that the subject has increased likelihood of cardiovascular disease if the level of said apoptosis-signaling receptors is increased relative to a reference value, or determining that the subject has decreased likelihood of cardiovascular disease if the level of said apoptosis-signaling receptors is decreased relative to a reference value.

Further Methods and Systems

Various embodiments provide a method of treating, reducing the severity of SLE in a subject, or of atherosclerosis in a subject with SLE, by administering to the subject an antibody or antibody fragment that binds to at least one fragment of apolipoprotein B100 (apoB100). In various embodiments, the method provides treatment of SLE in a subject, or of atherosclerosis in a subject with SLE, by passive immunization. Further embodiments provide the atherosclerosis is accelerated atherosclerosis, with which a patient presents earlier, and may develop more quickly, atherosclerotic lesions, compared to non-diseased age matched controls.

Various embodiments provide a method of reducing the likelihood of having SLE, or having atherosclerosis in a subject with SLE, by administering to the subject an antibody or antibody fragment that binds to at least one fragment of apolipoprotein B100 (apoB100). In various embodiments, the method provides passive immunity to the subject to reduce the likelihood of having SLE.

Various embodiments provide the antibody or antibody fragment in the methods disclosed herein binds to a native and/or an oxidized epitope P45 of apoB100. Various embodiments provide the antibody or antibody fragment in the methods disclosed herein only binds to a native and/or an oxidized epitope P45 of apoB100. P45 of apoB100 has a polypeptide sequence of IEIGLEGKGFEPTLEALFGK (SEQ ID NO: 45). An oxidized epitope or oxidized lipoprotein includes but is not limited to a modification on the epitope or lipoprotein to carry malone-di-aldehyde (MDA) groups on lysines and histidines, a modification that is induced by oxidation by copper (e.g., CuOxLDL), a modification to carry hydroxynonenal, or a modification to carry a hapten of an aldehyde. Another embodiment provides the antibody or antibody fragment in the method disclosed herein further binds one or more fragments of apoB100.

Various embodiments provide that the method of treating or reducing the severity of SLE in a subject, or of atherosclerosis in a subject with SLE, in a subject includes but is not limited to administering orticumab or a variant of orticumab that has identical heavy chain and/or light chain to those of orticumab, or identical complementarity determining regions to those of orticumab.

Various embodiments provide that the method of reducing the likelihood of SLE in a subject, or of atherosclerosis in a subject with SLE, in a subject includes but is not limited to administering orticumab or a variant of orticumab that has identical heavy chain and/or light chain to those of orticumab, or identical complementarity determining regions to those of orticumab. In further aspect, the method provides passive immunity to the subject to reduce the likelihood of having SLE.

The complementarity determining regions (CDRs) of orticumab are described above in relation to FIG. 21B and FIG. 21C. The heavy chain complementarity determining region (HCDR) 1 (HCDR1), 2 (HCDR2) and 3 (HCDR3) are set forth in SEQ ID Nos: 318, 319 and 320, respectively; and light chain complementarity determining regions (LCDR) 1 (LCDR1), 2 (LCDR2) and 3 (LCDR3) are set forth in SEQ ID Nos: 321, 322 and 323, respectively. Orticumab contains a variable heavy region ($V_H$) amino acid sequence of SEQ ID No: 324, and a variable light region ($V_L$) amino acid sequence of SEQ ID No: 325. Orticumab contains a heavy chain amino acid sequence of SEQ ID No: 316, a light chain amino acid sequence of SEQ ID No: 317, as shown in FIG. 21B and FIG. 21C.

```
HCDR1, i.e., SEQ ID NO: 318, is:
FSNAWMSWVRQAPG.

HCDR2, i.e., SEQ ID NO: 319, is:
SSISVGGHRTYYADSVKGR.

HCDR3, i.e., SEQ ID NO: 320, is:
ARIRVGPSGGAFDY.

LCDR1, i.e., SEQ ID NO: 321, is:
CSGSNTNIGKNYVS.

LCDR2, i.e., SEQ ID NO: 322, is:
ANSNRPS.

LCDR3, i.e., SEQ ID NO: 323, is:
CASWDASLNGWV.
```

Variable heavy region ($V_H$), i.e., SEQ ID NO:324, is as shown:

```
EVQLLESGGG LVQPGGSLRL SCAASGFTFS NAWMSWVRQA
PGKGLEWVSS ISVGGHRTYY ADSVKGRSTI SRDNSKNTLY
LQMNSLRAED TAVYYCARIR VGPSGGAFDY WGQGTLVTVS.
```

Variable light region ($V_L$), i.e., SEQ ID NO: 325, is as shown:

```
QSVLTQPPSA SGTPGQRVTI SCSGSNTNIG KNYVSWYQQL
PGTAPKLLIY ANSNRPSGVP DRFSGSKSGT SASLAISGLR
SEDEADYYCA SWDASLNGWV FGGGTKLTVL.
```

Methods are provided of treating or reducing the severity of SLE in a subject, or of atherosclerosis in a subject with SLE, in a subject including administering to the subject an effective amount of an antibody or antibody fragment that binds a fragment set forth in SEQ ID NO: 45 of apoB100, and the antibody contains one or more of HCDR1, HCDR2, HCDR3, LCDR1, LCDR2 and LCDR3 as set forth in SEQ ID Nos.: 318-323, respectively.

Methods of treating or reducing the severity of SLE in a subject, or of atherosclerosis in a subject with SLE, in a subject are also provided including administering to the subject an effective amount of an antibody or antibody fragment that binds a fragment set forth in SEQ ID NO: 45 of apoB100, and the antibody contains one or more of HCDR1, HCDR2, HCDR3, LCDR1, LCDR2 and LCDR3 as set forth in SEQ ID Nos.: 318-323, respectively.

One aspect of the disclosed methods provides administering an antibody comprising at least one CDR that has the amino acid sequence of the corresponding CDR of orticumab. More preferably, the antibody has two or three or four or five CDRs that have the sequence of the corresponding CDRs of orticumab. If the antibody has three or four CDRs that have the sequence of the corresponding CDRs of orticumab, it is preferred if the antibody has all three heavy chain or all three light chain CDRs that have the sequence of the corresponding CDRs of orticumab. Thus this aspect of the methods includes an antibody comprising three light chain CDRs that have the sequence of the corresponding three light chain CDRs of orticumab, or three heavy chain CDRs that have the sequence of the corresponding three heavy chain CDRs of orticumab. Yet more preferably, the antibody comprises three light chain CDRs and three heavy chain CDRs that have the sequence of the corresponding CDRs of orticumab.

If the antibody does not comprise all six CDRs that have the sequence of the corresponding CDRs of orticumab, it is preferred if some or all of the 1, 2, 3, 4 or 5 "non-identical" CDRs comprise a variant of the sequence of the corresponding CDRs of orticumab. By "a variant," we include the meaning that the variant has at least 50% sequence identity with the sequence of the corresponding CDR, more preferably at least 70%, yet more preferably at least 80% or at least 90% or at least 95%. Most preferably, the variant has 96% or 97% or 98% or 99% sequence identity with the sequence of the corresponding CDR of orticumab. Typically the "variant" CDR sequence has 5 or 4 or 3 or 2 or only 1 amino acid residue difference from the sequence of the corresponding CDR of orticumab. This aspect of the invention includes administering orticumab for the intended treatment or prophylaxis.

The antibody containing "one or more of HCDR1, HCDR2, HCDR3, LCDR1, LCDR2 and LCDR3" encompasses embodiments that the antibody contains one, any two, any three, any four, any five or all six of the CDRs (i.e., HCDR1, HCDR2, HCDR3, LCDR1, LCDR2 and LCDR3). For example, one aspect of the embodiment provides that the administered antibody contains HCDR1 as set forth in SEQ ID NO: 318. Another aspect provides that the administered antibody contains HCDR2 as set forth in SEQ ID NO: 319. Another aspect provides that the administered antibody contains HCDR3 as set forth in SEQ ID NO: 320. Yet another aspect provides that the administered antibody contains LCDR1 as set forth in SEQ ID NO: 321. Another aspect provides that the administered antibody contains LCDR2 as set forth in SEQ ID NO: 322. Another aspect provides that the administered antibody contains LCDR3 as set forth in SEQ ID NO:323. Yet another aspect provides that the administered antibody contains HCDR1 as set forth in SEQ ID NO:318 and HCDR2 as set forth in SEQ ID NO: 319. Another aspect provides that the administered antibody contains HCDR1 as set forth in SEQ ID NO:318 and HCDR3 as set forth in SEQ ID NO: 320. Another aspect provides that the administered antibody contains HCDR1 as set forth in SEQ ID NO:318 and LCDR1 as set forth in SEQ ID NO: 321. Another aspect provides that the administered antibody contains HCDR1 as set forth in SEQ ID NO:318 and LCDR2 as set forth in SEQ ID NO: 322. Another aspect provides that the administered antibody contains HCDR1 as set forth in SEQ ID NO:318 and LCDR3 as set forth in SEQ ID NO: 323. Another aspect provides that the administered antibody contains HCDR2 as set forth in SEQ ID NO:319 and HCDR3 as set forth in SEQ ID NO: 320. Another aspect provides that the administered antibody contains HCDR2 as set forth in SEQ ID NO:319 and LCDR1 as set forth in SEQ ID NO: 321. Another aspect provides that the administered antibody contains HCDR2 as set forth in SEQ ID NO:319 and LCDR2 as set forth in SEQ ID NO: 322. Another aspect provides that the administered antibody contains HCDR2 as set forth in SEQ ID NO:319 and LCDR3 as set forth in SEQ ID NO: 323. Another aspect provides that the administered antibody contains HCDR3 as set forth in SEQ ID NO:320 and LCDR1 as set forth in SEQ ID NO: 321. Another aspect provides that the administered antibody contains HCDR3 as set forth in SEQ ID NO:320 and LCDR2 as set forth in SEQ ID NO: 322. Another aspect provides that the administered antibody contains HCDR3 as set forth in SEQ ID NO:320 and LCDR3 as set forth in SEQ ID NO: 323. Another aspect provides that the administered antibody contains LCDR1 as set forth in SEQ ID NO:321 and LCDR2 as set forth in SEQ ID NO: 322. Another aspect provides that the administered antibody contains LCDR1 as set forth in SEQ ID NO:321 and LCDR3 as set forth in SEQ ID NO: 323. Another aspect provides that the administered antibody contains LCDR2 as set forth in SEQ ID NO:322 and LCDR3 as set forth in SEQ ID NO: 323. Another aspect provides that the administered antibody contains HCDR1, HCDR2 and HCDR3 as set forth in SEQ ID Nos.: 318-320, respectively. Another aspect provides that the administered antibody contains HCDR1, HCDR2 and LCDR1 as set forth in SEQ ID Nos.: 318, 319 and 321, respectively. Another aspect provides that the administered antibody contains HCDR1, HCDR2 and LCDR2 as set forth in SEQ ID Nos.: 318, 319 and 322, respectively. Another aspect provides that the administered antibody contains HCDR1, HCDR2 and LCDR3 as set forth in SEQ ID Nos.: 318, 319 and 323, respectively. Another aspect provides that the administered antibody contains HCDR1, HCDR3 and LCDR1 as set forth in SEQ ID Nos.: 318, 320 and 321, respectively. Another aspect provides that the administered antibody contains HCDR1, HCDR3 and LCDR2 as set forth in SEQ ID Nos.: 318, 320 and 322, respectively. Another aspect provides that the administered antibody contains HCDR1, HCDR3 and LCDR3 as set forth in SEQ ID Nos.: 318, 320 and 323, respectively. Another aspect provides that the administered antibody contains HCDR1, LCDR1 and LCDR2 as set forth in SEQ ID Nos.: 318, 322 and 323, respectively. Another aspect provides that the administered antibody contains HCDR1, LCDR1 and LCDR3 as set forth in SEQ ID Nos.: 318, 321 and 323, respectively. Another aspect provides that the administered antibody contains HCDR1, LCDR2 and LCDR3 as set forth in SEQ ID Nos.: 318, 322 and 323, respectively. Another aspect provides that the administered antibody contains HCDR2, HCDR3 and LCDR1 as set forth in SEQ ID Nos.: 319, 320 and 321, respectively. Another aspect provides that the administered antibody contains HCDR2, HCDR3 and LCDR2 as set forth in SEQ ID Nos.: 319, 320 and 322, respectively. Another aspect provides that the administered antibody contains HCDR2, HCDR3 and LCDR3 as set forth in SEQ ID Nos.: 319, 320 and 323, respectively. Another aspect provides that the administered antibody contains HCDR2, LCDR1 and LCDR2 as set forth in SEQ ID Nos.: 319, 321 and 322, respectively. Another aspect provides that the administered antibody contains HCDR2, LCDR1 and LCDR3 as set forth in SEQ ID Nos.: 319, 321 and 323, respectively. Another aspect provides that the administered antibody contains HCDR2, LCDR2 and LCDR3 as set forth in SEQ ID Nos.: 319, 322 and 323, respectively. Another aspect provides that the administered antibody contains HCDR3, LCDR1 and LCDR2 as set forth in SEQ ID Nos.: 320, 321 and 322, respectively. Another aspect provides that the administered antibody contains HCDR3, LCDR1 and LCDR3 as set forth in SEQ ID Nos.: 320, 321 and 323, respectively. Another aspect provides that the administered antibody contains HCDR3, LCDR2 and LCDR3 as set forth in SEQ ID Nos.: 320, 322 and 323, respectively. Another aspect provides that the administered antibody contains LCDR1, LCDR2 and LCDR3 as set forth in SEQ ID Nos.: 321-323, respectively. Yet another aspect provides that the administered antibody contains HCDR1, HCDR2, HCDR3 and LCDR1 as set forth in SEQ ID Nos.: 318-321, respectively. Another aspect provides that the administered antibody contains HCDR1, HCDR2, HCDR3 and LCDR2 as set forth in SEQ ID Nos.: 318-320 and 322, respectively. Another aspect provides that the administered antibody contains HCDR1, HCDR2, HCDR3 and LCDR3 as set forth in SEQ ID Nos.: 318-320 and 323, respectively. Another aspect provides that the administered antibody contains HCDR1, HCDR2, LCDR1 and LCDR2 as set forth in SEQ ID Nos.: 318, 319, 321 and 322, respectively. Another aspect provides that the administered antibody contains HCDR1, HCDR2, LCDR1 and LCDR3 as set forth in SEQ ID Nos.: 318, 319, 321 and 323, respectively. Another aspect provides that the administered antibody contains HCDR1, HCDR2, LCDR2 and LCDR3 as set forth in SEQ ID Nos.: 318, 319, 322 and 323, respectively. Another aspect provides that the administered antibody contains HCDR1, HCDR3, LCDR1 and LCDR2 as set forth in SEQ ID Nos.: 318, 320, 321 and 322, respectively. Another aspect provides that the administered antibody contains HCDR1, HCDR3, LCDR1 and LCDR3 as set forth in SEQ ID Nos.: 318, 320, 321 and 323, respectively. Another aspect provides that the administered antibody contains HCDR1, HCDR3, LCDR2 and LCDR3 as set forth in SEQ ID Nos.: 318, 320, 322 and 323, respectively. Another aspect provides that the administered antibody contains HCDR1, LCDR1, LCDR2 and LCDR3 as set forth in SEQ ID Nos.: 318, 321, 322 and 323, respectively. Another aspect provides that the administered antibody contains HCDR2, HCDR3, LCDR1 and LCDR2 as set forth in SEQ ID Nos.: 319-322, respectively. Another aspect provides that the administered antibody contains HCDR2, HCDR3, LCDR1 and LCDR3 as set forth in SEQ ID Nos.: 319-321 and 323, respectively. Another aspect provides that the administered antibody contains HCDR2, HCDR3, LCDR2 and LCDR3 as set forth in SEQ ID Nos.: 319, 320, 322 and 323, respectively. Another aspect provides that the administered antibody contains HCDR2, LCDR1, LCDR2 and LCDR3 as set forth in SEQ ID Nos.: 319, 321, 322 and 323, respectively. Another aspect provides that the administered antibody contains HCDR3, LCDR1, LCDR2 and LCDR3 as set forth in SEQ ID Nos.: 320-323, respectively. Yet another aspect provides that the administered antibody contains HCDR1, HCDR2, HCDR3, LCDR1 and LCDR2 as set forth in SEQ ID Nos.: 318-322 respectively. Another aspect provides that the administered antibody contains HCDR1, HCDR2, HCDR3, LCDR1 and LCDR3 as set forth in SEQ ID Nos.: 318-321 and 323 respectively. Another aspect provides that the administered antibody contains HCDR1, HCDR2, HCDR3, LCDR2 and LCDR3 as set forth in SEQ ID Nos.: 318-320, 322 and 323 respectively. Another aspect provides that the administered antibody contains HCDR1, HCDR2, LCDR1, LCDR2 and LCDR3 as set forth in SEQ ID Nos.: 318, 319, 321-323, respectively. Another aspect provides that the administered antibody contains HCDR1, HCDR3, LCDR1, LCDR2 and LCDR3 as set forth in SEQ ID Nos.: 318, 320-323, respectively. Another aspect provides that the administered antibody contains HCDR2, HCDR3, LCDR1, LCDR2 and LCDR3 as set forth in SEQ ID Nos.: 319-323, respectively. Yet another aspect provides that the administered antibody contains HCDR1, HCDR2, HCDR3, LCDR1, LCDR2 and LCDR3 as set forth in SEQ ID Nos.: 318-323, respectively.

Methods are provided of treating or reducing the severity or likelihood of SLE in a subject, or of atherosclerosis in a subject with SLE, including administering to the subject an effective amount of an antibody or antibody fragment that binds a fragment set forth in SEQ ID NO: 45 of apoB100, and the antibody contains a variable heavy region ($V_H$) as set forth in SEQ ID NO: 324 and a variable light region ($V_L$) containing LCDR1, LCDR2 and LCDR3 as set forth in SEQ ID Nos.: 321-323, respectively. A further aspect provides that the method of treating or reducing the severity of SLE in a subject, or of atherosclerosis in a subject with SLE, and/or provide passive immunity, includes administering to the subject an effective amount of an antibody or antibody fragment that binds a fragment set forth in SEQ ID NO: 45 of apoB100, and the antibody contains a variable light region ($V_L$) of SEQ ID NO: 325 and a variable heavy region ($V_H$) that contains HCDR1, HCDR2 and HCDR3 as set forth in SEQ ID Nos.: 318-320, respectively. Yet another aspect of the invention provides that the method of treating, reducing the severity or likelihood of SLE in a subject, or of atherosclerosis in a subject with SLE, includes administering to the subject an effective amount of an antibody or antibody fragment that binds a fragment set forth in SEQ ID NO: 45 of apoB100, and the antibody contains a variable heavy region ($V_H$) of SEQ ID NO: 324 and a variable light region ($V_L$) of SEQ ID NO:325.

Methods are also provided of treating or reducing the severity or likelihood of SLE in a subject, or of atherosclerosis in a subject with SLE, which includes administering to the subject an effective amount of an antibody or antibody fragment that binds a fragment set forth in SEQ ID NO: 45 of apoB100, and the antibody contains a heavy chain of SEQ ID NO: 316 and a light chain containing LCDR1, LCDR2 and LCDR3 as set forth in SEQ ID Nos.: 321-323, respectively. A further aspect of the embodiment provides that the method includes administering to the subject an effective amount of an antibody or antibody fragment that binds a fragment set forth in SEQ ID NO: 45 of apoB100, and the antibody contains a heavy chain of SEQ ID NO: 316 and a light chain that contains a variable light region ($V_L$) of SEQ ID NO: 325. Another aspect of the invention provides the method includes administering to the subject an effective amount of an antibody or antibody fragment that binds a fragment set forth in SEQ ID NO: 45 of apoB100, and the antibody contains a light chain of SEQ ID NO: 317 and a heavy chain that contains HCDR1, HCDR2 and HCDR3 as set forth in SEQ ID Nos.: 318-320, respectively. Yet another aspect provides the method includes administering to the subject an effective amount of an antibody or antibody fragment that binds a fragment set forth in SEQ ID NO: 45 of apoB100, and the antibody contains a light chain of SEQ ID NO: 317 and a heavy chain that contains a variable heavy region ($V_H$) of SEQ ID NO: 324. Alternatively, the method includes administering to the subject an effective amount of an antibody or antibody fragment that binds a fragment set forth in SEQ ID NO: 45 of apoB100, and the antibody contains a heavy chain of SEQ ID NO: 316 and a light chain of SEQ ID NO: 317.

Further embodiments of the methods include administering an inhibitor of native LDL, oxidized LDL (oxLDL) or MDA-modified LDL, which are suitable for treatment of a subject diagnosed with SLE and reducing the severity or likelihood of SLE, and optionally also reducing the severity or the likelihood of developing atherosclerosis in a subject with SLE. In one embodiment, the inhibitor is an anti-oxLDL antibody or an antigen-binding fragment thereof capable of binding an oxidized fragment of apolipoprotein B100. In another embodiment, the inhibitor of oxidized LDL is a small molecule, a polypeptide, a peptide, or a nucleic acid molecule, which is capable of binding an oxidized fragment of apolipoprotein B100. In other embodiments, the inhibitor of oxidized LDL is an antibody or an antigen-binding fragment capable of binding a malondialdehyde-modified LDL. In exemplary embodiments, the inhibitor of oxidized or malondialdehyde-modified LDL is a monoclonal antibody, such as orticumab, targeting an oxidized or MDA-modified form of a LDL.

Patient Selection

The methods disclosed herein, in some embodiments, include treating or inhibiting one or more forms of SLE, or of atherosclerosis in a subject with SLE, with administering an effective amount of orticumab to a subject in need thereof.

Some embodiments provided in the disclosed methods further include selecting a subject showing symptoms of SLE or having been diagnosed with SLE. For example, subjects with SLE can be characterized by having a positive test for antinuclear antibody (ANA) in combination with one or more symptoms such as rash (e.g., malar rash, discoid skin rash), arthritis, or edema in the ankles; having an abnormal sound called a heart friction rub or pleural friction rub; having an abnormally high creatinine; photosensitivity, mucous membrane ulcers, arthritis, pleuritic or pericarditis, kidney abnormalities, brain irritation, blood-count abnormalities, immunologic disorder, and positive antinuclear antibodies in the blood.

Also provided with the methods are embodiments where the subject does not have, has not been diagnosed with, or does not show symptoms of atherosclerosis.

Combination Therapy

Further embodiments provide that the methods of treating or reducing the severity or likelihood of SLE in a subject, or of atherosclerosis in a subject with SLE, include administering an effective amount of an antibody or antibody fragment in combination with another therapeutic agent to the subject. Exemplary therapeutic agents for use in this combination include an anti-malarial therapeutic (e.g., hydroxychloroquine), glucocorticoid, mycophenolate mofetil, or a disease-modifying antirheumatic drug (DMARD; such as azathioprine, cyclophosphamide, cyclosporine, hydroxychloroquine sulfate, leflunomide, methotrexate, mycophenolate mofetil, and sulfasalazine).

The methods may also include administering an antibody or antibody fragment that binds SEQ ID NO:45, another therapeutic agent, and commonly used adjuvants to enhance absorption of the antibody or mixture of antibodies.

In various embodiments, the composition to be administered in the disclosed methods are formulated for delivery via any route of administration. For example, the methods include administration via an aerosol, nasal, oral, transmucosal, transdermal, parenteral or enteral route. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection.

Dosage

Typically, an effective amount of the anti-oxLDL or an anti-LDL antibody, or the antibody that binds SEQ ID NO:45, in the method disclosed herein, results in a plasma concentration of at least 4 µg/mL, preferably at least 12 µg/mL in the subject.

Embodiments provide the method of treating or reducing the severity of SLE in a subject, or of atherosclerosis in a subject with SLE, in a subject includes administering to the subject an antibody or antibody fragment disclosed above subcutaneously at about 330 mg/month for about 3, 4, 5, 6, 7, 8, 9, 10, 11 or 12 months or longer, and the subject is an adult human.

Other embodiments provide administering the antibody or antibody fragment to treat SLE, or treat atherosclerosis in a subject with SLE, or provide passive immunity at least 5, 6, 7, or 8 mg orticumab/kg of a patient (e.g., 664 mg for an averaged human patient of 83 kg). Some embodiments provide administering the antibody or antibody fragment at between 5 mg orticumab/kg of a patient (e.g., 415 mg for an averaged human patient of 83 kg) and 8 mg/kg. Some embodiment provides administering orticumab at a monthly dosing regimen at the above-mentioned dosage.

Other embodiments provide administering the antibody or antibody fragment to treat SLE, or treat atherosclerosis in a subject with SLE, weekly at no less than 2 mg/kg/week (166 mg for an averaged human patient of 83 kg); preferably, 4 mg/kg/week (332 mg for an averaged human patient of 83 kg). In another aspect, the composition of an anti-oxLDL antibody is administered biweekly at >2.5 mg/kg/two weeks (e.g., 208 mg for an averaged human patient of 83 kg). In yet another aspect, the composition of an anti-oxLDL antibody is administered monthly at about 6 mg/kg/month (e.g., about 498 mg for an averaged human patient of 83 kg). For example, the monthly dosing may be carried out for 12 months or 3 months.

Yet other embodiments provide administering an antibody or antibody fragment to treat SLE, or treat atherosclerosis in a subject with SLE, with at least an initial dose of 800-900 mg, 900-1000 mg, 1000-1100 mg, 1100-1200 mg, 1200-1300 mg, 1300-1400 mg, 1400-1500 mg, or 1500-1600 mg. In some aspects, the effective amount in the method described herein includes an initial dose of orticumab of approximately 1000-1500 mg, followed by subsequent doses of the antibody at 700-900 mg administered weekly for 2, 3, 4 or 5 weeks and/or even administered monthly for 1, 2 or 3 months.

Other embodiments provide administering step-wise escalating doses of an antibody against native or oxidized LDL (e.g., binding SEQ ID NO:45). In this embodiment, an exemplary (starting) dose of a single-dose administration of an antibody (e.g., orticumab) against native or oxidized LDL is between 0.005 and 0.01 mg/kg (e.g., intravenously); and other exemplary dosage levels to be administered in the single-dose administration are between 0.01 and 0.15, between 0.15 and 0.75, between 0.75 and 2.5 and 7.5, and between 7.5 and 30 mg/kg (e.g., intravenously).

For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of an antibody against native or oxidized LDL is between 0.5 and 5 mg/kg, and a multiple-dose subcutaneous administration is also between 0.5 and 5 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (such as orticumab) against native or oxidized LDL is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion.

Further embodiments include administering to a subject an effective amount of an antibody or antibody fragment that binds SEQ ID NO:45 and having a sequence of one or more of SEQ ID Nos: 316-325, which is in the range of about 10-50 µg/period, 50-100 µg/period, 100-150 µg/period, 150-200 µg/period, 100-200 µg/period, 200-300 µg/period, 300-400 µg/period, 400-500 µg/period, 500-600 µg/period, 600-700 µg/period, 700-800 µg/period, 800-900 µg/period, 900-1000 µg/period, 1000-1100 µg/period, 1100-1200 µg/period, 1200-1300 µg/period, 1300-1400 µg/period, 1400-1500 µg/period, 1500-1600 µg/period, 1600-1700 µg/period, 1700-1800 µg/period, 1800-1900 µg/period, 1900-2000 µg/period, 2000-2100 µg/period, 2100-2200 µg/period, 2200-2300 µg/period, 2300-2400 µg/period, 2400-2500 µg/period, 2500-2600 µg/period, 2600-2700 µg/period, 2700-2800 µg/period, 2800-2900 µg/period or 2900-3000 µg/period. A period is a day, a week, a month, or another length of time. One aspect is the antibody (e.g., orticumab) is administered at a weekly, biweekly or monthly frequency of any of above-mentioned dosage per period.

In some embodiments, the methods include administering an inhibitor of oxidized LDL (e.g., orticumab) to the subject for 1-5 days, 1-5 weeks, 1-5 months, or 1-5 years. For example, the antibody is administered to the subject in 3, 4, 5, 6, 7, 8, 9, 10, 11, 12, 13, 14, 15, 16, 17, 18, 19 or 20 doses, each dose separated by at least 3 days, 5 days, one week, two weeks, one month, two months, or a combination thereof. In other embodiments, the second dose is administered about 2-3 weeks, or about 3 weeks after the first dose and the third dose is administered about 5-6 weeks or about 6 weeks after the first dose, etc. In another embodiment, the second dose is administered about 2-3 months, about 2 months, about 3 months or about 4 months after the first dose and the third dose is administered about 4-6 months, about 5-6 months, about 5 months or about 6 months after the first dose.

Other embodiments provide administering step-wise escalating doses of an antibody against native or oxidized LDL to treat SLE, or treat atherosclerosis in a subject with SLE, or provide passive immunity. In this embodiment, an exemplary (starting) dose of a single-dose administration of an antibody (e.g., orticumab) against native or oxidized LDL is between 0.005 and 0.01 mg/kg (e.g., intravenously); and other exemplary dosage levels to be administered in the single-dose administration are between 0.01 and 0.15, between 0.15 and 0.75, between 0.75 and 2.5, between 2.5 and 7.5, and between 7.5 and 30 mg/kg (e.g., intravenously). For example, a starting dose of orticumab in a single-dose intravenous administration is 0.007 mg/kg; and other exemplary dosages can be 0.05, 0.25, 1.25, 5.0 or 15.0 mg/kg in subsequent single-dose intravenous administration. In another embodiment, a single-dose subcutaneous administration of an antibody against native or oxidized LDL is between 0.5 and 5 mg/kg, and a multiple-dose subcutaneous administration is also between 0.5 and 5 mg/kg. For example, an antibody against native or oxidized LDL at 1.25 mg/kg is administered subcutaneously. In various embodiments, the dosage is administered within a specified hour range of the day in each administration, and each dose in a multiple-dose treatment (e.g., 4 doses, 3 doses, 5 doses, or 6 doses) is administered at weekly intervals with a time window of ±1 day. In another example, an antibody (such as orticumab) against native or oxidized LDL is administered at between 300 mg and 450 mg (e.g., 360 mg) to a human subject, optionally followed by another dose between 300 mg and 450 mg (e.g., 360 mg) to the human subject where the second dose is at least 70 days (up to 91 days) apart from the first dose. The antibody (such as orticumab) may be formulated at a concentration of 100-170 mg/mL (e.g., 150 mg/mL) and for use in subcutaneous administration without further dilution, or diluted to a large volume for intravenous infusion. In some embodiments, the therapeutically effective amount of an anti-LDL antibody or an anti-oxLDL antibody, or analogs, pharmaceutical equivalents or a peptidomimetics thereof, for use with the methods described herein is per dose: 1-10 µg/kg, 10-100 µg/kg, 100-500 µg/kg, 200-500 µg/kg, 300-500 µg/kg, 400-500 µg/kg, 1-5 mg/kg, 5-10 mg/kg, 10-15 mg/kg, 15-20 mg/kg, 20-25 mg/kg, 25-50 mg/kg, 50-75 mg/kg of the subject; where each dose is administered daily, weekly, monthly, or at other intervals.

In some embodiments, an instruction manual for use, a vial for diluent, or both are also included in the kit, in addition to the one or the plurality of vials/doses of the antibody or antibody fragment to treat SLE or treat atherosclerosis in a subject diagnosed with SLE.

Pharmaceutical Composition or Medicaments

In various embodiments, the present invention provides a pharmaceutical composition for use in the methods of treating, reducing the severity or likelihood of SLE in a subject, or of atherosclerosis in a subject with SLE, described herein. The pharmaceutical composition includes an inhibitor of oxidized LDL, such as an anti-oxLDL antibody that binds to an epitope of SEQ ID NO:45 of ApoB100, and a pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof. Generally, each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Further embodiments provide that a composition or medicament for use in treating, reducing the severity of, or promoting prophylaxis of SLE, or treating, reducing the severity of, or promoting prophylaxis atherosclerosis in a subject exhibiting symptoms of or having been diagnosed with SLE, where the composition of medicament contains an anti-oxLDL antibody that binds to an epitope of SEQ ID NO:45 of ApoB100, as disclosed above, in an amount of between 300 mg and 400 mg, preferably about 330 mg, per dosage (or vial), optionally with a pharmaceutically acceptable carrier, each (e.g., for a monthly subcutaneous administration to a subject) for 1, 2, 3, 4, 5, 6, 7, 8, 9, 10, 11, 12 months or longer. Other embodiments provide the composition or medicament contains an anti-oxLDL antibody that binds to an epitope of SEQ ID NO:45 of ApoB100, as disclosed above, in an amount of at least 5, 6, 7, or 8 mg orticumab/kg of a patient in one dosage (or vial), and optionally more dosages (or vials) of at least 2 mg/kg/week, at least 2.5 mg/kg/two weeks, or at least 6 mg/kg/month, for 3, 4, 5, 6, 7, 8, 9, 10, 11, 12 months or longer. Further embodiments provide the composition or medicament contains the antibody (such as orticumab) at a concentration of 100-170 mg/mL (e.g., 150 mg/mL) and for use in subcutaneous administration without further dilution, or diluted to a large volume for intravenous infusion.

Prepare Antibodies in the Methods

In some embodiments, the aforementioned methods involve antibodies that bind to a specific antigen epitope, where the antibodies contain one or more defined sequences. For example, modern recombinant library technology is used to prepare therapeutic antibodies against native ApoB, oxidized ApoB or MDA-modified ApoB. While murine hybridomas cells produce large amounts of identical antibodies, these non-human antibodies are recognized by human body as foreign, and as a consequence, their efficacy and plasma half-lives are decreased in addition to eliciting allergic reactions. To solve this problem, one approach is to make chimeric antibodies where the murine variable domains of the antibody are transferred to human constant regions resulting in an antibody that is mainly human. A further refinement of this approach is to develop humanized antibodies where the regions of the murine antibody that contacted the antigen, the so called Complementarity Determining Regions (CDRs) are transferred to a human antibody framework, resulting in a humanized antibody. Another approach is to produce completely human antibodies using recombinant technologies, which does not rely on immunization of animals to generate the specific antibody. Instead recombinant libraries comprise a huge number of pre-made antibody variants and it is likely that a library will have at least one antibody specific for any antigen. A phage display system may be used where antibody fragments are expressed, displayed, as fusions with phage coat proteins on the surface of filamentous phage particles, while the phage display system simultaneously carries the genetic information encoding the displayed molecule. Phage displaying antibody fragments specific for a particular antigen may be selected through binding to the antigen in question. Isolated phage may then be amplified and the gene encoding the selected antibody variable domains may optionally be transferred to other antibody formats as e.g. full length immunoglobulin and expressed in high amounts using appropriate vectors and host cells well known in the art. The format of displayed antibody specificities on phage particles may differ. The most commonly used formats are Fab and single chain (scFv) both containing the variable antigen binding domains of antibodies. The single chain format is composed of a variable heavy domain ($V_H$) linked to a variable light domain ($V_L$) via a flexible linker. Before use as analytical reagents, or therapeutic agents, the displayed antibody specificity is transferred to a soluble format, e.g., Fab or scFv, and analyzed as such. In later steps the antibody fragment identified to have desirable characteristics may be transferred into yet other formats such as full length antibodies.

Antibody Production Using Hybridomas

The cell fusions are accomplished by standard procedures well known to those skilled in the field of immunology. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

An anti-oxidized LDL antibody can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

Recombinant Expression of Anti-Oxidized LDL Antibodies

Recombinant murine or chimeric murine-human or human-human antibodies that inhibit oxidized LDL can be provided according to the present invention using known techniques based on the teaching provided herein. See, e.g., Ausubel et al., eds. Current Protocols in Molecular Biology, Wiley Interscience, N.Y. (1987, 1992, 1993); and Sambrook et al. Molecular Cloning: A Laboratory Manual, Cold Spring Harbor Laboratory Press (1989).

The DNA encoding an anti-oxidized LDL antibody can be genomic DNA or cDNA which encodes at least one of the heavy chain constant region (Hc), the heavy chain variable region (Hc), the light chain variable region (Lv) and the light chain constant regions (Lc). A convenient alternative to the use of chromosomal gene fragments as the source of DNA encoding the murine V region antigen-binding segment is the use of cDNA for the construction of chimeric immunoglobulin genes, e.g., as reported by Liu et al. (Proc. Natl. Acad. Sci., USA 84:3439 (1987) and J. Immunology 139: 3521 (1987). The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1. Efficacy Study of CVX-12 in Female GLD.APOE$^{-/-}$ Mice

The inventors tested the athero-protective effects of the prototype vaccine, CVX-210-B (CVX-12), comprised of a human ApoB100 derived peptide, P210, conjugated to a carrier protein (cBSA), and formulated with an adjuvant (Alum) in selected strains of mice.

As described herein, the ApoB peptide vaccine CVX-12 has shown atheroprotective benefits in mouse models of atherosclerosis. We hypothesized that these benefits would extend to mouse models of lupus with accelerated atherosclerosis (gld and gld.apoE−/− strains), and we investigated the impact of CVX-12 (Formulation 21 (CVX-210-B) formulated at 1.0 mg conjugate/mL: P-C-A ratio is 1-1-6.9; 0.2 mL administered) immunization on atherosclerosis, splenocyte immune cell populations and cytokine production, and autoimmune disease phenotypes in these animals. CVX-12 immunization reduced the extent of atherosclerotic plaque in apoE−/− mice. Anti-nuclear antibody reactivity was reduced by CVX-12 in gld.apoE−/− mice maintained on normal chow diet.

The gld.apoE−/− mouse strain is an acceptable model of accelerated atherosclerosis in the background of systemic lupus erythematosus. The test article used in this study was to determine its potential atheroprotective effect in this model.

Experimental Methods

CVX-12 in concentration of either 2 mg/ml P210 conjugate (CVX-3-84) or 2.1 mg/ml P210-B conjugate (CVX-3-123) were used in this study. Rosiglitazone (Ro) was used as a positive control.

Vehicle and test article were stored at 4° C. Test article was prepared by dispensing 0.5 mL of alum adjuvant into a 0.5 ml vial of P210-B with a sterile syringe. The combination was mixed by pipetting until uniform. Alum control was directly administered from the storage vial.

The rosiglitazone to be used as in-house positive control was prepared for administration in normal chow diet. 8 mg rosiglitazone tablets were pulverized by mortar and pestle and incorporated into normal diet chow (50 mg rosiglitazone/1 kg food). Rosiglitazone diet was stored at 4° C.

Experimental Design

Three strains of female mice were evaluated in this study: ApoE$^{-/-}$ (n=60), gld (n=60) and gld.ApoE$^{-/-}$ (n=200). The total number of animals on study was 320. Gld mice are mice that have a mutation in Fas ligand (FasL), a death factor that binds to its receptor, Fas, and induces apoptosis. Gld mice experience accelerated autoimmune disease and may be used as a mouse species to study SLE.

Mice received either normal chow diet or a combination of normal and high cholesterol chow diet (0.20% cholesterol, 21% fat). In the latter group, 150 female mice, 60 ApoE$^{-/-}$ and 90 gld.ApoE$^{-/-}$, were maintained on normal chow diet throughout the immunization period from Day 0 (7 weeks of age) until Day 41. At Day 42, the diet was switched to high cholesterol chow and continued until euthanasia. In the normal chow-only group, 170 female mice, 60 gld and 90 gld.ApoE$^{-/-}$, plus an additional 20 gld.ApoE$^{-/-}$ as a positive control group, received a normal chow diet for the duration of the study (Day 0 until euthanasia).

Each animal dosed with a test article received subcutaneous primary immunization in the dorsal interscapular area at Day 0 (7 weeks of age), followed by a booster on Day 21 and 35 (10 and 12 weeks of age). CVX-3-84 was used to dose ApoE$^{-/-}$ (n=20), gld mice (n=20). CVX-3-123 was used to dose gld.ApoE$^{-/-}$ (n=30 on high cholesterol chow; n=30 on normal chow diet).

20 gld.ApoE$^{-/-}$ mice in the positive control group received an oral dose of rosiglitazone at 10 mg/kg/day in normal chow starting on Day 0 (7 weeks of age) and continuing for the duration of the study period. Mice receiving Rosiglitazone were sacrificed at Day 126 (25 weeks of age).

Gld, ApoE$^{-/-}$, and gld.ApoE$^{-/-}$ mice on normal diet were euthanized on Day 126 (25 weeks of age). Gld.ApoE$^{-/-}$ on high cholesterol chow diet were sacrificed at either Day 126 (25 weeks of age) or Day 98 (21 weeks of age). Due to severe disease observed in the gld.ApoE$^{-/-}$ strain of mice receiving the high cholesterol diet, the duration of the in-life period for this group was reduced from 126 days (25 weeks of age) to 98 days (21 weeks of age). As a result of the earlier endpoint for these mice, the time on the high cholesterol diet was reduced from 84 days to 56 days.

All apoE$^{-/-}$ and gld study mice (n=60 each) had a 1 week period of acclimation before study enrollment.

Mice were enrolled into the study based on their date of birth, and age-matched mice were divided among the test article and control cohorts (i.e., PBS, Alum, and CVX-12) to supply date-matched controls at each endpoint date. The health of all mice was monitored by veterinary staff on a daily basis.

Animals were dosed according to the schedule in Table 2:

TABLE 2

Test Article Administration

| Mouse Model | N (320) | Diet | Formuation # | Test Article | Conjugate (mg/mL) | Conjugate (mg/admin) | Aluminum (mg/admin) | Dose Volume (mL) | Admin. Sequence (day) | Sacrifice (day) |
|---|---|---|---|---|---|---|---|---|---|---|
| ApoE$^{-/-}$ | 20 | Normal Diet day 0-41 HC Diet day 42-126 | A | PBS Control | 0 | 0 | 0 | 0.2 | 0, 21, 35 | 126 |
| ApoE$^{-/-}$ | 20 | Normal Diet day 0-41 HC Diet day 42-126 | B | Alum Control | 0 | 0 | 1.38 | 0.2 | 0, 21, 35 | 126 |
| ApoE$^{-/-}$ | 20 | Normal Diet day 0-41 HC Diet day 42-126 | 21 | CVX-210-B | 1.0 | 0.2 | 1.38 | 0.2 | 0, 21, 35 | 126 |
| Gld | 20 | Normal Diet day 0-126 | A | PBS Control | 0 | 0 | 0 | 0.2 | 0, 21, 35 | 126 |
| Gld | 20 | Normal Diet day 0-126 | B | Alum Contol | 0 | 0 | 1.38 | 0.2 | 0, 21, 35 | 126 |
| Gld | 20 | Normal Diet day 0-126 | 21 | CVX-210-B | 1.0 | 0.2 | 1.38 | 0.2 | 0, 21, 35 | 126 |
| gld.ApoE$^{-/-}$ | 30 | Normal Diet day 0-41 HC Diet day 42-98 | A | PBS Control | 0 | 0 | 0 | 0.2 | 0, 21, 35 | 98 or 126 $^a$ |
| gld.ApoE$^{-/-}$ | 30 | Normal Diet day 0-41 HC Diet day 42-98 | B | Alum Control | 0 | 0 | 1.38 | 0.2 | 0, 21, 35 | 98 or 126 $^a$ |
| gld.ApoE$^{-/-}$ | 30 | Normal Diet day 0-41 HC Diet day 42-98 | 21 | CVX-210-B | 1.0 | 0.2 | 1.38 | 0.2 | 0, 21, 35 | 98 or 126 $^a$ |
| gld.ApoE$^{-/-}$ | 30 | Normal Diet day 0-126 | A | PBS Control | 0 | 0 | 0 | 0.2 | 0, 21, 35 | 126 |
| gld.ApoE$^{-/-}$ | 30 | Normal Diet day 0-126 | B | Alum Control | 0 | 0 | 1.38 | 0.2 | 0, 21, 35 | 126 |
| gld.ApoE$^{-/-}$ | 30 | Normal Diet day 0-126 | 21 | CVX-210-B | 1.0 | 0.2 | 1.38 | 0.2 | 0, 21, 35 | 126 |
| gld.ApoE$^{-/-}$ | 20 | Normal Diet day 0-126 | R | Rosiglitazone* | 0 | 0 | 0 | * | 0-126 | 126 |

In Table 2 above: 1) Alum (Imject Alum) adjuvant stock solution is prepared using a 50% dilution to a concentration of 6.9 mg Al/mL in order to standardize administered dose volumes. 2) Formulation 21 (CVX-210-B) formulated at 1.0 mg conjugate/mL: P-C-A (peptide, conjugate, adjuvant) ratio is 1-1-6.9. Formulation A is PBS control. Formulation B is Alum. 3) An asterisk (*) denotes: *Positive Control (Rosiglitazone) to be administered orally in normal chow at a dose of 10 mg/kg/day. 4) A superscript "a" denotes: $^a$Due to high stress levels demonstrated in the gld.ApoE$^{-/-}$ strain of mice receiving the high cholesterol diet, the duration of the in-life period for this group was reduced from 126 days (25 weeks of age) to 98 day (21 weeks of age). Similarly, the time on the high cholesterol diet was reduced from 84 days to 56 days.

Cageside Observations:

All animals were observed for morbidity, mortality, injury, and the availability of food and water at least twice daily. On occasion, veterinary consultations were conducted during the course of the study. All treatments and observations were recorded.

Detailed Clinical Observations:

Clinical observations were recorded on the day of dosing, three days after dosing, and weekly between doses.

Body Weights:

Body weights for all animals were measured and recorded prior to randomization and weekly during the study. Food intake was measured on a weekly basis per cage, and intake was calculated per mouse.

Physical Examinations:

A complete physical examination was conducted on all animals by a staff veterinarian pretest.

Serum Analysis:

Serum and urine was collected at day 63 of the study (16 weeks of age). Serum collected at day 63 of the study was analyzed for anti-P210 IgM and IgG antibodies. Levels of oxidized phospholipid was also measured in gld.apoE$^{-/-}$ mice maintained on normal diet.

Postmortem Study Evaluations:

Serum and urine was collected at euthanasia. Endpoint serum was analyzed for anti-nuclear antibody (ANA) titers, total cholesterol, triglycerides, anti-P210 IgM antibodies, and anti-P210 IgG antibodies. Endpoint serum from gld.A-poE$^{-/-}$ animals maintained on normal diet was also analyzed for anti-cardiolipin antibodies. Anti-nuclear antibody titers were tested using the NOVA-lite Hep2 ANA assay, and serum dilutions of 1:100, 1:1000, 1:10000, 1:30000, and 1:90000 were tested for nuclear-localized antibody reactivity to human epithelial cells. Reactivity was detected using FITC-conjugated goat anti-mouse IgG antibody. ANAs were scored based on the presence or absence of antibody signal at each titer. Total cholesterol was assessed using Cholesterol E reagent according to the manufacturer's protocol. Triglyceride levels were assessed with Triglyceride Reagent and with a glycerol standard. Anti-P210 antibodies were detected by ELISA using reconstituted P210 peptide.

Lymph nodes and spleen were harvested and weighed. Splenocytes were isolated and analyzed for T-regulatory cell populations by immunofluorescence staining and flow cytometry. Splenocytes were also cultured and T-cells activated in vitro by Mouse T-Activator CD3/CD28. Production of cytokines INF-γ, IL-6, IL-10, IL-12, and TGF-β by activated T-cells were assessed with immunoassays.

Kidneys were fixed, sectioned, and stained with hematoxylin and eosin to assess glomerular tuft size and cell count. Extent of atherosclerosis was quantified by oil red O stained en face prepared aorta, and oil red O stained aortic root sections.

Table 3 below defines the set of comparisons used in the statistical analyses on this study.

TABLE 3

Statistical Analysis Comparisons

| Group | Comparison Group |
| --- | --- |
| Formulation A (PBS controls) | All Formulation A groups from different mouse models |
| Formulation B (Alum) | All Formulation B groups from different mouse models |
| Formulation 21 (CVX-210-B or CVX-12) | All Formulation 21 groups from different mouse models |
| Within each mouse model | Formulation 21 vs. Formulation B vs. Formulation A |

Mortality:

2 apoE$^{-/-}$ mice and 1 gld mouse, on PBS or Alum treatments, were euthanized due to hunched posture and decreased mobility. 19 gld.apoE$^{-/-}$ mice on normal diet, 37 gld.apoE$^{-/-}$ mice on western diet, and 7 gld.apoE$^{-/-}$ mice on rosiglitazone treatment were euthanized due to health concerns or found dead prior to their scheduled sacrifice. Unscheduled deaths were distributed among the treatment groups (PBS, Alum, and CVX-12), and CVX-12 did not impact the incidence of unscheduled deaths.

Body and Organ Weights:

Body weight data are illustrated in FIG. 1. Average food consumption measurements are presented in FIG. 2. There were no test article-related body weight or food intake changes. All groups had fluctuations in body weight that are within the normal range for the species.

Anti-P210 IgM and IgG levels were assessed at the midpoint of the study (Day 63) and the endpoint (at euthanasia), and their levels in gld or apoE$^{-/-}$ did not change as a result of Alum or CVX-12 treatment (Table 4). Anti-P210 IgG levels in gld mice are intrinsically higher than IgG levels in apoE$^{-/-}$ mice. Overall anti-P210 IgM levels decreased over time in the apoE$^{-/-}$ mice between the midpoint and endpoint regardless of the treatment group (PBS, Alum, and CVX-12). On the contrary, anti-P210 IgG levels increased over time in the gld mice between the midpoint and endpoint analyses in all three treatment groups (PBS, Alum, and CVX-12).

TABLE 4

Relative anti-P210 antibody levels in gld mice and apoE−/− mice.
Values = anti-P210 OD at 405 nm ± SEM.

| | Midpoint | | Endpoint | |
| --- | --- | --- | --- | --- |
| | IgM | IgG | IgM | IgG |
| apoE$^{-/-}$ PBS | 3.37 ± 0.014 | 0.73 ± 0.19 | 2.60 ± 0.19 [a] | 0.47 ± 0.05 |
| apoE$^{-/-}$ Alum | 3.34 ± 0.15 | 1.27 ± 0.47 | 2.37 ± 0.19 [a] | 0.47 ± 0.06 |
| apoE$^{-/-}$ CVX-12 | 3.29 ± 0.14 | 0.90 ± 0.24 | 2.38 ± 0.22 [a] | 0.38 ± 0.04 [a] |
| gld PBS | 3.29 ± 0.14 | 1.28 ± 0.19 | 3.20 ± 0.19 | 2.75 ± 0.26 [a] |
| gld Alum | 3.78 ± 0.11 | 1.37 ± 0.53 | 3.34 ± 0.20 | 2.78 ± 0.27 [a] |
| gld CVX-12 | 3.23 ± 0.15 | 1.46 ± 0.22 | 3.61 ± 0.12 | 3.14 ± 0.20 [a] |

[a] $p < 0.05$ for midpoint vs endpoint

Anti-P210 antibodies did not increase in gld.apoE$^{-/-}$ mice immunized with CVX-12 (Table 5). Instead, immunization with CVX-12 decreased anti-P210 IgM in gld.apoE$^{-/-}$ mice on western diet. Rosiglitazone treatment had a similar effect on anti-P210 IgM antibodies, decreasing their levels in gld.apoE$^{-/-}$ relative to PBS-treated mice on either normal or high cholesterol diet protocols.

TABLE 5

Relative anti-P210 antibody levels in gld.apoE−/− mice.
Values = anti-P210 OD at 405 nm ± SEM.

| | Midpoint | | Endpoint | |
| --- | --- | --- | --- | --- |
| | IgM | IgG | IgM | IgG |
| gld.apoE$^{-/-}$ (ND) PBS | 0.60 ± 0.03 | 0.57 ± 0.05 | 0.58 ± 0.04 | 0.66 ± 0.06 |
| gld.apoE$^{-/-}$ (ND) Alum | 0.59 ± 0.02 | 0.55 ± 0.04 | 0.50 ± 0.03 [a] | 0.61 ± 0.04 |
| gld.apoE$^{-/-}$ (ND) CVX-12 | 0.62 ± 0.03 | 0.59 ± 0.05 | 0.53 ± 0.04 | 0.65 ± 0.04 |
| gld.apoE$^{-/-}$ (WD) PBS | 0.76 ± 0.04 [b] | 0.57 ± 0.06 | 0.66 ± 0.04 | 0.69 ± 0.04 |
| gld.apoE$^{-/-}$ (WD) Alum | 0.70 ± 0.02 [b] | 0.55 ± 0.05 | 0.61 ± 0.04 [a] | 0.76 ± 0.05 [a] |
| gld.apoE$^{-/-}$ (WD) CVX-12 | 0.64 ± 0.05 | 0.54 ± 0.06 | 0.53 ± 0.03 [c] | 0.69 ± 0.05 |
| Rosiglitazone | 0.64 ± 0.03 | 0.68 ± 0.07 | 0.42 ± 0.06 [a, c] | 0.68 ± 0.07 |

[a] $p < 0.05$ for midpoint vs endpoint.
[b] $p < 0.05$ for ND vs WD.
[c] $p < 0.05$ for treatment relative to PBS control.

Since peptides derived from ApoB100 are thought to be antigens for pathogenic T cells, it is thought that they can tolerize against these responses. As a readout, we would expect to see reduced antibodies to ApoB100-related antigens. Here measurements of apoB, oxidized phospholipid (OxPL), measure by E06 antibody, reveal a significant increase in oxPL with CVX-12 administration in gld.a- poE$^{-/-}$ mice on normal diet (FIG. 3), which demonstrates that the immunization had an effect.

Anti-Nuclear Antibody Titer.

Figure 4:
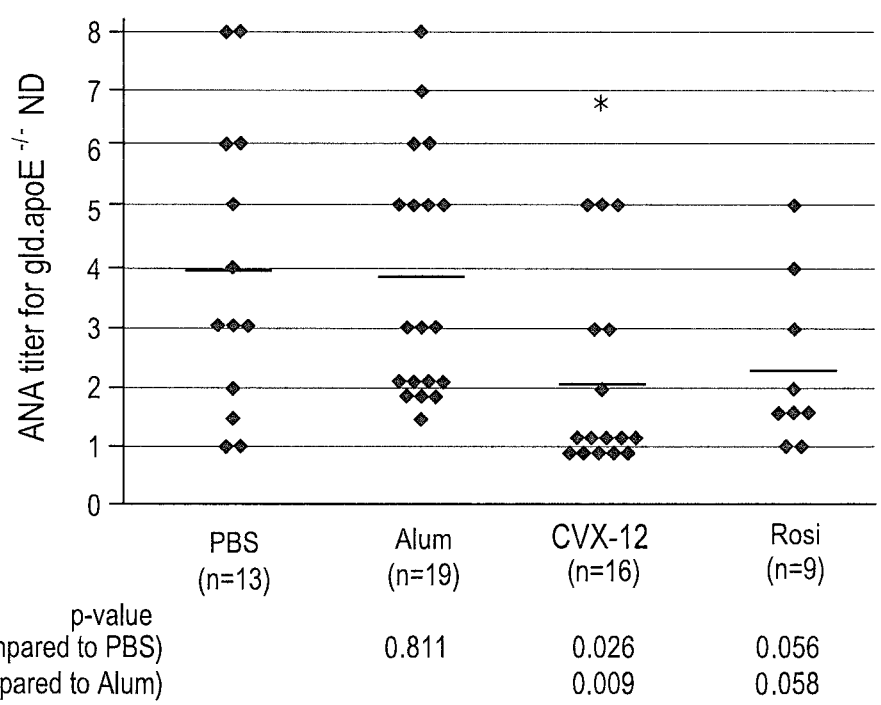
FIG. 4 depicts in accordance with various embodiments of the invention, anti-nuclear antibody reactivity detected in Example 1. Values correspond to the maximum serum dilution at which ANA reactivity is detectable, where 1=1:100, 2=1:1000, 4=1:10000, 6=1:30000, and 8=1:90000.
Figure 23:
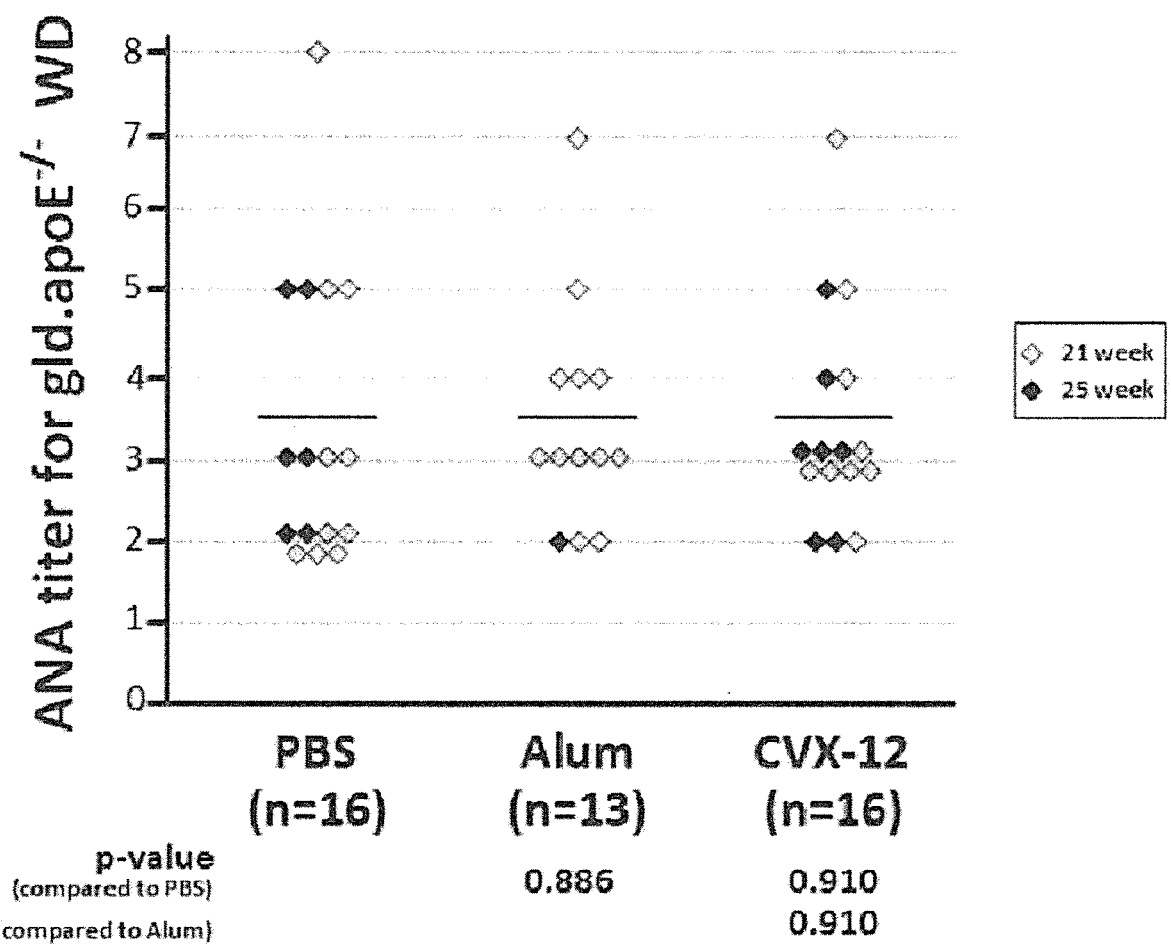
FIG. 23 depicts anti-nuclear antibody (ANA) reactivity in mice fed with western diet (WD) detected in Example 1. Values correspond to the maximum serum dilution at which ANA reactivity is detectable, where 1=1:100, 2=1:1000, 4=1:10000, 6=1:30000, and 8=1:90000.

CVX-12 immunization reduced the anti-nuclear antibody titer in gld.apoE$^{-/-}$ mice on normal diet (FIG. 4 compared to mice on western diet as shown in FIG. 23). This demonstrates that CVX-12 is beneficial for lupus disease, an application of which has not previously been tested.

Anti-Cardiolipin Analysis.

Figure 5:
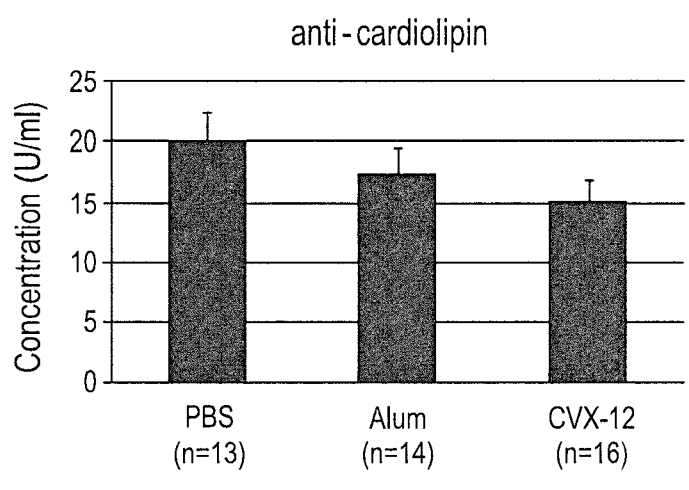
FIG. 5 depicts in accordance with various embodiments of the invention, serum anti-cardiolipin antibody reactivity. Anti-cardiolipin antibodies in serum of gld.apoE−/− mice on normal diet.
Figure 7A:
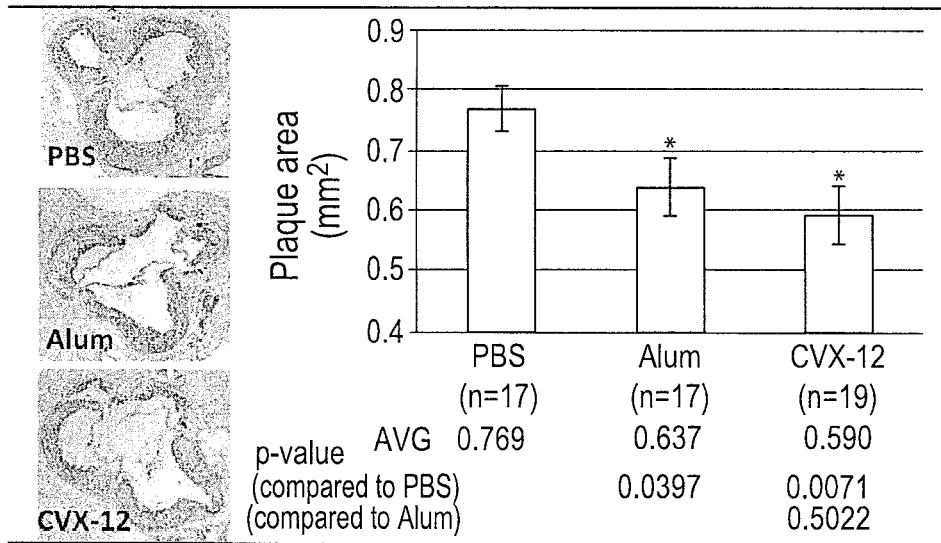
FIG. 7A-FIG. 7C depicts in accordance with various embodiments of the invention described in example 1, atherosclerotic lesion area in aortic roots. Oil-red-O-stained cross-sections of aortic roots from apoE$^{-/-}$ (FIG. 7A), gld.apoE$^{-/-}$ normal diet (FIG. 7B), and gld.apoE$^{-/-}$ western diet (FIG. 7C) mice. Representative images of each treatment group (PBS, Alum, and CVX-12) and a measurement of cross-sectional plaque area (mm$^2$) are shown. P<0.05 for apoE$^{-/-}$-Alum (*) and apoE$^{-/-}$-CVX-12 (*) compared to apoE$^{-/-}$-PBS.
Figure 7B:
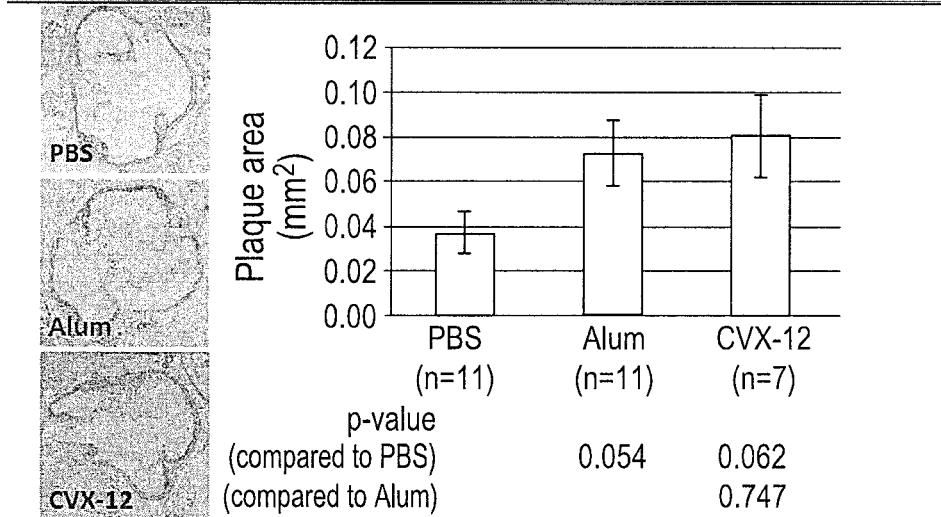
Figure 7C:
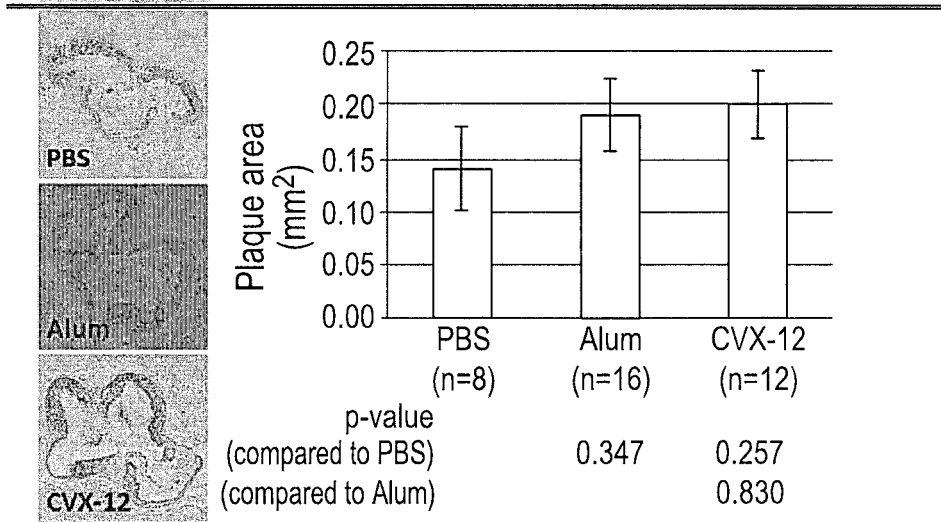

Because anti-nuclear antibody titers were reduced in CVX-12 immunized gld.apoE$^{-/-}$ mice on normal diet, anti-cardiolipin antibody reactivity was also assessed (FIG. 5). While not significantly reduced, we observed a trend towards decreased anti-cardiolipin antibodies in CVX-12 immunized gld.apoE$^{-/-}$ mice on normal diet. These data suggest a larger sample size would likely demonstrate a statistically significant effect.

Postmortem Study Evaluations:

Aortic en face and root plaque measurements are illustrated in FIGS. 6A-6D and FIGS. 7A-7C. Gld mice did not develop atherosclerotic lesions, and CVX-12 did not trigger spontaneous lesion formation in these mice. In apoE$^{-/-}$ mice, en face coverage of atherosclerotic lesions was similar among treatment groups, but aortic root section measurements indicated that atherosclerotic plaque depth was reduced by Alum and CVX-12 immunization in apoE$^{-/-}$ mice. In gld.apoE$^{-/-}$ mice, coverage of atherosclerotic lesions quantified by en face measurements of lesion area was unaffected by CVX-12 relative to control mice. A trend towards decreased lesion area was observed in gld.apoE−/− mice maintained on normal diet when treated with both Alum and CVX-12, however these changes were not statistically significant.

Organ Weights.

Figure 8:
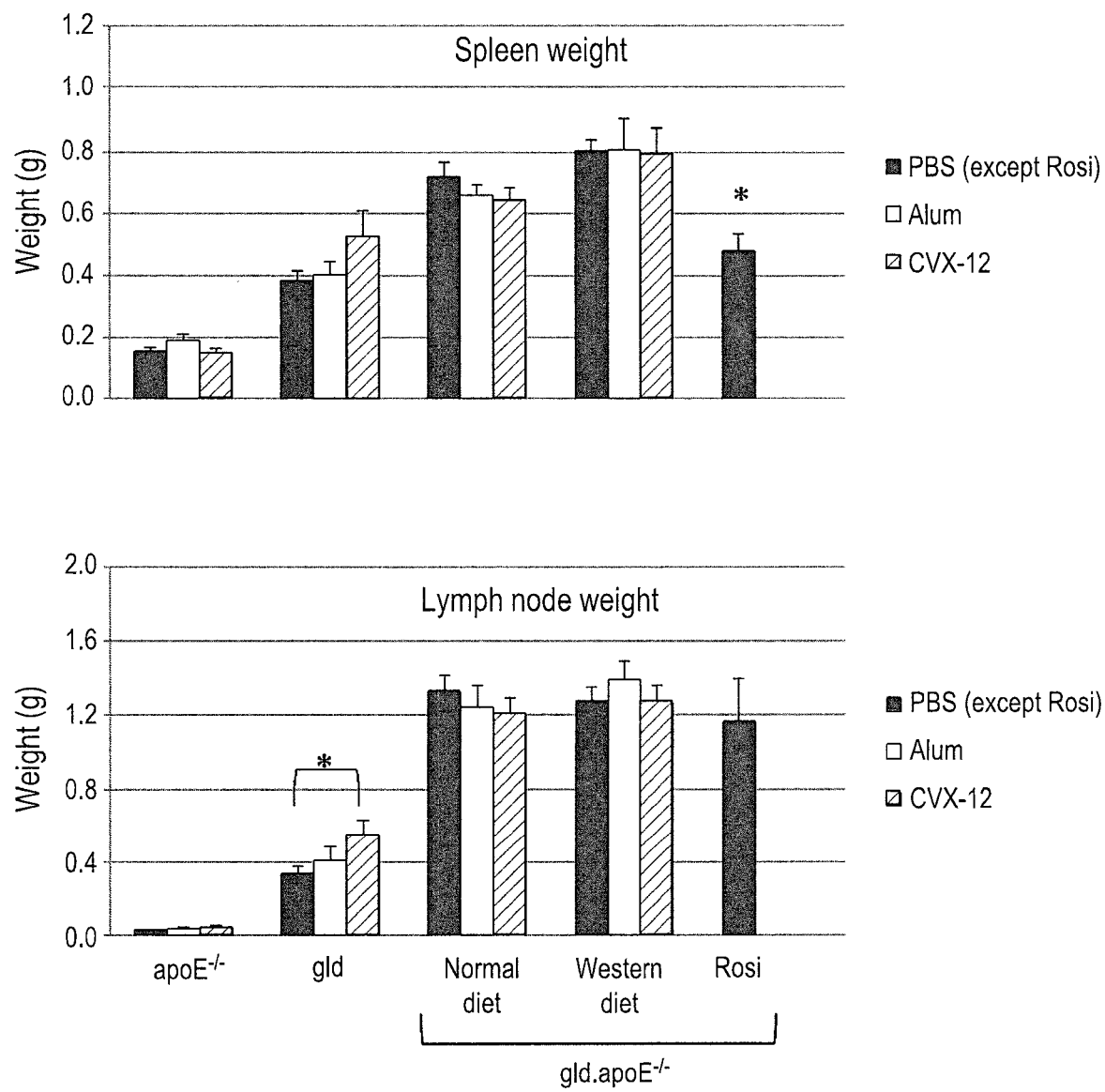
FIG. 8 depicts in accordance with various embodiments of the invention described in example 1, spleen and lymph node weights at sacrifice. Values=averages±SEM. P=0.017 for gld treated with CVX-12 versus gld treated with PBS and P=0.002 for rosiglitazone versus normal diet gld.apoE−/− treated with PBS (*).

Spleen and lymph node weights are illustrated in FIG. 8. CVX-12 immunization increased submandibular lymph node size in gld mice but had no impact on lymph node size in apoE$^{-/-}$ or gld.apoE$^{-/-}$ mice. CVX-12 did not affect spleen size.

Kidney Analysis.

Kidney glomerular tuft area was measured in the autoimmunity-elevated gld mice and gld.apoE$^{-/-}$ mice (FIG. 9). Average glomerular tuft area was unaffected by CVX-12 immunization in gld or gld.apoE$^{-/-}$ mice fed either a normal or Western diet.

Splenocyte Analysis.

CVX-12 immunization is hypothesized to impact atherosclerosis via modulation of T-cell cytokine release. Thus cytokine release by cultured splenocytes activated by CD3 and CD28 was assessed for the cytokines IFNγ, IL-6, IL-10, IL-12 (p70), and TNFα (Tables 6-12). CVX-12 immunization increased IL-6 and IL-10 cytokine release from spleen T-cells in apoE$^{-/-}$ mice. CVX-12 immunization did not impact levels of the assayed cytokines in gld mice. Rosiglitazone decreased IFNγ and IL-6 production by splenocytes from gld.apoE$^{-/-}$ mice, whereas CVX-12 treatment increased IFNγ release by splenocytes from gld.apoE$^{-/-}$ fed normal diet chow. IL-10 release from gld.apoE$^{-/-}$ splenocytes was decreased by CVX-12 immunization of gld.apoE$^{-/-}$ mice on western diet.

TABLE 6

Cytokine Production from Spleen T-cells from apoE−/− mice. All values are pg/mL.

| | | IFN-γ | | | IL-6 | | | IL-10 | |
|---|---|---|---|---|---|---|---|---|---|
| | | PBS | Alum | CVX-12 | PBS | Alum | CVX-12 | PBS | Alum |
| Unstimulated | Avg | 33.9 | 581.0 | 845.0 | 269.9 | 549.0 | 893.1* | 34.8 | 43.1 |
| | SEM | ±19.5 | ±385.6 | ±23.0 | ±121.8 | ±124.8 | ±182.2 | ±12.3 | ±9.5 |
| Stimulated | Avg | 12545 | 11411 | 12507 | 1689.6 | 3861.0* | 2925.2* | 1206.7 | 1390.2 |
| | SEM | ±716.7 | ±1027.1 | ±683.9 | ±295.4 | ±828.8 | ±350.3 | ±144.3 | ±314.3 |

| | | IL-10 | IL-12 (p70) | | | TNFα | | |
|---|---|---|---|---|---|---|---|---|
| | | CVX-12 | PBS | Alum | CVX-12 | PBS | Alum | CVX-12 |
| Unstimulated | Avg | 85.8* | 52.2 | 12.0 | 12.3 | 8.0 | 23.3 | 7.5 |
| | SEM | ±10.1 | ±40.4 | ±0.5 | ±0.7 | ±4.3 | ±14.8 | ±0.9 |
| Stimulated | Avg | 1676.3* | 12.9 | 12.9 | 13.6 | 75.7 | 540.9 | 80.7 |
| | SEM | ±171.3 | ±0.4 | ±0.6 | ±0.7 | ±4.0 | ±265.1 | ±4.8 |

*P < 0.05 compared to PBS.

TABLE 7

Cytokine Production (pg/mL) from Spleen T-cells from gld mice.

| | | IFN-γ | | | IL-6 | | | IL-10 | |
|---|---|---|---|---|---|---|---|---|---|
| | | PBS | Alum | CVX-12 | PBS | Alum | CVX-12 | PBS | Alum |
| Unstimulated | Avg | 171.0 | 112.6 | 82.9 | 302.4 | 576.5 | 152.4 | 142.9 | 147.5 |
| | SEM | ±55.9 | ±48.8 | ±48.1 | ±99.7 | ±323.4 | ±43.9 | ±34.8 | ±65.8 |
| Stimulated | Avg | 11145 | 12509 | 13780 | 2115.5 | 2290.4 | 1538.3 | 945.5 | 1132.5 |
| | SEM | ±894.4 | ±1119.7 | ±1098.7 | ±246.9 | ±462.2 | ±217.2 | ±127.1 | ±187.5 |

TABLE 7-continued

Cytokine Production (pg/mL) from Spleen T-cells from gld mice.

|  |  | IL-10 | IL-12 (p70) | | | TNFα | | |
|---|---|---|---|---|---|---|---|---|
|  |  | CVX-12 | PBS | Alum | CVX-12 | PBS | Alum | CVX-12 |
| Unstimulated | Avg | 74.1 | 434.0 | 233.4 | 169.7 | 8.4 | 57.9 | 3.7 |
|  | SEM | ±22.2 | ±153.4 | ±155.6 | ±73.1 | ±4.5 | ±38.0 | ±0.4 |
| Stimulated | Avg | 1255.3 | 451.4 | 142.7 | 254.2 | 46.7 | 106.9 | 49.9 |
|  | SEM | ±198.3 | ±152.7 | ±47.0 | ±139.0 | ±6.8 | ±43.8 | ±5.0 |

TABLE 8

IFN-γ Production from Spleen T-cells from gld.apoE−/− mice. All values are pg/mL.

|  |  | Normal Diet | | | Western Diet | | | |
|---|---|---|---|---|---|---|---|---|
|  |  | PBS | Alum | CVX-12 | PBS | Alum | CVX-12 | Rosi |
| Unstimulated | Avg | 65.9 | 79.8 | 85.4 | 127.9 | 139.0 | 132.3 | 24.2* |
|  | SEM | ±9.4 | ±23.7 | ±19.3 | ±83.3 | ±52.8 | ±56.3 | ±8.4 |
| Stimulated | Avg | 12053.5 | 11111.9 | 14852.3* | 12957.2 | 13721.5 | 9755.3 | 11419.9 |
|  | SEM | ±1047.4 | ±1202.1 | ±421.0 | ±1431.8 | ±679.1 | ±1745.3 | ±2002.3 |

*P < 0.05 compared to normal diet PBS

TABLE 9

IL-6 Production from Spleen T-cells from gld.apoE−/− mice. All values are pg/mL.

|  |  | Normal Diet | | | Western Diet | | | |
|---|---|---|---|---|---|---|---|---|
|  |  | PBS | Alum | CVX-12 | PBS | Alum | CVX-12 | Rosi |
| Unstimulated | Avg | 612.3 | 542.1 | 674.8 | 572.0 | 1024.0 | 1855.2 | 255.9* |
|  | SEM | ±98.8 | ±121.1 | ±268.3 | ±127.2 | ±315.5 | ±731.9 | ±84.6 |
| Stimulated | Avg | 2642.1 | 2972.8 | 2703.0 | 2556.8 | 3208.1 | 3476.3 | 385.0* |
|  | SEM | ±309.7 | ±701.4 | ±539.4 | ±450.4 | ±511.1 | ±771.7 | ±79.0 |

*P < 0.05 compared to normal diet PBS

TABLE 10

IL-10 Production from Spleen T-cells from gld.apoE−/− mice. All values are pg/mL.

|  |  | Normal Diet | | | Western Diet | | | |
|---|---|---|---|---|---|---|---|---|
|  |  | PBS | Alum | CVX-12 | PBS | Alum | CVX-12 | Rosi |
| Unstimulated | Avg | 147.5 | 177.3 | 158.1 | 302.8 | 230.4 | 215.6 | 196.0 |
|  | SEM | ±24.4 | ±42.4 | ±42.4 | ±156.8 | ±84.5 | ±89.2 | ±100.6 |
| Stimulated | Avg | 1603.7 | 1472.1 | 1723.3 | 1696.9 | 1671.0 | 1023.5* | 1528.3 |
|  | SEM | ±240.7 | ±224.3 | ±194.2 | ±323.9 | ±237.0 | ±188.0 | ±233.9 |

*P < 0.05 compared to WD alum and ND CVX-12

TABLE 11

IL-12 (p70) Production from Spleen T-cells from gld.apoE−/− mice. All values are pg/mL.

|  |  | Normal Diet | | | Western Diet | | | |
|---|---|---|---|---|---|---|---|---|
|  |  | PBS | Alum | CVX-12 | PBS | Alum | CVX-12 | Rosi |
| Unstimulated | Avg | 121.1 | 160.2 | 145.9 | 427.4 | 212.0 | 404.7 | 89.2 |
|  | SEM | ±39.7 | ±51.0 | ±61.8 | ±281.2 | ±83.2 | ±223.7 | ±40.3 |
| Stimulated | Avg | 147.9 | 235.0 | 70.1 | 743.1 | 148.7 | 225.3 | 44.7 |
|  | SEM | ±64.7 | ±124.0 | ±19.1 | ±414.1 | ±48.5 | ±131.4 | ±30.0 |

TABLE 12

TNFα Production from Spleen T-cells from gld.apoE−/− mice. All values are pg/mL.

| | | Normal Diet | | | Western Diet | | | |
|---|---|---|---|---|---|---|---|---|
| | | PBS | Alum | CVX-12 | PBS | Alum | CVX-12 | Rosi |
| Unstim-ulated | Avg | 9.4 | 29.4 | 11.4 | 7.5 | 25.0 | 4.6 | 8.9 |
| | SEM | ±1.2 | ±17.0 | ±2.1 | ±1.3 | ±18.6 | ±0.6 | ±1.5 |
| Stim-ulated | Avg | 50.1 | 42.9 | 58.3 | 59.0 | 68.4 | 53.5 | 39.5 |
| | SEM | ±6.0 | ±4.3 | ±6.8 | ±7.4 | ±26.5 | ±18.0 | ±8.7 |

Figure 22:
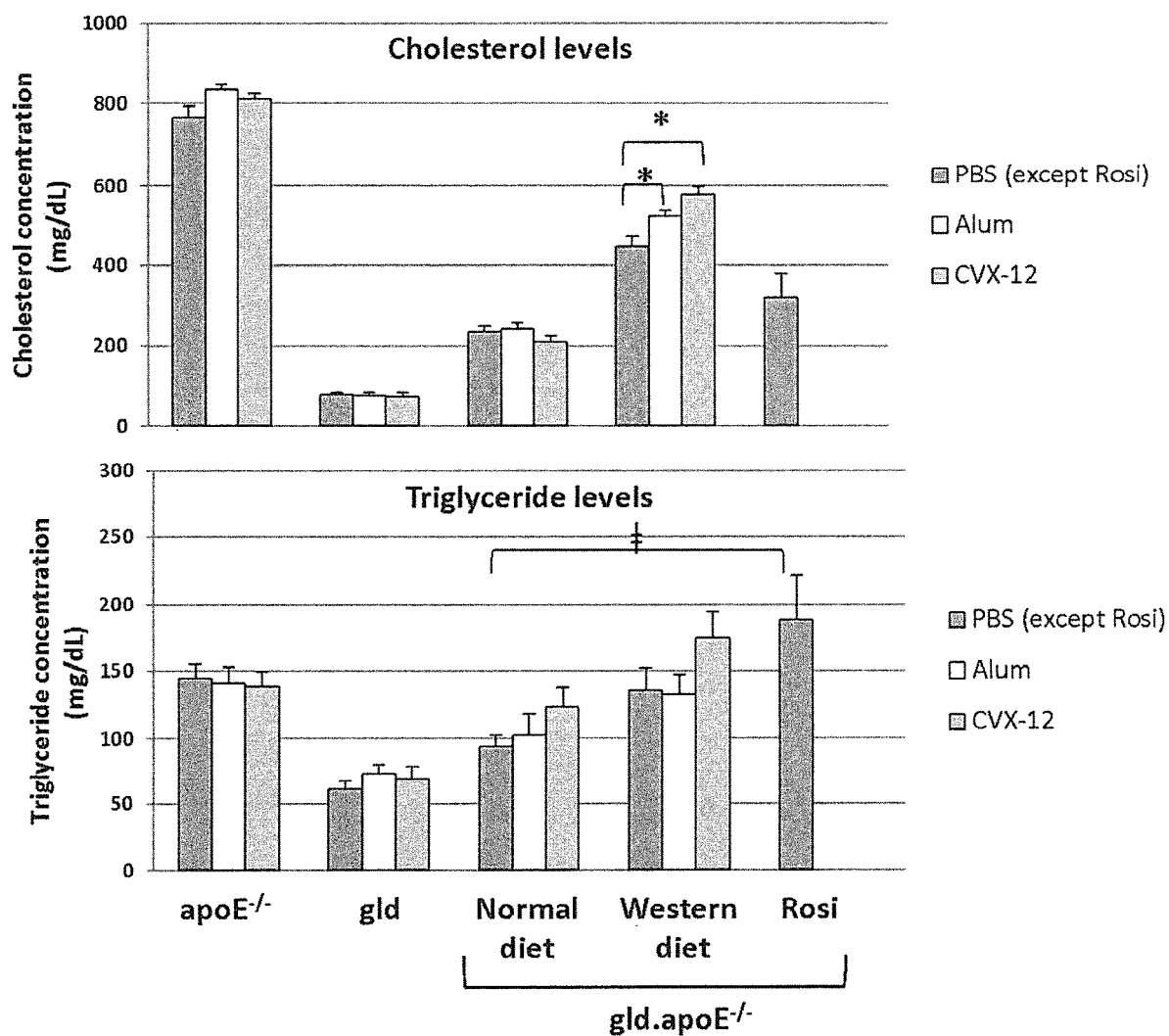
FIG. 22 depicts serum cholesterol and triglyceride levels at euthanasia. Values=averages±SEM. P<0.05 for cholesterol levels of gld.apoE−/− mice on western diet for PBS versus Alum and PBS versus CVX-12 (*). P<0.001 for triglyceride levels gld.apoE−/− mice on rosiglitazone compared to PBS control mice (#).

Serum Analysis:

Cholesterol and triglyceride results are displayed in FIG. 22. CVX-12 and alum treatments significantly increased cholesterol levels in gld.apoE−/− mice on western diet, but did not affect cholesterol levels in apoE−/− or gld mice nor in gld.apoE−/− mice on normal diet. Triglyceride levels were increased in gld.apoE−/− as a result of rosiglitazone treatment, but the test article treatment did not significantly alter triglyceride levels relative to controls in any of the cohorts.

Figure 24:
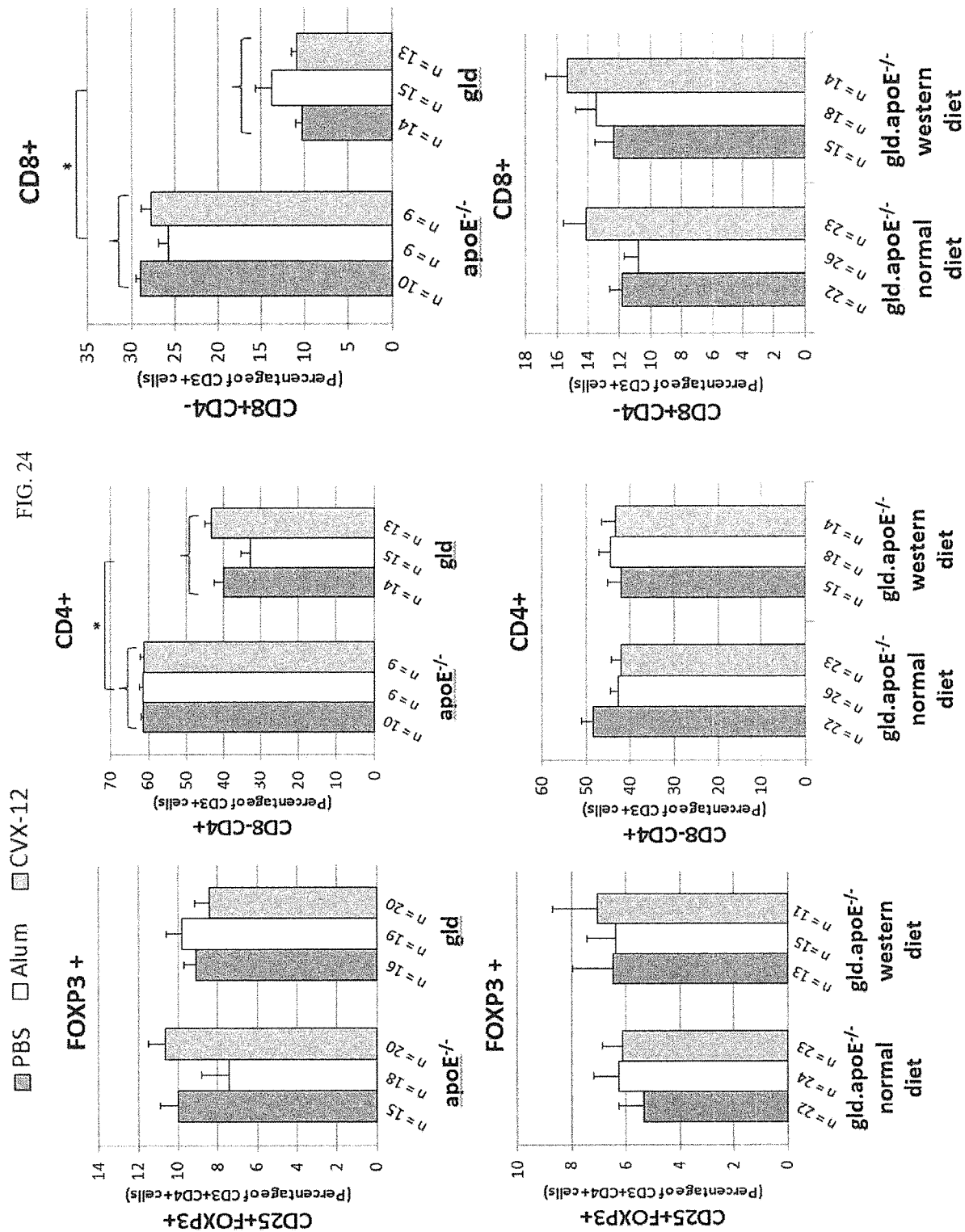
FIG. 24 depicts T-regulatory cell populations from spleen. P<0.0001 for CD8+ cell populations in gld mice versus apoE−/− mice (*).

Analysis of Regulatory T-Cells:

T-regulatory cell populations within the spleen were assessed as a potential mechanism for conveying the atherosclerosis benefits of CVX-12 immunization, and thus all study mice were assessed for populations of T-regulatory CD3+CD4+CD25+FOXP3+ splenocytes and for CD8+ or CD4+ splenocytes (FIG. 24). CD3+CD4+CD25+FOXP3+ T-regulatory cell populations were not significantly impacted by CVX-12 immunization in gld, apoE−/−, or gld.apoE−/− mice. gld mice produce significantly smaller CD4+ and CD8+ populations compared to apoE−/−, but no significant differences among the treatment groups (PBS, Alum, and CVX-12) were observed in CD4+ or CD8+ cell populations in gld, apoE−/−, or gld.apoE−/− mice.

CVX-12 immunization reduced the anti-nuclear antibody titer levels in gld.apoE$^{-/-}$ mice on normal diet, demonstrating its applicability for treatment for patients with SLE, independent of cardiovascular disease involvement. Anti-P210 IgM was decreased by CVX-12 in gld.apoE$^{-/-}$ on western diet. Glomerular tuft area, as a first measurement of kidney dysfunction, was not affected in a positive nor negative manner by Alum or CVX-12 treatment. Taken together, CVX-12 immunization in a mouse model of lupus with lupus-associated accelerated atherosclerosis appears to be safe, and effectively diminishes anti-nuclear antibody titer.

Example 2. Increased Levels of Soluble Death Receptors are Associated with Cardiovascular Disease in Systemic Lupus Erythematosus Since dysregulation of apoptosis has been implicated in atherosclerosis the present study investigated if plasma levels of the death receptors Fas, TRAIL receptor 2 (TRAIL-R2) and TNF-R1 are related to the presence of cardiovascular disease (CVD) in patients with SLE.

Experimental Methods

Patients and Controls.

Patients and controls were included between January 2004 and October 2013. All patients who fulfilled four or more of the 1982 revised American College of Rheumatology (ACR) classification criteria for SLE [Tan E M et al. The 1982 revised criteria for the classification of systemic lupus erythematosus. *Arthritis Rheum* 1982; 25:1271-7]. Patients were required to be older than 18 years, otherwise there were no exclusion criteria. Population controls, individually matched to the first 322 SLE patients were identified in the population registry. Matching was performed within one year of age, for sex, and region of living. Controls were contacted and asked to participate through a letter. The only exclusion criterion among controls was a diagnosis of SLE. Due to limitation of the analytical platform 69 randomly selected controls were excluded from the present study.

Data Collection.

All patients and controls were investigated in person by a rheumatologist. Traditional risk factors for CVD were tabulated. Hypertension was defined as a systolic BP>140 mm Hg and/or a diastolic BP>90 mm Hg or use of antihypertensive treatment. Diabetes was considered present if patients were previously diagnosed with diabetes. History of vascular events, defined as a history of objectively verified myocardial infarction, ischemic cerebrovascular disease or peripheral vascular disease was obtained though interview and review of medical files. In SLE patients, age at diagnosis, duration of disease, and lupus manifestations including autoantibodies were recorded. Lupus nephritis was defined according to the 1982 revised ACR classification criteria for nephritis [Tan E M, Cohen A S, Fries J F, et al. The 1982 revised criteria for the classification of systemic lupus erythematosus. *Arthritis Rheum* 1982; 25: 1271-7]. Organ damage was assessed with Systemic Lupus International Collaborating Clinics/ACR Damage index (SDI) [Gladman D, et al. The development and initial validation of the Systemic Lupus International Collaborating Clinics/American College of Rheumatology damage index for systemic lupus erythematosus. *Arthritis Rheum* 1996; 39: 363-9]. All blood samples were taken after overnight fasting and laboratory examinations were performed blinded, either on fresh blood samples or after storage in −70° C.

Analysis of Circulating Death Receptors in Plasma.

Plasma levels of Fas, TNF-R1 and TRAIL-R2 were analyzed by the Proximity Extension Assay (PEA) technique using the Proseek Multiplex CVD$^{96 \times 96}$ reagents kit. Oligonucleotide-labeled antibody probe pairs were allowed to bind to their respective targets present in the plasma sample and addition of a DNA polymerase led to an extension and joining of the two oligonucleotides and formation of a PCR template. Universal primers were used to pre-amplify the DNA templates in parallel. Finally, the individual DNA sequences were detected and quantified using specific primers by microfluidic real-time quantitative PCR chip. The mean coefficients of variance for intra-assay variation and inter-assay variation were 8% and 12% for Fas, 7% and 11% for TNF-R1, and 7% and 15% for TRAIL-R2. All samples were analyzed in the same run. Data analysis was performed by a preprocessing normalization procedure using Olink Wizard for GenEx. All data are presented as arbitrary units (AU). General calibrator curves to calculate the approximate concentrations are available on the OLINK homepage.

Determination of P45, P210 and β2GPI Autoantibodies.

Peptides corresponding to the amino acids from 661 to 680 (P45; IEIGLEGKGFEPTLEALFGK) and amino acids 3136-3155 (P210; KTTKQSFDLSVKAQYKKNKH) of human ApoB100 were synthesized and used in ELISA. The peptides were modified by 0.5 M MDA for 3 h at 37° C. and dialyzed against PBS containing 1 mM EDTA as described [Fredrikson G N, et al. Identification of immune responses against aldehyde-modified peptide sequences in Apo B-100 associated with cardiovascular disease. *Arterioscler Thromb Vasc Biol* 2003; 23: 872-8]. Native and MDA-modified peptides diluted in PBS pH 7.4 (20 µg/ml) were absorbed to microtiter plate wells in an overnight incubation at 4° C. After washing with PBS containing 0.05% Tween-20 (PBS-T) the coated plates were blocked with SuperBlock in TBS for 30 min at RT followed by an incubation of test plasma, diluted 1/100 in TBS-0.1% Tween-20 and 10% Superblock (TBS-T) for 2 hr at RT and overnight at 4° C. After rinsing, deposition of autoantibodies directed to the peptide was detected using biotinylated rabbit anti-human IgM or IgG antibodies appropriately diluted in TBS-T. After another incubation for 2 hr at RT the plates were washed and the bound biotinylated antibodies detected by alkaline phosphatase conjugated streptavidin, incubated for 2 hr at RT. The colour reaction was developed by using phosphatase substrate kit and the absorbance at 405 nm was measured after 90 and 120 min of incubation at RT for IgM and IgG, respectively. Data regarding the specificity and variability of the antibody ELISA have been published previously [Fredrikson G N, et al. Identification of immune responses against aldehyde-modified peptide sequences in apo B-100 associated with cardiovascular disease. *Arterioscler Thromb Vasc Biol* 2003; 23: 872-8; Fredrikson G N, et al. Autoantibody against the amino acid sequence 661-680 in apo B-100 is associated with decreased carotid stenosis and cardiovascular events. *Atherosclerosis* 2007; 194: e188-92].

Anti-$\beta_2$GPI antibodies IgM/IgG were determined with the multiplex immunoassays, BioPlex 2200 APLS (Bio-Rad Laboratories Inc., Hercules, Calif., USA). Results were reported in the ranges between 1.9-160 U/mL for IgM and 1.9-160 U/mL for IgG. Results were handled as continuous variables. The multiplex assays are regarded as positive if ≥20 U/mL. This cut-off level corresponded to at least the 99th percentile of healthy blood donors.

Human Peripheral Blood Mononuclear Cell (PBMCs) Isolation.

PBMCs from SLE patients (n=6, x female and x male, age x+/−x years) and matched healthy controls (n=6, x female and x male, age x+/−x years) as well as from a healthy donor were isolated using FicollPaque Plus (GE healthcare, Waukesha, Wis., USA) density gradient centrifugation according to manufacturer's instructions. The cells from SLE patients and controls were resuspended in 40% autologous serum, 40% RPMI 1640 medium (Thermo Fisher Scientific, Waltham, Mass., USA) and 20% dimethyl sulfoxide (Sigma Aldrich, St. Louis, Mich., USA) and frozen in liquid nitrogen.

Death Receptor Activation of Human Donor PBMC.

Cells from healthy donors were seeded freshly at a density of 0.5×10⁶ cells per well in complete RPMI (10 U/ml Penicillin/streptomycin, 1% L-glutamine, 1% sodium pyruvate, 1% Hepes and 0.1% mercaptoethanol) with 2% FBS (HyClone South Logan, Utah, USA). For death receptor activation, IL-1β, soluble Fas ligand, TNF (Peprotech, Rocky Hill, N.J., USA) and LPS (Sigma Aldrich) were used at a concentration of 10 ng/ml, 0.5 µg/ml, 10 ng/ml and 10 µg/ml respectively.

Flow Cytometry.

Cells from a healthy donor were seeded freshly at a density of 0.5×10⁶ cells per well in complete RPMI (10 U/ml Penicillin/streptomycin, 1% L-glutamine, 1% sodium pyruvate, 1% Hepes and 0.1% mercaptoethanol) with 2% FBS (HyClone South Logan, Utah, USA). For death receptor activation, IL-1β, soluble Fas ligand, TNFα (Peprotech, Rocky Hill, N.J., USA) and LPS (Sigma Aldrich) were used at a concentration of 10 ng/ml, 0.5 µg/ml, 10 ng/ml and 10 µg/ml respectively.

Cell Supernatant Soluble Death Receptor Analysis.

Cell supernatants from death receptor activated PBMCs from a healthy donor and SLE patients/controls were used for measurement of soluble Fas, TNF-R1 and TRAIL-R2 with a magnetic bead system multiplex assay (R&D Systems, Minneapolis, Minn., USA) obtained by Luminex machine (Bio-Rad). For SLE patients and controls, TNF-R1 concentration was measured with ELISA (Abcam) according to manufacturer's recommendations.

Statistics.

Clinical characteristics are presented as median (interquartile range, IQR) for continuous variables and as percentages for categorical variables. Continuous variables that were not normally distributed were log transformed. If not become normally distributed after log transformation, non-parametric tests were used. Depending on data type, Students' t-test, Mann Whitney or Chi square test were used to compare differences between groups. Correlations were investigated through calculating the Spearman rank correlation coefficients. Multivariable-adjusted logistic regression models were performed to evaluate the associations between autoantibodies and cardiovascular/organ damage outcomes.

Plasma Levels of Soluble Death Receptors are Elevated in SLE Patients and Associated with the Severity of Organ Damage.

We analyzed the plasma levels of soluble death receptors in a cohort of 484 patients with SLE and 253 healthy controls. There was no significant age-difference between SLE patients and controls but the percent of females was higher in the control group (Table 13). Circulating levels of Fas, TRAIL-R2 and TNF-R1 were increased by 34.1%, 13.6% and 47.4%, respectively (p<0.001 for all) in patients with SLE as compared to the controls (Table 13).

TABLE 13

Circulating death receptor levels in SLE patients and controls. Distributions are given as median (interquartile range) or percentages. Differences between groups were analyzed by Mann-Whitney U test. Fas, TRAIL receptor 2 and TNF receptor 1 values are given as arbitrary units.

| TABLE 13 | SLE patients (n = 484) | Controls (n = 253) | P |
|---|---|---|---|
| Age (years) | 46.4 (33.7-57.6) | 49.3 (36.0-58.8) | ns |
| Female sex (%) | 86.7 | 93.3 | 0.006 |
| Death receptors | | | |
| Fas | 181 (143-234) | 135 (114-166) | <0.001 |
| TRAIL receptor 2 | 2.5 (1.9-3.5) | 2.2 (1.9-2.7) | <0.001 |
| TNF receptor 1 | 5873 (4576-7750) | 3984 (3362-4689) | <0.001 |

There were 69 CVD cases in the SLE group and 8 in the control group (Table 14).

TABLE 14

Clinical characteristic of SLE patients and controls. Distributions are given as median (interquartile range) or percentages. CVD data missing for 14 SLE patients.

| TABLE 14 | SLE patients No CVD (n = 401) | SLE patients CVD (n = 69) | P | Controls No CVD (n = 245) | Controls CVD (n = 8) | P |
|---|---|---|---|---|---|---|
| Age (yrs) | 43.9 (31.9-56.1) | 56.8 (49.5-66.1) | <0.001 | 50.0 (35.9-58.8) | 54.3 (50.1-61.6) | ns |
| Female sex % | 85 | 91 | ns | 93 | 88 | ns |
| SLE characteristics | | | | | | |
| Disease duration year | 6.5 (1.7-13.6) | 17.2 (7.8-32.2) | <0.001 | NA | NA | |
| SLICC damage index (SDI) | 1 (1-2) | 3 (2-5) | <0.001 | NA | NA | |
| Risk factors | | | | | | |
| Smoking (%) | 49 | 71 | 0.002 | 48 | 50 | ns |
| Systolic BP (mm Hg) | 120 (110-135) | 130 (120-150) | <0.001 | 120 (110-137) | 140 (125-168) | 0.02 |
| Diastolic BP (mm Hg) | 78 (70-80) | 80 (70-85) | ns | 75 (70-80) | 85 (85-90) | 0.003 |
| Hypertension treatment (%) | 28.9 | 59.4 | <0.001 | 15.1 | 50 | 0.008 |
| Body mass index (kg/m$^2$) | 23.8 (21.4-27.1) | 25.3 (21.9-29.8) | 0.04 | 24.2 (22.0-27.5) | 31.3 (27.0-35.1) | 0.001 |
| Diabetes (%) | 1.4 | 0 | ns | | | |
| HDL (mmol/L) | 1.3 (1.1-1.6) | 1.2 (1.0-1.6) | ns | 1.5 (1.2-1.8) | 1.4 (1.1-1.5) | ns |
| LDL (mmol/L) | 3.0 (2.5-3.6) | 2.9 (2.3-3.6) | ns | 3.3 (2.6-4.0) | 3.7 (3.0-4.4) | ns |
| Triglycerides (mmol/L) | 1.0 (0.6-1.4) | 1.4 (1.0-1.7) | <0.001 | 0.8 (0.6-1.1) | 0.8 (0.7-1.7) | ns |
| Glucose | 4.8 (4.4-5.2) | 5.1 (4.6-56) | 0.001 | 4.9 (4.6-5.2) | 5.3 (5.0-6.3) | 0.02 |
| High-sensitivity CRP | 1.5 (0.6-5.0) | 2.4 (1.0-7.0) | 0.04 | 0.9 (0.5-2.2) | 3.2 (2.5-7.6) | 0.006 |
| Creatinine | 67 (57-80) | 76 (64-94) | 0.001 | 65 (60-72) | 70 (56-89) | ns |

SLE patients with a prevalent CVD event were older, had a longer duration of SLE, a higher SLICC damage index and more cardiovascular risk factors. In the SLE group those with prevalent CVD had significantly higher levels of Fas, TRAIL-R2 and TNF-R1 than those without CVD (Table 15). This difference remained significant for TRAIL-R2 and TNF-R1, but not for Fas, when controlling for the influence of age and sex in logistic regression models. There were no significant differences between those with and without prevalent CVD in the control group for Fas (144 (IQR 137-201) versus 134 AU (IQR 114-166)), TRAIL-R2 (2.3 (IQR 2.1-2.9) versus 2.2 AU (IQR 1.9-2.7)) or TNF-R1 (4211 (IQR 3956-4898) versus 3984 AU (IQR 3350-4689)). To determine if increased levels of soluble death receptors represent a general marker of organ damage we finally analyzed their relation with permanent organ damage measures as a SLICC score>1. A SLICC>1 was found to be associated with increased plasma levels of Fas, TRAIL-R2 and TNF-R1 and these differences remained statistically significant when controlling for age and sex (Table 15).

Association Between Soluble Death Receptors and Cardiovascular Risk Factors.

The plasma levels of soluble death receptors increased with age in both SLE patients and controls (Table 16). In spite of this, there was only a modest or no association with SLE disease duration. Associations with blood pressure, BMI, LDL (only Fas), triglycerides, glucose, hsCRP and creatinine were observed both in SLE and controls. There was an inverse association with HDL for TRAIL-R2 and TNF-R1 in the SLE group and for TNF receptor 1 in the control group. Smokers (current or former) had higher levels than those that had never smoked (Fas: 187 (IQR 152-247) versus 170 AU (IQR 134-219); p=0.001, TRAIL-R2: 2.5 (IQR 1.9-3.5) versus 2.2 AU (IQR 1.8-3.0); p=0.004 or TNF-R1: 6252 (IQR 4738-8720) versus 5386 AU (IQR 4375-6712); p=0.003).

TABLE 15

Circulating death receptor levels on SLE patients with and without nephritis and SLICC > 1. Distributions are given as median (interquartile range).

| TABLE 15 | Fas | TRAIL receptor 2 | TNF receptor 1 |
|---|---|---|---|
| No CVD (n = 401) | 177 (141-229) | 2.4 (1.8-3.4) | 5557 (4513-7564) |
| CVD (n = 69) | 209 (162-272) | 3.3 (2.2-4.5) | 6562 (5480-9090) |
| P | 0.004 | <0.001 | 0.001 |
| OR (95% C.I.) age and sex adjusted | 1.44 (0.87-2.38) | 1.63 (1.16-2.29) | 1.84 (1.12-3.01) |
| SLICC ≤ 1 | 170 (134-215) | 2.3 (1.8-3.2) | 5367 (4292-6985) |
| SLICC > 1 | 209 (165-280) | 3.0 (2.0-4.4) | 6608 (5203-9027) |
| P | <0.001 | ns | <0.001 |
| OR (95% C.I.) age and sex adjusted | 2.34 (1.60-3.43) | 1.56 (1.20-2.03) | 2.53 (1.72-3.72) |

TABLE 16

Association between risk factors and circulating death receptor levels. Spearman rank correlation coefficients.

|  | SLE patients | | | Controls | | |
| --- | --- | --- | --- | --- | --- | --- |
|  | Fas | TRAIL receptor 2 | TNF receptor 1 | Fas | TRAIL receptor 2 | TNF receptor 1 |
| Age (years) | 0.26*** | 0.21*** | 0.19*** | 0.31*** | 0.23*** | 0.16* |
| Disease duration year | 0.10* | ns | ns | NA | NA | NA |
| Systolic BP (mmHg) | 0.26*** | 0.21*** | 0.23*** | 0.36*** | 0.22*** | 0.16* |
| Diastolic BP (mmHg) | 0.17*** | ns | 0.13** | 0.29*** | ns | ns |
| BMI (kg/m$^2$) | 0.20*** | 0.13* | 0.14** | 0.21** | 0.16** | 0.22** |
| HDL (mmol/L) | ns | −0.14** | −0.19*** | ns | ns | −0.14* |
| LDL (mmol/L) | 0.14** | ns | ns | 0.19** | ns | ns |
| Triglycerides (mmol/L) | 0.37*** | 0.37*** | 0.45*** | 0.16* | 0.19** | ns |
| Glucose | 0.18*** | ns | 0.12** | 0.22*** | 0.19** | 0.22*** |
| High-sensitivity CRP | 0.18*** | 0.29*** | 0.43*** | 0.22** | 0.14* | 0.14* |
| Creatinine | 0.35*** | 0.27*** | 0.43*** | 0.15* | 0.15* | 0.20** |

*P < 0.05,
**P < 0.01,
***P < 0.001.

Association Between Soluble Death Receptors and Immune Biomarkers.

High levels of soluble Fas, TRAIL-R2 and TNF-R1 correlated with higher neutrophil and lower lymphocyte counts (Table 17). There were also significant associations between some of the soluble death receptors and the plasma levels of immune biomarkers of SLE such as C3dg, cardiolipin IgG and β2GP1 IgG. We have shown that antibodies against apolipoprotein (apo) B have a protective role in atherosclerosis and that SLE patients have reduced levels of the apo B P210 IgG. Interestingly, we observed an inverse association between soluble death receptors and P210 IgG in the present study (Table 17).

TABLE 17

Association of circulating death receptor levels with blood cells, complement and autoantibodies in SLE patients. Spearman rank correlation coefficients.

| TABLE 17 | Fas | TRAIL receptor 2 | TNF receptor 1 |
| --- | --- | --- | --- |
| White blood cells | | | |
| Lymphocytes | −0.15** | −0.11* | −0.15** |
| Neutrophils | 0.19** | 0.24*** | 0.26*** |
| Complement | | | |
| C1q | −0.02 | −0.09 | −0.08 |
| C3 | −0.11* | −0.06 | −0.10* |
| C3dg | 0.34*** | 0.09 | 0.33*** |
| Autoantibodies | | | |
| Cardiolipin IgG | ns | 0.09* | 0.15** |
| Cardiolipin IgM | ns | ns | ns |
| β2GP1 IgG | ns | 0.09* | 0.15** |
| β2GP1 IgM | ns | ns | ns |
| Apo B P210 IgG | −0.21*** | −0.15** | −0.13** |
| Apo B P210 IgM | ns | −0.11* | ns |

*P < 0.05,
**P < 0.01,
***P < 0.001.

Fas Ligand Activates Release of Soluble Death Receptors from Peripheral Blood Mononuclear Cells (PBMC)

Figure 10A:
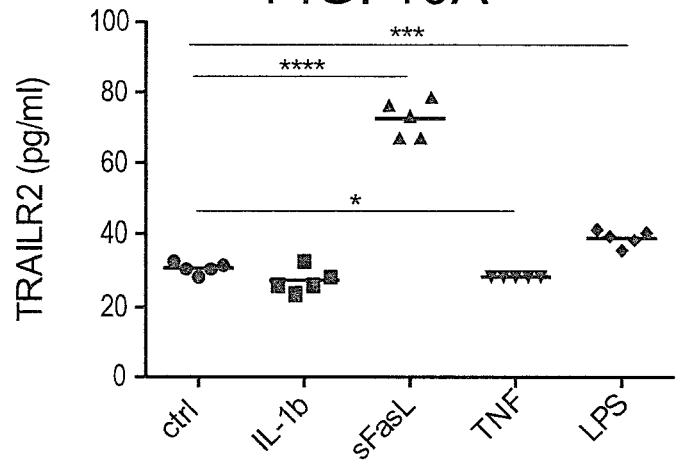
FIG. 10A-FIG. 10C depict in accordance with various embodiments of the invention, that death receptors ligands induces the release of soluble death receptors in cell supernatant. The levels of the soluble death receptors (FIG. 10A) TRAILR2, (FIG. 10B) Fas and (FIG. 10C) TNFR1 obtained from cell supernatant from freshly cultured healthy donor PBMC treated with IL-1β (10 ng/ml), soluble Fas ligand (0.5 μg/ml), TNF (10 ng/ml) or LPS (10 μg/ml).
Figure 10B:
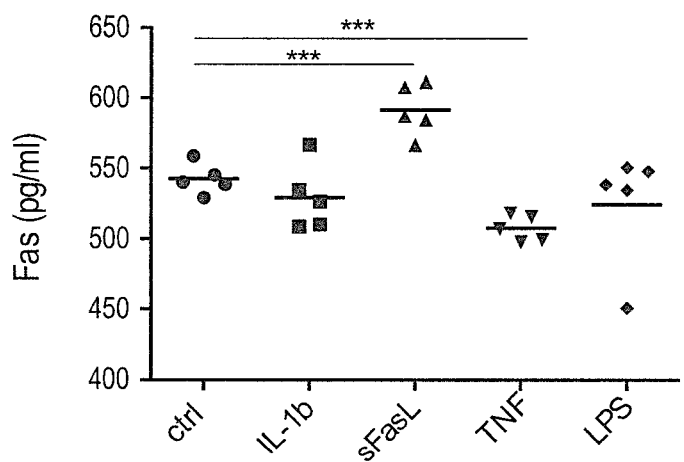
Figure 10C:
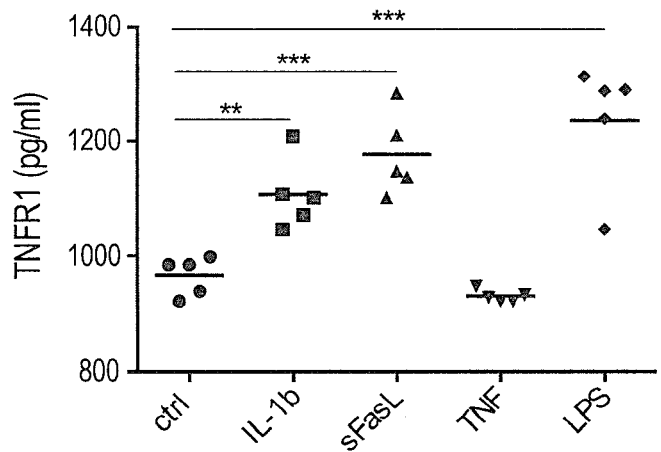

The role of cell surface death receptors in apoptosis signaling is well characterized but the factors that regulate the release of the soluble forms of these receptors have not been extensively studied. Hence, we cultured human PBMC in presence of different death receptor ligands and pro-inflammatory factors. Exposure of cells to Fas ligand stimulated the release of Fas, and TRAIL-R2 into the culture medium, while exposure to IL-1β no effect and LPS only induced a small increase in the release if TRAIL-R2 (FIGS. 10A and 10B). Incubation with TNF-α resulted in a modest inhibition of the release of TRAIL-R2, but had no effect on the release of Fas from PBMC. Fas ligand, IL-1β and LPS all stimulated the release of TNF-R1, whereas no effect was seen in response to TNF-α (FIG. 10C). These observations demonstrate that the release of Fas and TRAIL-R2 is induced by activation of the Fas ligand/Fas pathway but not in response to pro-inflammatory factors. In contrast, the release of TNF-R1 is stimulated both by Fas ligand and pro-inflammatory factors.

PBMC from SLE Patients and Healthy Controls Differ in Response to Fas Ligand Stimulation.

Figure 11A:
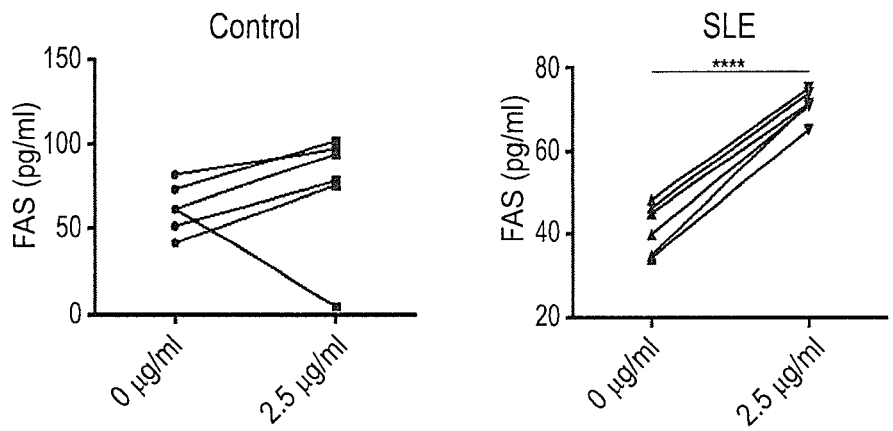
FIG. 11A-FIG. 11F depicts in accordance with various embodiments of the invention, that treatment of PBMC with soluble Fas ligand does not activate apoptosis as extensively in SLE patients as in controls. The levels of the soluble death receptors (FIG. 11A) FAS (FIG. 11B) TRAIL and (FIG. 11C) TNFR1.
Figure 11B:
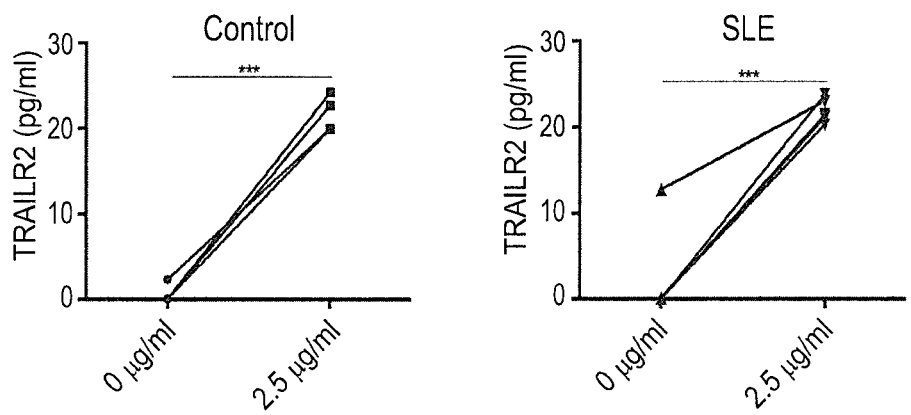
Figure 11C:
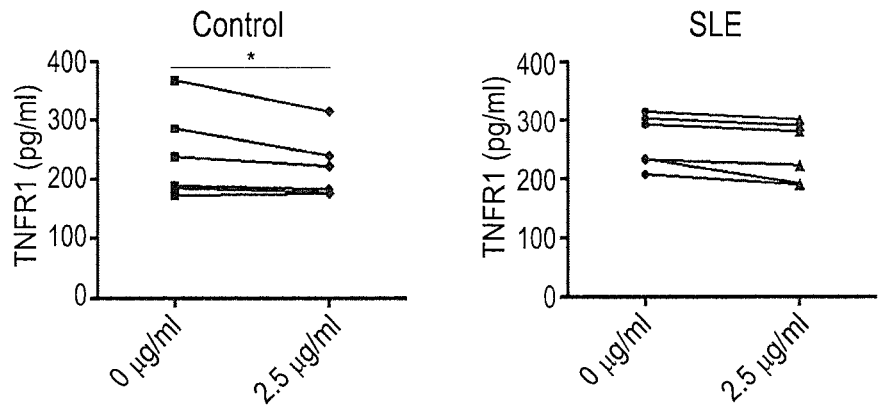
Figure 11D:
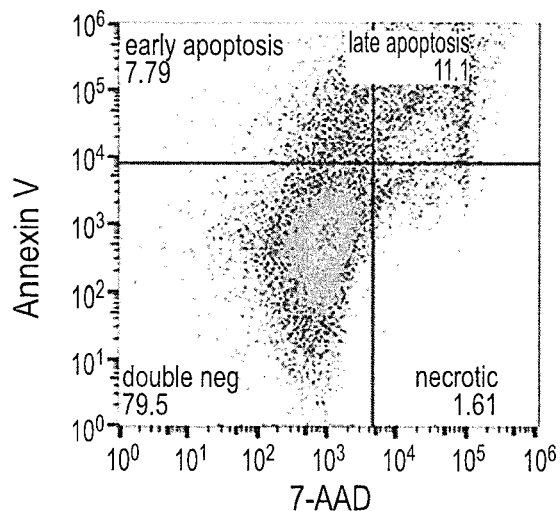
Figure 11E:
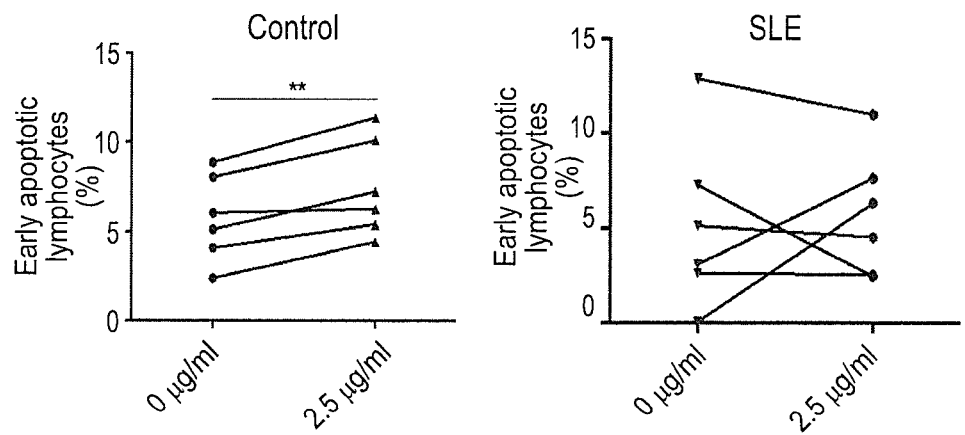
Figure 11F:
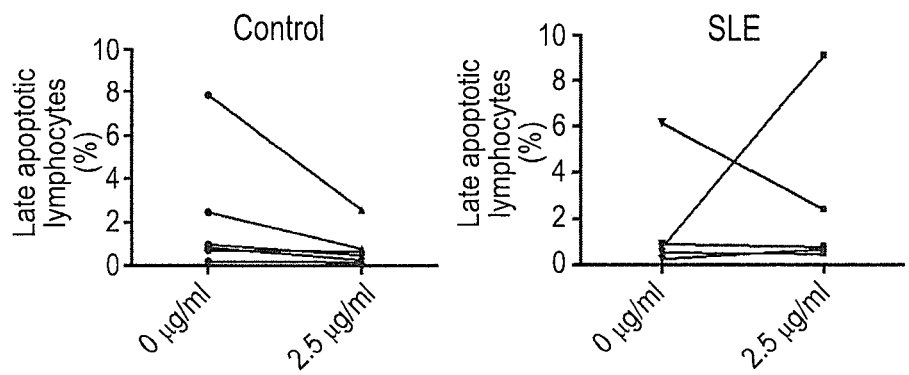

Stimulation of PBMCs from SLE patients with Fas ligand resulted in a 73% increase in the release of FAS and a seven-fold increase in TRAIL-R2 release (FIG. 11A and FIG. 11B). A similar increase in the release of TRAIL-R2 was seen in healthy controls exposed to Fas ligand, whereas the effect on Fas was less pronounced and did not reach statistical significance in paired t-test. Stimulation with Fas ligand did not activate secretion of TNF-R1 (FIG. 11C) Incubation with Fas ligand increased the frequency of apoptotic lymphocytes in PBMCs obtained from healthy controls but not in PBMCs from SLE patients (FIG. 11C).

The present study demonstrates that patients with SLE have increased plasma levels of soluble Fas, TNF-R1 and TRAIL-R2 as compared to age- and sex-matched healthy controls. Moreover, patients with previous nephritis and higher organ damage scores had higher plasma levels of Fas, TNF-R1 and TRAIL-R2 than those with milder disease manifestations.

Activation of death receptors by their respective ligands (primarily FasL, TNF-α and TRAIL) are of importance for several types of physiological apoptosis including deletion of activated T cells at the end of an immune response and killing of virus infected cells as well as cancer cells. However, dysfunctional activation of death receptor signaling has also been associated with autoimmunity. Autoimmune lymphoproliferative syndrome is a rare disease caused by mutations in the Fas gene leading to high expression of autoantibodies, recurrent autoimmune cytopenia as well as other autoimmune organ complications. Several lines of evidence have also implicated FasL/Fas signaling in the pathogenesis of SLE. In particular, altered FasL/Fas signaling is considered to play an important role in the disease process by contributing to an impaired clearance of autoreactive lymphocytes and increased exposure of hidden self-antigens. Mice with functional mutations in the Fas (lpr mice) and FasL (gld mice) genes develop SLE-like phenotypes. Moreover, T and B cells from SLE patients are characterized by increased cell surface expression of Fas and this expression has been shown to correlate with disease activity.

Death receptors can also be released by the cells in a soluble form. The factors that induce the release of soluble Fas and TRAIL-R2 have to our knowledge previously not been studied in detail. In the present study we demonstrate that the release of soluble Fas and TRAIL-R2 from human PBMCs is enhanced by FasL, but not by IL-1β or TNF-α. This implies that the observed significant associations between soluble Fas and TRAIL-R2 and CRP in SLE patients reflect inflammation caused by impaired regulation of apoptosis rather than a release of these death receptors in response to inflammation. The cause of the increased levels of soluble TNF-R1 in SLE is more complex since the release of this receptor from PBMCs is stimulated by both FasL and pro-inflammatory factors, such as IL-β and LPS. This suggests that increased levels of TNF-R1 may be a marker of both extrinsic apoptosis signaling and inflammation. We have previously studied sTNF-R1 in SLE from a systemic inflammatory perspective and demonstrated that together with sTNF-R2 and TNF-α, it is a good marker of SLE disease activity and it was also associated with CVD. Interestingly, we did not observe an increased release of TNF-R1 in response to stimulation with TNF-α, which is in contrast to previous studies on polymorphonuclear leukocytes and microvessel endothelial cells.

The soluble form of Fas has been shown to inhibit apoptosis by blocking the binding of FasL to the membrane-bound form of Fas. Thus, it is likely that the increased levels of soluble Fas found in subjects with SLE may contribute to development of SLE disease characteristics in the same way as inhibition of FasL/Fas signaling contributes to development of an SLE-like phenotype in experimental animals. In this context it is interesting to note that FasL-induced apoptosis in PBMCs from control subjects was not associated with a significant increase in the amount of secreted Fas, while in PBMCs from SLE subjects stimulation with FasL stimulated the release of Fas without affecting apoptosis. One possible explanation to this observation could be that SLE PBMCs can block FasL-induced apoptosis by releasing soluble Fas, which competes with membrane-bound Fas for the binding of FasL. The lack of significant effect of FasL on the release of Fas in the experiment comparing SLE and control PBMCs in FIG. 11A could be seen as contradictory to the findings presented in FIG. 10B that stimulation with FasL induced a significant increase of Fas secretion in control PBMCs. However, it should be kept in mind that all cells in the latter experiment came from the same individual and that the increase was only about 10%.

SLE patients with clinical manifestations of CVD had higher levels of soluble death receptors than those without. Notably, an impaired regulation and handling of apoptosis represents an interesting common feature of SLE and atherosclerosis, the main cause of acute cardiovascular events. Enhanced apoptosis of smooth muscle cells in atherosclerotic plaques increases the risk for plaque rupture, which is considered as the main cause of acute myocardial infarction. However, there is experimental evidence that also inhibition of apoptotic signaling as well as impaired clearance of apoptotic material contribute to atherosclerosis development. In line with this notion ApoE$^{-/-}$ mice lacking FasL or Fas both demonstrate enhanced atherosclerosis development. Also TNF-R1 deficient mice are more susceptible to atherosclerosis. TNF-α$^{-/-}$/ApoE$^{-/-}$ mice are characterized by reduced formation of atherosclerotic plaques suggesting that while TNF-α signaling through TNF-R1 is atheroprotective the net effect of other TNF receptors is pro-atherogenic.

The role of TRAIL-R2 in atherosclerosis remains relatively unknown but observations that both TRAIL and TRAIL receptors are present in atherosclerotic plaques suggests that it may play a role in the disease process. The positive association between increased levels of soluble death receptors and a SLICC score above one suggest that these mechanisms also contribute to organ damage outside the cardiovascular system. These observations are thus in line with previous reports of elevated soluble Fas levels in SLE patients with organ manifestations.

A striking observation in the present study was the clear association between increased levels of soluble death receptors and factors associated with the metabolic syndrome including high BMI, glucose, triglycerides, systolic blood pressure and low HDL. The mechanisms responsible these associations remain to be fully elucidated. In the present study we also identified an inverse association between soluble death receptors and autoantibodies against the LDL antigen ApoB P210. High levels of this type of autoantibodies have been associated with a lower risk of CVD and we recently reported that patients with SLE have reduced levels of ApoB autoantibodies. Moreover, recombinant IgG against Apo B have been shown to reduce atherosclerosis in experimental animal models. It is an interesting possibility that these autoantibodies in some way may reduce death receptor signaling and through this mechanism affect atherosclerosis development.

The present findings demonstrate an increased release of the soluble forms of the apoptosis-signaling receptors Fas, TNF-R1 and TRAIL-R2 in SLE and that the plasma levels of these receptors are associated with the presence of CVD as well as other types of SLE-related organ complications. Our findings also suggest that the plasma levels of soluble Fas and TRAIL-R2 reflect signaling through membrane-bound death receptors and that increased levels of soluble Fas may inhibit apoptosis induction in SLE through binding to FasL. Since impaired regulation of apoptosis also has been shown to promote atherosclerosis development in general we propose that increased expression of soluble death receptors may contribute to cardiovascular complications in SLE.

Example 3. Low Levels of Apolipoprotein B-100 Autoantibodies are Associated with Increased Risk of Coronary Events Previous smaller studies have indicated inverse associations between autoantibodies to oxidized low-density lipoprotein epitopes, and cardiovascular disease. The present study investigated associations between autoantibodies against the apolipoprotein B-100 peptides P45 and P210, respectively, and risk of incident cardiovascular disease in a large population-based cohort.

Apolipoprotein B-100 autoantibodies were analyzed by ELISA in a prospective study, including 5393 individuals (aged 46-68 years) belonging to the cardiovascular arm of the Malmö Diet and Cancer study with a follow-up time of >15 years. Subjects that suffered an acute coronary event during follow-up (n=382) had lower levels at baseline of IgM autoantibodies recognizing the native and malondialdehyde-modified apolipoprotein B-100 peptides P45 and P210 and also lower IgG levels recognizing native P210, whereas no association was found with risk for stroke (n=317). Subjects in the highest compared with lowest tertile of IgM-P45$_{MDA}$ (hazard ratio [95% confidence interval]: 0.72 [0.55, 0.94]; P=0.017) and IgG-P210$_{native}$ (hazard ratio [95% confidence interval]: 0.73 [0.56, 0.97]; P=0.029) had lower risk for incident coronary events after adjustment for cardiovascular risk factors in Cox proportional hazard regression models. Moreover, subjects with high levels of IgG-P210$_{native}$ were less likely to have carotid plaques as assessed by ultrasonography at baseline (odds ratio=0.81, 95% confidence interval 0.70-0.95, P=0.008 after adjustment for risk factors).

This large prospective study demonstrates that subjects with high levels of apolipoprotein B-100 autoantibodies have a lower risk of coronary events supporting a protective role of these autoantibodies in cardiovascular disease.

We investigated the relationships of plasma levels of IgM and IgG autoantibodies against native P45 (IgMP45 native and IgG-P45native), native P210 (IgM-P210native and IgG-P210native), MDA-modified P45 (IgM-P45MDA and IgGP45 MDA), and MDA-modified P210 (IgM-P210MDA and IgGP210MDA) and incidence of cardiovascular events. The findings establish that high levels of ApoB100 autoantibodies are associated with a lower incidence of coronary events.

Experimental Methods

The Malmö Diet and Cancer Study (MDCS) is a prospective population-based cohort (n=28,449) study examining the association between diet and cancer [Berglund G, et al. The Malmo Diet and Cancer Study. Design and feasibility. J Intern Med. 1993; 233:45-51]. Subjects born between 1926 and 1945 and living in Malmö were eligible for inclusion in the study. Between October 1991 and February 1994, every other participant was also invited to take part in a sub-study focusing on the epidemiology of carotid artery disease (MDCS cardiovascular cohort, n=6,103) [Hedblad B, et al. Relation between insulin resistance and carotid intima-media thickness and stenosis in non-diabetic subjects. Results from a cross-sectional study in Malmo, Sweden. Diabet Med. 2000; 17:299-307]. In the present study, plasma samples for assessments of ApoB100 autoantibodies were available in a random subsample of 5,393 subjects participating in the cardiovascular cohort of MDCS (FIG. 12), aged 46 to 68 years old (mean age 57.6). Participants were followed from baseline examination until first event of cardiovascular disease (CVD), emigration from Sweden or death, up until Dec. 31, 2009. Ascertainment of cases and validity of the registries used (the Swedish Discharge Registry, the Stroke Register of Malmö and the Cause of Death Registry of Sweden) have been proven to be high. A coronary event was defined as a fatal or non-fatal myocardial infarction, on the basis of the International Classification of Diseases 9th and 10th revisions (ICD-9 and ICD-10) codes 410 and I21, respectively. Death due to ischemic heart disease was defined on the basis of codes 412 and 414 (ICD-9) or I22, I23 and I25 (ICD-10). A stroke event was defined as a fatal- or non-fatal stroke (ICD-9: 430, 431, 434 and 436), hemorrhagic stroke as ICD-9: 430, 431 or ICD-10: I60, I61 and ischemic stroke as ICD-9:434, 436 or ICD-10: I63. Throughout the follow-up period 668 incident first event CVD cases (398 coronary events and 329 strokes, whichever came first) were identified. Within the 398 incident coronary events, 66 fatal myocardial infarctions, 293 non-fatal myocardial infarctions and 39 ischemic heart diseases were identified. Moreover, within the 329 incident stroke events, 25 fatal and 304 non-fatal strokes, whereof 269 ischemic strokes, 52 hemorrhagic strokes and 8 unspecified were recognized. Hypertension was defined as blood pressure≥140/90 mmHg or blood pressure lowering medication, high cholesterol as >5 mmol/L, smoking as current smoking. Blood pressure, smoking habits and lipid levels were determined as previously described [Hedblad B, et al. Relation between insulin resistance and carotid intima-media thickness and stenosis in non-diabetic subjects. Results from a cross-sectional study in Malmo, Sweden. Diabet Med. 2000; 17:299-307]. The study was approved by the Regional Ethical Review Board in Lund (LU 51-90) and was conducted in accordance with the Helsinki Declaration. All subjects gave written consent. The reporting of this cohort study is in accordance with the STROBE guidelines.

B-mode ultrasound. Analysis of the common and bifurcation carotid arteries was performed using an Acuson 128 CT system with a 7-MHz transducer as described previously [Hedblad B, Nilsson P, Janzon L and Berglund G. Relation between insulin resistance and carotid intima-media thickness and stenosis in non-diabetic subjects. Results from a cross-sectional study in Malmo, Sweden. Diabet Med. 2000; 17:299-307]. Briefly, the right carotid bifurcation was scanned within a predefined window comprising 3 cm of the distal common carotid artery, the bifurcation, and 1 cm of the internal and external carotid arteries. All images for measurement of plaque thickness were obtained in the longitudinal projection showing the thickest intima-media complex. Plaque was defined as a focal thickening of the intima-media exceeding 1.2 mm.

Determination of P45 and P210 Autoantibodies.

Peptides corresponding to the amino acids from 661 to 680 (P45; IEIGLEGKGFEPTLEALFGK, SEQ ID NO: 45) and amino acids 3136-3155 (P210; KTTKQSFDLSVKAQYKKNKH, SEQ ID NO: 210) of human ApoB100 were synthesized (K J Ross Petersen A S, Horsholm, Denmark) and used in ELISA. The peptides were modified by 0.5 M MDA for 3 h at 37° C. and dialyzed against PBS containing 1 mM EDTA as described [Palinski W, Witztum J L. Immune responses to oxidative neoepitopes on LDL and phospholipids modulate the development of atherosclerosis. J Intern Med. 2000; 247:371-380]. Native and MDA-modified peptides diluted in PBS pH 7.4 (20 µg/ml) were absorbed to microtiter plate wells (Nunc MaxiSorp, Nunc, Roskilde, Denmark) in an overnight incubation at 4° C. After washing with PBS containing 0.05% Tween-20 (PBS-T) the coated plates were blocked with SuperBlock in TBS (Thermo Scientific, #37535) for 30 min at room temperature (RT) followed by an incubation of test plasma, diluted ¹/₁₀₀ in TBS containing 0.1% Tween-20 (Thermo Scientific, #28320) and 10% Superblock (TBS-T) for 2 h at RT and overnight at 4° C. After rinsing, deposition of autoantibodies directed to the peptide was detected using biotinylated rabbit polyclonal secondary antibody to human IgG (Abcam ab7159) or IgM antibodies (ICN 67-321, Biomedicals, Inc., Aurora, Ohio) appropriately diluted in TBST. After another incubation for 2 h at RT the plates were washed and the bound biotinylated antibodies detected by alkaline phosphatase conjugated streptavidin (BioLegend 405211), incubated for 2 h at RT. The colour reaction was developed by using phosphatase substrate kit (Thermo Scientific, #37620) and the absorbance at 405 nm was measured after 90 and 120 min for IgM and IgG, respectively, of incubation at RT. A ratio between the absorbance unit of the individual plasma sample and the absorbance unit of the control plasma (a plasma pool from voluntary healthy blood donors run on each ELISA-plate) was calculated and used for the analysis. Data regarding the specificity and variability of the antibody ELISA have been published previously [Fredrikson G N, et al. Identification of immune responses against aldehydemodified peptide sequences in apoB associated with cardiovascular disease. Arterioscler Thromb Vasc Biol.

2003; 23:872-878; Fredrikson G N, et al. Autoantibody against the amino acid sequence 661-680 in ApoB100 is associated with decreased carotid stenosis and cardiovascular events. Atherosclerosis. 2007; 194:e188-e192]. In the present study, the intra-assay coefficient of variation was 9-10% for all eight apo-B100 autoantibodies and the inter-assay coefficient 25% for IgM-P45$_{native}$ and IgM-P45$_{MDA}$, 23% for IgG-P45$_{native}$ and IgG-P45$_{MDA}$, 13% for IgM-P210$_{native}$ and IgM-P210$_{MDA}$, 22% for IgG-P210$_{native}$ and IgG-P210$_{MDA}$, respectively. The intra-assay coefficient of variation was calculated by using the absorbance values of the control plasma pool run on each plate of the same day and the inter-assay by using all the absorbance values of the control plasma pool run during the whole period of analysis.

Figure 12:
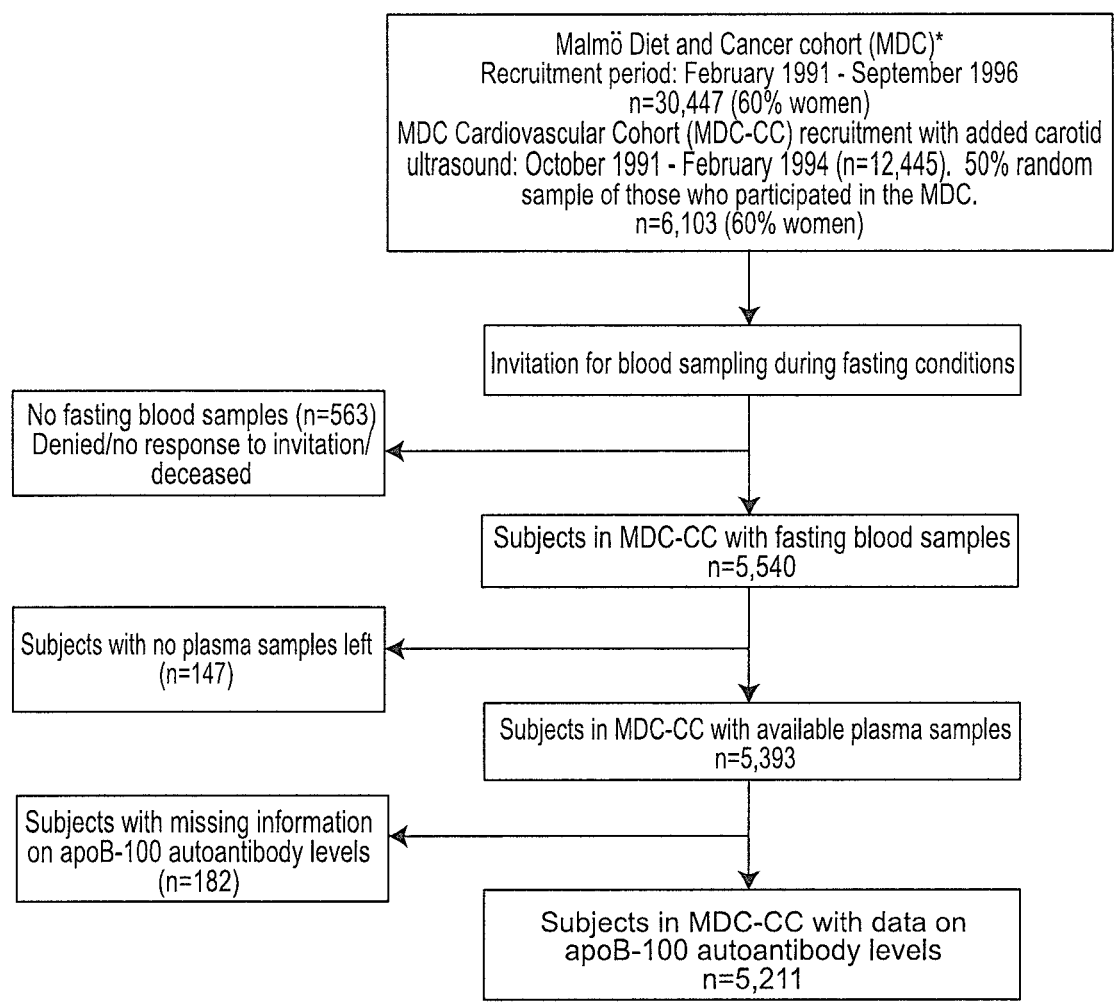
FIG. 12 depicts in accordance with various embodiments of the invention, a flow chart showing the recruitment of the Malmo Diet and Cancer cardiovascular cohort and the study participants of Example 3. See, *1. Manjer J, Elmståhl S, Janzon L, Berglund G. Invitation to a population-based cohort study: differences between subjects recruited using various strategies. Scand J Public Health. 2002; 30(2):103-112. 2. Manjer J, Carlsson S, Elmståhl S, Gullberg B, Janzon L, Lindström M, Mattisson I, Berglund G. The Malmö Diet and Cancer study: representativity, cancer incidence and mortality in participants and non-participants. Eur J Cancer Prev. 2001 December; 10(6):489-499.
Figure 13A:
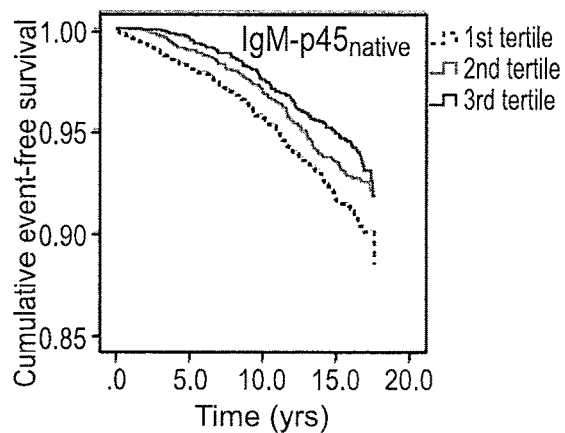
FIG. 13A-FIG. 13E depicts in accordance with various embodiments of the invention, coronary event-free survival of autoantibody tertiles recognizing the apolipoprotein B-100 (ApoB100) peptides P45 and P210 during a 15-year follow-up. Kaplan-Meier event-free survival curves of tertiles of autoantibodies to ApoB100 peptides P45 and P210 revealed a significant positive linear trend showing lower incidence of coronary events with increasing autoantibody levels. Tertiles of IgM-P45$_{native}$ (FIG. 13A) IgM-P45$_{MDA}$, (FIG. 13B) IgM-P210$_{native}$, (FIG. 13C) IgM-P210$_{MDA}$, (FIG. 13D) and IgG-P210$_{native}$, (FIG. 13E) Log rank (Mantel Cox)] tests were used to calculate P for linear trends.
Figure 13B:
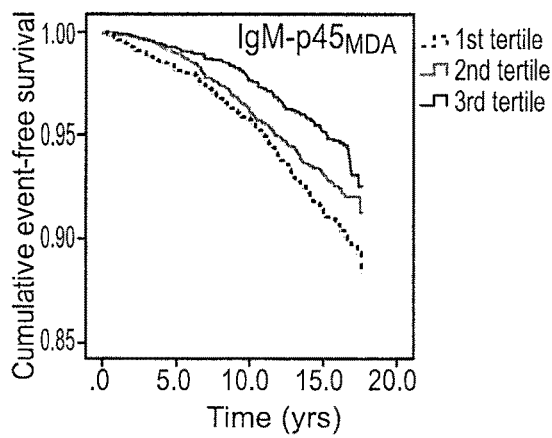
Figure 13C:
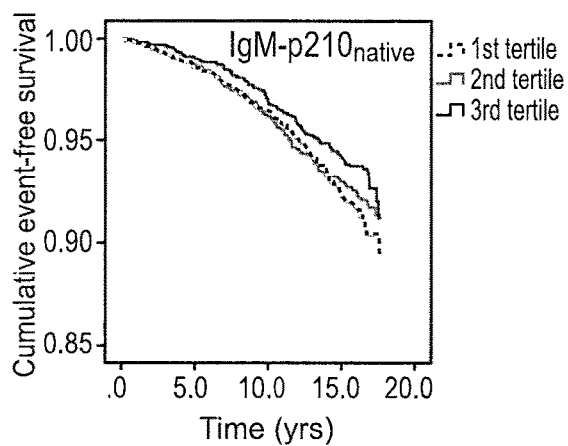
Figure 13D:
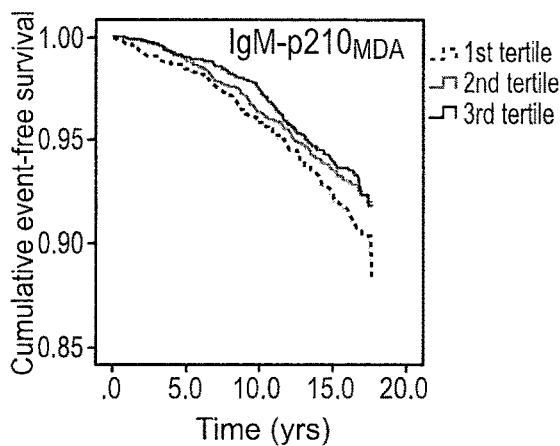
Figure 13E:
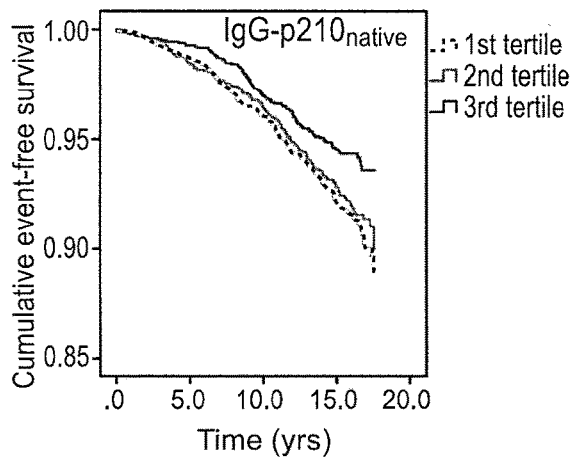

Statistics. Clinical characteristics are presented as median (interquartile range, IQR) for continuous variables and as percentages for categorical variables. The 182 missing data due to technical reasons in the measurements of ApoB100 autoantibody levels were excluded from analysis (FIG. 12). Skewed continuous variables were logarithmically transformed. An independent sample t test was used to assess normally distributed continuous variables and a Chi-square test for proportions between subjects with and without an incident cardiovascular event. Non-parametric test (Mann-Whitney) was used to assess non-normally distributed continuous variables. Spearman's correlation coefficient was used to examine the relationship among continuous variables as appropriate. No correction for multiple testing of the eight apo-B100 autoantibodies has been performed. Several of the baseline clinical characteristics that significantly differed between cases and controls (Table 18) were selected as potential confounders: age, sex, triglycerides, LDL, HDL (but not cholesterol, LDL/HDL ratio or apoB), hs-CRP, current smoking, prevalent diabetes mellitus (but not glucose or HbA1c), systolic blood pressure (but not diastolic blood pressure) and blood pressure lowering medication. The confounders not included are represented by related risk factors included in the model. A linear regression model was used to calculate independent associations and logistic regression analyses (with the selected potential confounders included as correction variables) were used to determine associations between ApoB100 autoantibodies and presence of carotid plaques. The Kaplan-Meier method was used to evaluate rates of coronary or stroke event-free survival of ApoB100 autoantibody tertiles, and differences were analyzed by log rank test. Cox proportional hazard regression models were used to compare incidence of coronary or stroke events between autoantibody tertiles and to calculate risk factor adjusted hazard ratios (95% confidence interval, CI). Plots of the hazard function in different groups over time did not indicate that the proportional-hazards assumption was violated.

Characteristics of the Study Cohort. In this cohort of 5393 individuals (aged 46-68 years) from the cardiovascular arm of MDCS (FIG. 12), 398 incident coronary events (66 fatal and 293 nonfatal myocardial infarctions and 39 ischemic heart disease) and 329 incident stroke events (25 fatal and 304 nonfatal strokes, whereof 269 ischemic strokes, 52 hemorrhagic strokes, and 8 unspecified) were registered during follow-up until Dec. 31, 2009. Baseline characteristics of noncases and CVD cases are shown in Table 18. In comparison with noncases, those with incident CVD (coronary or stroke events) were older; included more males, more smokers, and hypertensive individuals; and had a higher prevalence of diabetes mellitus. Also blood lipids, hemoglobin A1c, and high sensitive C-reactive protein were increased among CVD cases (Table 18).

TABLE 18

Baseline Clinical Characteristics of the Study Cohort:

| | Noncases (n = 4666) | Cases (n = 398),* Coronary | Cases (n = 329),* Stroke |
|---|---|---|---|
| Age at screening, y | 57.6 (52.2-62.5) | 61.6 (57.2-64.7)† | 62.1 (58.0-64.4)† |
| Sex, % men | 39.8 | 61.6† | 50.8† |
| Current smoker, % | 26.1 | 33.8† | 32.8† |
| Diabetes mellitus, %§ | 7.4 | 19.8† | 18.2† |
| Hypertension, %‖ | 62.5 | 81.2† | 85.1† |
| Glucose, mmol/L | 4.9 (4.6-5.3) | 5.1 (4.7-5.6)† | 5.1 (4.7-5.5)† |
| Triglycerides, mmol/L | 1.2 (0.9-1.6) | 1.4 (1.0-1.9)† | 1.3 (1.0-1.9)† |
| Cholesterol, mmol/L | 6.1 (5.4-6.8) | 6.3 (5.6-7.0)† | 6.1 (5.5-6.9) |
| HDL, mmol/L | 1.4 (1.1-1.6) | 1.2 (1.0-1.4)† | 1.2 (1.0-1.4)† |
| LDL, mmol/L | 4.1 (3.5-4.8) | 4.4 (3.7-5.0)† | 4.2 (3.6-4.9) |
| LDL/HDL, ratio | 3.1 (2.3-3.9) | 3.8 (2.9-4.7)† | 3.6 (2.6-4.4)† |
| apoB, mg/L¶ | 1042 (883-1205) | 1136 (997-1266)† | 1074 (923-1232) |
| Systolic BP, mm Hg | 140 (126-152) | 150 (138-160)† | 150 (140-160)† |
| Diastolic BP, mm Hg | 86 (80-92) | 90 (82-95)† | 90 (85-98)† |
| HbA1c, % | 4.8 (4.5-5.1) | 5.0 (4.6-5.4)† | 5.0 (4.6-5.3)† |
| hs-CRP, mg/L | 1.3 (0.7-2.7) | 2.0 (1.0-4.1)† | (1.0-3.8)† |

For Table 18 Above: Values presented as median and interquartile range or percentages. ApoB indicates apolipoprotein B; BP, blood pressure; HbA1c, Hemoglobin A1c; HDL, high-density lipoprotein; hs-CRP, high-sensitive C-reactive protein; and LDL, low-density lipoprotein. *Mann-Whitney test or $\chi 2$ test for categorical data. †P<0.001. ‡P<0.05. § History of diabetes mellitus, medication, or fasting glucose≥6.1 mmol/L. ¶Blood pressure≥140/90 mm Hg or blood pressure-lowering treatment. noncases, 167 coronary, and 137 stroke events.

ApoB100 Autoantibodies and Incident CVD. CVD cases were found to have lower levels of IgM against both native and MDA-modified ApoB100 P45 and P210, respectively, as well as lower levels of IgG against native ApoB100 P210, whereas the other IgG autoantibody levels did not differ between groups. When subjects with incident coronary events and incident stroke were analyzed separately, the same pattern of differences was observed between noncases and those with coronary events. However, no association was seen between ApoB100 peptide autoantibodies and risk for total stroke (Table 19).

TABLE 19

Ratio of ApoB100 Autoantibody Levels in Noncases and CVD Cases:

| ApoB100 Abs, | Noncases (n = 4512) | Cases (n = 382), Coronary | Cases (n = 317), Stroke |
|---|---|---|---|
| IgM-P45$_{native}$ | 0.307 (0.135-0.579) | 0.237 (0.089-0.497)† | 0.292 (0.119-0.512) |
| IgM-P45$_{MDA}$ | 0.434 (0.260-0.685) | 0.360 (0.211-0.588)† | 0.406 (0.243-0.605) |
| IgM-P210$_{native}$ | 0.668 (0.518-0.818) | 0.649 (0.493-0.781)‡ | 0.659 (0.488-0.811) |
| IgM-P210$_{MDA}$ | 0.750 (0.606-0.881) | 0.721 (0.571-0.852)† | 0.723 (0.593-0.853) |
| IgG-P45$_{native}$ | 0.231 (0.105-0.468) | 0.217 (0.092-0.452) | 0.224 (0.090-0.455) |
| IgG-P45$_{MDA}$ | 0.368 (0.241-0.564) | 0.341 (0.226-0.530) | 0.351 (0.228-0.575) |
| IgG-P210$_{native}$ | 0.395 (0.290-0.530) | 0.372 (0.266-0.478)† | 0.392 (0.275 0.520) |
| IgG-P210$_{MDA}$ | 0.649 (0.489-0.830) | 0.619 (0.465-0.840) | 0.651 (0.462-0.873) |

For Table 19 Above: Abs indicates antibodies; ApoB100, apolipoprotein B-100; CVD, cardiovascular disease; IgG, immunoglobulin; IgM, immunoglobulin M; and MDA, malondialdehyde. *Ratio of the individual plasma sample and the control plasma pool. Values presented as median and interquartile range of the ratio of the ApoB100 autoantibody levels. Skewed variables were log-transformed before analysis. †P<0.01, Student t test. ‡P<0.05.

Also, no association was detected when only individuals with incident ischemic stroke were analyzed.

To determine if there were time-dependent associations between autoantibodies and incident coronary events, the autoantibody levels were divided into tertiles that were plotted into Kaplan-Meier survival curves. The survival curves revealed a significant positive linear trend over tertiles of the IgM-P45$_{native}$, IgM-P45$_{MDA}$, IgM-P210$_{native}$, IgM-P210$_{MDA}$, and IgG-P210$_{native}$ autoantibodies (Log rank [Mantel Cox] tests, P for linear trend<0.05; FIG. 13A-13E). No significant linear trend was found for IgG-P45$_{native}$, IgG-P45$_{MDA}$, or IgG-P210$_{MDA}$. In a Cox proportional hazard regression model, a significant association was identified between high levels of IgM-P45$_{MDA}$ and lower risk of incident coronary events after adjustment for several potential confounders, for example, age, sex, LDL, HDL, triglycerides, high-sensitive C-reactive protein, current smoking, prevalent diabetes mellitus, blood pressure-lowering medication, and systolic blood pressure (hazard ratio [95% confidence interval (CI)]: 0.72 [0.55, 0.94], P=0.02 for the third tertile versus first; Table 20). Furthermore, a significant association between high levels of IgG-P210$_{native}$ and decreased risk of coronary events was found after adjustment of the model with the same risk factors (hazard ratio [95% CI]: 0.73 [0.56, 0.97], P=0.03; for the third tertile versus first; Table 20).

TABLE 20

Hazard Ratios (HR) and 95% Confidence Intervals (CI) for Incident Coronary Event by Tertiles of IgM-P45$_{MDA}$ and IgG-P210$_{native}$ Autoantibodies:

| Model | | First Tertile | Second Tertile | Third Tertile | P for Trend |
|---|---|---|---|---|---|
| | IgM-P45$_{MDA}$, ratio* | <0.313 | 0.313-0.578 | >0.579 | |
| | Coronary events, numbers | 159 | 126 | 97 | <0.0001 |
| 1 | Cornony events, HR (95% CI) | 1.00 | 0.79 (0.62-0.99)† | 0.59 (0.46-0.76)‡ | 0.001 |
| 2 | Cornony events, HR (95% CI) | 1.00 | 0.94 (0.73-1.20) | 0.72 (0.55-0.94)† | 0.112 |
| | IgM-P210$_{native}$, ratio* | <0.324 | 0.324-0.475 | >0.476 | |
| | Coronary events, numbers | 148 | 137 | 97 | 0.001 |
| 1 | Cornony events, HR (95% CI) | 1.00 | 0.91 (0.72-1.15) | 0.66 (0.51-0.85)‡ | 0.005 |
| 2 | Cornony events, HR (95% CI) | 1.00 | 1.10 (0.86-1.40) | 0.73 (0.56-0.97)† | 0.051 |

Table 20 above: Associations between tertiles of IgM-P45$_{MDA}$ and IgG-P210$_{native}$ autoantibodies and incident coronary event was calculated using Cox proportional hazard regression unadjusted (Model 1) and adjusted for age, sex, LDL, HDL, systolic blood pressure, triglycerides, hs-CRP, current smoking, blood pressure-lowering medication, and prevalent diabetes mellitus (Model 2). Significant associations between number of events and tertiles of autoantibodies were determined with a χ2 test for linear trend. CI indicates confidence interval; HbA1c, Hemoglobin A1c; HDL, high-density lipoprotein; HR, hazard ration; hs-CRP, high-sensitive C-reactive protein; IgG, immonoglobulin; IgM, immunoglobulin M; LDL, low-density lipoprotein; and MDA, malondialdehyde. *Ratio of the individual plasma sample and the control plasma pool. †P<0.05. ‡P<0.001 vs first tertile, highlighted in bold.

No significant differences between tertiles for the other ApoB100 autoantibodies were detected (Table 21).

TABLE 21

Hazard ratios (HR) and 95% confidence intervals (CI) for incident coronary event by tertiles of apo-B100 autoantibodies:

|  | 1st tertile | 2nd tertile | 3rd tertile | P for trend |
|---|---|---|---|---|
| IgM-P45$_{native}$, ratio† | | | | |
| Coronary events, numbers | 137 | 109 | 95 | 0.004 |
| Coronary events HR (95% CI) | 1.00 | 0.84 (0.64-1.09) | 0.76 (0.58-1.03) | 0.010 |
| IgG-P45$_{native}$, ratio† | | | | |
| Coronary events, numbers | 140 | 119 | 123 | 0.269 |
| Coronary events HR (95% CI) | 1.00 | 0.87 (0.67-1.14) | 1.02 (0.79-1.32) | 0.167 |
| IgG-P45$_{MDA}$, ratio† | | | | |
| Coronary events, numbers | 138 | 118 | 113 | 0.098 |
| Coronary events HR (95% CI) | 1.00 | 0.85 (0.66-1.11) | 0.89 (0.68-1.16) | 0.892 |
| IgM-P210$_{native}$ ratio† | | | | |
| Coronary events, numbers | 144 | 129 | 109 | 0.023 |
| Coronary events HR (95% CI) | 1.00 | 1.07 (0.83-1.38) | 0.90 (0.67-1.18) | 0.298 |
| IgM-P210$_{MDA}$ ratio† | | | | |
| Coronary events, numbers | 147 | 121 | 114 | 0.032 |
| Coronary events HR (95% CI) | 1.00 | 0.95 (0.73-1.23) | 1.04 (0.80-1.35) | 0.368 |
| IgG-P210$_{MDA}$ ratio† | | | | |
| Coronary events, numbers | 144 | 113 | 125 | 0.216 |
| Coronary events HR (95% CI) | 1.00 | 0.81 (0.63-1.06) | 0.96 (0.74-1.23) | 0.289 |

Table 21 above: Associations between tertiles of ApoB100 autoantibodies and incident coronary event was calculated using Cox proportional hazard regression adjusted for age, sex, LDL, HDL, systolic blood pressure, triglycerides, hs-CRP, current smoking, blood pressure lowering medication and prevalent diabetes. Significant associations between number of events and tertiles of autoantibodies were determined with a $\chi2$ test for linear trend. Tertiles of the ratio of the individual plasma sample and the control plasma pool. Significant P-values for trend across tertiles are highlighted in bold text.

The association between high levels of IgM-P45$_{MDA}$ and lower risk of incident coronary events was independent of the levels of the IgG-antibody recognizing the same antigen (IgG-P45$_{MDA}$; hazard ratio [95% CI]: 0.59 [0.46, 0.76]; P<0.001). In line, high levels of IgG-P210$_{native}$ were independent of the levels of IgM-P210$_{native}$ (hazard ratio [95% CI]: 0.71 [0.54, 0.93]; P=0.01). All together, the results suggest that some of the ApoB100 autoantibodies are associated with a lower incidence of coronary events.

Individuals with presence of carotid plaques had lower levels of 3 of the apo-B100 autoantibodies; IgM-P210$_{native}$ (0.66±0.21 absorbance ratio versus 0.68±0.22; P<0.01), IgM-P210$_{MDA}$ (0.73±0.20 absorbance ratio versus 0.75±0.20; P<0.001), and IgG-P210$_{native}$ (0.41±0.22 absorbance ratio versus 0.44±0.22; P<0.001), in comparison to subjects with no carotid plaques. Moreover, chi-squared tests identified significant linear trends for presence of carotid plaques across the tertiles of these 3 ApoB100 autoantibodies and also in IgG-P45$_{MDA}$ (Table 22).

TABLE 22

Associations between presence of carotid plaques and tertiles of ApoB100 autoantibodies.

|  | 1st tertile | 2nd tertile | 3rd tertile | P for trend |
|---|---|---|---|---|
| IgM-P45$_{native}$, ratio† | | | | |
| Carotid plaques n (%) | 689 (45.4) | 659 (43.3) | 654 (43.0) | 0.169 |
| IgM-P45$_{MDA}$, ratio† | | | | |
| Carotid plaques n (%) | 768 (46.3) | 702 (42.2) | 731 (43.5) | 0.114 |
| IgG-P45$_{native}$, ratio† | | | | |
| Carotid plaques n (%) | 749 (44.7) | 736 (44.4) | 716 (43.0) | 0.319 |
| IgG-P45$_{MDA}$, ratio† | | | | |
| Carotid plaques n (%) | 760 (46.1) | 713 (43.5) | 695 (42.5) | 0.039 |
| IgM-P210$_{native}$ ratio† | | | | |
| Carotid plaques n (%) | 770 (46.0) | 732 (44.3) | 699 (41.7) | 0.011 |
| IgM-P210$_{MDA}$ ratio† | | | | |
| Carotid plaques n (%) | 778 (46.7) | 742 (44.4) | 681 (40.9) | 0.001 |
| IgG-P210$_{native}$ ratio† | | | | |
| Carotid plaques n (%) | 801 (48.1) | 729 (43.7) | 671 (40.2) | <0.001 |
| IgG-P210$_{MDA}$ ratio† | | | | |
| Carotid plaques n (%) | 748 (45.0) | 721 (43.1) | 732 (43.9) | 0.525 |

Table 22 above: Numbers represent individuals with presence of carotid plaques (n) and the percentage (%) the percent of individuals with presence of carotid plaques within the tertile, respectively. Significant associations between presence of carotid plaques and tertiles of autoantibodies were determined with a $\chi^2$ test for linear trend. †Tertiles of the ratio of the individual plasma sample and the control plasma pool. Significant P-values for trend across tertiles are highlighted in bold text.

In a logistic regression model (adjusted for the same risk factors as mentioned above), there were fewer individuals with presence of carotid plaques in the upper compared with the lowest tertile of IgG-P210$_{native}$ (OR=0.813, 95% CI 0.70-0.95; P=0.008), whereas no associations were found for the other autoantibodies. All autoantibodies except for IgM-P45$_{native}$ correlated inversely with LDL levels, whereas only antibodies recognizing P210 showed a significant inverse correlation with apoB (Table 23).

TABLE 23

Spearman Bivariate Correlations (r) Between ApoB100 Autoantibody Levels and LDL or ApoB.

| Apo B-100 Abs, Ratio* | LDL,† mmol/L | apoB,‡ mg/L |
|---|---|---|
| IgM-P45$_{native}$ | NS | NS |
| IgM-P45$_{MDA}$ | r = −0.032§ | NS |
| IgM-P210$_{native}$ | R = −0.064 ‖ | R = −0.080 ‖ |
| IgM-P210$_{MDA}$ | R = −0.046 | R = −0.083 ‖ |
| IgG-P45$_{native}$ | R = −0.032§ | NS |
| IgG-P45$_{MDA}$ | R = −0.04 | NS |
| IgG-P210$_{native}$ | R = −0.069 ‖ | R = −0.083 ‖ |
| IgG-P210$_{native}$ | R = −0.042 | R = −0.047§ |

For Table 23 above: Abs indicates antibodies; ApoB100, apolipoprotein B-100; IgG, immonoglobulin; IgM, immonoglobulin M; LDL, low-density lipoprotein; MDA, malondialdehyde; and NS, not significant. *Ratio of the individual plasma sample and the control plasma pool. †Includes 4512 noncases, 382 coronary, and 317 stroke events. ‡Includes 1842 noncases, 167 coronary, and 137 stroke events. § P<0.05. ¶P<0.01. ‖P<0.001.

This Swedish prospective population-based study including 5393 white individuals represents the hitherto largest study investigating the role of autoantibodies recognizing ApoB100 peptides in CVD. Several of the previous studies have had retrospective case-control design and included small selected patient populations, such as individuals demonstrating different established cardiovascular risk factors. The present study design, however, made it possible to determine whether the autoantibody levels can predict risk of future cardiovascular events in subjects of the general community. The findings verified that IgG autoantibodies recognizing the native form of P210 are cross-sectionally associated with a lower presence of carotid plaques. Moreover, the IgM-P45$_{MDA}$ and the IgG-P210$_{native}$ autoantibodies, respectively, demonstrated independent association with lower risk for a future coronary event.

Previous studies analyzing autoantibodies against the whole oxidized LDL particle and their associations with CVD have demonstrated contradictory findings. The inconclusive results may depend on difficulties in the standardization of the antigen. During the oxidation process of the LDL particle, neoepitopes are formed and others degraded. This process may deviate depending on the differences in the composition of the LDL particle isolated from diverse individuals, resulting in a poorly defined antigen. Studies using single LDL-derived antigens as phosphorylcholine or ApoB100 peptides have revealed a clearer picture. Previous studies analyzing ApoB100 peptide autoantibodies have demonstrated an inverse association between the autoantibodies and CVD, also in diabetic and systemic lupus erythematosus patients. Thus, the clinical studies suggest a protective role of antibodies recognizing specific antigens in oxidized LDL. This is supported by experimental studies, where treatment of atherosclerosis-prone mice with human recombinant IgG recognizing the MDA-P45 epitope was found to reduce aortic plaque area and plaque inflammation.

High plasma levels of IgG-P210$_{native}$ have previously been associated with less severe coronary lesions, both in nondiabetic and diabetic patients, lower risk of developing myocardial infarction, less severe subclinical atherosclerosis, decreased risk of postoperative cardiovascular death in carotid endarterectomy patients as well as a lower prevalence of CVD in systemic lupus erythematosus patients. We now extend these findings by demonstrating that low levels of IgG-P210$_{native}$ autoantibodies predict risk of coronary events in a large population-based, prospective study. Interestingly, only antibodies recognizing the P210 epitope, and not the P45 epitope, showed an inverse correlation with apoB. It could be speculated that P210 may be visible for the immune system in the intact LDL particle, whereas the P45 epitope may be hidden in the phospholipid layer and only visible after the oxidation process. Furthermore, it might be that the IgG-P210$_{native}$ autoantibody recognizes a native or mildly modified P210 peptide and that this epitope plays a more important role in atherogenesis than the more extensively MDA-modified one.

In previous studies, we have detected an inverse association between high levels of autoantibodies recognizing P210$_{MDA}$ and subclinical atherosclerosis as well as less severe carotid disease in women. In both cases, the epitope was recognized by IgM autoantibodies. An open question is if these represent natural IgM antibodies that have previously been shown to recognize other endogenously generated structures, such as oxidation-specific epitopes, or if they are classical IgM antibodies. T cell-activated B2 cells are known to secrete adaptive IgMs, whereas B1 cells spontaneously secrete natural IgM antibodies. Experimental studies have suggested that B2 cells have a proatherogenic role, whereas B1 cells are atheroprotective depending on their secretion of natural IgM antibodies. Altogether, this may indicate that the IgM antibodies recognizing a modified ApoB100 epitope represent atheroprotective natural IgM antibodies. Interestingly, we have previously demonstrated that subjects with low levels of IgM recognizing methylglyoxal-modified peptide p220 in ApoB100 have an increased risk to develop cardiovascular events and that anti-methylglyoxal-p220 IgM is produced by B1 cells. Another important oxidation-specific epitope on oxidized LDL, the phosphorylcholine epitope, has been found to be recognized by anti-phosphorylcholine IgM that represents an extensively characterized natural IgM antibody. This natural IgM antibody against the phosphorylcholine epitope has been shown to confer protection in experimental atherosclerosis in mice and also to be associated with reduced cardiovascular risk in humans. In support, the present study demonstrated an inverse association between high levels of IgM-P45$_{MDA}$ and reduced risk of future coronary events. High levels of this IgM antibody have also in a previous study showed an association with a lower prevalence of CVD in systemic lupus erythematosus patients. Furthermore, in patients with type-2 diabetes mellitus, high levels of IgM autoantibodies recognizing AGE-modified ApoB100 were found to be associated with less severe coronary disease. Taken together, both IgM and T cell-dependent IgG antibodies recognizing oxidized LDL epitopes seem to have a protective role in atherogenesis, suggesting important contributions of both innate and adaptive immune responses. The reason why only 2 of the autoantibodies recognizing ApoB100 epitopes measured in the present study were associated with lower risk of incident coronary events may be that these 2 epitopes appear at different stages of the modification of the LDL particle and become presented in a way that is important for activation of immune responses, reflecting that the extent of LDL oxidation influences the plasma autoantibody levels.

Both inflammation and immune responses have been found to influence the pathogenesis of coronary artery disease, as well as the risk and causation of stroke. Induced oxidative stress in the myocardium with a subsequent LDL oxidation may rapidly activate an antibody response in already primed individuals and that these antibodies are consumed directly resulting in baseline levels the day after the event.

Levels of natural IgM antibodies to oxidation-specific epitopes have shown inverse correlation with CVD in several human studies. Their atheroprotective properties may be dependent on the ability to recognize the oxidation-specific epitopes on oxidized LDL. Thus, the IgM-P45$_{MDA}$ autoantibody may represent a natural IgM antibody explaining its association with lower risk of future coronary events.

The strengths of the present study were the large size of the population and the prospective design together with a 15-year follow-up time, including >600 events, making it unique by allowing for an evaluation if these ApoB100 epitope autoantibodies predict risk for future cardiovascular events. The findings demonstrated an association between high levels of IgM-P45$_{MDA}$ or IgG-P210$_{native}$ autoantibodies and a lower risk of coronary events. Taken together, and in the light of previous smaller studies, the present findings establish that high levels of ApoB100 autoantibodies have a protective role in CVD.

Example 4. Decreased Levels of Autoantibodies Against Apolipoprotein B-100 Antigens are Associated with Cardiovascular Disease in Systemic Lupus Erythematosus Increased production of autoantibodies is a characteristic feature of systemic lupus erythematosus (SLE) and there is evidence that several of these autoantibodies may contribute to increased cardiovascular disease (CVD) in SLE. Autoantibodies against the apolipoprotein (apo) B-100 peptides P45 and P210 have been associated with a lower CVD risk in non-SLE cohorts. The aim of the present study was to investigate how SLE affects the occurrence of these potentially protective autoantibodies. The study cohort consisted of 434 SLE patients and 322 age- and sex-matched population controls. Antibodies against native and malondialdehyde (MDA)-modified P45 and P210 were measured by enzyme-linked immunosorbant assay (ELISA). SLE patients had significantly lower levels of P210 immunoglobulin (Ig)G and P45 IgM (both the native and malondialdehyde (MDA)-modified forms). SLE patients with manifest CVD (myocardial infarction, ischaemic cerebrovascular disease or peripheral vascular disease) had lower levels P210 IgG and P45 IgM than SLE patients without CVD. Decreased levels of these autoantibodies were also observed in SLE patients with permanent organ damage, as assessed by the Systemic Lupus International Collaborating Clinics/American College of Rheumatology (ACR) Damage Index (SDI). The present findings show that patients with SLE, a condition generally characterized by abundance of autoantibodies of multiple specificities, have reduced levels of antibodies against the apo B-100 antigens P45 and P210 and that the levels of these antibodies are reduced further in SLE patients with CVD. These observations suggest the possibility that an impaired antibody-mediated removal of damaged LDL particles may contribute to the development of vascular complications and organ damage in SLE.

In the present study we analyzed plasma levels of IgG and IgM against native and MDA-modified P45 and P210 in a cohort of SLE patients and matched controls. The result demonstrates that patients with SLE have decreased levels of P45 IgM and P210 IgG autoantibodies and that this is associated with an increased risk of CVD and other organ complications.

Experimental Methods

Patients and Controls.

Patients and controls were included between January 2004 and October 2013. All patients who fulfilled four or more of the 1982 revised American College of Rheumatology (ACR) classification criteria for SLE [Tan E M, Cohen A S, Fries J F et al. The 1982 revised criteria for the classification of systemic lupus erythematosus. Arthritis Rheum 1982; 25:1271-7] and who received care for SLE at the Department of Rheumatology, Karolinska University Hospital Solna during this period were asked to participate. Patients were required to be older than 18 years, otherwise there were no exclusion criteria. Population controls, individually matched to the first 322 SLE patients were identified in the population registry. Matching was performed within one year of age, for sex, and region of living. Controls were contacted and asked to participate through a letter. The only exclusion criterion among controls was a diagnosis of SLE. The Local Ethics Committee of the Karolinska University Hospital approved the study protocol. All participants gave informed written consent to participate.

Data Collection.

All patients and controls were investigated in person by a rheumatologist. Traditional risk factors for CVD were tabulated. Hypertension was defined as a systolic BP>140 mm Hg and/or a diastolic BP>90 mm Hg or use of antihypertensive treatment. Diabetes was considered present if patients were previously diagnosed with diabetes. History of vascular events, defined as a history of objectively verified myocardial infarction, ischemic cerebrovascular disease or peripheral vascular disease was obtained though interview and review of medical files. In SLE patients, age at diagnosis, duration of disease, and lupus manifestations including autoantibodies were recorded. Lupus nephritis was defined according to the 1982 revised ACR classification criteria for nephritis [Tan E M, et al. The 1982 revised criteria for the classification of systemic lupus erythematosus. Arthritis Rheum 1982; 25:1271-7]. Organ damage was assessed with Systemic Lupus International Collaborating Clinics/ACR Damage index (SDI) [Gladman D, et al. The development and initial validation of the Systemic Lupus International Collaborating Clinics/American College of Rheumatology damage index for systemic lupus erythematosus. Arthritis Rheum 1996; 39:363-9]. All blood samples were taken after overnight fasting and laboratory examinations were performed blinded, either on fresh blood samples or after storage in −70° C.

Intima-Media Wall Thickness Measurements.

Three hundred and two patients were investigated with carotid ultrasound using a duplex scanner (Acuson 128XP, Mountain View, Calif., USA) with a 7.0 MHz ART linear array transducer. Left and right carotids were examined. The IM thickness was defined as the distance between the leading edge of the luminal echo to the leading edge of the media/adventitia echo [Wikstrand J, Wendelhag I. Methodological considerations of ultrasound investigation of intima-media thickness and lumen diameter. J Intern Med 1994; 236:555-9]. IM thickness was measured over one cm length just proximal to the bulb. The mean intima-media thickness (IMT) values for both sides were calculated for each subject. One technician recorded all measurements.

Determination of P45, P210 and β$_2$GPI Autoantibodies.

Peptides corresponding to the amino acids from 661 to 680 (P45; IEIGLEGKGFEPTLEALFGK, SEQ ID NO: 45) and amino acids 3136-3155 (P210; KTTKQSFDLSVKAQYKKNKH, SEQ ID NO: 210) of human ApoB100 were synthesized (K J Ross Petersen A S, Horsholm, Denmark) and used in ELISA. The peptides were modified by 0.5 M MDA for 3 h at 37° C. and dialyzed against PBS containing 1 mM EDTA as described [Fredrikson G N, et al. Identification of immune responses against aldehyde-modified peptide sequences in apo B-100 associated with cardiovascular disease. Arterioscler Thromb Vasc Biol 2003; 23:872-78]. Native and MDA-modified peptides diluted in PBS pH 7.4 (20 μg/ml) were absorbed to microtiter plate wells (Nunc MaxiSorp, Nunc, Roskilde, Denmark) in an overnight incubation at 4° C. After washing with PBS containing 0.01% Tween-20 (PBS-T) the coated plates were blocked with SuperBlock in TBS (Pierce, Rockford, Ill.) for 30 min at RT followed by an incubation of test plasma, diluted ¹⁄₁₀₀ in TBS-0.01% Tween-20 (TBS-T) for 2 h at RT and overnight at 4° C. After rinsing, deposition of autoantibodies directed to the peptide was detected using biotinylated rabbit anti-human IgM (ICN, Biomedicals, Inc., Aurora, Ohio) or IgG antibodies (Abcam, ab 7159) appropriately diluted in TBS-T. After another incubation for 2 h at RT the plates were washed and the bound biotinylated antibodies detected by alkaline phosphatase conjugated streptavidin (BioLegend, 405211), incubated for 2 h at RT. The colour reaction was developed by using phosphatase substrate kit (Pierce) and the absorbance at 405 nm was measured after 1 h of incubation at RT. Values are presented as the ratio against a standard reference plasma. Data regarding the specificity and variability of the antibody ELISA have been published previously [Fredrikson G N, et al. Identification of immune responses against aldehyde-modified peptide sequences in apo B-100 associated with cardiovascular disease. Arterioscler Thromb Vasc Biol 2003; 23:872-78; Fredrikson G N, et al. Autoantibody against the amino acid sequence 661-680 in apo B-100 is associated with decreased carotid stenosis and cardiovascular events. Atherosclerosis 2007; 194:e188-92].

Anti-$\beta_2$GPI antibodies IgM/IgG were determined with the multiplex immunoassays, BioPlex 2200 APLS (Bio-Rad Laboratories Inc., Hercules, Calif., USA). Results were reported in the ranges between 1.9-160 U/ml for IgM and 1.9-160 U/ml for IgG. Results were handled as continuous variables. The multiplex assays are regarded as positive if $\geq$20 U/ml. This cut-off level corresponded to at least the 99th percentile of healthy blood donors.

Statistics.

Clinical characteristics are presented as median (interquartile range, IQR) for continuous variables and as percentages for categorical variables. Continuous variables that were not normally distributed were log transformed. If not normally distributed after log transformation, non-parametric tests were used. Depending on data type, Students' t-test, Mann Whitney or Chi square test were used to compare differences between groups. Correlations were investigated through calculating the Spearman rank correlation coefficients. Multivariable-adjusted logistic regression models were performed to evaluate the associations between autoantibodies and cardiovascular/organ damage outcomes. Partial correlations were calculated to determine the associations between autoantibodies and IMT controlling for age and sex.

The clinical characteristics of the SLE patient and control groups are shown in Table 24. Around 90% of the study subjects were females and the median age was just below 50 years. The prevalence of clinically manifest CVD (myocardial infarction, stroke or peripheral artery disease) was 13-fold higher in the SLE group.

TABLE 24

Clinical characteristic of systemic lupus erythematosus (SLE) patients and controls

|  | SLE patients (n = 434) median (IQR)* | Controls (n = 322) median (IQR)* | P-value |
|---|---|---|---|
| Age (years) | 47.2 (34.2-57.8) | 48.2 (35.4-58.6) | n.s. |
| Female sex % | 86 | 92 | 0.01 |
| SLE characteristics |  |  |  |
| Number of SLE criteria | 6 (5-7) 17 missing | n.a. |  |
| Disease duration year | 10.6 (2.8-20.9) | n.a. |  |
| SLICC damage index (SDI) | 1 (IQR: 0-2, range 0-10) | n.a. |  |
| Traditional risk factors and laboratory tests |  |  |  |
| Current smoking (%) | 18.8 | 14.6 | n.s. |
| Systolic blood pressure (mmHg) | 120 (110-140) | 120 (110-135) | n.s. |
| Diastolic blood pressure (mmHg) | 78 (70-80) | 75 (70-82) | n.s. |
| Hypertension treatment (%) | 37.2 | 13.7 | <0.0001 |
| Body mass index (kg/m2) | 24.0 (21.4-27.2) | 24.3 (22.0-27.6) | n.s. |
| Diabetes (%) | 1.4 | 0.9 | n.s. |
| Total cholesterol (mmol/l) | 4.9 (4.2-5.7) | 5.1 (4.4-5.9) | 0.009 |
| High-density lipoprotein (mmol/l) | 1.1 (1.1-1.6) | 1.5 (1.2-1.8) | 0.006 |
| Low-density lipoprotein (mmol/l) | 3.0 (2.5-3.6) | 3.2 (2.6-3.9) | 0.0002 |
| Triglycerides (mmol/l) | 1.0 (0.7-1.5) | 0.78 (0.55-1.10) | <0.0001 |
| Apolipoprotein A1 (mg/ml) | 1.5 (1.3-1.7) | 1.7 (1.4-1.9) | <0.0001 |
| Apolipoprotein B (mg/ml) | 0.81 (0.69-0.96) | 0.81 (0.66-0.97) | n.s. |
| Glucose | 4.8 (4.5-5.2) | 4.9 (4.6-5.2) | n.s. |
| High-sensitivity CRP | 1.7 (0.7-5.3) | 0.9 (0.4-0.9) | <0.0001 |
| Creatinine | 69 (58-84) | 66 (59-73) | 0.0005 |
| Cardiovascular disease |  |  |  |
| Cardiovascular event† (%) | 16.1 | 1.2 | <0.0001 |
| Ischaemic heart disease (%) | 6.5 | 0.3 | <0.0001 |
| Ischaemic cerebrovascular disease (%) | 8.7 | 1.6 | <0.0001 |

TABLE 24-continued

Clinical characteristic of systemic lupus erythematosus (SLE) patients and controls

| | SLE patients (n = 434) median (IQR)* | Controls (n = 322) median (IQR)* | P-value |
|---|---|---|---|
| Ischaemic peripheral vascular disease (%) | 2.8 | 0.6 | <0.0001 |
| IMT mm (mean of both sides) | 0.053 (0.048-0.063) | n.a. | |
| Treatment (ongoing) | | | |
| Prednisolone % | 61.4 | | |
| Anti-malarials % | 37.1 | | |
| Azathioprine % | 17.4 | | |
| Mycophenolate mofetil % | 11.4 | | |

For Table 24 above: *Distributions are given as median [interquartile range (IQR)] unless indicated otherwise. †Includes myocardial infarction, ischaemic cerebrovascular and peripheral artery disease. IMT=intima-media thickness; CRP=C-reactive protein; SLIC=Systemic Lupus International Collaborating Clinics; n.a.=not applicable; n.s.=not significant.

SLE patients have lower levels of apo B P45 IgM and P210 IgG. We first studied if there were differences in the expression of autoantibodies against apo B between SLE patients and controls. This was determined by analyzing IgM and IgG antibodies against the native and malondialdehyde (MDA)-modified apo B sequences P45 and P210. Autoantibodies against $\beta_2$GPI (also called apo H) were used to compare the pattern of apo B peptide autoantibodies with those against another antigen which binds to lipoproteins and to membrane phospholipids. SLE patients had significantly lower levels of P210 IgG and P45 IgM (both the native and MDA-modified forms), while IgM against native and MDA-P210 were increased (Table 25).

TABLE 25

Apolipoprotein B and $\beta_2$-glycoprotein-I (GPI) autoantibodies in systemic lupus erythematosus (SLE) patients and controls.

| Apolipoprotein B antibodies | SLE patients (n = 434) median (IQR)* | Controls (n = 322) median (IQR)* | P |
|---|---|---|---|
| P45 IgM | 0.64 (0.30-1.29) | 0.86 (0.47-1.72) | 0.001 |
| MDA-P45 IgM | 0.72 (0.37-1.43) | 0.92 (0.56-0.92) | 0.001 |
| P45 IgG | 0.49 (0.23-1.03) | 0.42 (0.20-0.90) | n.s. |
| MDA-P45 IgG | 0.52 (0.28-1.02) | 0.43 (0.23-0.95) | n.s. |
| P210 IgM | 0.77 (0.52-1.06) | 0.70 (0.53-0.89) | 0.007 |
| MDA-P210 IgM | 0.87 (0.63-1.03) | 0.79 (0.62-0.93) | 0.002 |
| P210 IgG | 0.48 (0.24-0.84) | 0.54 (0.35-0.89) | 0.02 |
| MDA-P210 IgG | 0.70 (0.51-0.98) | 0.82 (0.61-1.05) | 0.005 |
| b2GPI antibodies | | | |
| b2GPI IgM | 1.9 (1.9-3.9) | 1.9 (1.9-2.5) | 0.002 |
| b2GPI IgG | 1.9 (1.9-10.2) | 1.9 (1.9-1.9) | 0.001 |

For Table 25 above: *Distributions are given as median [interquartile range (IQR)]. Ig=immunoglobulin; MDA=malondialdehyde; n.s.=not significant.

Antibody levels against native peptides generally correlated strongly with the level of antibodies against the MDA-modified form of the same peptide but much more weakly with antibodies against the other apo B peptide. As an example, the Spearman correlation coefficient for P210 IgG against MDA-P210 IgG was 0.85, while it was only 0.13 and 0.14 for P210 IgG against P45 IgG and MDA-P45 IgG, respectively. Similar trends were also observed for P45 and P210 IgM. As expected, SLE patients also had significantly elevated levels of anti-$\beta_2$GPI IgG and IgM. The levels of both P210 and MDA-P210 IgM correlated with $\beta_2$-GP-I IgG (r=0.19, P<0.001 and r=0.18, P<0.001; respectively) and b2-GP-I IgM levels (r=0.23, P=0.001 and r=0.21, P<0.01; respectively). The levels of P45 and MDA-P45 IgM both correlated with $\beta_2$-GP-I IgM levels (r=0.13, P=0.001 and r=0.14, P<0.001; respectively), but otherwise there were no association between autoantibody levels against apo B peptides and anti-$\beta_2$GPI. None of the common SLE medications were associated with autoantibodies against apoB, with the exception of antimalarials, which were negatively associated with MDA-P45 IgG (P=0.03).

Figure 14:
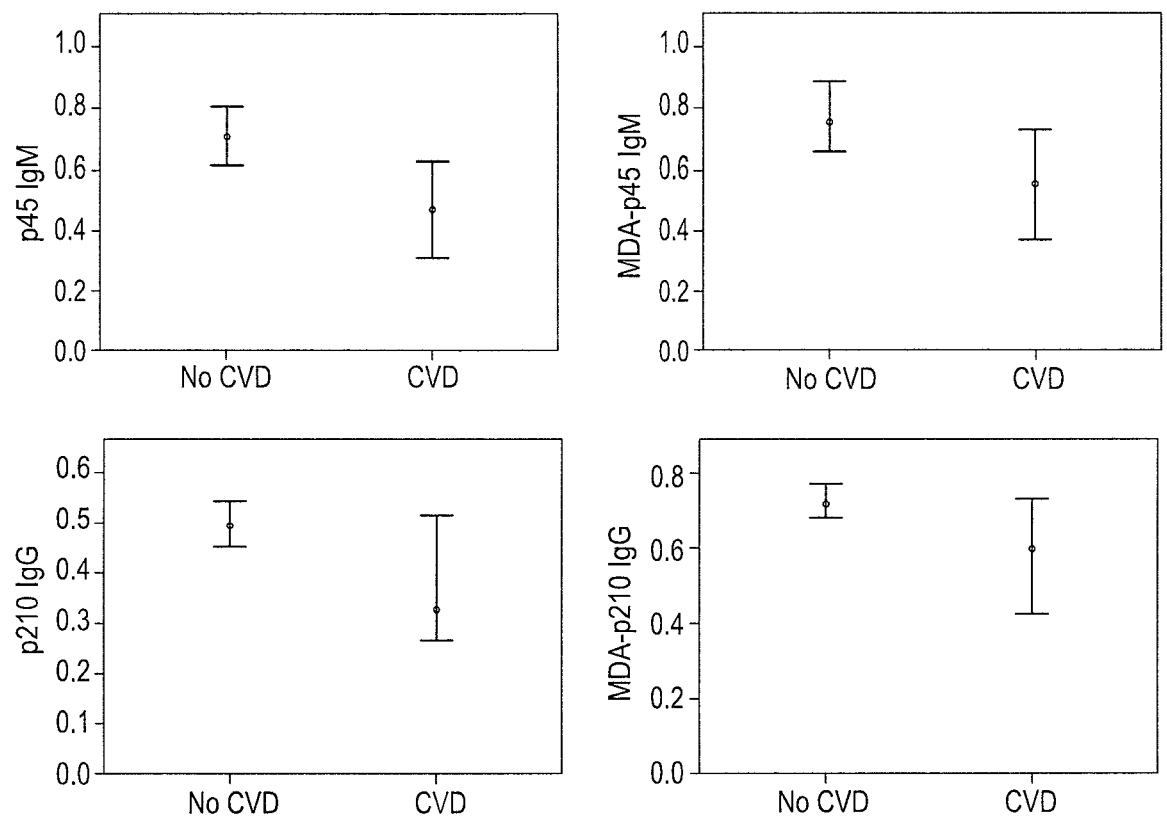
FIG. 14 depicts in accordance with various embodiments of the invention, one-dimensional box-plots showing median and 95% confidence interval for P45 immunoglobulin (Ig)M, malondialdehyde (MDA)-P45 IgM, P210 IgG and MDA-P210 IgG in systemic lupus erythematosus (SLE) patients with and without cardiovascular disease (CVD).

Low levels of apo B P45 IgM and P210 IgG are associated with CVD in SLE. Next we compared autoantibody levels against apo B peptides and $\beta_2$GPI in SLE patients with and without prevalent CVD. CVD patients had lower levels of native and MDAP45 IgM, native P210 IgM, native and MDA-P210 IgG, whereas $\beta_2$GPI IgG levels were higher. MDA-P45 IgM, MDA-P210 IgG and $\beta_2$GPI IgG levels remained significantly different when adjusting for age and sex (Table 26 and FIG. 14).

TABLE 26

Apolipoprotein B and $\beta_2$-glycoprotein-I (GPI) autoantibodies in systemic lupus erythematosus (SLE) patients with and without cardiovascular disease.

| | CVD (n = 62) median (IQR)* | SLE | No CVD (n = 370) median (IQR)* | P | P adjusted |
|---|---|---|---|---|---|
| Apo B antibodies | | | | | |
| P45 IgM | 0.47 (0.19-1.17) | | 0.70 (0.33-1.29) | 0.01 | n.s. |
| MDA-P45 IgM | 0.55 (0.24-1.02) | | 0.75 (0.41-1.48) | 0.003 | 0.04 |
| P45 IgG | 0.36 (0.17-0.90) | | 0.54 (0.23-1.05) | n.s. | n.s. |

TABLE 26-continued

Apolipoprotein B and β₂-glycoprotein-I (GPI) autoantibodies in systemic lupus erythematosus (SLE) patients with and without cardiovascular disease.

| | CVD (n = 62) median (IQR)* | SLE | No CVD (n = 370) median (IQR)* | P | P adjusted |
|---|---|---|---|---|---|
| MDA-P45 IgG | 0.46 (0.29-0.84) | | 0.54 (0.28-1.04) | n.s. | n.s. |
| P210 IgM | 0.64 (0.42-0.99) | | 0.78 (0.53-1.07) | 0.03 | n.s. |
| MDA-P210 IgM | 0.80 (0.51-1.02) | | 0.54 (0.28-1.04) | n.s. | n.s. |
| P210 IgG | 0.32 (0.10-0.64) | | 0.50 (0.25-0.88) | 0.004 | n.s. |
| MDA-P210 IgG | 0.60 (0.3-0.84) | | 0.72 (0.53-1.00) | 0.001 | 0.05 |
| Apo H antibodies | | | | | |
| β₂GPI IgM | 1.9 (1.9-3.5) | | 1.9 (1.9-4.0) | n.s. | n.s. |
| β₂GPI IgG | 4.0 (1.9-30.9) | | 1.9 (1.9-8.7) | 0.02 | 0.01 |

Table 26 above: *Distributions are given as median [interquartile range (IQR)]. Ig=immunoglobulin; MDA=malondialdehyde; CVD=cardiovascular disease; n.s.=not significant.

To further determine the association between these autoantibodies and cardiovascular disease in patients with SLE we used measurements of carotid IMT as assessed by ultrasonography. Associations were in a negative direction between carotid IMT and all apo B autoantibodies. For P45, both native and MDA modified, IgM antibodies became significant after age and gender adjustments, but these association were generally so weak that the biological relevance is questionable. Crude associations for all P210 antibodies were significant, but these associations were not independent of age and sex (Table 27).

TABLE 27

Associations between apolipoprotein B and β₂-glycoprotein-I (GPI) autoantibodies and carotid intima-media thickness (IMT) in SLE patients.

| | SLE patients (n = 302) | P | P adjusted for age and gender |
|---|---|---|---|
| Apolipoprotein B antibodies | | | |
| P45 IgM | −0.05 | n.s. | 0.02 |
| MDA-P45 IgM | −0.08 | n.s. | 0.02 |
| P45 IgG | −0.10 | n.s. | n.s. |
| MDA-P45 IgG | −0.07 | n.s. | n.s. |
| P210 IgM | −0.23 | 0.001 | n.s. |
| MDA-P210 IgM | −0.16 | 0.005 | n.s. |
| P210 IgG | −0.20 | 0.001 | n.s. |
| MDA-P210 IgG | −0.19 | 0.001 | n.s. |
| Apolipoprotein H antibodies | | | |
| β₂GPI IgM | 0.04 | n.s. | n.s. |
| β₂GPI IgG | −0.03 | n.s. | n.s. |

Table 27 above: Partial correlations were calculated to determine independent associations between autoantibodies and IMT when controlling for age and sex. Ig=imm- uno- globulin; MDA=malondialdehyde; n.s.=not significant.

Low levels of apoB autoantibodies are associated with manifestation of organ damage in SLE. Finally we determined if plasma levels of apo B autoantibodies were associated with clinical signs of organ damage in SLE. SLE patients with permanent organ damage (SDI>1) had lower levels of P45 IgM (both native and MDA-modified), P210 IgM and P210 IgG (both native and MDA-modified) than SLE patients with a SDI≤1 (Table 28). When controlling for age and sex only the difference in MDA-P210 IgG remained significantly different between the groups (Table 28). In contrast, SLE patients with permanent organ damage had elevated levels of β₂GPI IgG (Table 28).

TABLE 28

Apolipoprotein B and β₂-glycoprotein-I (GPI) autoantibodies in systemic lupus erythematosus (SLE) patients with and without organ damage (SDI > 1).

| | SDI > 1 median (IQR)* | SDI ≤ 1 median (IQR)* | P | P adjusted for age |
|---|---|---|---|---|
| Apolipoprotein B | | | | |
| P45 IgM | 0.53 (0.24-1.19) | 0.72 (0.36-1.38) | 0.02 | n.s. |
| MDA-P45 IgM | 0.60 (0.28-1.22) | 0.79 (0.44-1.55) | 0.003 | n.s. |
| P45 IgG | 0.48 (0.19-0.91) | 0.50 (0.24-1.04) | n.s. | n.s. |
| MDA-P45 IgG | 0.50 (0.30-0.97) | 0.56 (0.27-1.03) | n.s. | n.s. |
| P210 IgM | 0.68 (0.44-1.02) | 0.83 (0.57-1.07) | 0.006 | n.s. |
| MDA-P210 IgM | 0.80 (0.55-1.02) | 0.89 (0.68-1.05) | n.s. | n.s. |
| P210 IgG | 0.37 (0.16-0.66) | 0.54 (0.28-0.95) | 0.001 | n.s. |
| MDA-P210 IgG | 0.61 (0.41-0.84) | 0.76 (0.56-1.05) | 0.001 | 0.005 |
| Apolipoprotein H antibody | | | | |
| β₂GPI IgM | 1.9 (1.9-5.9) | 1.9 (1.9-3.1) | n.s. | n.s. |
| β₂GPI IgG | 2.1 (1.9-21.5) | 1.9 (1.9-7.6) | 0.02 | 0.006 |

Table 28 Above: *Distributions are given as median [interquartile range (IQR)]. Ig=immunoglobulin; MDA=malondialdehyde; SDI=Systemic Lupus International Collaborating Clinics damage index; n.s.=not significant.

Since many of the associations between antibody levels and organ complications, including the cardiovascular, were found to be dependent on age we specifically analyzed the relationships between antibody levels and age. All apo B autoantibodies were found to decrease with age both in SLE patients and in controls, while no such trend was observed for $\beta_2$GPI antibodies (Table 29).

TABLE 29

Associations between apolipoprotein B and $\beta_2$-glycoprotein-I (GPI) autoantibodies and age in systemic lupus erythematosus (SLE) patients and controls.

|  | SLE patients (n = 434) | P | Controls (n = 322) | P |
| --- | --- | --- | --- | --- |
| Apolipoprotein B antibodies | | | | |
| P45 IgM | −0.19 | 0.001 | −0.24 | 0.001 |
| MDA-P45 IgM | −0.22 | 0.001 | −0.24 | 0.001 |
| P45 IgG | −0.17 | 0.001 | −0.12 | 0.04 |
| MDA-P45 IgG | −0.16 | 0.001 | −0.07 | n.s. |
| P210 IgM | −0.26 | 0.001 | −0.26 | 0.001 |
| MDA-P210 IgM | −0.19 | 0.001 | −0.21 | 0.001 |
| P210 IgG | −0.29 | 0.001 | −0.28 | 0.001 |
| MDA-P210 IgG | −0.30 | 0.001 | −0.27 | 0.001 |
| Apolipoprotein H antibodies | | | | |
| $\beta_2$GPI IgM | 0.07 | n.s. | 0.12 | 0.04 |
| $\beta_2$GPI IgG | 0.01 | n.s. | 0.09 | n.s. |

For Table 29 above: Ig=immunoglobulin; MDA=malondialdehyde; n.s.=not significant.

Production of a multitude of autoantibodies is a characteristic feature of SLE and there is evidence that several of these autoantibodies, in particular aPL, contribute to increased CVD in SLE. Autoantibodies against the apo B-100 peptides P45 and P210 are found in most individuals and have on the contrary been associated with a lower CVD risk in observational studies. The present study investigated how SLE affects the occurrence of these potentially protective antibodies. Our findings demonstrate that subjects with SLE have reduced levels of P45 IgM and P210 IgG. Moreover, SLE patients with clinically manifest CVD had lower levels of P45 IgM and P210 IgG than those without CVD, but only the levels of MDA-P45 IgM and MDA-P210 IgG remained significantly after controlling for age and sex. One possible explanation for the stronger association with autoantibodies recognizing the MDA-peptides could be that these are more specific for epitopes present in oxidized LDL. Also SLE patients with clinical manifestations of permanent organ damage as assessed by a SDI score>1 had lower levels of MDA-P210 IgG. In comparison, anti-$\beta_2$GPI IgG levels were increased in SLE patients and those with prevalent CVD had higher levels than those without. Taken together these observations demonstrate that SLE is associated with suppression of a set of naturally occurring autoantibodies with potential protective effects and suggest that this may contribute to increased risk for development of organ damage and CVD in SLE. There is evidence that some medications used to treat SLE also have athero-protective effects. However, we found no association between treatment with prednisolone, azathioprine or mycophenolate mofetil and apoB peptide autoantibodies in the present study while the use of antimalarias was associated with lower levels of MDA-P45 IgG.

There are several mechanisms through which autoantibodies to apoB antigens could protect against atherosclerosis and other types of organ damage in SLE. First, it is likely that such antigens are recognized by the immune system first when LDL is modified by oxidation. This oxidation is associated with degradation of the apo B protein into smaller peptide fragments as well as aldehyde-modifications. Aldehyde-modified apo B peptides are readily identified by the immune system but also non-modified apo B peptide sequences may be targeted by the immune system if normally embedded into phospholipid LDL membrane. Oxidized LDL is cytotoxic for vascular cells and promotes the inflammation that leads to development and destabilization of atherosclerotic plaques. Factors that facilitate an early removal of oxidized LDL are therefore likely to have an athero-protective effect. Both P45 and P210 IgG have been shown to promote the uptake of oxidized LDL in human monocyte/macrophages and treatment of LDLr$^{-/-}$/human apoB$^{+/+}$ mice with MDA-P45 IgG lowers the plasma level of oxidized LDL. Oxidized LDL/MDAP45 immune complexes have anti-inflammatory properties through activation of the inhibitory Fc$\gamma$RII receptor. Treatment of hypercholesterolemic mice with recombinant malondialdehyde-P45 IgG has been shown to inhibit development of atherosclerosis and to promote plaque regression when combined with lowering of plasma cholesterol levels. Low levels of autoantibodies against apoB peptides have been associated with more severe atherosclerosis and an increased risk for development of myocardial infarction. Also IgM autoantibodies targeting phosphorylcholine (PC) in oxidized LDL have been attributed a protective role in cardiovascular disease. Several studies have shown that subclinical carotid disease in SLE patients is associated with lower levels of these autoantibodies adding further support to the notion that autoantibodies against oxidized LDL antigens may protect against cardiovascular complications in SLE. In line with the notion that oxidized LDL contributes to vascular damage in autoimmune disease and that anti-PC antibodies may protect against this damage Ajeganova and coworkers reported that development of cardiovascular events in rheumatoid arthritis is associated with both elevated plasma levels of oxidized LDL and lower levels of anti-PC IgM.

$\beta_2$GPI is an evolutionary conserved protein, which occurs abundantly in the human circulation. The function of $\beta_2$GPI is still under investigation, but recent data indicate that $\beta_2$GPI is mainly a scavenger molecule with capacity to bind and remove harmful bacterial products e.g. LPS. It is also involved in clearance of endogenous waste such as micro particles and cellular debris. There is growing evidence that low affinity anti-$\beta_2$GPI, in similarity to some anti-apoB antibodies, belong to the natural antibody repertoire, which defends us against well-conserved pathogenic structures e.g. bacterial antigens or products of oxidation. In most previous studies anti-$\beta_2$GPI antibodies are regarded as present or absent according to cut-offs used in the APS criteria. In this study, however, we have in similarity to anti-apoB antibodies investigated continuous titers and isotypes. Our results demonstrate that only anti-$\beta_2$GPI antibodies of the IgG isotype occurred at higher titers in SLE patients as compared to controls, and high titers are especially common in the SLE subgroup with previous CVD. We also note that, unlike anti-apoB antibodies, anti-$\beta_2$GPI antibodies do not decline with age, rather in the control group titers were higher among older subjects.

Loss of tolerance against abundant apoptotic cell antigens is an important pathogenic factor in SLE. In atherosclerosis the loss of tolerance against apoptotic cell antigens appears to take place primarily within the environment of the atherosclerotic plaque where there is a similar loss of tolerance against antigens in oxidized LDL. Taken together, these findings imply that the issue of tolerance control may be particularly critical in SLE atherosclerotic lesions. Oxidized LDL is enhanced in SLE and may further aggravate pro-inflammatory responses to apoptotic cells in SLE atherosclerotic lesions by competing with the binding to phagocytic receptors, which mediate clearance of both apoptotic cells and oxidized LDL. It is likely that these mechanisms play a role in the accelerated atherosclerosis in SLE and that antibody-mediated removal of oxidized LDL could help to limit vascular and possibly also the general systemic inflammation in SLE.

We report that patients with SLE, a condition generally characterized by a high production of auto-antibodies, have reduced levels of athero-protective autoantibodies against the apo B-100 peptides P45 and P210. The level of these antibodies was further reduced in SLE patients that had developed CVD. We propose that an impaired antibody-mediated removal of oxidized LDL may contribute to loss of tolerance and increased inflammation in vascular tissues in SLE.

Example 5. Immunization with ApoB100 Peptide Vaccine Reduces Atherosclerosis Development in a Mouse Model of Systemic Lupus Erythematosus In the present study we investigated if immunization with CVX-4, a prototype vaccine consisting of the apoB peptide P210, a bovine serum albumin (BSA) carrier and the aluminum phosphate adjuvant Adjuphos, affects atherosclerosis development in MRL/lpr/ApoE$^{-/-}$ mice that display both hypercholesterolemia and a SLE-like phenotype.

Experimental Methods

Mice:

Animal care and experimental procedures were approved by the local committee of Animal Care and Use at Lund University. MRL/lpr ApoE$^{-/-}$ mice on a C57bl/6 background (originally from Jackson Laboratories, Charles River Laboratories, Germany) were bred in the animal facility and female mice were used for the present study. High fat diet (HFD, 0.15% cholesterol, 21% fat, Lantmännen, Sweden) was introduced from 12 weeks of age until the experimental end point. Mice were given subcutaneous injections (200 µL) of P210 conjugated to bovine serum albumin (BSA, CVX-14) together with aluminium phosphate gel (Adjuphos) as adjuvant at 6, 9, 11 and 21 weeks of age. Injections of phosphate-buffered saline (PBS) or Adjuphos alone served as controls. Mice were killed at 22 weeks of age by intraperitoneal injection of ketamine and xylazine. Spleens were harvested and stored in PBS on ice and plasma was collected by cardiac puncture and stored at −80° C. until analysis. Mice were then whole-body perfused with PBS followed by Histochoice (Amresco, Solon, Ohio, USA), and the descending aorta was then dissected free of connective tissue and fat, cut longitudinally, mounted en face and stored in Histochoice [Schiopu, A., et al. 2004. Recombinant human antibodies against aldehyde-modified apolipoprotein B-100 peptide sequences inhibit atherosclerosis. Circulation 110: 2047-2052]. The hearts were collected and snap frozen in liquid nitrogen for storage or sectioning.

Staining of the Descending Aorta:

En face preparations of the descending aorta were washed in distilled water, dipped in 78% methanol and stained for 40 min in 0.16% Oil Red O dissolved in 78% methanol/0.2 mol L) 1 NaOH. The Oil Red O stained plaque areas were quantified blindly using BioPix iQ 2.3.1 (BioPix AB).

Immunohistochemistry:

Frozen hearts were embedded in Tissue Tek (Sakura Fine Tek., Japan) and sections of 10 µm were cut from the aortic root for immunohistochemical staining of atherosclerotic plaques. Sections were fixed in ice-cold acetone for 10 minutes followed by permeabilized in 0.5% TritonX-100 (Merck, Millipore, US) with PBS washing for 5 minutes between each step. Further, sections were blocked in 10% mouse serum in PBS for 30 minutes. Immunohistochemical staining of macrophages using rabbit anti-CD68 (Abcam, Cambridge, UK) detected by secondary biotinylated goat anti-rabbit (Abcam) with diaminobenzene (DAB, Vector Labs, CA, USA) was performed. The primary or secondary antibodies were omitted as controls. Immune stained areas were quantified blindly in BioPix 2.0 Software (BioPix AB, Goteborg, Sweden).

Spleen Cell Preparation and Cell Culture:

Splenocytes in single cell suspension were prepared by pressing the spleen through a 70-µm cell strainer (BD Falcon, Franklin Lakes, N.J., USA). Erythrocytes were removed using red blood cell lysing buffer (Sigma, St. Louis, Mo., USA). Cells were cultured in culture medium (RPMI 1640 medium containing 10% heat-inactivated foetal calf serum, 1 mmol L$^{-1}$ sodium pyruvate, 10 mmol$^{-1}$ Hepes, 50 U penicillin, 50 µg/mL streptomycin, 0.05 mmol L$^{-1}$ β-mercaptoethanol and 2 mmol L$^{-1}$ L-glutamine; GIBCO, Paisley, UK) in 96-well, round-bottom plates (Sarstedt, Nümbrecht, Germany).

Flow Cytometry:

Splenocytes were stained with fluorochrome-conjugated antibodies and measured with a CyAn ADP flow cytometer (Beckman Coulter). The following antibodies phycoerythrin/Cy7-conjugated anti-CD3, pacific blue-conjugated anti-CD4, allophycocyanin-conjugated anti-CD25, phycoerythrin-conjugated anti-Foxp3 and allophycocyanin/Cy7-conjugated anti-CD8 were used for T cells and fluorescein isothiocyanate-conjugated anti-B220, pacific blue-conjugated anti-CD11b, phycoerythrin/Cy7-conjugated anti-CD11c and allophycocyanin-conjugated anti-CD115. The analysis was performed with FlowJo V10 software (Tree Star).

Measurements of IgG:

A 96-well ELISA plate was coated with 20 □g/ml P210 diluted in Na$_2$CO$_3$—NaHCO$_3$ and incubated at 4° C. overnight. After three cycles of washing, the plate was blocked with 2% goat serum in PBS for 60 minutes. After a single wash plasma samples diluted 1:50 was added to the plate and incubated for 1 hour in 37° C. After three washing cycles, detection antibody (anti-mouse IgG-biotin) was added and the plate was incubated for 1 hour in 37° C. After three more washing cycles, streptavidin-HRP was then added and incubated for 20 minutes in the dark. Stop solution (1M H$_2$SO$_4$) was then added and the absorbance was read at 450 nm.

Plasma Cholesterol and Triglyceride:

Total plasma cholesterol and triglyceride levels were quantified with colorimetric assays, Infinity™ Cholesterol and Triglyceride (INT), respectively (Thermo Scientific).

Plasma Cytokines:

Cytokine (IL-2, IL-4, IL-5, IL-6 and IL-10) concentrations in plasma were determined with multiplex technology (Luminex Assay, R&D Systems Inc.) according to the manufacturer's instructions.

Statistics:

Data are presented as mean±standard deviation. Student's two-tailed t-test was used for normally distributed samples and the Mann-Whitney rank sum test for skewed data. Statistical significance was considered at the level P<0.05.

Figure 15B:
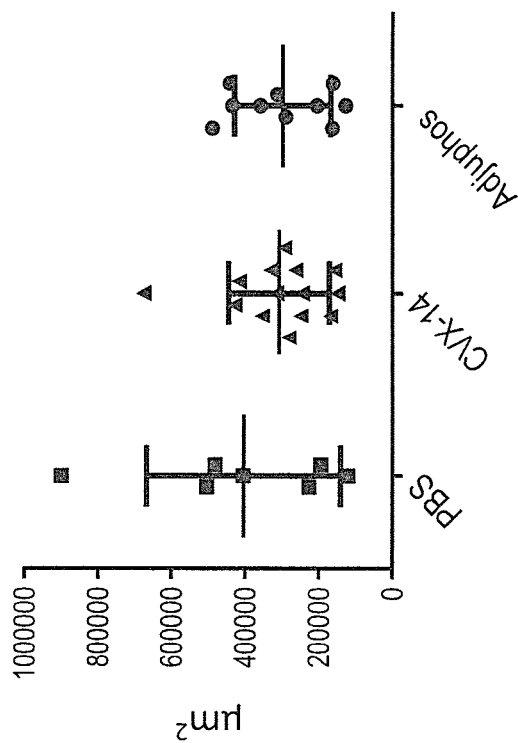
FIG. 15A-FIG. 15G depicts in accordance with various embodiments of the invention, plaque composition and features in aortic arch sections of MRL/lpr/Apoe$^{-/-}$ mice after treatment with PBS, CVX-14 or Adjuphos. Oil Red O lipid staining fraction of aortic arch (FIG. 15A), plaque area (FIG. 15B), and CD68 fraction (FIG. 15C-FIG. 15D) in PBS, CVX-14 or Adjuphos treated groups. Carotid artery mRNA gene expression of FOXP3 (FIG. 15E), TGF-β (FIG. 15F) and TNF-α (FIG. 15G).
Figure 15D:
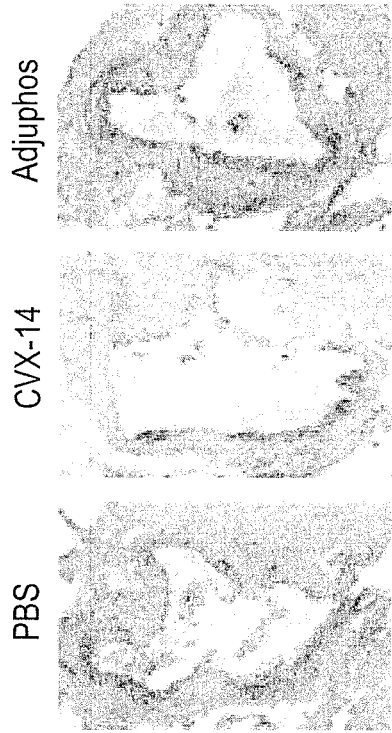
Figure 15A:
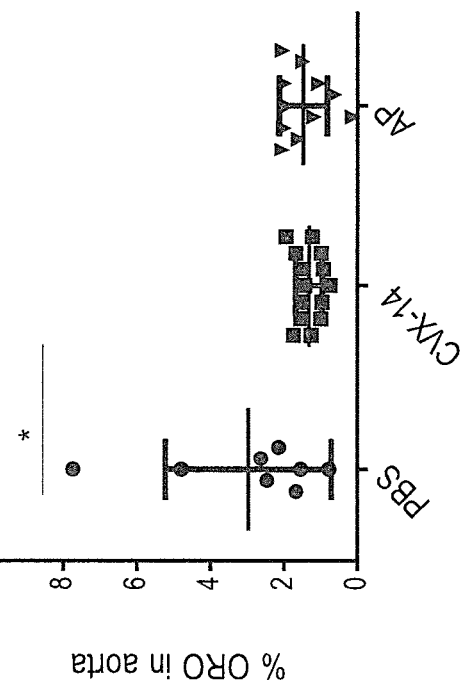
Figure 15C:
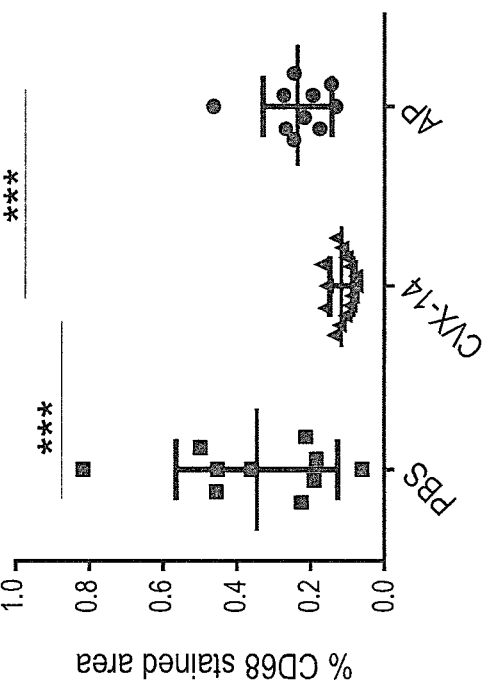
Figure 15E:
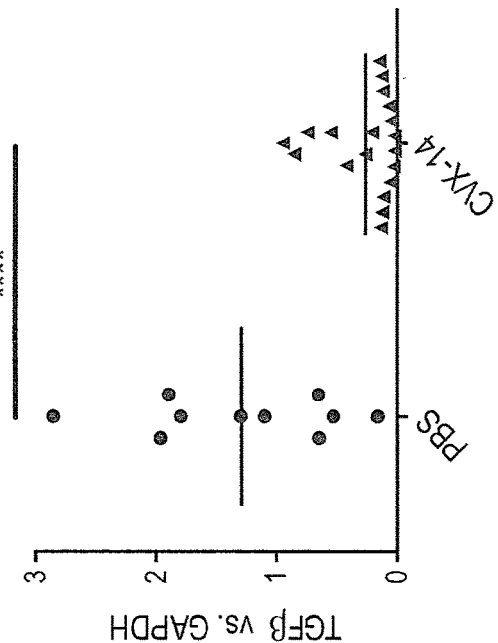
Figure 15F:
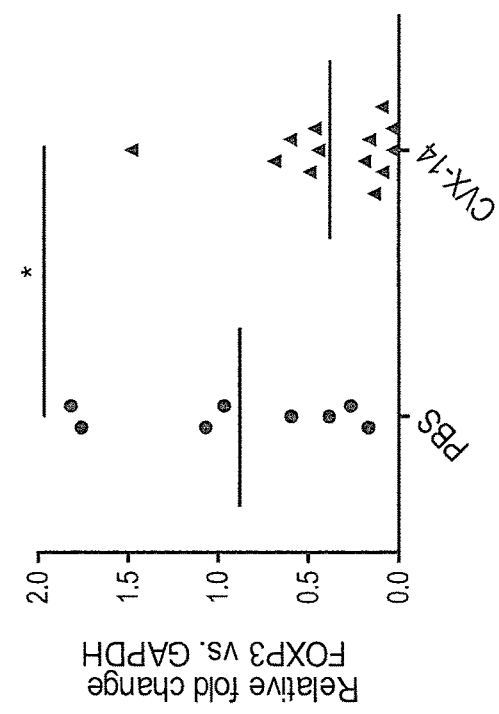
Figure 15G:
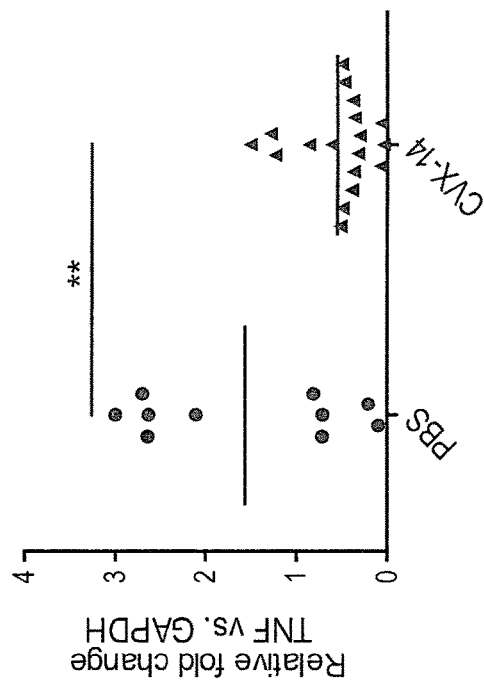

MRL/lpr/ApoE−/− mice received 4 subcutaneous injections with PBS, CVX-14 or adjuphos alone at week 6, 9, 11 and 21 of age. Mice were killed at week 22 of age and atherosclerosis assessed by Oil Red O (ORO) en face staining of the aorta and measurement of the cross-sectional plaque area at the aortic root. Immunization with CVX-14 reduced plaque development in the aorta by 55.5% as compared to the PBS (1.32±0.36 versus 2.97±2.26% ORO stained area, p=0.0133; FIG. 15A). A trend towards reduced atherosclerosis was also observed in the mice give adjuphos alone. There was no significant difference in aortic root plaque area between the PBS and CVX-14 treated groups (FIG. 15B), but CVX-14 treatment reduced the plaque area with positive macrophage staining (CD68) by 66.2% as compared with the PBS control (11.2±6.9 versus 34.6±6.9%, p=0.005; FIG. 15C and FIG. 15D). There was no effect on plaque macrophage staining by giving adjuphos alone. The effect of CVX-14 treatment on vascular inflammation was further assessed by analyzing cytokine mRNA expression in the carotid artery. Arteries from CVX-14 treated mice were found to have reduced expression of TNF-α and TGF-β mRNA, as well as of Foxp3 mRNA (FIG. 15E-FIG. 15G).

Plasma cholesterol was increased in CVX-14 treated mice compared to PBS control, whereas no difference was observed in triglyceride levels or body weights (Table 30). There were also no significant differences between P210 IgG1 between the Groups (Table 30).

TABLE 30

|  | PBS | CVX-14 | Adjuphos |
| --- | --- | --- | --- |
| Cholesterol | 2.80 ± 2.22 | 4.77 ± 1.41 | 4.30 ± 0.69 |
| Triglycerides | 0.63 ± 0.55 | 0.92 ± 0.21 | 0.99 ± 0.22 |
| P210-IgG1 | 0.47 ± 0.32 | 0.45 ± 0.32 | 0.51 ± 0.48 |

Figure 16A:
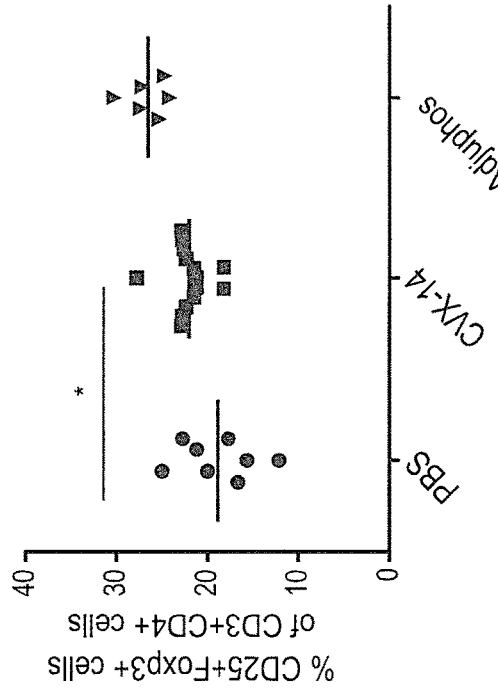
FIG. 16A-FIG. 16E depict in accordance with various embodiments of the invention, assessment of immune cells with flow cytometry after treatment of MRL/lpr/Apoe$^{-/-}$ mice with PBS, CVX-14 or Adjuphos. Splenocytes amount of regulatory T cells (CD25+Foxp3+CD3+CD4+ cells, FIG. 16A), T helper cells (CD4+CD3+ cells, FIG. 16B), cytotoxic T cells (CD8+CD3+ cells, FIG. 16C), peripheral dendritic cells (B220+CD11c+, FIG. 16D) and monocytes (CD11b+CD115+, FIG. 16E) cell populations in treated mice.
Figure 16C:
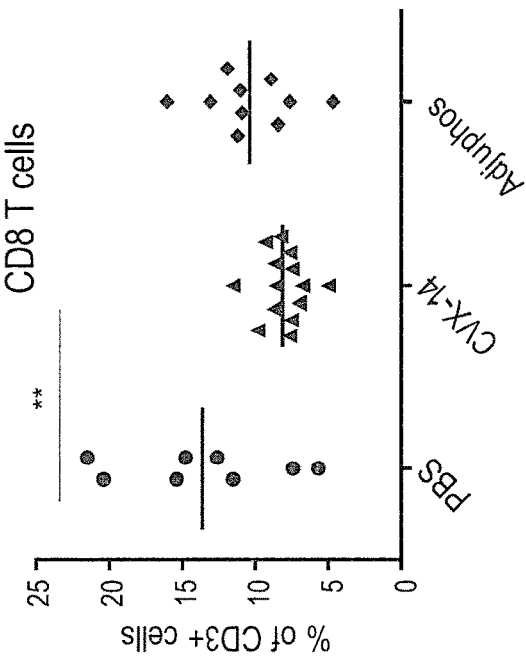
Figure 16B:
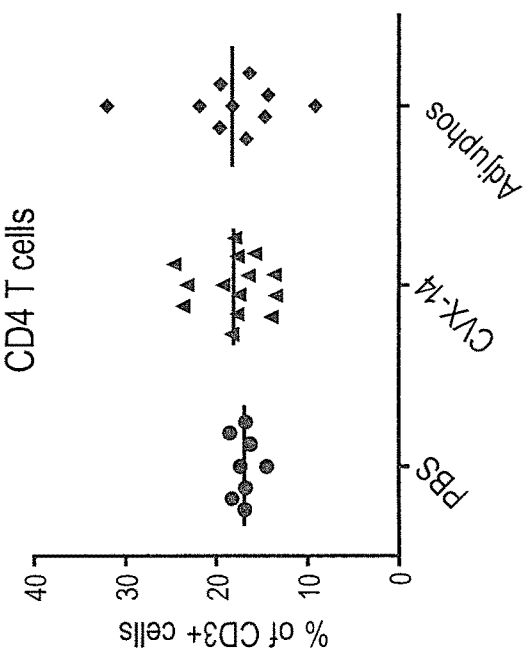
Figure 16E:
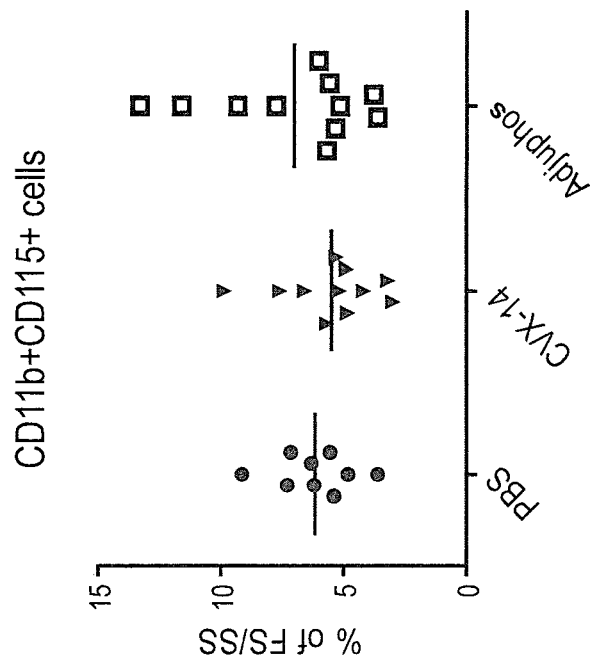
Figure 16D:
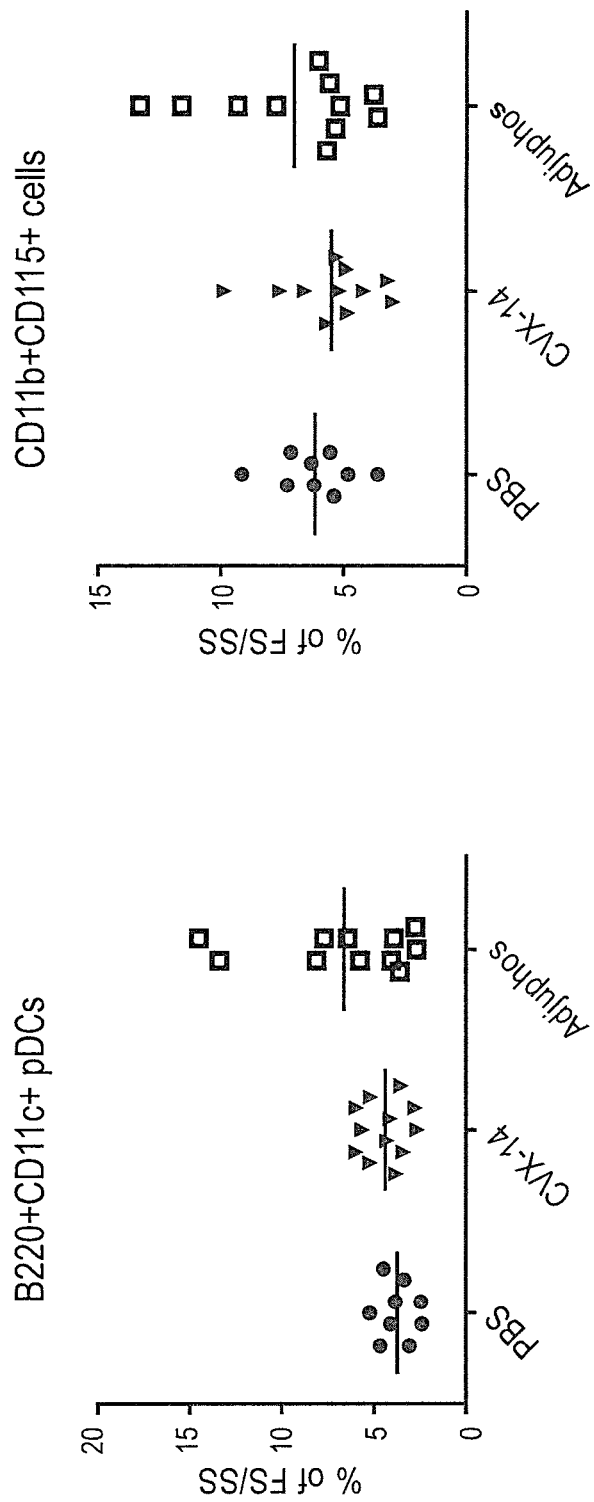

Splenocytes were analyzed with flow cytometry to determine systemic changes of the immune system in immunized mice. There was an increased frequency of regulatory T cells, defined as $CD3^+CD4^+CD25^+Foxp3^+$ cells, in mice immunized with CVX-14 as compared to the PBS controls, but a similar increase was also observed with Adjuphos alone (FIG. 16A). Immunization with CVX-14 also reduced the fraction of $CD8^+$ T cells (FIG. 16C), whereas no effect was seen on the fraction of splenic plasmacytoid dendritic cells and $CD11b^+CD115^+$ (FIG. 16D-FIG. 16E).

There is accumulating evidence that autoimmune responses against modified LDL particles aggravate arterial inflammation and development of atherosclerosis. As loss of tolerance against self-antigens is an important feature of SLE and atherosclerosis it reasonable to assume that autoimmune responses against LDL trapped in the vascular extracellular matrix contributes to the development of cardiovascular complications in SLE. In the present study we found that immunization with the ApoB peptide P210 reduces plaque development and inflammation in an atherosclerosis-prone mouse model of SLE. This effect was associated with reduced arterial cytokine expression and an expansion of Tregs in the spleen, whereas no change was observed in the levels of P210 IgG. These observations are in good agreement with previous studies demonstrating that immunization with apoB peptide and oxidized LDL inhibits atherosclerosis through activation of Tregs and promotion of LDL tolerance. An expansion of Tregs in the spleen and a trend towards reduced atherosclerosis was also observed in mice injected with adjuphos alone. Athero-protective effects of aluminum-based adjuvants have previously been identified in several studies and have been suggested to be explained by an uptake of oxidized LDL by the adjuvant subcutaneously. Irrespective of this, aluminum-based adjuvants represent attractive candidate adjuvants for possible future atherosclerosis vaccines.

There is a considerable unmet clinical need for improved prevention of cardiovascular complications in SLE. Treatment with statins has not affected the progression of carotid disease in randomized clinical trials involving subjects with SLE and it remains unclear to what extent other medications used in treatment of SLE reduces the cardiovascular risk. In this context, oxidized LDL represents an interesting possible target as it has been implicated both in SLE and atherosclerosis. Autoantibodies against oxidized LDL-associated phospholipid antigens are common in SLE. Oxidized LDL and apoptotic cells compete for binding to the same scavenger receptors on macrophages suggesting that presence of large amounts of oxidized LDL may further impair handling of apoptotic cells in SLE. Human atherosclerotic plaques contains T cells specific for oxidized LDL antigens and T cells recognizing epitopes in apo B have been shown to accelerate atherosclerosis in experimental mouse models. Immunizations with the ApoB100 derived peptides could potentially represent an attractive approach not only for preventing damage to the cardiovascular system in SLE because it may also have effects on other organs. As previous studies have shown that immunizations with the ApoB100 derived peptides promotes generation of LDL specific Tregs it is likely that these cells would have an immune-suppressive effect in any organ where they encounter native or oxidized LDL.

The results from this study show that immunizations with P210-containing vaccines reduce atherosclerosis development in $Apoe^{-/-}$ mice with a SLE like phenotype. In accordance with previous studies using P210-containing vaccines in hypercholesterolemic $Apoe^{-/-}$ mice without SLE, regulatory T cells are increased systemically after the P210 immunization. ApoB peptide based vaccines represents a possible novel approach for prevention of CVD in SLE that warrants further investigation.

Example 6

Inflammatory responses in the autoimmune disorder systemic lupus erythematosus (SLE) results in severe clinical manifestations of peripheral inflammation. Atherosclerosis, one inflammatory manifestation of the disease, arises as a result of lipid accumulation and modification of lipoproteins in the arterial wall. Underlying both myocardial infarction (MI) and stroke, it is one of the main causes of further cardiovascular disease (CVD) events and mortality. The incidence of CVD is significantly increased in SLE patients suggesting that the enhanced systemic inflammation contributes to the dysfunctional protection against oxidized low-density lipoproteins (LDL) and other atherogenic antigens. A vaccine formulation containing a peptide sequence of the LDL antigen was used to evaluate the effects of atherosclerosis in a hypercholesterolemic SLE mouse to assess the immune responses. We assessed the atherosclerosis by examining plaque development in the aorta. The response to immunization was investigated by flow cytometry of spleen and lymph node cells. Plaque progression in the aorta was significantly decreased in the mice treated with the vaccine. Further, inflammatory immune cell populations were significantly decreased. This vaccine candidate represents as a possible new therapy against CVD in SLE for the future.

Systemic lupus erythematosus (SLE) is a complex autoimmune disease in which the individual displays various immune responses against own tissue. (1) The inflammatory response given by this autoimmune condition results in severe clinical manifestations leading to complications such as atherosclerosis, renal failure and hypertension amongst other things.

Atherosclerosis is a chronic inflammatory disease arising as a result of lipid accumulation and modification in the arterial wall. Underlying both myocardial infarction (MI) and stroke, it is one of the main causes of clinical manifestations of cardiovascular disease (CVD). The atherosclerotic process is initiated when low-density lipoproteins (LDL) particles is entrapped in the vascular wall and modified by enzymes or reactive oxygen species forming oxidized LDL (oxLDL). Macrophages attempt to remove oxLDL by engulfing them and eventually this leads to foam cell accumulation, immune cell activation and arterial lesions in the vessel wall.

The incidence of CVD is significantly increased in SLE patients suggesting that the enhanced systemic inflammation contributes to the dysfunctional protection against oxLDL and other atherogenic antigens. For example, females with SLE have up to 50-fold increased risk of getting a MI, underlining the need for alternative preventives to inhibit atherosclerosis in SLE. Systemic autoimmune manifestations such as SLE are suggested to go hand in hand with immunodeficiency. The deficiencies arise from defects of the immune system and features genetic variations, environmental factors and immune cell activation. General characteristics of autoimmunity is antinuclear antibodies (ANA), anti-smith/ribonuclear proteins (anti-sm/RNP) and the 'interferon (IFN) signature', where peripheral blood cells display a significant upregulation of type I IFN-inducible genes.

Vaccines has been used a long time clinically to induce the individuals own immune protection against an antigen. Therefore, a vaccine through antigen-specific modulation would be of great interest as a therapy. We investigated whether immunomodulation therapies with the ApoB100 peptide 45 are able to reduce atherosclerosis and apoptosis in experimental SLE.

Experimental Methods

Mice.

Female MRL/lpr ApoE$^{-/-}$ mice (purchased from Jackson Laboratories, Charles River Laboratories, Germany) were bred in the animal facility. High fat diet (HFD, 0.15% cholesterol, 21% fat, Lantmännen, Sweden) was introduced from 6 weeks of age until the experimental end point. ApoB100 peptide 45 (P45) was coupled to cholera toxin B (P45-CTB), as previously described (Sun J B, Czerkinsky C and Holmgren J. B lymphocytes treated in vitro with antigen coupled to cholera toxin B subunit induce antigen-specific Foxp3(+) regulatory T cells and protect against experimental autoimmune encephalomyelitis. J Immunol. 2012; 188: 1686-9). Treatments with 30, 15, 5 µg P45-CTB conjugate, 30 µg CTB or PBS started at 18 weeks of age at day 0 and were orally administered at day 0, 2, 5, 7, 14, 21, 28, 35, 42 and 49. Blood and urine was collected at day 0, 14, 28, 42 and 56. Weight was monitored at day 0, 28 and 56. At day 56 of treatment, the mice were killed by ketamin/xylazine injection at 26 weeks of age. Blood for plasma was collected before a whole-body perfusion with PBS followed by collection of heart, kidney, carotids and mesenterial lymph node, which was snap frozen in liquid nitrogen and consequently stored at −80° C. until analysis. Aorta was dissected free from surrounding tissues and fixed in Histochoice (Amresco, Solon Ohio, USA). Spleens and remaining mesenterial lymph node were collected and kept on ice until further analysis. Animal care and experimental procedures were approved by the local committee of Animal Care and Use at Lund University.

Lipid Staining of the Aortic Arch.

The aortic arch was prepared en face and washed in distilled water, 78% methanol and stained for 40 minutes in 0.16% Oil-Red-O dissolved in 78% methanol (0.2 mol/L NaOH). The quantification was performed blindly using BioPix i.Q 2.0 software (Biopix AB, Gothenburg, Sweden) where bordeaux coloured regions were referred to the content of neutral lipids in plaques.

Cytokine Determination of Spleen and Lymph Node Cells.

Spleens and lymph nodes were pressed trough a 70 uM single cell mesh, washed in RPMI and centrifuged 700×g for 5 minutes. Red blood cells from spleens were lysed with Red Blood Cell Lysis buffer (Sigma). Cells were calculated, washed in RPMI and centrifuged 700×g for 5 minutes followed by resuspension in cRPMI supplemented with 2% FBS and seeding at a density of 0.5×10(6) cells/well. Cells were stimulated with CD3/28 beads (Life Technologies) and incubated for 72 h in 37*c, 5% CO2. The cytokine determination will be performed with a multiplex assay.

Flow Cytometry Analysis of Blood, Spleen and Lymph Node Cells.

Blood cells from day 42 were stained with CD3-PeCy7, CD4-PB, CD25-APC, FoxP3-PE IL-17-APC and IFN-γ-PE (Biolegend) for regulatory T-cell panel and T helper-1/T-helper 17 panel. Blood cells (20 µl) were also seeded in a round bottomed 96-well plate in cRPMI supplemented with 10% FBS together with 100 ug/ml Brefeldin A (Sigma Aldrich) for 24 h, consequently stained for flow cytometry analysis with CD3-PeCy7, CD4-PB, CD8-APC, IL-17-APC and IFN-γ-FITC (Biolegend) for T helper-1/T-helper 17 panel.

Spleen and lymph node cells were stained for flow cytometry analysis with anti CD3-PeCy7, CD4-PB, CD25-APC, FoxP3-PE, CD44-AF488, CD62L-PE, CD8-APC/Cy7, B220-FITC, B220-PB, CD24-PE, CD5-PE/Cy7, CD23-PB, CD21/35-APC/Cy7, CD1d-AF488, CD40-PE, mTGFβ-APC and CD86-APC/Cy7 (all Biolegend), run on Gallios Flow cytometer (Backman Coulter) and analyzed with FlowJo software (Tree star).

Immunohistochemistry.

Frozen hearts and kidneys were embedded in Tissue Tek (Sakura Fine Tek., Japan) and cross sections from the aortic root were collected with a thickness of 10 and 5 µm, respectively. Macrophage, CD3 and CD8 stainings were performed using rabbit anti-CD68 (Abcam, Cambridge, UK), rat anti-CD3 (Abeam, Cambridge, UK) and rat anti-CD8a (BD Parmingen,), respectively, and detected by diaminobenzene (DAB). Briefly, sections were permeabilized in 0.5% Triton X-100 (Merck Millipore, United States) and incubated in 3% $H_2O_2$ in PBS. Sections were blocked with 10% goat (CD68) or mouse (CD3 and CD8) serum (Sigma-Aldrich, United States) in PBS followed by incubation with 1 µg/ml of the primary anti-CD68, -CD3 or -CD8 antibodies overnight at 4° C. in a pre-wet chamber.

Immunoglobulin G and M stainings of aortic arch and/or kidney will be performed by using biotinylated anti-mouse IgG/IgM (Vector Laboratories) as primary antibodies, respectively. For detection of the anti-CD68, a secondary biotinylated anti-rabbit IgG (Vector Lab) produced in goat was used and a biotinylated mouse anti rat (Vector Lab) for the detection of CD3 and CD8. Color was developed with DAB Detection Kit (Vector Labs, CA, USA) binding to the biotinylated antibody and immune stained areas were quantified in BioPix i.Q 2.0 software.

In Vitro Induction of Tregs Through Antigen Presentation

CD11c+ dendritic cells were isolated from a MRL/lpr ApoE-/- spleen using CD11c positive selection kit and EasySep magnetic beads (StemCell Technologies). CD4+ T cells were isolated using CD4 negative selection kit (StemCell Technologies) followed by isolation of $CD25^-CD4^+$ cells were isolated using CD25 positive selection kit (StemCell Technologies). Cells were cultured in complete RPMI (RPMI-1640 medium containing 2% heat-inactivated fetal bovine serum (FBS), 1 mmol L-1 sodium pyruvate, 10 mmol L-1 Hepes, 50 U penicillin, 50 µg mL-1 streptomycin, 0.05 mmol L-1 b-mercaptoethanol and 2 mmol L-1 L-glutamine; all from GIBCO) for all experiments.

CD11c+ cells were pulsed with 5, 15, 30 µg/ml P45-CTB, 30 µg/ml CTB or PBS for two hours in 37° C. and thereafter washed three times in PBS. $CD25^-CD4^+$ cells were incubated with Celltrace Violet proliferation marker (Thermo Scientific) for one hour in 37° C. 100 000 CD11c+ cells were then cocultured with 100 000 CD4+CD25- T effector cells in complete RPMI for 72 hours. IL-2 and TGF-β (Peprotech) were added to all wells at 25 U/ml and 10 ng/ml respectively, to induce Tregs. Dendritic cells and Treg induction was verified by flow cytometry using the antibodies anti CD123 PE, CD86-PeCy7, CD3-PeCy7, CD25-APC, FoxP3-PE, CD4-AF488, CD8a-APC/Cy7 as previously described above.

Previous studies using P45 in hypocholesterolemic mice have shown that immunization is associated with inhibited atherosclerosis progression as well as eliciting a protective immunoresponse with anti-inflammatory properties. Moreover, there is clinical evidence of an association between P45 IgG autoantibody levels and atherosclerotic plaque inflammation, repair and cardiovascular events in endarterectomy patients. To investigate if the ApoB100 peptide 45 is able to induce atheroprotection and reduce apoptosis in experimental SLE, MRL/lpr ApoE$^{-/-}$ mice were orally immunized with P45-CTB (5, 15 or 30 µg/ml), CTB (30 µg/ml) or PBS at treatment day 0, 2, 5, 7, 14, 21, 28, 35, 42 and 49.

En face mounted aorta were analysed with Oil Red O (ORO) where the aortic arch demonstrated decrease of plaques with 5 and 15 ug/ml P45-CTB compared to the PBS control (FIG. 17). Immunization with 5 and 15 µg/ml P45-CTB reduced the ORO positive staining for lipids with 58.1 and 58.5% respectively (12.1±5.0% and 12.1±4.1%, p<0.01 in both) compared to the PBS treated group (20.8±4.9%). However, no reduction observed in the group treated with 30 µg/ml P45-CTB compared to PBS. No significant difference between each treatment group and CTB, although a trend of reduction can be seen between 5 and 15 µg/ml P45-CTB compared to CTB.

The populations of immune cells in spleen and lymph node at the day of sacrifice were influenced by the treatment, especially the groups of 5 and 15 µg/ml P45-CTB. The central memory helper T cells ($CD3^+CD4^+CD62L^+CD44^{int-hi}$) were reduced in spleen in the 15 and 30 µg/ml P45-CTB groups compared to CTB (7.6±7.7% and 7.5±6.1% versus 19.4±5.2% p<0.001 and p<0.01 respectively) but not PBS (FIG. 18A-FIG. 18I). In lymph node, the central memory T cells were reduced in 15 µg/ml P45-CTB compared to CTB (18.8±11.5% versus 34.5±10.6%, (FIG. 19A-FIG. 19I). Interestingly, the cytolytic T cell populations ($CD3^+CD8^+CD62L^+CD44^{int-hi}$) in spleen displayed an increase in the 5 and 15 µg/ml P45-CTB groups compared to both PBS (29.4±13.3% and 31.9±15.1% respectively versus 17.0±5.1%, p<0.05 in both) and CTB (18.2±3.7%, p<0.05 in both). In contrast, a reduction was observed in lymph node for 15 µg/ml P45-CTB compared to PBS (23.0±16.3% versus 41.3±7.6%, p<0.05 (FIG. 18A-18I, FIG. 19A-19I).

No differences in the amount of Tregs in spleen and LN were observed at the day of sacrifice. However, staining blood cells for Tregs mid-treatment at day 42, a trend can be seen between the treatment groups and PBS and CTB controls where an slight increase can be observed in the 5 and 15 µg/ml P45-CTB groups, although not significant.

Previous observations suggest there is a possibility to develop an ApoB100 peptide-conjugated vaccine targeting atherosclerosis. SLE patients has a significant increased incidence of CVD as a result of systemic inflammation and thus in need of specific therapies. In this study provide data that an ApoB100 peptide (P45) coupled to CTB have immune-modulating properties and reduces atherosclerosis in the aortic arch in MRL/lpr ApoE$^{-/-}$.

Plaque formations in the 5 and 15 µg/ml P45-CTB treatment groups were decreased compared to PBS control, suggesting atheroprotection is elicited by the vaccine candidate in lower doses. The immune cell populations seen in spleen and lymph node reveals how the vaccine influence the immune system, thus there were differences in the T cell populations. Central memory helper T cells were reduced in spleen after treatment with 5 and 15 µg/ml P45-CTB compared to CTB. In the lymph node, the effects were not as pronounced, only a reduction in the 15 µg/ml P45-CTB group was seen. The activated central memory cytolytic T cells in spleen were increased in the 5 and 15 µg/ml P45-CTB treatment groups and similarly in the lymph node. This might suggest an expansion of the CD8$^+$ portion of T cells resulting in less CD4$^+$ cells in the periphery after exposure to peptide vaccine. Immune protection would rather be elicited through cytolytic T cell activation from antigen specificity initiated by the vaccine rather than regulatory T cell suppression, even though a slight trend in populations can be seen.

Taken the results from Oil Red O and the flow cytometry immune cell population characteristics together, it is distinct that an effect of the immunizations with the vaccine candidate in lower doses is observed, either compared to PBS and/or to CTB. As seen in our previous studies using P45-CTB as a therapy against atherosclerosis, we can now see immunomodulating effects in an SLE setting as well. This peptide vaccine represents a possible new therapy for treatment of CVD in SLE patients.

Example 7. Passive Immunization with Recombinant Human IgG1 Against an ApoB100 Peptide Decreased Atherosclerosis Development in a Mouse Model of SLE Background.

Systemic lupus erythematosus (SLE) in an autoimmune disease characterized by inflammation in several organs, such as blood, joint, kidneys, skin and the nervous system. In SLE, increased generation and impaired clearance of apoptotic material is believed to be one disease promoting mechanism leading to activation of autoimmune cells. SLE patients have an increased risk of cardiovascular disease (CVD) (e.g., an about 50-fold increased risk of myocardial infarction) and CVD is the main cause of death in these patients. Traditional preventive CVD therapies such as statins do not lower the incidence of CVD in SLE patients stressing the fact that novel therapies targeting other disease mechanisms is needed. Patients suffering from SLE typically have increased Th1, Th17 and CD4$^-$CD8$^-$ cells; decreased CD8+ cells and Tregs, more reactive T effector cells; and decreased activation threshold.

Aim.

To test if orticumab (BI-204; a recombinant human IgG against peptide sequence 45 in ApoB100) reduced atherosclerosis development in a mouse model of SLE.

Results.

Figure 25A:
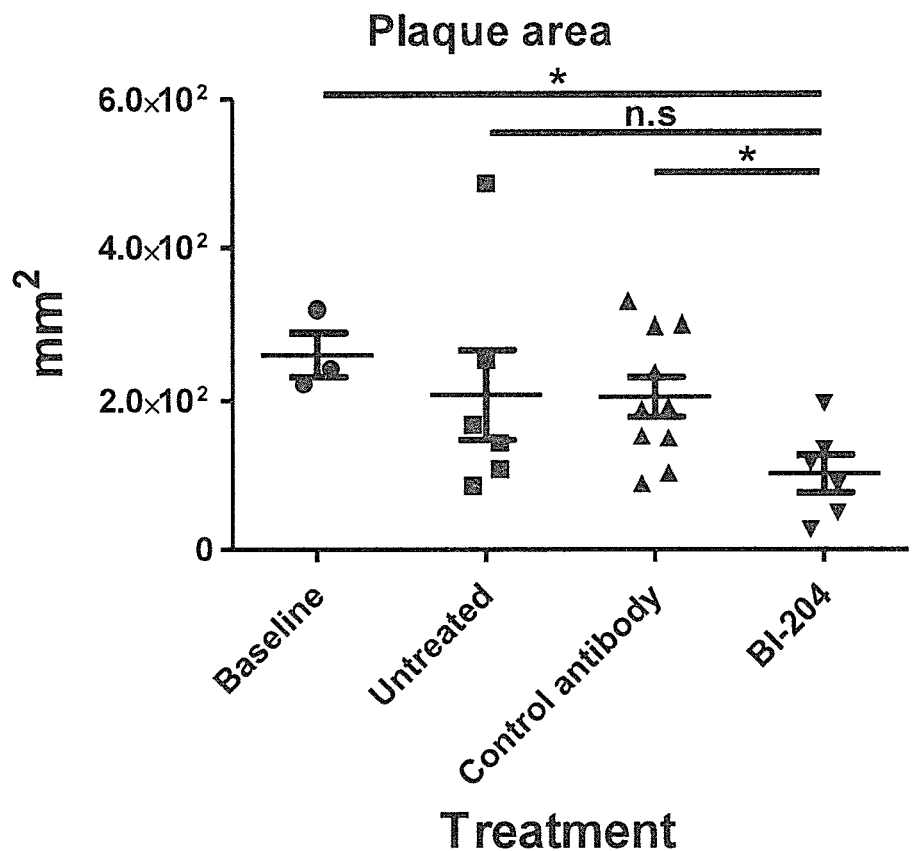
FIG. 25A depicts the plaque area (mm$^2$) in SLExApoE$^{-/-}$ mice. Progression of total plaque area (mm$^2$) after passive immunization with baseline, untreated, control IgG and human recombinant IgG against P45. Baseline, n=3; Untreated, n=6; Control antibody, n=10; BI-204 (orticumab), n=6. Statistical analysis was performed using GraphPad Prism Software 5 with nonparametric two-tailed Mann-Whitney's t-test where *p<0.05. Quantitative data are presented as mean±S.E.M.
Figure 25B:
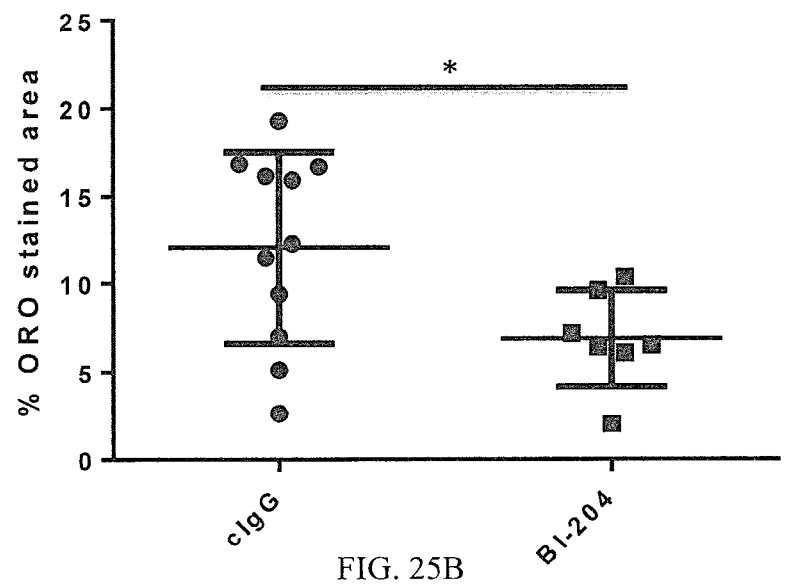
FIG. 25B depicts the area of Oil-Red-O (ORO) staining (%) in SLExApoE$^{-/-}$ mice injected with a control antibody or with orticumab (BI-204).
Figure 27:
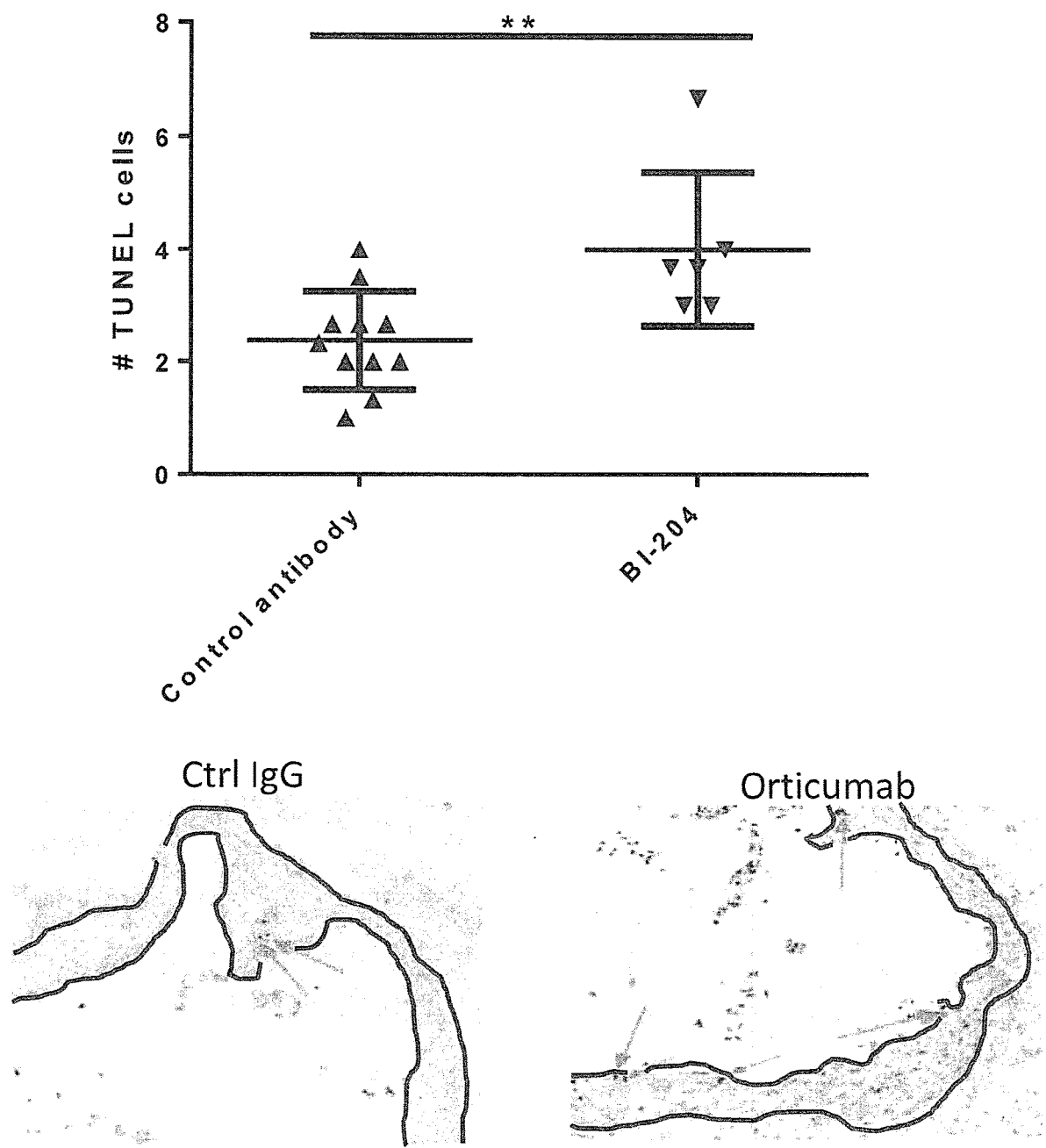
FIG. 27 depicts the quantification and the staining micrographs of TUNEL cells in SLExApoE$^{-/-}$ mice injected with a control antibody or with orticumab (BI-204).
Figure 28:
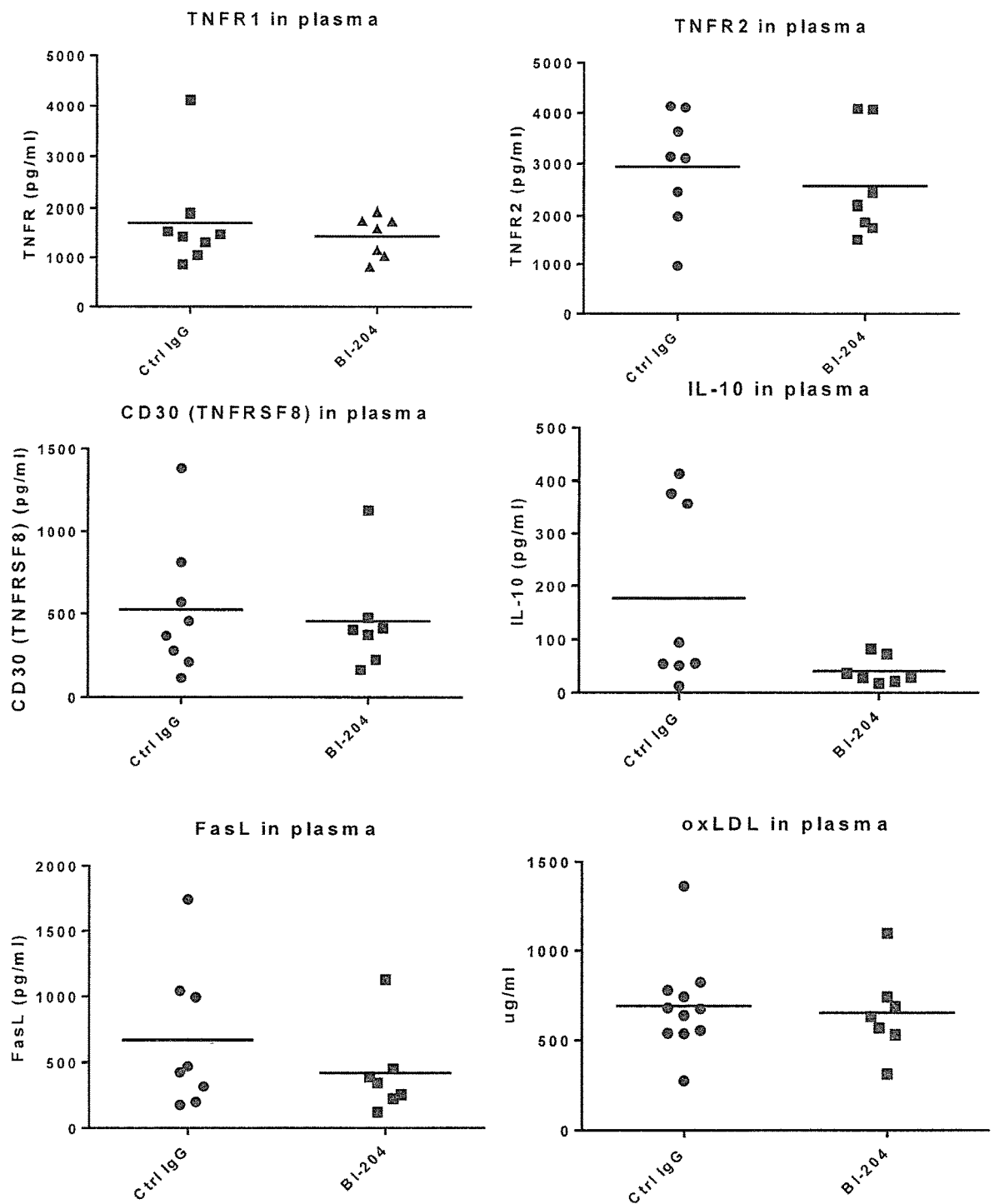
FIG. 28 depicts the quantifications of biomarkers in plasma in SLExApoE$^{-/-}$ mice injected with a control antibody or with orticumab (BI-204).

SLE ApoE$^{-/-}$ mice were treated with three weekly injections of either orticumab or an irrelevant antibody as control. Six-week old mice were fed with HFD, and were injected at weeks 18, 19 and 20 with orticumab (one dose of 1 mg per week, IP injections), and sacrificed for analysis in week 22. Plaque area and composition were determined in the aortic root. Mice treated with orticumab had significantly smaller plaques with less macrophages (FIG. 25A). Flat preps of the aorta showed a reduction, although not significant, in lipid staining after treatment with orticumab (FIG. 25B). Orticumab-treated mice also had a reduced CD68+ area compared to mice treated with a control antibody (FIG. 26). There was also increased apoptosis in plaque areas in orticumab-treated mice as quantified by the number of TUNEL cells (FIG. 27). There were no differences in spleen monocytes or B cells at the end of experiment. Furthermore, no differences in plasma levels of oxidized LDL and plasma cytokines could be detected (FIG. 28).

Conclusions.

Orticumab treatment in SLE ApoE mice has the potential to reduce atherosclerosis development.

Example 8. Phase I Study: Double-Blind, within-Group Randomized Dose-Escalation Trial Evaluated Single and Multiple Doses of Orticumab Study population: 80 healthy subjects with elevated LDL cholesterol.

Orticumab was provided as a sterile liquid and contained no preservatives. Each single-use, 10 mL vial was designed to deliver 250 mg of MLDL1278A. The Drug Product was formulated as 25 mg/mL orticumab in 20 mM sodium acetate, 0.15 M sodium chloride, pH 5.5.

Route of Administration: intravenous injection (Subcutaneous injection was also examined).

Figure 29:
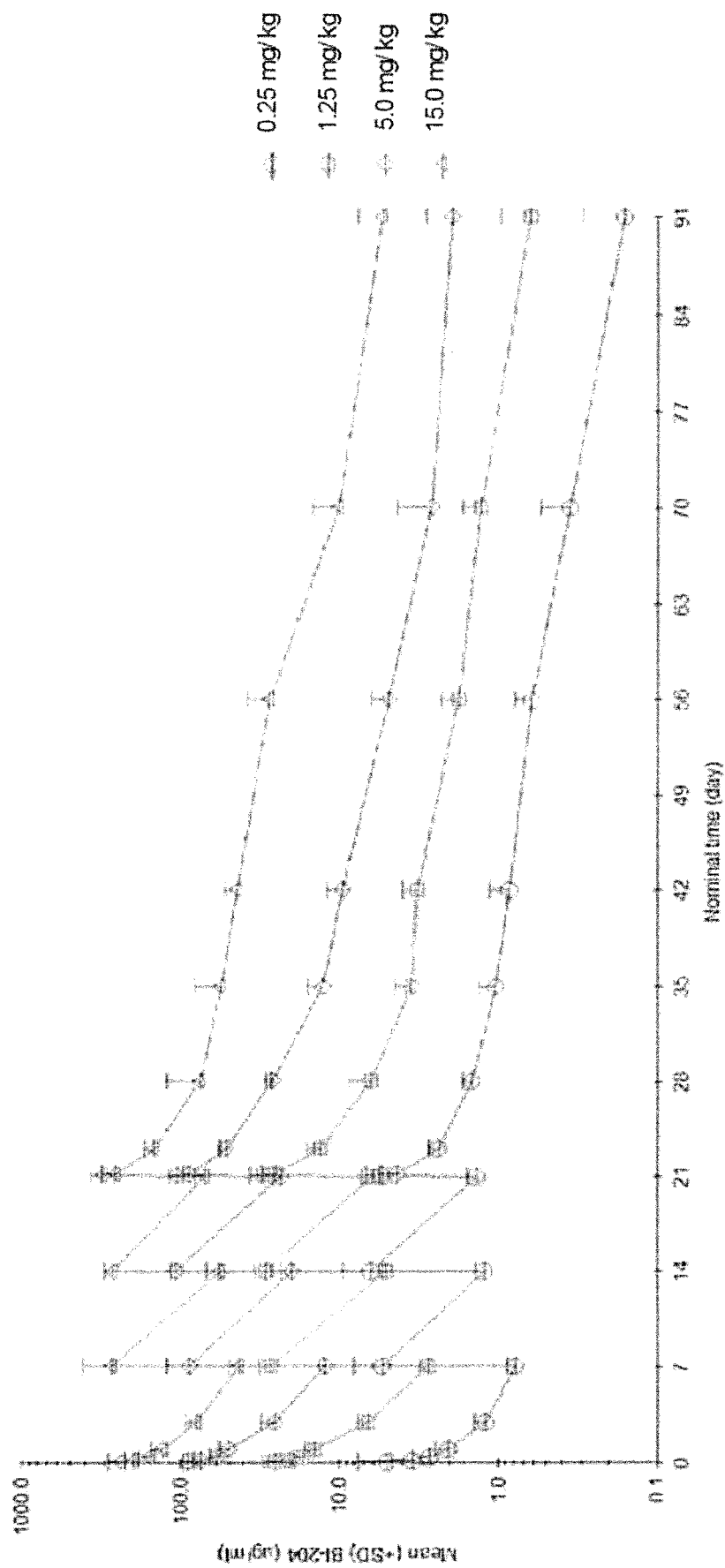
FIG. 29 depicts the serum concentration of orticumab over time following multiple-dose intravenous administration of orticumab to human subjects in a Phase I study.

Overall, the data obtained from single- and multiple-dose IV administration exhibited a clearance (CL) of approximately 8.96-12.1 mL/kg/day, which is higher than the CL of a typical IgG1 antibody (typical CL, 2-5 mL/kg/day). See FIG. 29. The terminal phase volume of distribution (Vz, 216-478 mL/kg) was also higher than that of a typical IgG1 antibody. The exact explanation for these unusual PK characteristics was unknown at that time. The mean terminal half-life was similar after both single and multiple administrations of orticumab and was generally in the range of 2-3 weeks and thus in agreement with other therapeutic monoclonal antibodies. The dose-normalized AUCinf, CL, volume of distribution, and terminal elimination half-life were similar after single and multiple IV doses, which indicated that the PK parameters did not change over time.

Safety: There were a total of 151 treatment-emergent adverse events. The majority of these (125; 82.8%) were mild in intensity; the rest (26; 17.2%) were moderate; none were severe. Of the 151 adverse events, 115 (76.2%) were reported by 44 of the 64 subjects on active treatment, whereas 36 (23.8%) were reported by 17 of the 24 subjects treated with placebo.

Efficacy (effect of orticumab on Biomarkers): The Phase I study involving healthy volunteers did not include any direct efficacy endpoints, but a panel of biomarkers and lipids was evaluated. The panel included: oxLDL, Lp-PLA2, hsCRP, sCD36, MCP-1, ICAM-1, IL-10, VCAM-1, IL-1ra, TNFα, insulin, and MMP-3. No treatment-induced general effects of MLDL1278A were observed in these biomarkers.

Example 9. Second Phase I: Open-Label, Single-Dose Bioavailability Study of Orticumab after Subcutaneous and Intravenous Administration Primary Objective:

to estimate the absolute systemic bioavailability of 150 mg/mL orticumab administered via subcutaneous (SC) injection. Secondary Objectives: to explore the possible effect of a prior intravenous (IV) dose on SC bioavailability; to further characterize the pharmacokinetics (PK) of orticumab; to further evaluate safety and tolerability following SC and IV administration of orticumab; to further characterize the immunogenicity of orticumab by measuring antibodies to orticumab.

Results

Following SC administrations of a single dose of 360 mg orticumab in Cohort A, Period 2 and Cohort B, the mean serum concentrations slowly reached a maximum in approximately 4 days (reaching 15.1 and 9.15 µg/mL, respectively). See FIG. 30. The absolute bioavailability of orticumab after a single SC dose of 360 mg orticumab, based on a statistical analysis of AUC(0-inf), was 47%. The bioavailability of orticumab after a single SC dose of 360 mg orticumab, which was administered after at least 70 days washout from an initial IV dose, was 56%. Therefore, a prior IV dose slightly increased (approximately 9%) the bioavailability of the subsequent SC dose. Orticumab was slowly absorbed after a single SC dose with a median tmax of 4 days. Orticumab t½ was about 20 days for both routes of administration.

There were no SAEs during the study and no subjects were withdrawn as a result of AEs. The most frequently reported TEAEs overall were mild intensity local site reactions following the SC injections (and similar in both groups, SC+/IV).

TABLE 31

Summary of pharmacokinetic parameters of orticumab.

| Parameters | Summary Statistics | Intravenous (Cohort A, Period 1) n = 12 | Subcutaneous (Cohort A, Period 2) n = 12 | Subcutaneous (Cohort B) n = 9 |
|---|---|---|---|---|
| $AUC_{(0-inf)}$ (μg * d/mL) | Mean (SD) | 412 (87.3) | 236 (69.7) | 194 (45.6) |
| $AUC_{(0-last)}$ (μg * d/mL) | Mean (SD) | 380 (76.4) | 215 (60.0) | 178 (39.6) |
| $C_{max}$ (μg/mL) | Mean (SD) | 84.3 (16.9) | 15.1 (4.50) | 9.15 (3.86) |
| $t_{max}$ (d) | Median (min-max) | 0.04 (0.04-0.04) | 3.99 (1.96-6.91) | 3.91 (1.00-4.02) |
| $t_{1/2}$ (d) | Mean (SD) | 20.3 (2.91) | 20.5 (2.84) | 19.6 (6.03) |
| MRT (d) | Mean (SD) | 16.9 (3.02) | NA | NA |
| CL (L/d) | Mean (SD) | 0.906 (0.168) | NA | NA |
| CL/F (L/d) | Mean (SD) | NA | 1.65 (0.491) | 1.96 (0.522) |
| $V_{ss}$ (L) | Mean (SD) | 15.2 (3.25) | NA | NA |
| $V_z$ (L) | Mean (SD) | 26.3 (5.34) | NA | NA |
| $V_z/F$ (L) | Mean (SD) | NA | 48.4 (14.6) | 53.6 (15.4) | min = minimum;
max = maximum;
NA = not applicable;
SD = standard deviation.
Notes:
Value of AUC(0-inf) in Cohort A Period 2 was corrected by subtracting the AUCresidual left from Cohort A Period 1.

Example 10. Phase IIa Study: Double-Blind, Placebo-Controlled, Randomized, Multicenter Study Involving Patients on Standard-of-Care Therapy for Atherosclerotic Cardiovascular Disease (CVD) with Evidence of Vascular Inflammation Overview:

Evidence of vascular inflammation was quantified by [18F]2-deoxyglucose positron emission tomography (FDG-PET) and computed tomography (CT).

The study enrolled 147 participants (83% male; mean age 63.0±9.0 years) with atherosclerosis and evidence of carotid or aortic plaque inflammation, measured by FDG-PET/computed tomography (CT). Because there is poor correlation between serum LDL levels and both serum and plaque oxLDL levels, patients were enrolled with a relatively wide range of serum LDL levels (fasting LDL>60 mg/dL at screening, which includes patients both above and below National Cholesterol Education Program Adult Treatment Panel III treatment goals). 139 patients completed the study.

All patients were on standard-of-care therapy that included 3-hydroxy-3methyl-coenzyme A (HMG-CoA) reductase inhibitor (statin). The dose and type of statin was unchanged for at least 6 weeks prior to initiation of screening, and patients remained on statin therapy without change to dose or type of statin throughout the study. If patients were receiving antihypertensive, antiplatelet agents, non-statin lipid-modifying agents, inhaled corticosteroids, leukotriene-modifying agents, or thiazolidenediones, those therapies were also kept stable for 6 weeks prior to screening and for the duration of the study. All patients who finished the study were treated with standard therapy.

A minimum of 10 patients with type 2 diabetes mellitus (T2DM) per arm (38 total) enrolled, to allow exploration of an effect on insulin/glucose homeostasis.

Trial Design (FIG. 31):

Patients were randomly allocated in a 1:1:1 ratio to receive either MLDL1278A single infusion (1245 mg intravenously [IV]×1, followed by placebo infusions to maintain blinding), MLDL1278A multiple infusions (1245 mg IV followed by 830 mg IV weekly×3 followed by 830 mg IV monthly×2), or placebo by IV infusions to maintain blinding. Random allocation was stratified by T2DM status and pre-diabetes status, presence of elevated screening tissue-to-background ratio TBR>2), and study site.

The study consisted of a 28-day screening period, a 78-day treatment period, and a 90-day follow-up period. Study assessments that coincided with study treatment days were to be performed prior to dosing unless otherwise specified. During the screening period, patient acceptability for the study was assessed on the basis of medical history, concomitant medications, physical examination, and clinical laboratory test results. Once a patient passed this initial screening phase, acceptability for study participation was confirmed on the basis of a TBR>1.8 in the qualifying vessel, as quantified by FDG-PET/CT. All FDG-PET/CT data were acquired on combination FDG-PET/CT scanners; the CT data were used for anatomic reference and localization.

Demographic and selected baseline characteristics for the safety-evaluable population, defined as all patients who received any dose of study drug, are presented in Table 32. The majority of patients were male (83.7%) and White (89.7%). The average age was 63.3 years (range, 40-80 years). All treatment groups were similar with respect to age, sex, and race. The orticumab single-dose group had higher percentage of patients with prediabetes (41.2%) compared with the orticumab multiple-dose (32.7%) and the placebo (27.7%) groups. All treatment groups were similar with respect to the other selected baseline characteristics.

TABLE 32

Demographic and baseline characteristics, safety evaluable patients. (MLDL1278A refers to orticumab)

| Characteristic | Placebo (n = 47) | MLDL1278A Single Dose (n = 51) | MLDL1278A Multiple Dose (n = 49) | All Patients (n = 147) |
|---|---|---|---|---|
| Age, in years | | | | |
| n | 47 | 51 | 49 | 147 |
| Mean (SD) | 63.9 (8.9) | 62.5 (8.6) | 63.3 (9.5) | 63.3 (9.0) |
| Median | 65.0 | 63.0 | 66.0 | 64.0 |
| Range | 41-80 | 40-80 | 43-80 | 40-80 |
| Sex, No. (%) of patients | | | | |
| n | 47 | 51 | 49 | 147 |
| Female | 8 (17.0) | 9 (17.6) | 7 (14.3) | 24 (16.3) |
| Male | 39 (83.0) | 42 (82.4) | 42 (85.7) | 123 (83.7) |
| Race, No. (%) of patients | | | | |
| n | 47 | 50 | 49 | 146 |
| Asian | 1 (2.1) | 0 (0.0) | 1 (2.0) | 2 (1.4) |
| Black | 5 (10.6) | 4 (8.0) | 4 (8.2) | 13 (8.9) |
| White | 41 (87.2) | 46 (92.0) | 44 (89.8) | 131 (89.7) |
| Baseline body mass index (kg/m$^2$) | | | | |
| n | 47 | 51 | 49 | 147 |
| Mean (SD) | 29.4 (4.6) | 29.2 (4.9) | 29.1 (3.5) | 29.2 (4.4) |
| Median | 29.1 | 29.0 | 29.5 | 29.1 |
| Range | 21.7-49.3 | 19.3-38.8 | 20.4-36.9 | 19.3-49.3 |
| Type 2 diabetes mellitus, no. (%) of patients | | | | |
| n | 47 | 51 | 49 | 147 |
| Yes | 14 (29.8) | 12 (23.5) | 12 (24.5) | 38 (25.9) |
| No | 33 (70.2) | 39 (76.5) | 37 (75.5) | 109 (74.1) |
| Prediabetes, no. (%) of patients | | | | |
| n | 47 | 51 | 49 | 147 |
| Yes | 13 (27.7) | 21 (41.2) | 16 (32.7) | 50 (34.0) |
| No | 34 (72.3) | 30 (58.8) | 33 (67.3) | 97 (66.0) |
| Potent Statin use, no. (%) of patients | | | | |
| n | 47 | 51 | 49 | 147 |
| Yes | 24 (51.1) | 23 (45.1) | 21 (42.9) | 68 (46.3) |
| No | 23 (48.9) | 28 (54.9) | 28 (57.1) | 79 (53.7) |
| LDL-C | | | | |
| n | 47 | 51 | 49 | 147 |
| Mean (SD) | 96.6 (35.0) | 91.9 (20.8) | 98.2 (29.8) | 95.5 (28.9) |
| Median | 93.0 | 95.0 | 95.0 | 94.0 |
| Range | 39.0-231.0 | 55.0-130.0 | 52.0-189.0 | 39.0-231.0 |

Primary Outcome Measures:

The primary outcome variable was change in index vessel MDS-TBR (most diseased segment-target to background ratio) measured by FDG-PET/CT from baseline to week 12. Arterial FDG uptake was assessed as target to-background ratio (TBR). Index Vessel was defined as the vessel with the highest mean-of-the-maximum TBR and acceptable image quality at baseline. The most diseased segment was defined as the vessel segment (3 contiguous slices) that included the highest TBR at baseline.

Secondary Outcome Measures:

Incidence and severity of adverse events and clinical laboratory abnormalities as a measure of safety and tolerability of orticumab. Effects of orticumab on inflammatory and metabolic biomarkers. Serum and EDTA plasma samples for soluble biomarker analysis were obtained at baseline and on Day 29 and Day 85. Biomarker assays were performed using the HumanMAP1.6 multiplex panel from Rules Based Medicine (RBM). IL-6 and TNFα immunoassays were performed at Pacific Biomarkers using Quantikine R&D High Sensitivity ELISA. IL-10, MPO and oxLDL immunoassays were performed at Pacific Biomarkers using immunoassay kits from MSA, Prognostix, and Mercodia, respectively. Presence of anti-therapeutic antibodies to orticumab.

Results:

MLDL1278A Did Not Reduce Either Imaging or Circulating Markers of Inflammation. Although high serum concentrations of orticumab were achieved throughout the study for both treatment groups, treatment did not significantly reduce arterial inflammation (primary endpoint of index vessel MDS-TBR) versus placebo. Baseline demographics were comparable among groups for the 117 patients with evaluable week 12 FDG-PET images included in the primary analyses. Orticumab was well tolerated, and there was no evidence of immunogenicity. Notably, a nominal increase in the levels of tumor necrosis factor alpha (p=0.03) and interleukin 6 (p=0.04) occurred at 4 weeks in the multiple-dose group. No significant decreases in lipid parameters or high-sensitivity C-reactive protein level were observed in either group. Further, none of the secondary outcomes were different between groups. No serious adverse events were reported that were related to the procedures or to the administration of orticumab in this Study. This Study did not demonstrate any clinically significant safety signals for orticumab, and the only imbalances in safety events between dose arms were minor numerical differences in dizziness, headache, and gastrointestinal (diarrhea) events, which were assessed as mild and not clinically significant by the Internal Monitoring Committee. No dose-limiting toxicities, deaths, or pregnancies were reported. No trends in laboratory values and significant clinical events were observed.

Example 11. Simulation and Actual Pharmacokinetics (PK)

The ability of orticumab to shut down macrophage pro-inflammatory activity locally in the plaque became the focus, as it was thought to be an important mechanism underlying its therapeutic activity. Initial hypothesis of using orticumab related to neutralizing oxLDL from the systemic compartment, which required 4 μg/mL=~28 nM=11 mg of orticumab to neutralize 90% systemic oxLDL. Further in vitro assays provided an insight into the minimum effective concentration of orticumab needed to achieve 50% or 90% inhibition of oxLDL-mediated cytokine release (i.e., inhibition of monocyte chemoattractant protein 1, MCP-1):

$IC_{50}$ for MCP-1 inhibition: ~10 nM=1.5 μg/mL=~4 mg $IC_{90}$ for MCP-1 inhibition: ~30-80 nM=4.5-12 μg/mL=12.4-33 mg.

The dosage (an initial dose of 1245 mg, followed by 830 mg weekly×3, then 830 mg monthly×2) in the clinical trial, compared to the lower range (12.4 mg orticumab) as $IC_{90}$ for MCP-1 inhibition, was 100 times and 67 times greater. The dosage in the clinical trial, compared to the higher range (33 mg orticumab) as $IC_{90}$ for MCP-1 inhibition, was 38 times and 25 times greater.

In atherosclerosis patient, it has been reported that there is an increased endothelial permeability to macromolecules, where uptake of injected macromolecules into the arterial wall is rapid and linear over time and the equilibrium against circulating blood stream is reached within 1 hour (Ross et al NEJM 1999).

Figure 32:
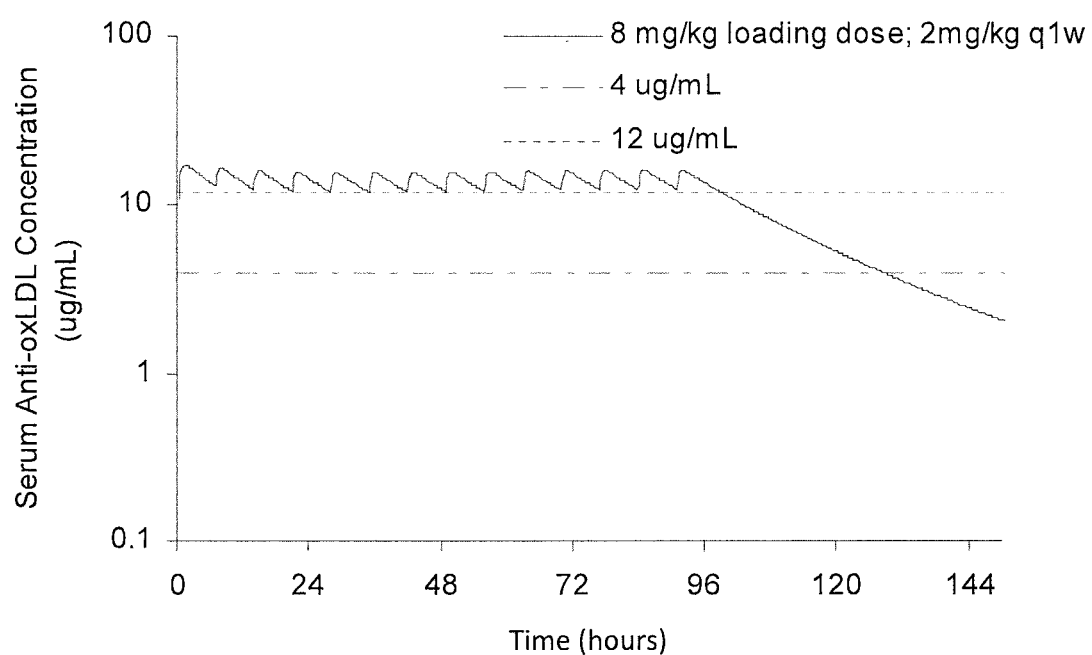
FIG. 32 depicts a simulated human pharmacokinetics (PK) profile after a subcutaneous (SC) loading dose of 8 mg/kg followed by a weekly SC dosing of 2 mg/kg (the solid line). Dashed lines indicate two desired thresholds (4 μg/mL, generally lowest line, and 12 μg/mL, the higher dashed line) of the serum concentration of orticumab.

Based on this background information, we proposed a loading dosage that would yield steady state plasma concentration of orticumab of at least 12 μg/mL for up to 96 hours in a simulation model (FIG. 32). The loading dose of 8 mg/kg (664 mg for an averaged patient of 83 kg), followed by bi-weekly to weekly 2 mg/kg (166 mg) subcutaneous (SC) dosing. This loading dose was 1.9 times less than the loading dose, and the weekly dosing was 5 times less than the weekly dosing.

Figure 33A:
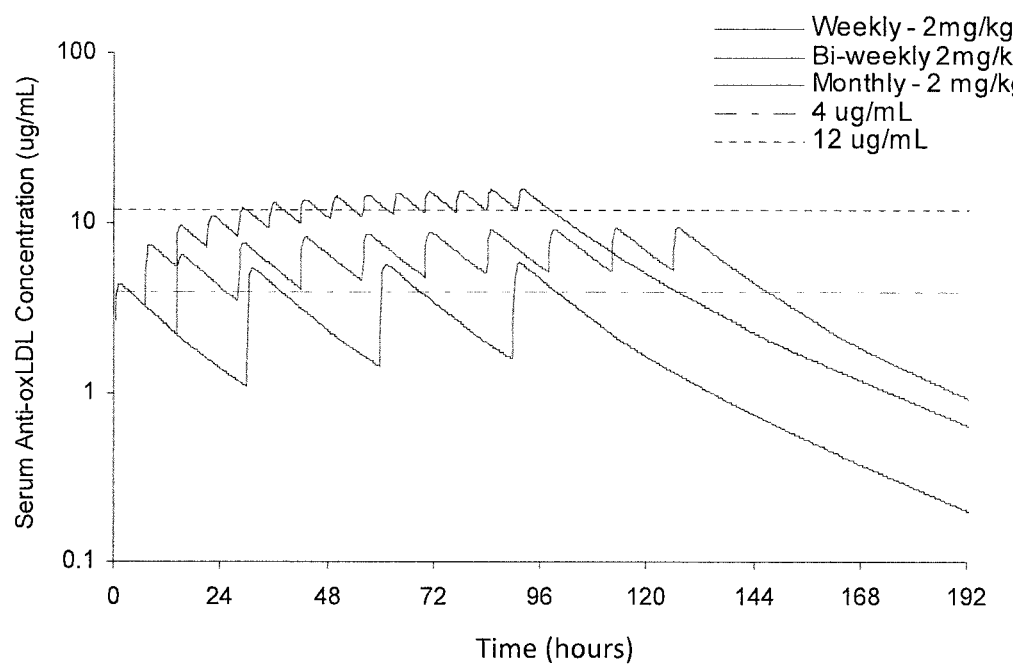
FIG. 33A and FIG. 33B depict simulated human PK profiles based on SC dosing.
Figure 33B:
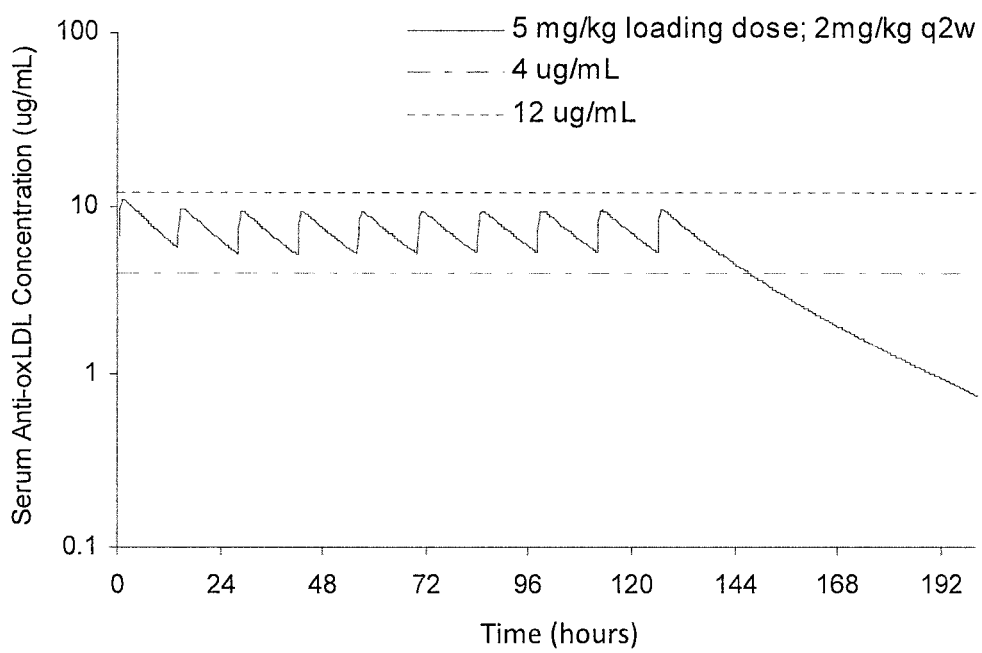

In another set of simulations based on SC dosing:
(1) Weekly dosing at 2 mg/kg (166 mg) achieved 12 μg/mL threshold between Day 2-4 (FIG. 33A);
(2) Biweekly dosing at 2 mg/kg did not achieve 12 μg/mL threshold, but did achieve 4 μg/mL threshold from Day 1-6 (FIG. 33B);
(3) Monthly dosing at 2 mg/kg did not achieve sustained exposure at the 4 μg/mL threshold (FIG. 33A);
(4) Loading Dose of 5 mg/kg (415 mg), followed by biweekly dosing at 2 mg/kg did not achieve 12 μg/mL threshold, but did maintain exposure above the 4 μg/mL through Day 6 (FIG. 33B).

In clinical trials of orticumab, Tables 33-36 below summarize the PK data.

TABLE 33

The PK data from a "FIH" trial with single dosing.

| Dose (mg/kg) | Route of Admin | $C_{max}$ (μg/mL) | C ≥ 1 μg/mL | C ≥ 4 μg/mL | C ≥ 12 μg/mL |
|---|---|---|---|---|---|
| 1.25 | SC | 2.99 | Day 28 | Not achieved | Not achieved |
| 1.25 | IV | 20.6 | Day 28 | Day 3 (<Day 7) | 11 hours |
| 5 | IV | 105 | Day 56 | Day 14 | Day 3 |
| 15 | IV | 286 | Day 70* | Day 42 | Day 28 |

(*Last day of assessment)

TABLE 34

The PK data from a "FIH" trial with multiple dosing.

| Dose (mg/kg) | Route of Admin | $C_{max}$ (μg/mL) | C ≥ 1 μg/mL | C ≥ 4 μg/mL | C ≥ 12 μg/mL |
|---|---|---|---|---|---|
| 1.25 | SC | 1.24 | Day 42 | Not achieved | Not achieved |
| 1.25 | IV | 29.6 | Day 70 | Day 28 | Day 23 |
| 5 | IV | 105 | Day 91* | Day 56 | Day 35 |
| 15 | IV | 303 | Day 91* | Day 91 | Day 56 |

(*Last day of assessment)

TABLE 35

The PK data from a "Ph1" trial with single dosing comparing subcutaneous (SC) and intravenous (IV) administration.

| Dose (mg) | Route of Admin | $C_{max}$ (μg/mL) | C ≥ 1 μg/mL | C ≥ 4 μg/mL | C ≥ 12 μg/mL |
|---|---|---|---|---|---|
| 360 | SC | 9.15 | Day 43 | Day 15 | Not achieved |
| 360 | SC 70-90 days after IV dosing | 15.1 | Day 57 | Day 15 | Day 8 |
| 360 | IV | 84.3 | Day 57* | Day 15 | Day 8 |

(*Last day of assessment)

TABLE 36

The PK data from a "Ph2" trial.

| Dose Group | Route of Admin | $C_{max}$ (μ/mL) D 1 | D 78* | C ≥ 1 μg/mL | C ≥ 4 μg/mL | C ≥ 12 μg/mL |
|---|---|---|---|---|---|---|
| Single Dose | IV | 297 | N/A | Day 106 | Day 50 | Day 22 |
| Multiple Dose | IV | 286 | 197 | Day 169 | Day 141 | Day 106 |

Dosing days: D 1, 8, 15, 22, 50, 78.
*Last day of dosing.

$C_{max}$, Single Dose at 1.25 mg/kg: 1.25 mg/kg=104 mg, which was 6.9 times greater max exposure with IV vs SC admin (½-life is 20 days for both); SC dose does not reach threshold of 4-12 μg/mL.

$C_{max}$, Single Dose at 360 mg: 360 mg=4.34 mg/kg (3.5 times FIH study), 9.2 times greater max exposure with IV vs SC admin (½-life is 33.5 vs 24.3 days, IV vs SC); SC dose falls within range of 4-12 μg/mL.

As a result, based on the simulated and actual PK data, 8 mg/kg (664 mg) is optimal, but 5 mg/kg (415 mg) is likely sufficient. Based on the ½-life of a single dose in the clinical studies (i.e., 24 days with a single SC dose of 360 mg), monthly dosing is reasonable.

Figure 34:
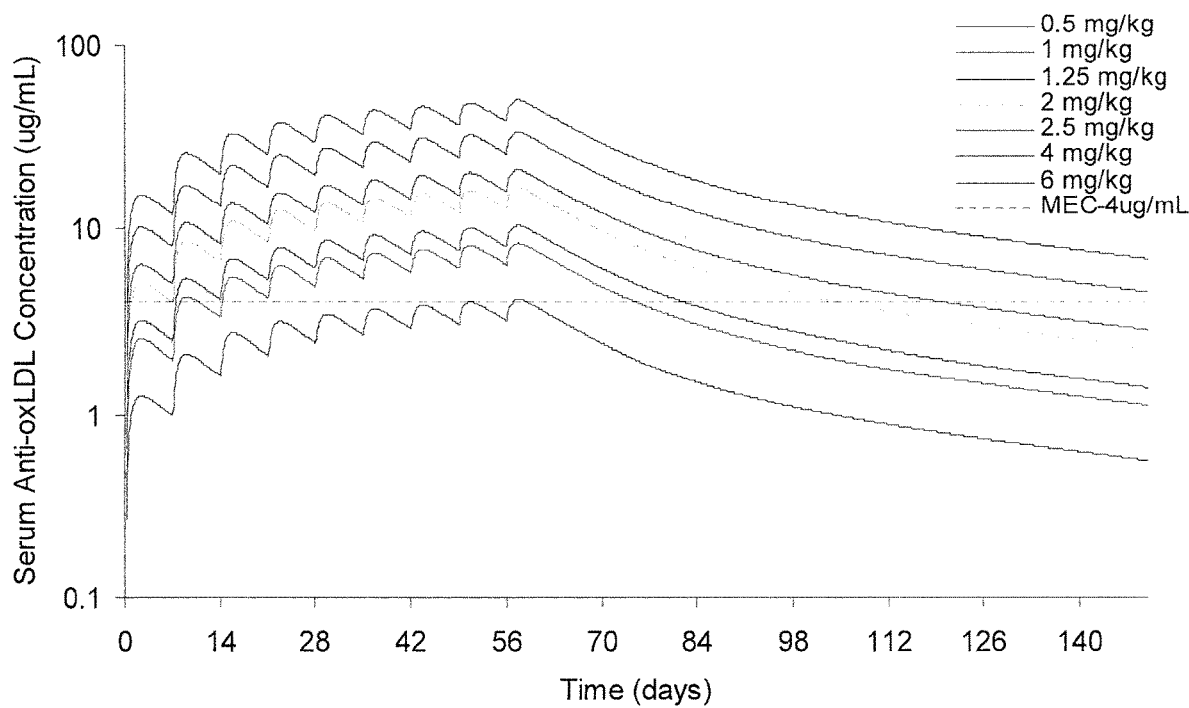
FIG. 34 depicts the simulated human PK profiles after weekly SC dosing, using PK parameters from Phase I data. The solid lines in the graph from low to high represent dosages at 0.5, 1, 1.25, 2, 2.5, 4 or 6 mg/kg.
Figure 35:
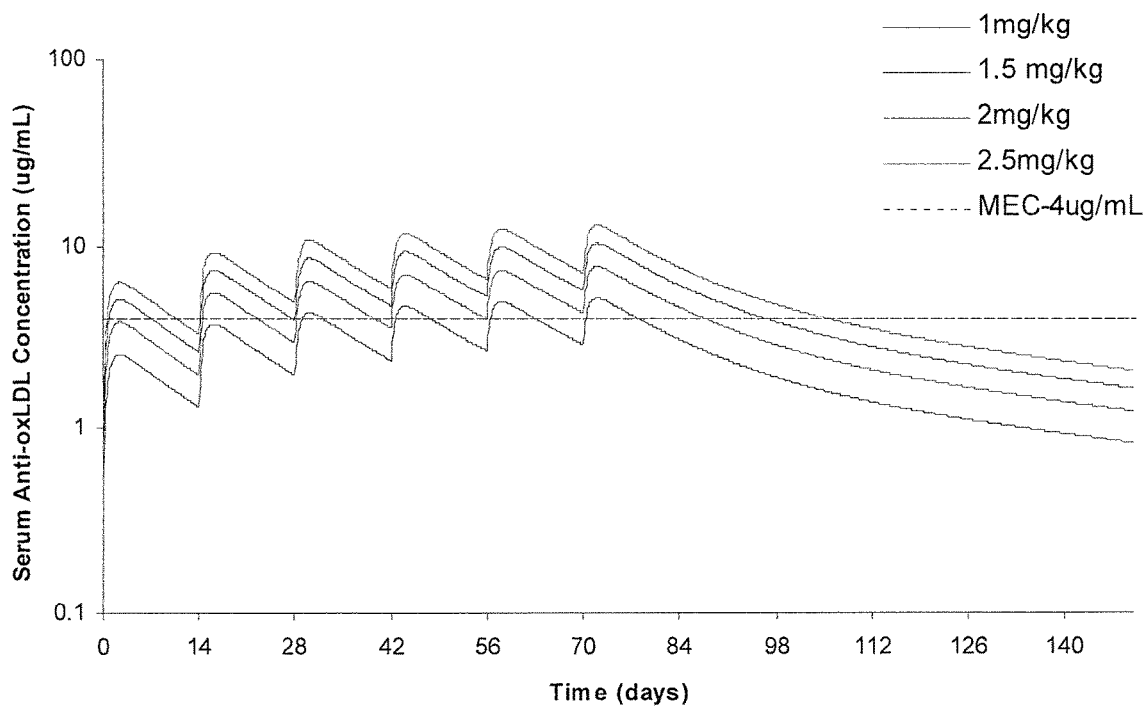
FIG. 35 depicts the simulated human PK profiles after bi-weekly SC dosing, using PK parameters from Phase I data. The solid lines in the graph from low to high represent dosages at 1, 1.5, 2 or 2.5 mg/kg.
Figure 36:
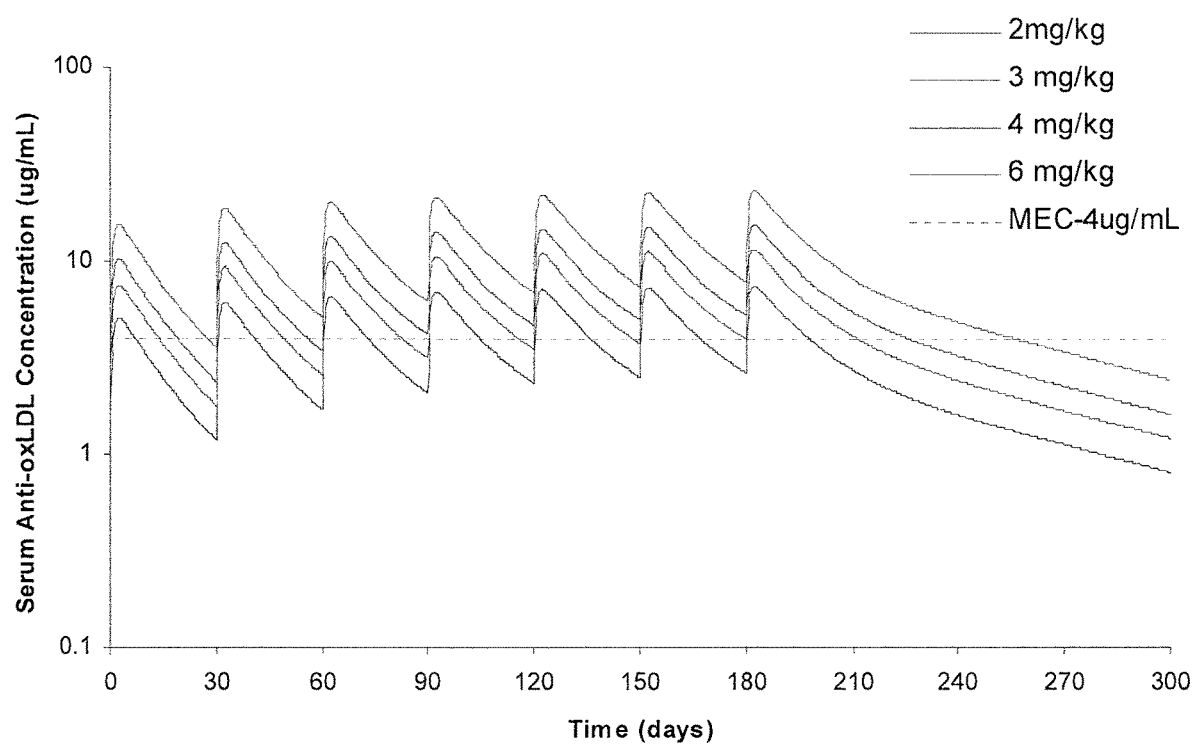
FIG. 36 depicts the simulated human PK profiles after monthly SC dosing, using parameters from Phase I data. The solid lines in the graph from low to high represent dosages at 2, 3, 4 or 6 mg/kg.

In another set of studies of orticumab:
(1) Weekly SC dose of 1 mg/kg and above maintained concentrations above 4 µg/mL at steady state. FIG. 34 depicts the simulated human PK profiles after weekly SC dosing, using PK parameters from Phase I data. Bioavailability after SC dose is 70%.
(2) Bi-weekly SC dose of 1.5 mg/kg and above maintained concentrations above 4 µg/mL at steady state. FIG. 35 depicts the simulated human PK profiles after bi-weekly SC dosing, using PK parameters from Phase I data.
(3) Monthly SC dose of ~3 to 4 mg/kg and above maintained concentrations above 4 µg/mL. FIG. 36 depicts the simulated human PK profiles after monthly SC dosing, using parameters from Phase I data.

Based on simulated PK data, and targeting a plasma concentration of 12 µg/mL threshold for maximum chance of success, weekly dosing should be no less than 2 mg/kg (166 mg); 4 mg/kg (332) would be preferable; biweekly dosing must be >2.5 mg/kg (208 mg); higher doses were not simulated; and monthly dosing should be 6 mg/kg (498 mg). In some embodiments, final recommendation is 500 mg, monthly via SC injection. Monthly dosing of 500 mg each month can be administered 12 doses over a 12-month dosing regimen, or 3 doses over a 3-month dosing regimen. Monthly dosing of 330 mg each month (to meet the minimum 4 µg/mL plasma concentration threshold) can be administered 12 doses over a 12-month dosing regimen, or 3 doses over a 3-month dosing regimen.

Example 12. Immune Responses Against Oxidized LDL as Targets for Prevention of Atherosclerosis in Systemic Lupus Erythematosus Abstract: Patients suffering from systemic lupus erythematosus (SLE) are at an increased risk of developing cardiovascular disease (CVD) and traditional therapies including statins provide insufficient protection. Impaired removal of apoptotic material is a common pathogenic mechanism in both SLE and atherosclerosis and is considered to be a key factor in the development of autoimmunity. We aimed to investigate if targeting oxidized LDL autoimmunity can affect atherosclerosis in SLE. Subjects with SLE and matched healthy controls had similar levels of oxidized LDL in plasma but the correlation with IL-6 was stronger in SLE subjects. Mucosal immunization of hypercholesterolemic mice with an SLE-like phenotype (B6.lpr.ApoE-/- mice) with the apolipoprotein B-100 peptide P45 (amino acids 661-680) coupled to the cholera toxin B-subunit increased regulatory T cells in mesenteric lymph nodes and reduced plaque development in the aorta by 32.5%. Targeting oxidized LDL by injection of an MDA-P45 specific antibody reduced aortic atherosclerosis by 42.8%, subvalvular plaque area by 50.3% and the macrophage content of remaining plaque by 30.5%. This exemplary study provides experimental and clinical support for targeting oxLDL in the prevention of cardiovascular complications in SLE.

INTRODUCTION

Accumulation and oxidation of low density lipoproteins (LDL) in the arterial wall is considered to be a pathogenic process of key importance in the development of atherosclerosis. Oxidized LDL (oxLDL) is strongly pro-inflammatory and has toxic effects on vascular cells. It can be removed by infiltrating monocytes that differentiate into scavenger receptor-expressing macrophages that ingest the oxLDL particles and store excess cholesterol in lipid droplets. These cells may also present antigens derived from oxLDL to T cells. Activation of Th1 cells results in aggravation of inflammation and progression of atherosclerosis, while activation of regulatory T cells (Tregs) has the opposite effect. To promote and/or mimic the protective oxLDL immunity, we and others have developed apolipoprotein B-100 peptide immune-suppressive vaccines and antibodies that reduce atherosclerosis in different mouse models.

Systemic lupus erythematosus (SLE) is a complex autoimmune disease characterized by autoimmune responses against a number of different tissues. The incidence of cardiovascular disease (CVD) is significantly increased in SLE patients with a 5-10 fold increased risk of myocardial infarction (MI) after adjusting for the Framingham Risk Factors. The pathogenic mechanisms responsible for the increased CVD risk in SLE remains to be fully understood. There is evidence that a dysfunctional clearance of autoreactive lymphocytes and apoptotic material in SLE is an important cause of autoimmunity in SLE. Similarly, an impaired clearance of apoptotic material contributes to the development of atherosclerosis. Macrophage scavenger receptors are of critical importance for the clearance of both apoptotic material and oxLDL indicating that both processes could be affected in SLE and that this can represent a link between SLE and CVD. We hypothesize that impaired removal of oxLDL and apoptotic material results in activation of autoimmunity against related antigens contributing to the development of cardiovascular complications in SLE.

Since oxidized LDL and apoptotic material bind to the same receptors, we aimed to investigate if targeting oxidized LDL autoimmunity can affect atherosclerosis in SLE. We thus compared peripheral blood mononuclear cell (PBMC) responses to oxidized LDL in subjects with SLE and matched healthy controls. We also used two different approaches to modulating immune responses against modified LDL (mucosal tolerance induction by an apoB100 peptide linked to the B subunit of cholera toxin (CTB) and administration of an antibody specific for the same peptide) to study the effect of atherosclerosis development in a hypercholesterolemic mouse model of SLE.

Materials and Procedures:

SLE patients and controls: All patients in the study were evaluated by a rheumatologist at the department of Rheumatology, Skånes Universitetssjukhus, Lund. Clinical measurements were performed and fresh blood samples were collected from SLE and healthy controls during 2014-2015. Peripheral blood mononuclear cells (PBMC) from 26 randomly selected SLE individuals with age and sex matched control individuals were isolated from heparin whole blood, using Ficoll Paque (GE Healthcare) according to manufacturer's instructions. Cell numbers were calculated and further the cells kept frozen into liquid nitrogen until all samples were collected. Serum from each individual was collected and saved in -80° C.

Plasma marker measurements: oxidized LDL was analysed according to manufacturers instructions (Mercodia, Uppsala, Sweden). Plasma cytokines were analyzed by the Proximity extension assay (PEA) technique at the Clinical biomarkers facility, (Science for Life Laboratory, Uppsala, Sweden) using their 96×96 Olink Inflammation panel. Briefly, oligonucleotides-labeled antibodies in pairs were allowed to bind to their plasma cytokine target. Upon targeting, DNA polymerase allowed for an extension and joining of the oligonucleotides creating a PCR DNA template. Universal primers were added to amplify the templates to a detectable amount. Each individual DNA sequence were then detected and quantified with specific primers in a microfluid real-time quantitative PCR chip on HD Biomark instrument (96×96, Dynamic Assay IFC, Fluidigm Biomark). Data analysis was performed by normalization in Olink Wizard for GenEx (Multid Analyses, Sweden) and expressed as arbitrary units (A.U).

Flow cytometry analysis of PBMCs stimulated with DIloxLDL and MDA.P45-IgG antibody: PBMCs were slowly thawed in 37° C. PBS with 2% autologous serum, counted and seeded into appropriate medium and conditions. Medium for each stimuli condition was prepared from complete RPMI (cRPMI, 10 U/ml Penicillin/streptomycin, 1% L-glutamine, 1% sodium pyruvate, 1% Hepes and 0.1% mercaptoethanol) with 2% autologous serum (Sigma Aldrich) including the respective stimuli conditions and pre-incubated in 37° C. for 1 h before stimulating the cells with it. Condition 1; unstimulated, condition 2; 10 μg/ml Dil-OxLDL (Thermo Scientific), condition 3; 10 μg/ml Dil-OxLDL with MDA.P45-IgG. (Dil-OxLDL refers to oxidized LDL complexed with Dil dye).

At time of experiment, cells were slowly thawed in 37° C. PBS containing 2% autologous serum. Cells were counted and all cells obtained were divided into three wells for respective condition mentioned above for 24 h at 37° C. in 5% CO2. After 24 h stimulation, medium was harvested and kept in −80° C. until cytokine analysis. Cells were washed twice in FACS buffer (PBS 1% bovine serum albumin 500 mM EDTA), then stained with Zombie Aqua viability dye for 20 minutes in room temperature (RT). This was followed by another wash then incubation with anti-HLA-DR APC-Cy7 anti-CD3-PECy7 and anti-CD14-AF700 for 30 minutes in RT prior acquisition in Gallios flow cytometer (Beckman Coulter, Brea, Calif., USA). Cell populations were manually gated in FlowJo LTT (Tree Star, San Diego, Calif., USA).

Multiplex analysis of PBMC cell culture medium: Cell culture medium from human SLE and control PBMCs were thawed on ice before analyzed using Multiplex Inflammation assay (Merck, Millipore, Burlington, Mass., USA) according to following kit instructions.

Mice: Female B6.lpr.ApoE−/− mice were generated and bought from Jackson Laboratories (Charles River Laboratories, Germany) before purchasing bred in our animal facility. High fat diet (HFD, 0.15% cholesterol, 21% fat, Lantmännen, Sweden) was introduced from 6 weeks of age until the experimental end point. The ApoB100 peptide 45 (P45) was coupled to cholera toxin B (P45-CTB). Female mice were used for the treatment with p45-CTB conjugate (5 μg/injection, n=13 or CTB (30 n=13) started at 18 weeks of age at day 0 and were orally administered three times the first week followed by once weekly until 26 weeks of age followed by sacrifice 27 weeks of age. Male B6.lpr.ApoE−/− mice were used for the IgG1 antibody study with administration of human recombinant malondialdehyde-modified P45 antibody (MDA-P45-IgG1, BioInvent, Lund, Sweden). HFD was introduced at 6 weeks of age until the experimental end point at 22 weeks of age. Mice were treated with 1 mg MDA-P45-IgG1 (IgG that binds to MDA-modified P45) once a week for three times with start at 18 weeks of age (n=9 in each group) followed by sacrifice at week 22. At euthanizing, urine and blood for plasma was collected before a whole-body perfusion with PBS followed by collection of heart, kidney and carotids. Mesenteric lymph node were collected from mice treated with P45-CTB. All organs were snap frozen in liquid nitrogen and stored at −80° C. until further analysis. Aortas were dissected free from surrounding tissues and fixed in Histochoice (Amresco, Solon Ohio, USA). Spleens and mesenteric lymph nodes were collected and kept on ice until further restimulation challenge in vitro.

Lipid staining of the aortic arch: The aortic arch was prepared en face and washed in distilled water, 78% methanol and stained for 40 minutes in 0.16% Oil-Red-O dissolved in 78% methanol (0.2 mol/L NaOH). The quantification was performed blindly using BioPix i.Q 2.0 software (Biopix AB, Gothenburg, Sweden) where bordeaux coloured regions were referred to the content of neutral lipids in plaques.

Immunohistochemistry: Frozen hearts and kidney were embedded in Tissue Tek (Sakura Fine Tek., Japan) and cross sections from the aortic root were collected with a thickness of 8 μm and 5 μm, respectively. Kidney sections were stained in Mayers hematoxyline for 3 minutes, followed by ddH2O wash twice followed by dehydration and mounting with Pertex (Sigma). For hearts sections, CD68 staining was performed using rabbit anti-CD68 (Abcam, Cambridge, UK). Briefly, sections were washed in between all steps with phosphate buffered saline (PBS) and Tris buffered saline (TBS) respectively. For permeabilization 0.5% Triton X-100 (Merck Millipore, United States) in PBS/TBS was used and further and incubated in 3% H2O2 in PBS/TBS. Sections were blocked with 10% goat serum (Sigma-Aldrich, United States) in PBS followed by incubation with 1 μg/ml of the primary anti-CD68 antibody overnight at 4° C. in a pre-wet chamber. For detection, a secondary biotinylated goat anti-rabbit IgG (Vector Labs, CA, USA) was stained with for 1 h in RT. Color was developed with DAB Detection Kit (Vector Labs) binding to the biotinylated antibody. Heart CD68 immune stained areas and kidney glomeruli cells and area were quantified in BioPix i.Q 2.0 software (Goteborg, Sweden).

Plasma cytokine analysis: Plasma from P45-CTB and MDA.P45-IgG treated mice was thawed on ice for multiplex analysis of cytokines using Milliplex Map Kit Mouse High Sensitivity T cell Magnetic Bead panel (Merck Millipore, Darmstadt, Germany) or MilliPlex (Billerica Mass., USA) respectively, according to instructions provided. Results were obtained by Luminex technique (Bio-Rad, CA, USA).

Splenocyte restimulation challenge in vitro: Spleens from P45-CTB treated mice were pressed trough a 70 μM single cell mesh, washed in RPMI and centrifuged 700×g for 5 minutes. Red blood cells were lysed with Red Blood Cell Lysis buffer (Sigma). Cells were calculated, washed in RPMI and centrifuged 700×g for 5 minutes followed by resuspension in cRPMI supplemented with 2% FBS and seeding at a density of 0.5×10⁶ cells/well. Cells were stimulated with CD3/28 beads (Life Technologies) and incubated for 72 h in 37° C., 5% CO2.

Plasma oxLDL, cholesterol and triglycerides assay: Plasma from all mice were thawed on ice and subsequently total plasma cholesterol and triglyceride levels were quantified with oxLDL ELISA kit (Cloud-Clone Corp) and colorimetric assays INFINITY™ Cholesterol and Triglyceride (INT) according to the manufacturer's instructions.

Plasma anti-nuclear antibody and anti-dsDNA measurement: Plasma anti-nuclear antibodies from P45-CTB treated mice were measured with Nova-lite Hep2 slides (Inova Diagnostics, San Diego, USA). Plasma (1:100) in PBS with 0.2% BSA were incubated on the Hep2 slides 1 h at room temperature. Slides were then washed with PBS 5 times using a squeeze bottle and put in a joplin jar filled with PBS for 5 minutes twice and then dipped 5 times in dH$_2$O. Slides were then incubated with 25 μl human IgG (H+L)-FITC (Southern Biotech, Birmingham, USA) diluted 1:100 in PBS with 0.2% BSA. Slides were then washed as previously and thereafter mounted with Vectashield (Vector Biolabs). ANA score was assessed according to a standard matrix from four individuals independently of each other.

Blood urea nitrogen and albumin/creatinine measurement in urine: Blood urea nitrogen from P45-CTB was measured in urine diluted 1:100 using BUN assay (Bioassay Systems, San Francisco, USA) and urine albumin and creatinine from all mice were measured with ELISA for albumin and creatinine (Abcam) respectively according to manufacturer's instructions provided in the kits.

Statistics: Clinical comparisons from human individuals were evaluated and statistically tested using SPSS software. For same-individual analyses, paired nonparametric Wilxocon rank test was used. For normally distributed data, Students t-test was used. For not normally distributed data, Mann-Whitney rank test was used. Numerical data is expressed as mean±standard deviation if normally distributed or median±intra-quartile range if not normally distributed. Carotid gene expressions were log transformed and expressed as arbitrary units (A.U) and relative fold change respectively. All data was plotted in GraphPad Prism and significance levels used are *=p<0.05 =p<0.01, *=p<0.001.

Results

The cohort consisted of a total of 51 SLE cases and 32 sex and age-matched healthy controls. Clinical characteristics of the SLE patients are shown in Table 37.

TABLE 37

Baseline characteristics SLE individuals Lund cohort.

| Baseline characteristics | SLE cases (n = 53) |
| --- | --- |
| Age (mean) | 54.3 ± 15.9 |
| Gender (f/m %) | 88.7/11.3 |
| Disease duration (median) | 17.3 (10.3-25.3) |
| SLEDAI disease score (mean) | 2.5 ± 2.4 |
| SLICC damage score (mean) | 1.2 ± 1.4 |
| ANA positive (%) | 79.2 |
| Corticosteroid treatm. (%) | 54.7 |
| Immunomodulating treatm. (%) | 62.3 |

Note:
f; female, m; male, SLEDAI; SLE disease activity index, SLICC; Systemic Lupus Collaborating Clinics, ANA; anti-nuclear antibody.

Figure 37A:
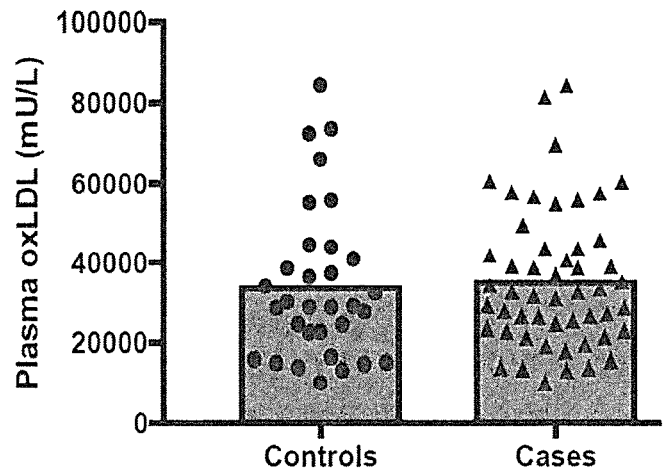
FIG. 37A-FIG. 37C depict response to oxLDL of PBMC from SLE patients and healthy controls, characterized by plasma levels of oxLDL (37A), IL-6 (37B) and MCP-1 (37C) in healthy controls (n=31) and SLE cases (n=53).
Figure 37B:
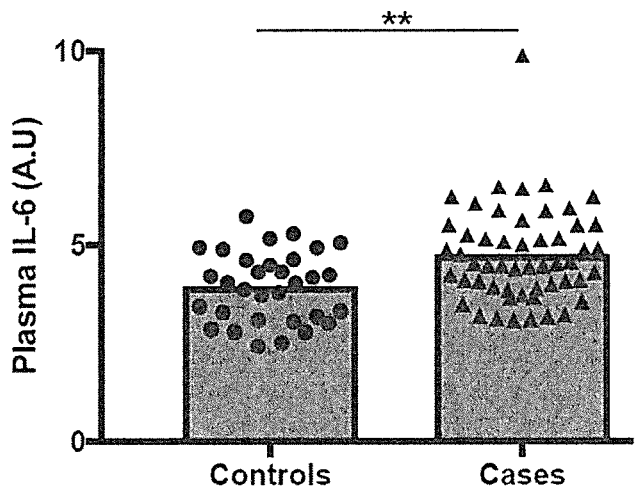
Figure 37C:
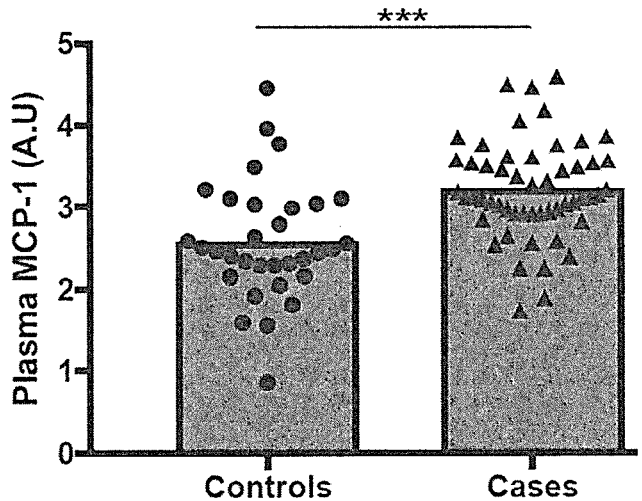

Response of PBMCs from SLE patients and healthy controls to oxLDL:

There was no difference in the plasma level of oxLDL between SLE patients and controls, while both interleukin (IL)-6 and monocyte chemoattractant protein (MCP)-1 levels were higher in SLE patients (FIGS. 37A-37C). The plasma level of IL-6 demonstrated a significant correlation with oxLDL in SLE patients (r=0.32, p<0.05) but not in controls (r=0.11, n.s.). No correlation was observed between the plasma levels of oxLDL and MCP-1.

Figure 38:
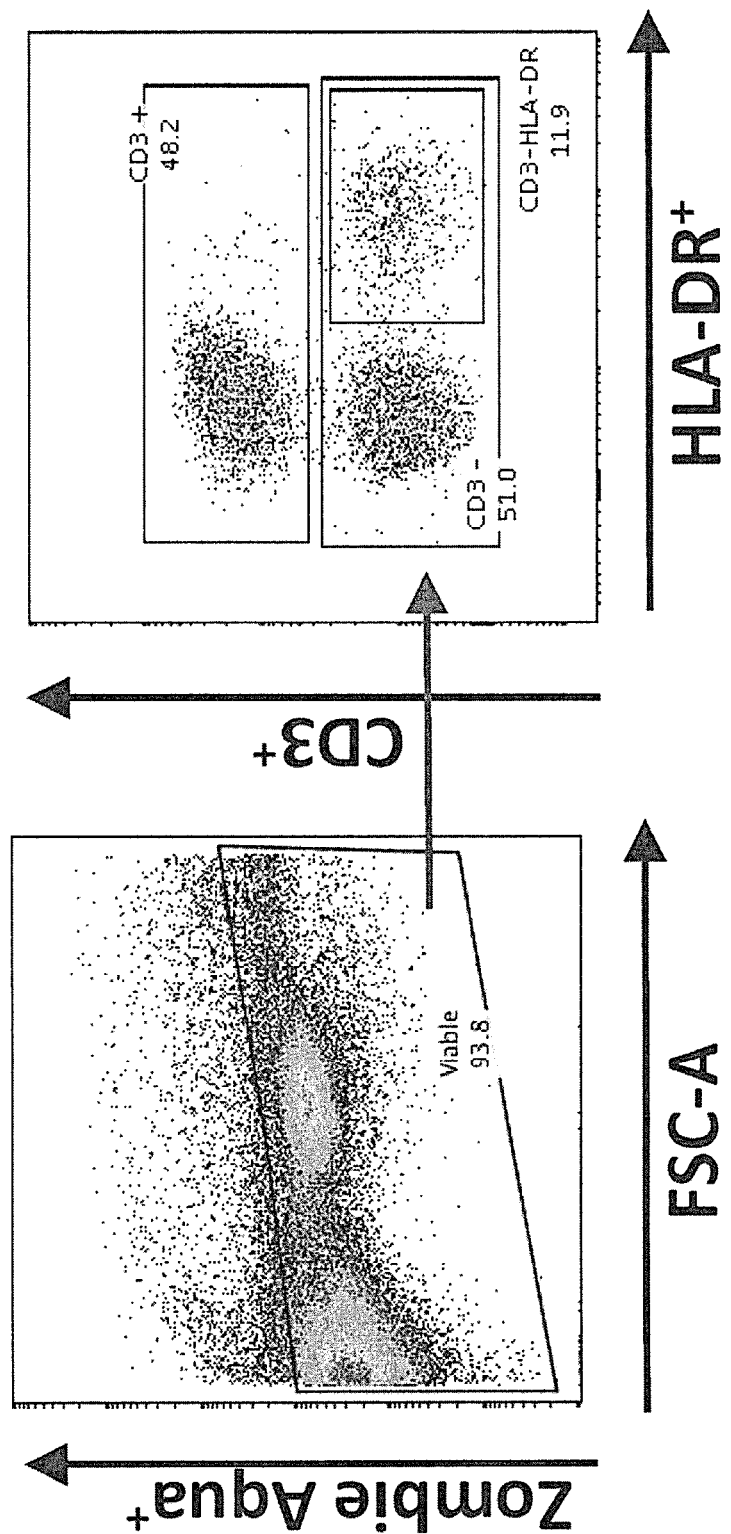
FIG. 38 depicts the gating strategy for $CD3^+$, $CD3^-$ and $CD3^-HLA-DR^+$ populations from all viable (Zombie Aqua-) PBMC.
Figure 39A:
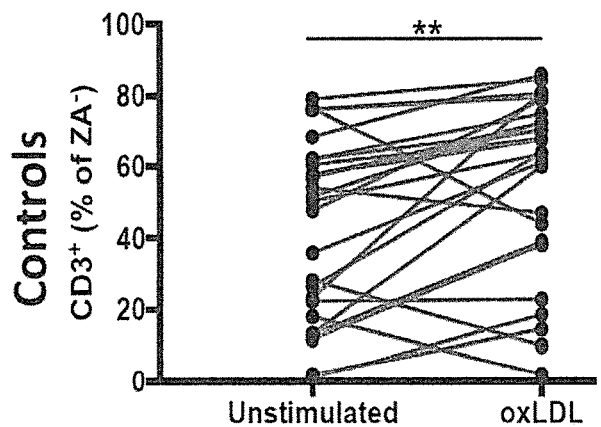
FIG. 39A-FIG. 39C depict $CD3^+$ T cell populations in healthy controls (39A) and in SLE cases (39B) with or without exposure to 10 µg/ml of oxLDL for 24 hours.
Figure 39B:
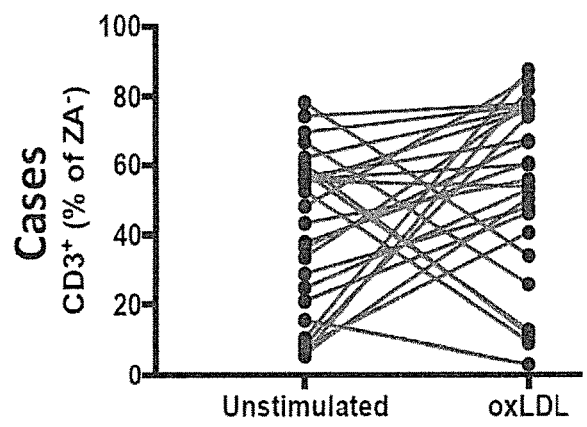
Figure 39C:
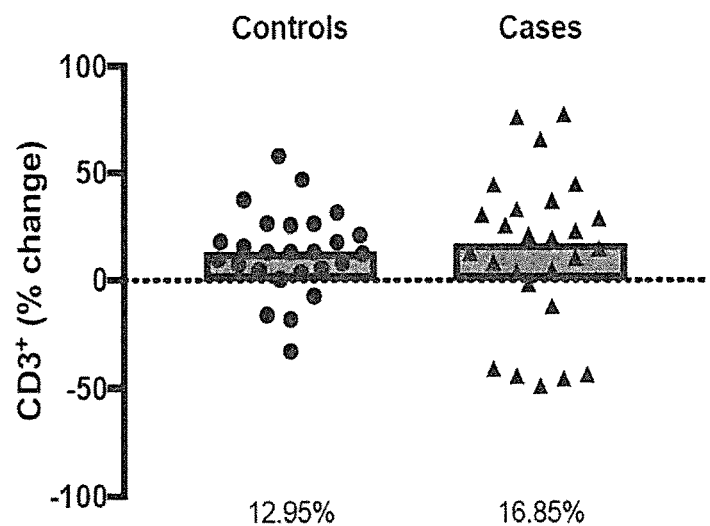
Figure 40A:
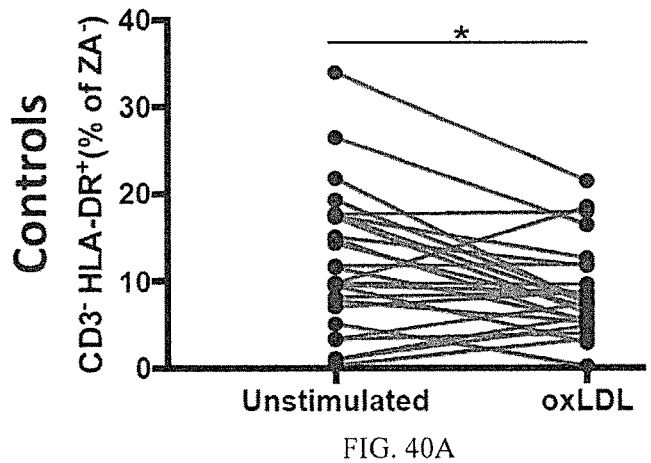
FIG. 40A-FIG. 40C depict $CD3^-$ $HLA-DR^+$ antigen-presenting cell populations in healthy controls (40A) and in SLE cases (40B) with or without exposure to 10 µg/ml of oxLDL for 24 hours.
Figure 40B:
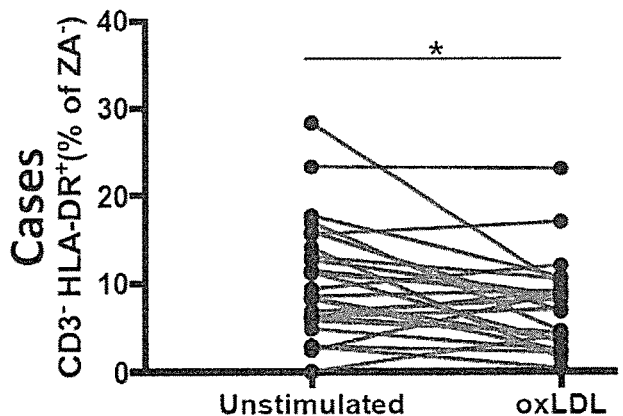
Figure 40C:
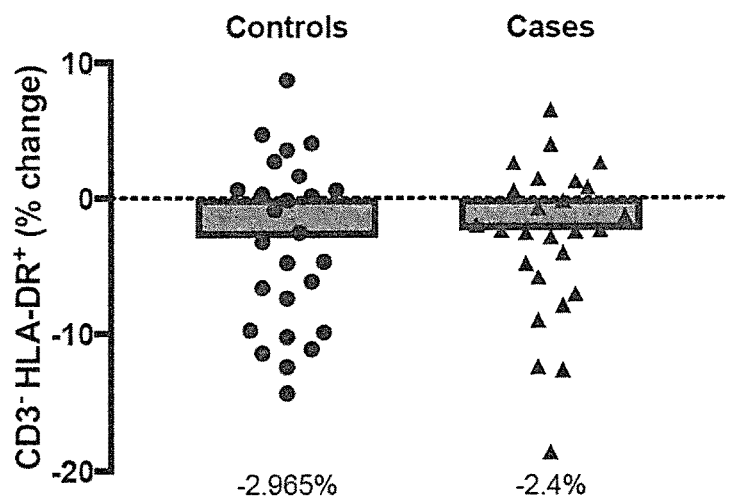
Figure 41A:
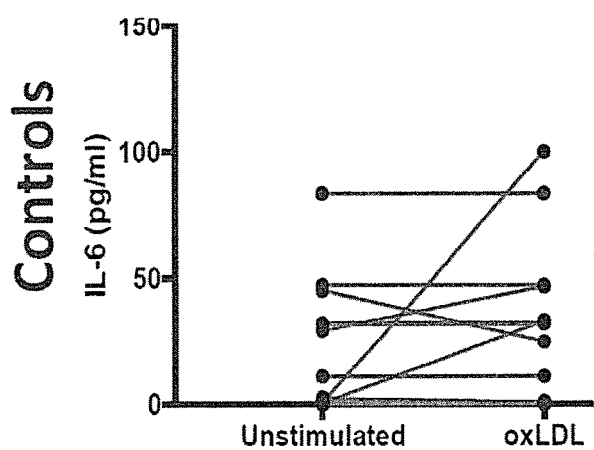
FIG. 41A-FIG. 41C depict release of IL-6 in healthy controls (41A) and in SLE (41B) PBMC with or without exposure to 10 µg/ml of oxLDL for 24 hours.
Figure 41B:
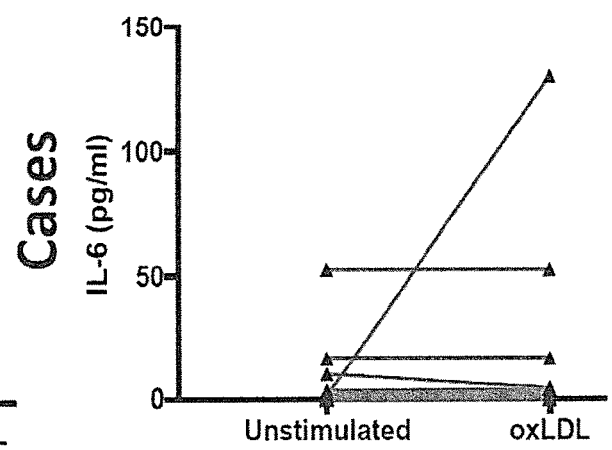
Figure 41C:
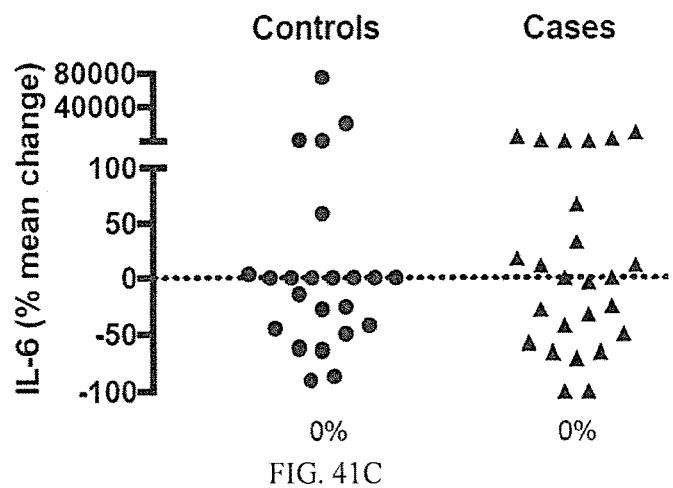
Figure 42A:
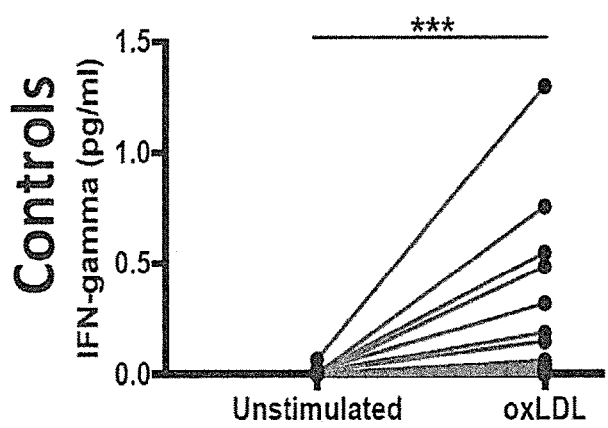
FIG. 42A-FIG. 42C depict release of IFN-γ in healthy controls (42A) and in SLE (42B) PBMC with or without exposure to 10 µg/ml of oxLDL for 24 hours.
Figure 42B:
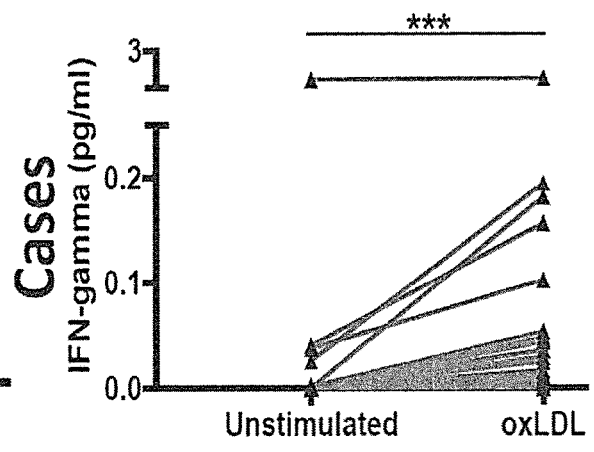
Figure 42C:
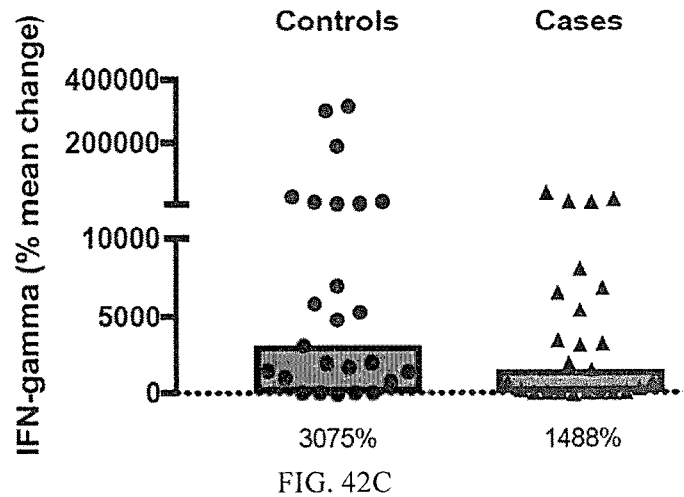
Figure 43A:
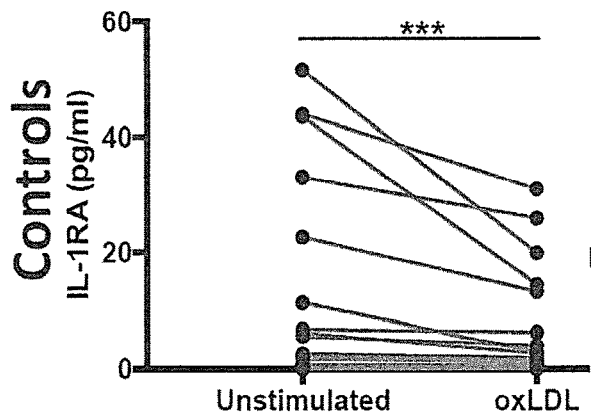
FIG. 43A-FIG. 43C depict release of IL-1RA in healthy controls (43A) and in SLE (43B) PBMC with or without exposure to 10 µg/ml of oxLDL for 24 hours.
Figure 43B:
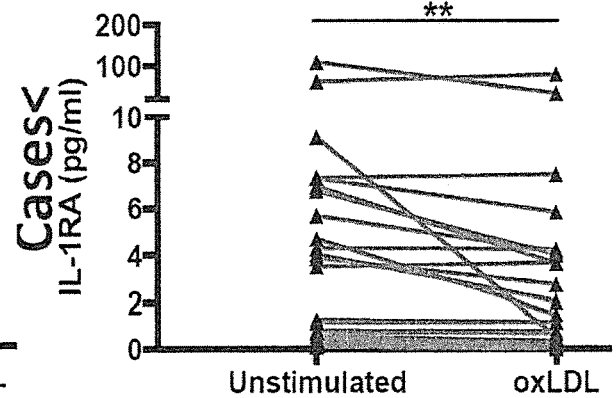
Figure 43C:
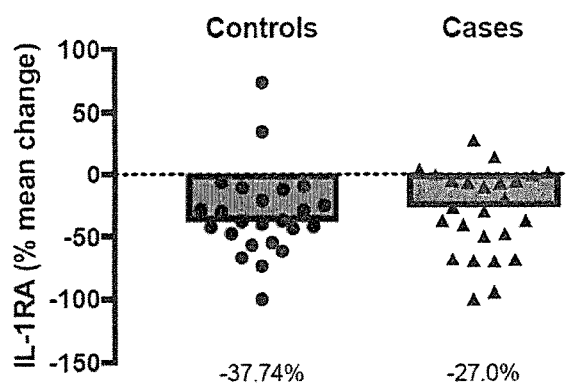
Figure 44A:
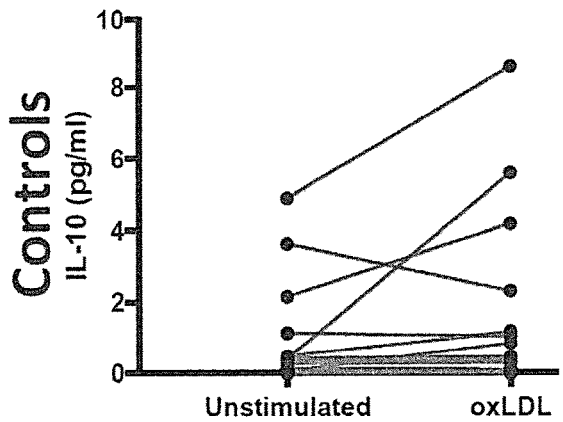
FIG. 44A-FIG. 44C depict release of IL-10 in healthy controls (44A) and in SLE (44B) PBMC with or without exposure to 10 µg/ml of oxLDL for 24 hours.
Figure 44B:
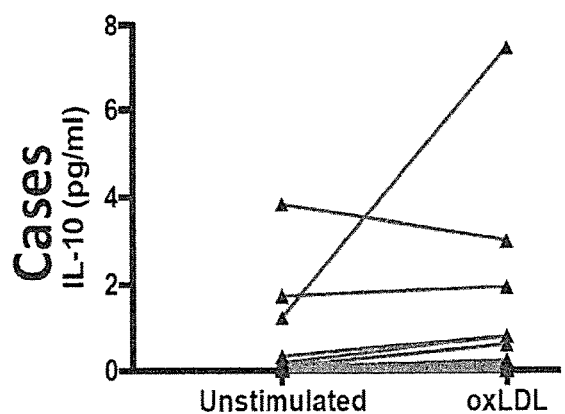
Figure 44C:
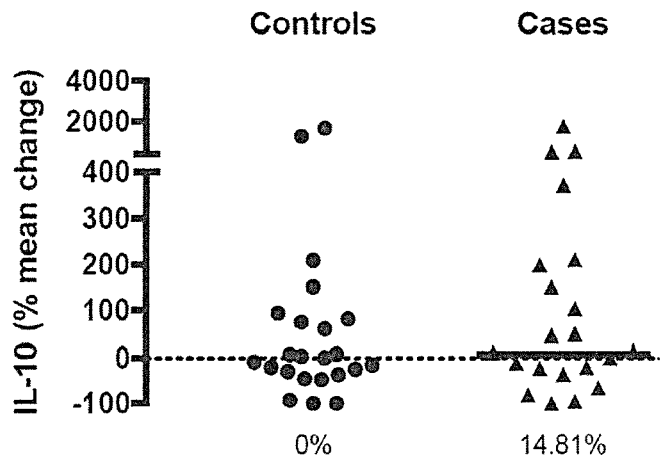

PBMC from 26 randomly selected SLE cases and 26 age- and sex-matched healthy controls were used for in vitro stimulation with oxLDL. The fraction of CD3+ T cells was similar in SLE and control PBMC (around 50% of all viable cells), but the T cell population was considerably more heterogeneous in the samples from SLE patients as assessed by t-Distributed Stochastic Neighbor Embedding (t-SNE), a 2-dimensionality reduction algorithm (FIG. 38). Exposure of PBMC to 10 μg/ml of oxLDL for 24 hours increased the fraction of CD3+ T cells in both groups (13.0 and 16.9% respectively in controls and cases) with no significant difference between the two groups (FIGS. 39A, 39B and 39C). In contrast, oxLDL exposure decreased the fraction of antigen-presenting cells (APCs, defined as CD3-HLA-DR+ cells) in both control and SLE PBMC, again with no significant difference between the two groups (FIGS. 40A, 40B and 40C). In view of the correlation between plasma levels of oxLDL and IL-6 found in SLE patients but not in controls (FIG. 41A-41C), we next analyzed if oxLDL induced a larger release of IL-6 from SLE than from control PBMC. However, exposure of the cells to 10 μg/ml of oxLDL for 24 hours did not affect the release of IL-6 from control or from SLE PBMC (FIG. 42A). In contrast, the release of interferon (IFN)-γ was markedly increased, while that of the anti-inflammatory cytokine IL-1 receptor a (IL-1RA) was reduced in both control and SLE PMBC with no significant difference between the groups for either cytokine (FIGS. 42A-42C and 43A-43C). There was no effect of oxLDL on the release of IL-10 (FIGS. 44A-44C).

Figure 45A:
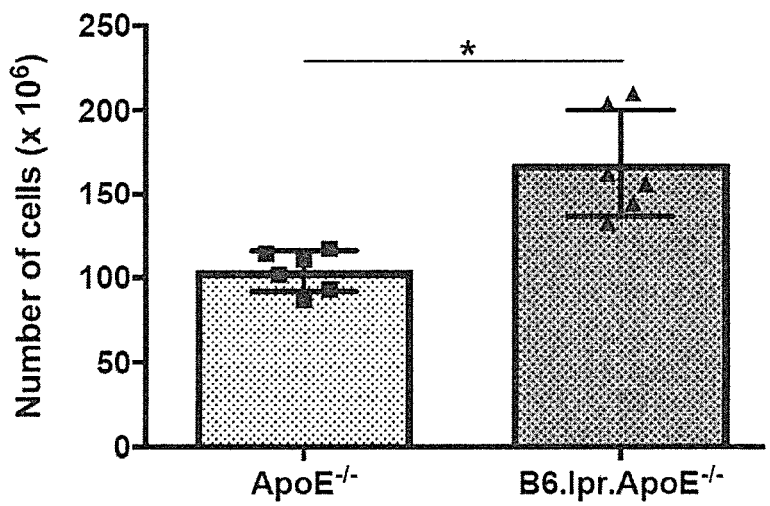
FIG. 45A and FIG. 45B depict that B6.lpr.ApoE-/- mice display a SLE phenotype, characterized by ApoE-/- and B6.lpr.ApoE-/- spleen cell count (45A), double negative T cells ($CD4^-CD8^-$ of $CD3^+$) (45B) and anti-nuclear antibody presence from plasma diluted 1:100.
Figure 45B:
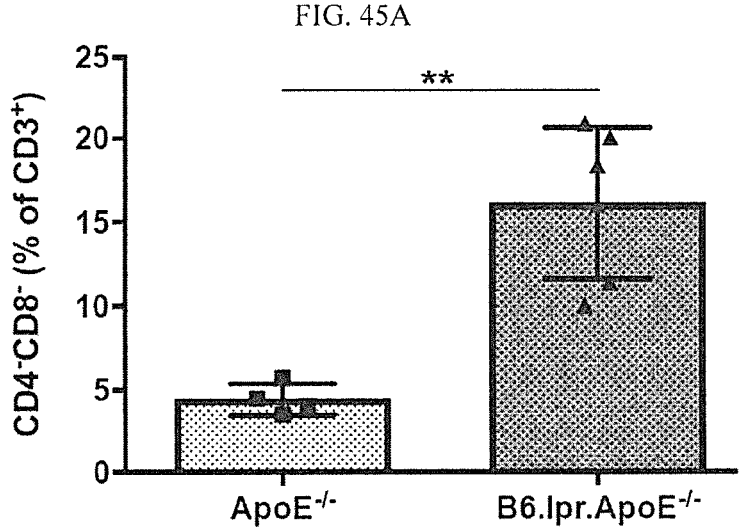

Effect of mucosal immunization with an ApoB100 peptide on atherosclerosis in hypercholesterolemic mice with a SLE-like phenotype:

With the exception of stronger correlation between circulating oxLDL and IL-6, the studies described above failed to identify a stronger immune response against oxLDL in SLE patients. However, since the response was comparable to that of controls and traditional approaches for cardiovascular prevention (such as statins) are less effective in SLE we decided that it still was justified to investigate the effect of LDL immunomodulatory therapy in a hypercholesterolemic mouse model with a SLE-like phenotype (B6.lpr.ApoE−/− mice). These mice display SLE-like characteristics with lymphadenopathy and splenomegaly (FIG. 45A) as a result of Fas receptor loss (lpr) and are atherosclerosis-prone due to apolipoprotein E-deficiency (ApoE−/−). Expansion of double negative T cells and detection of plasma anti-nuclear antibodies further confirmed the SLE phenotype of the B6.lpr.ApoE−/− mice (FIG. 45B).

Figure 46:
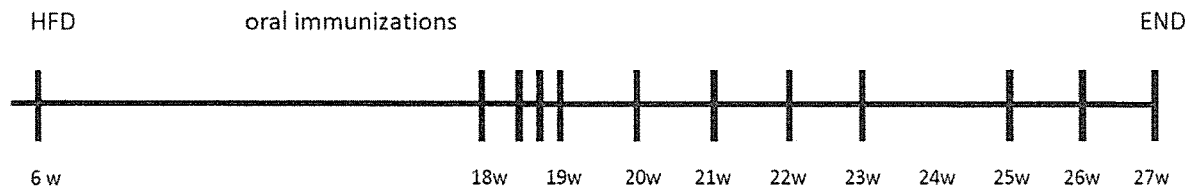
FIG. 46 depicts an experimental setup, where female B6.lpr.ApoE$^{-/-}$ mice were fed high-fat diet (HFD) from 6 weeks of age until termination of the study at 27 weeks of age. Mice were orally administered by gavage with CTB (30 µg, n=13) or p45-CTB conjugate (5 µg, n=13) starting at 18 weeks of age at day 0, 3, and 5 followed by once weekly administrations until 26 weeks of age.
Figure 47A:
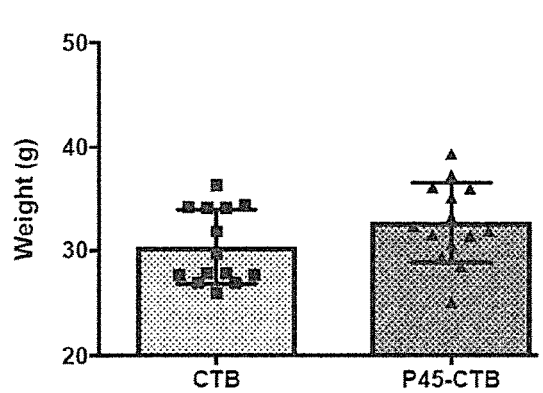
FIG. 47A-FIG. 47C depict the weight (47A), plasma triglyceride levels (47B) and plasma cholesterol levels (47C).
Figure 47B:
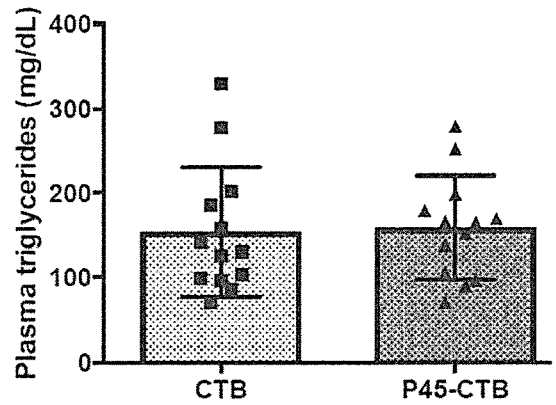
Figure 47C:
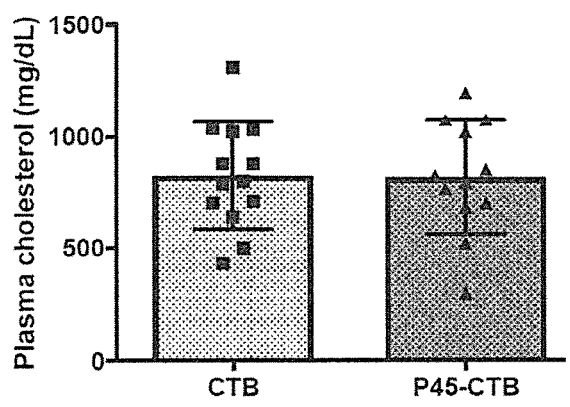
Figure 48A:
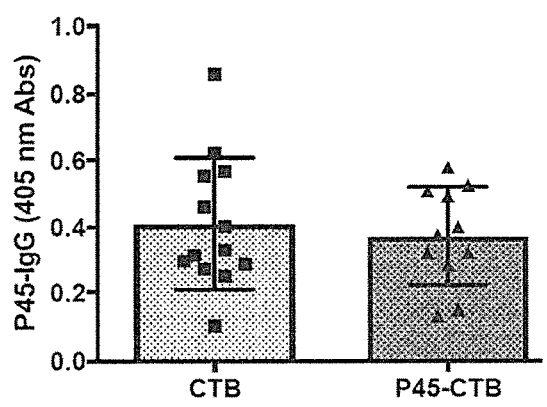
FIG. 48A and FIG. 48B depict plasma P45-IgG and P45-IgM antibodies, respectively, at termination of the study. Each dot represents one mouse and data are shown as mean±standard deviation, $*p \le 0.05$ with Students t-test on normally distributed data or Mann-Whitney rank test on not normally distributed data.
Figure 48B:
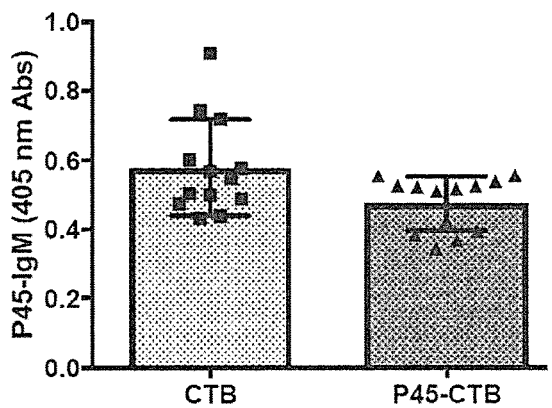
Figure 49A:
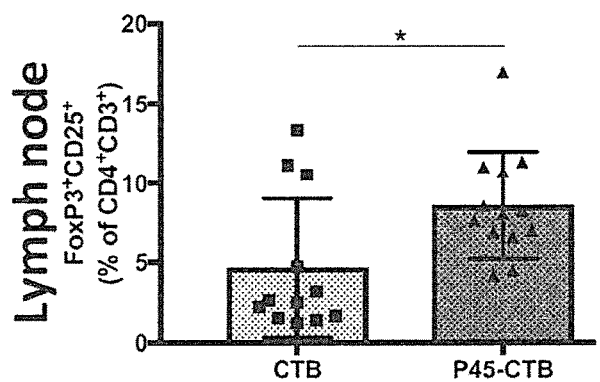
FIG. 49A and FIG. 49B demonstrate the mucosal immunization with p45-CTB is associated with a regulatory effect in draining mesenteric lymph node, which is depicted by cell frequencies in mesenteric lymph node (49A) and in spleen (49B) of regulatory T cells ($CD25^+FoxP3^+$ gated from $CD3^+CD4^+$).
Figure 49B:
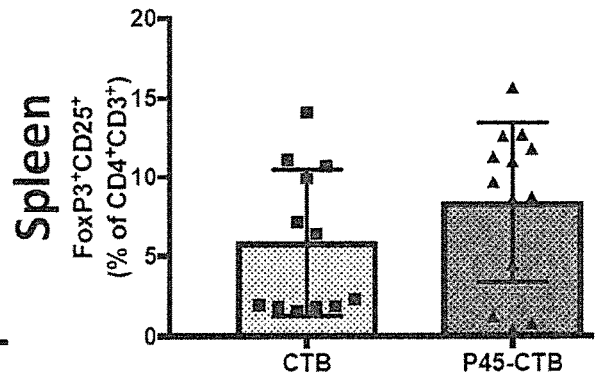
Figure 50A:
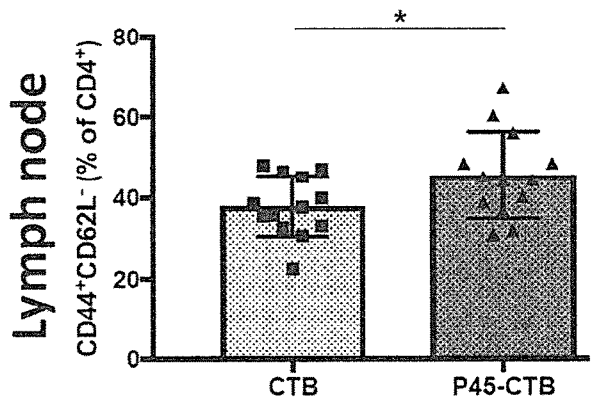
FIG. 50A and FIG. 50B depict cell frequencies in mesenteric lymph node (50A) and in spleen (50B) of T effector memory cells ($CD44^+CD62L^-$ gated from $CD3^+$ $CD4^+$).
Figure 50B:
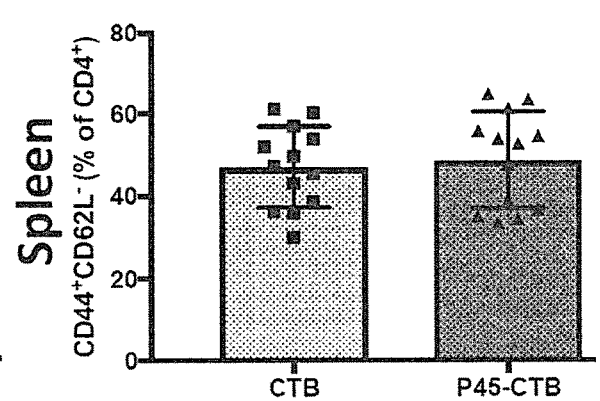
Figure 51B:
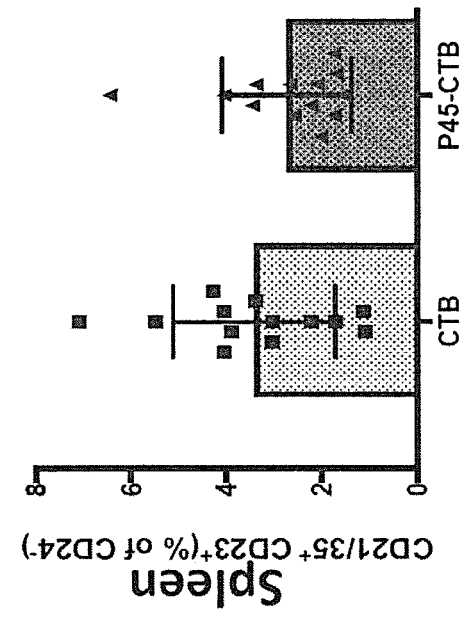
FIG. 51A and FIG. 51B depict cell frequencies in mesenteric lymph node (51A) and in spleen (51B) of follicular B cells ($CD21/35^+CD23^+$ gated from B220 positive $CD24^-$ cells).
Figure 52B:
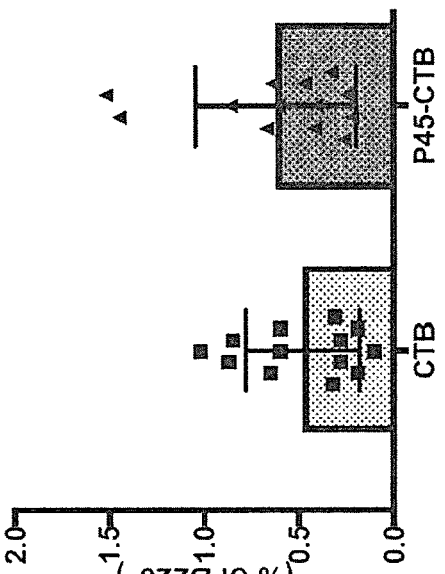
FIG. 52A and FIG. 52B depict cell frequencies in mesenteric lymph node (52A) and in spleen (52B) of regulatory B cells ($CD1d^{hi}CD5^+$ gated from $B220^+$). Each dot represents one mouse and data is shown as mean±standard deviation, $*p \le 0.05$ and $***p \le 0.001$ with Students t-test on normally distributed data or Mann-Whitney rank test on not normally distributed data.
Figure 51A:
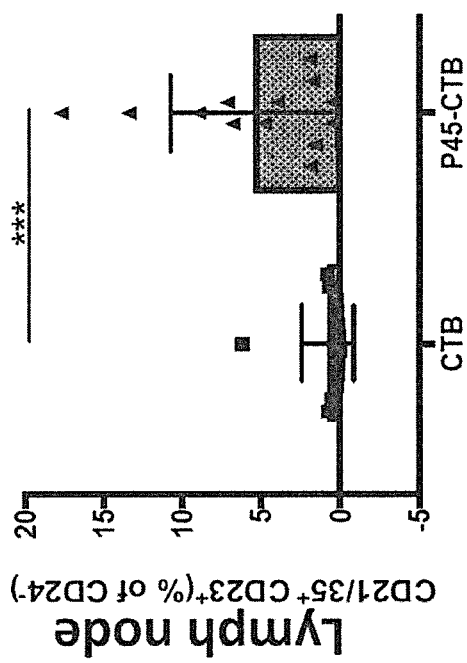
Figure 52A:
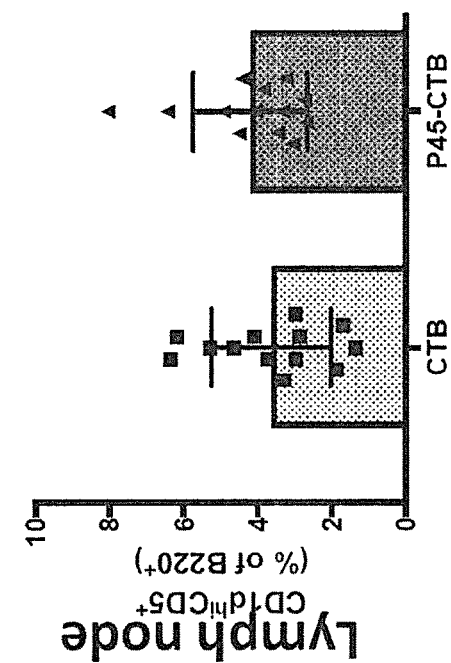
Figure 53:
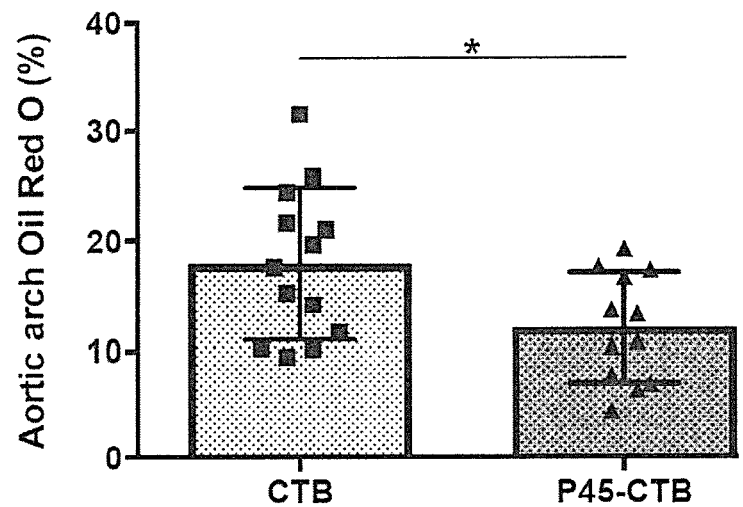
FIG. 53-FIG. 56, FIG. 57A and FIG. 57B demonstrate p45-CTB treatment reduced development of atherosclerotic plaques. Atherosclerosis in the aortic arch as assessed by en face percent Oil Red O lipid stained area (FIG. 53), by subvalvular plaque area (FIG. 54), by Oil Red O lipid stained area of subvalvular plaques (FIG. 55), by CD68 positive area of subvalvular plaques (FIG. 56), and by carotids artery mRNA expression of FoxP3 (FIG. 57A) and IL-10 (FIG. 57B) at termination of the study expressed as log transformed relative fold change to CTB, normalized to 18S as housekeeping gene. Gene expression data was log transformed before analysis. Each dot represents one mouse and data is shown as mean±standard deviation, $*p \le 0.05$ and $**p \le 0.01$ with Students t-test on normally distributed data or Mann-Whitney rank test on not normally distributed data.
Figure 54:
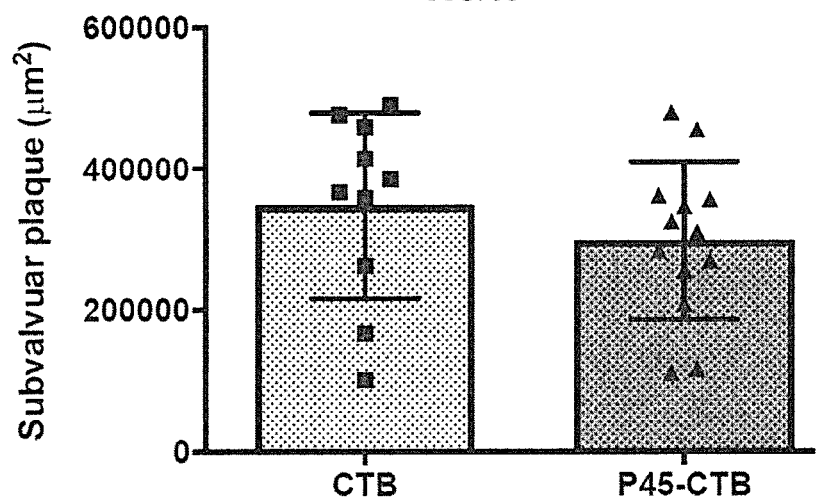
Figure 55:
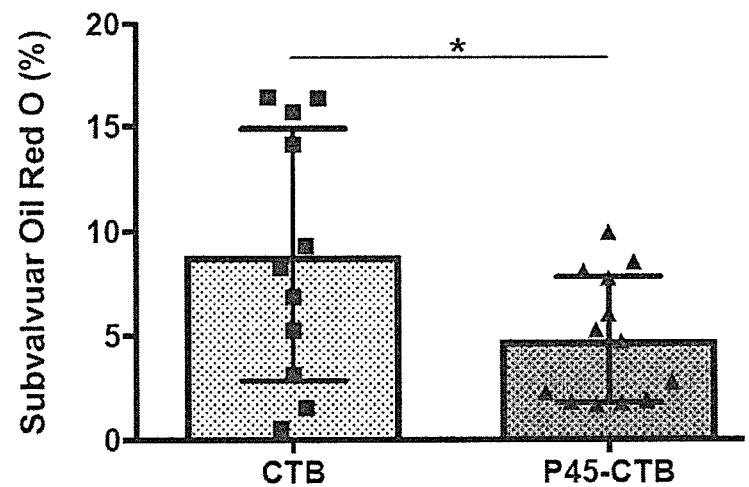
Figure 56:
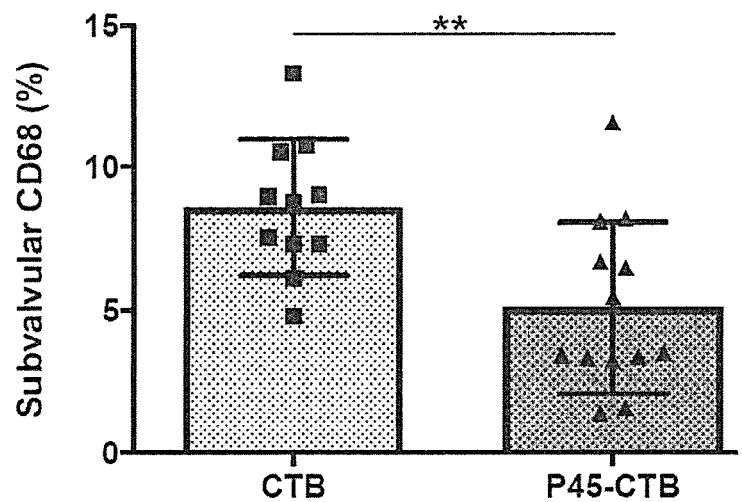
Figure 57A:
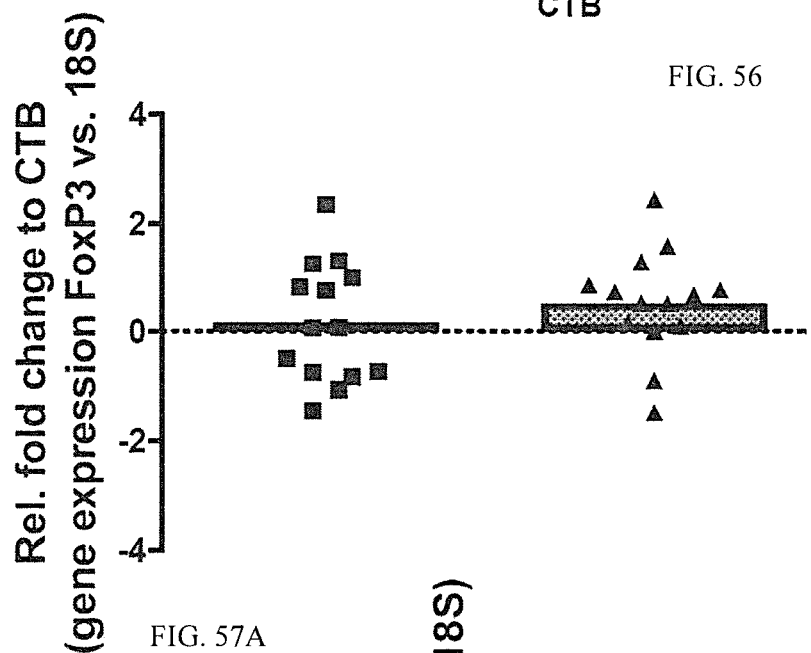
Figure 57B:
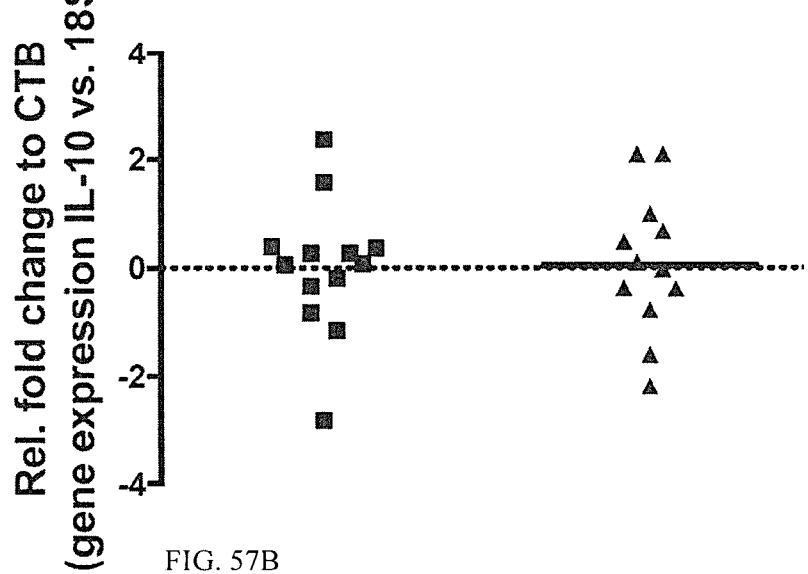

Since SLE involves an impaired ability to control for activation of autoimmunity we first tested an immune suppressive approach. To achieve this we generated a fusion protein of a peptide sequence in ApoB100 (P45; amino acids 661-680) and the cholera toxin B subunit (CTB) in which CTB facilitates mucosal uptake through binding to the GM1 ganglioside on gut epithelial cells. B6.lpr.ApoE−/− mice were first fed high-fat diet for 12 weeks, and then given three oral administrations of p45-CTB or CTB alone during one week followed by weekly administrations for another 8 weeks (FIG. 46). The treatment did not affect total body weight, plasma cholesterol or triglyceride levels (FIGS. 47A-47C). There was also no effect on P45 antibody levels (FIGS. 48A and 48B). Analyses of cell populations in mesenteric lymph nodes by flow cytometry demonstrated that p45-CTB treatment was associated an increased fraction of FoxP3+/CD25+ Tregs, CD44hi/CD62− effector memory T cells and CD21/35+/CD23+/CD24− follicular B cells, while there was no effect of the CD1dhi/CD5+ regulatory B cell population (FIGS. 49A, 50A, 51A, 52A). There was no effect on any of these cell populations in the spleen (FIGS. 49B, 50B, 51B, 52B). These observations are in line with activation of an immunosuppressive, regulatory response against an orally administered antigen. Analysis of the aortic arch by en face Oil Red O staining demonstrated that treatment with p45-CTB was associated with a 32.5% decrease atherosclerosis (FIG. 53). There was no change in subvalvular plaque area (FIG. 54), but the subvalvular plaque Oil Red O and CD68 macrophage stained area was reduced by 50.3% and 40.3% respectively in response to p45-CTB treatment (FIGS. 55 and 56). In order to investigate presence of immune regulatory activity in arterial tissue we analyzed FoxP3 and IL-10 mRNA levels in the carotid arteries but found no difference between CTB and p45-CTB treated mice (FIGS. 57A and 57B).

To address the question whether p45-CTB treatment caused adverse effects on other SLE manifestations, we analyzed the expression of anti-nuclear antibodies (ANA) and anti-double stranded DNA antibodies (anti-dsDNA) as well as the renal function markers albumin/creatinine ratio and blood urea nitrogen (BUN). We observed no effect of treatment on ANA, anti-dsDNA antibodies or the albumin/creatinine ratio (ACR) (FIGS. 58-60), but the mice treated with p45-CTB had significantly lower blood urea nitrogen (BUN) levels indicating an improved renal function (FIG. 61).

Figure 62:
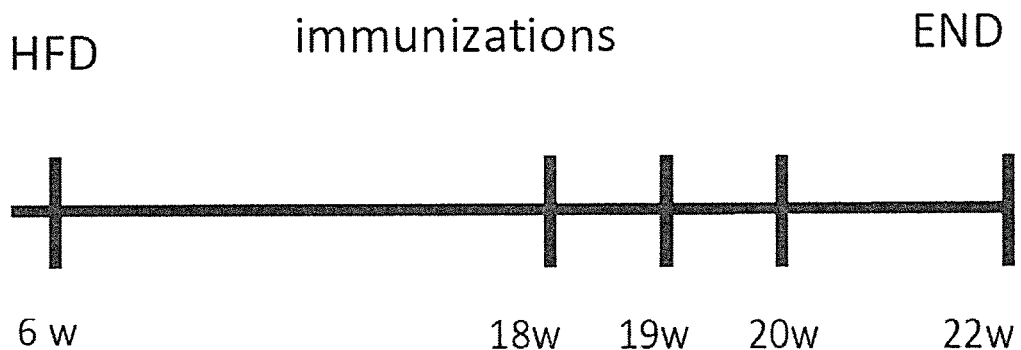
Figure 63A:
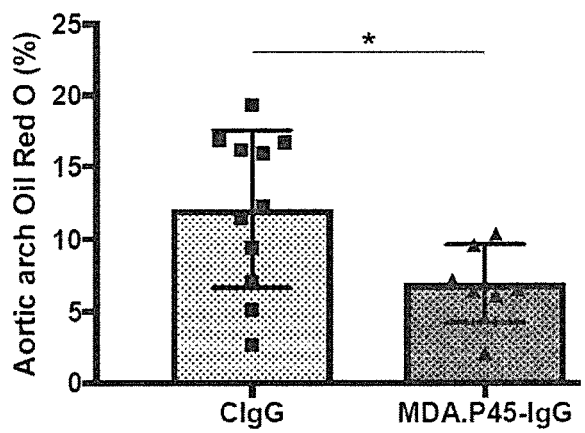
Figure 63B:
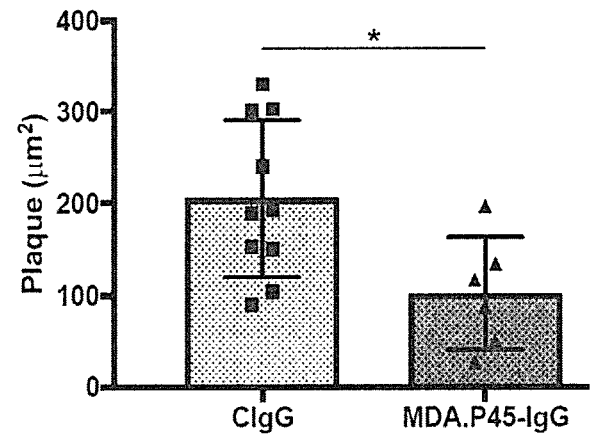
Figure 64:
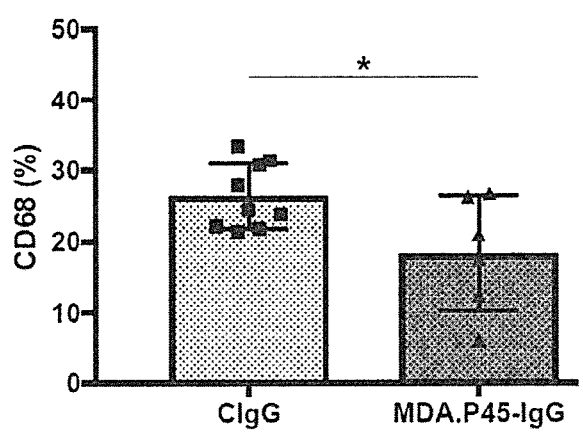
Figure 67A:
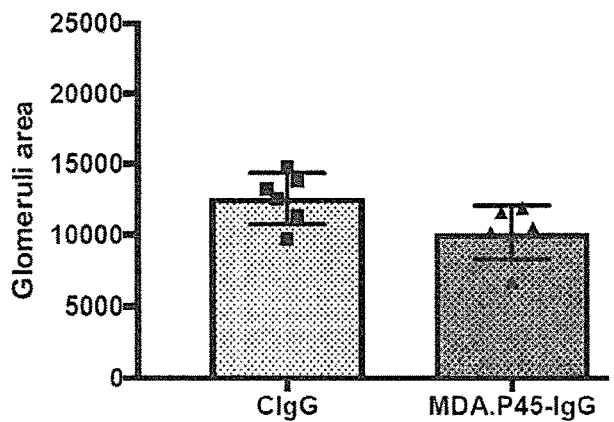
Figure 67B:
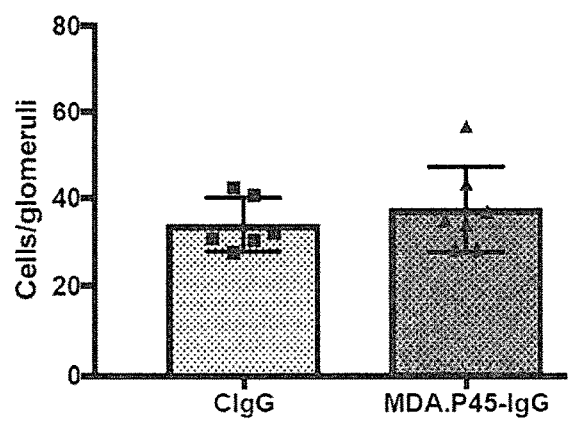

Effect of passive immunization with an anti-ApoB100 peptide antibody on atherosclerosis in hypercholesterolemic mice with a SLE-like phenotype:

In our second approach to influencing immune responses against oxLDL in B6.lpr.ApoE−/− mice, we applied a passive immunization strategy using a recombinant human IgG1 antibody targeting malondialdehyde (MDA)-modified p45 (MDA-p45 IgG). B6.lpr.ApoE−/− mice were thus fed high-fat diet for 12 weeks and then given weekly intraperitoneal injections of 1 mg of MDA-p45 or control IgG for three weeks (FIG. 62). Treatment with MDA-p45 IgG reduced atherosclerosis in the aortic arch by 42.8% and CD68-macrophage subvalvular plaque staining by 30.5% and there was also a trend towards decreased lipid accumulation in subvalvular plaques (FIGS. 63A, 63B and 64). We observed no effect on the mRNA expression of IL-10 or MCP-1 in carotid arteries (FIGS. 65A and 65B). Moreover, there were no significant differences in plasma cholesterol, triglycerides or oxLDL between the two treatment groups (FIGS. 66A-66D). To search for signs of possible renal damage by MDA-p45 IgG/oxLDL immune complexes we analyzed glomerular area and cellularity in the kidneys but found no difference between the groups (FIGS. 67A and 67B). There was also no difference in the urine albumin/creatinine ratio between the groups.

Figure 68A:
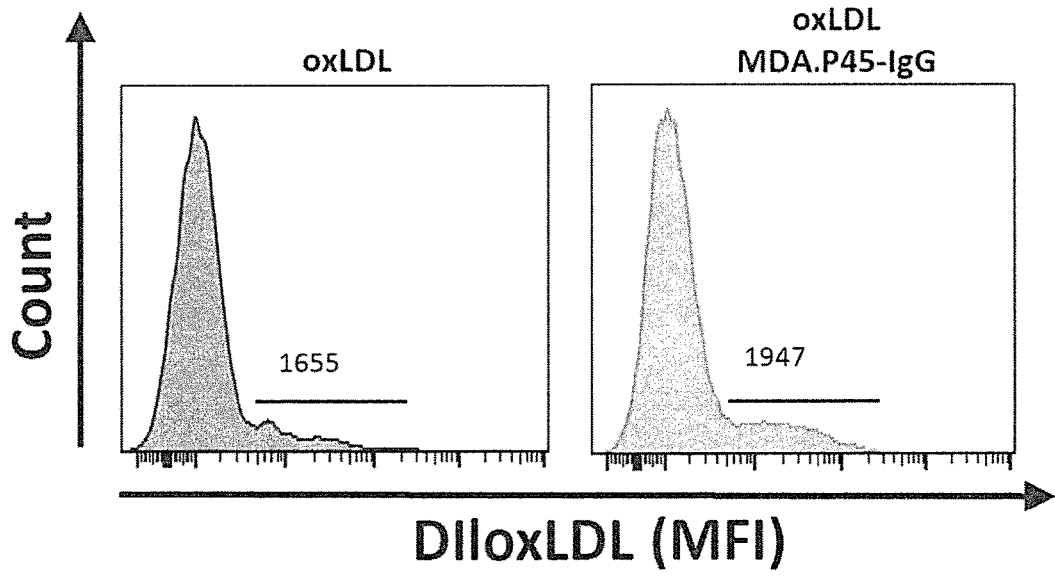
Figure 68B:
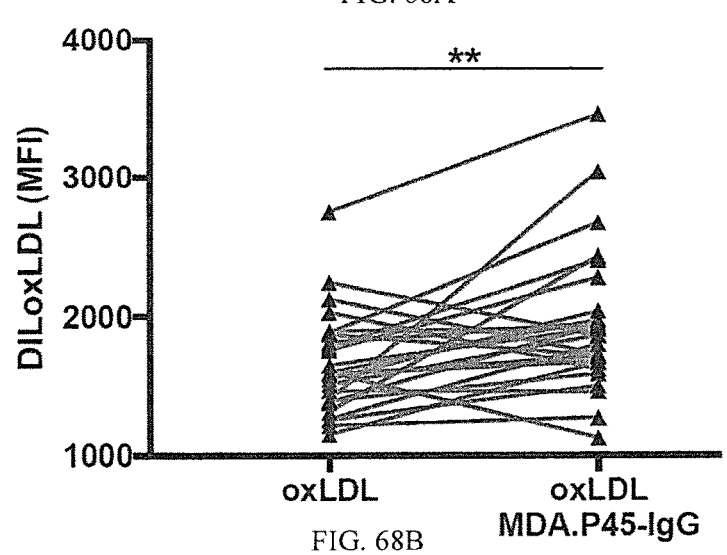
Figure 73C:
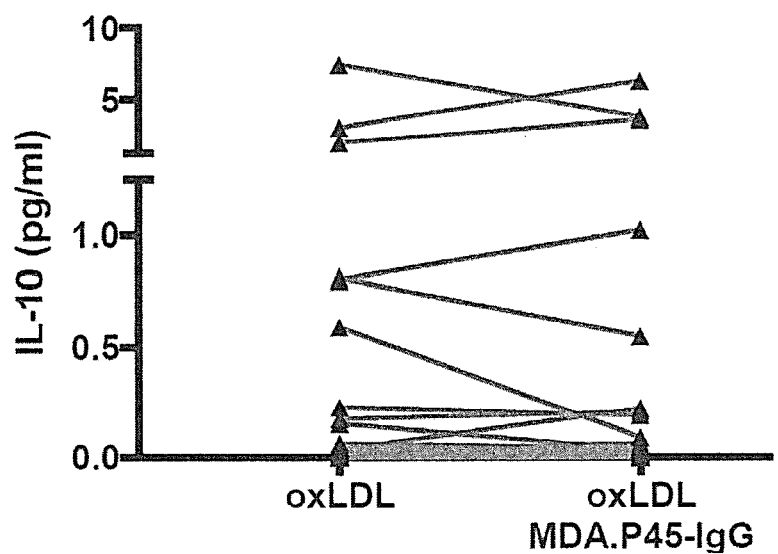
Figure 73D:
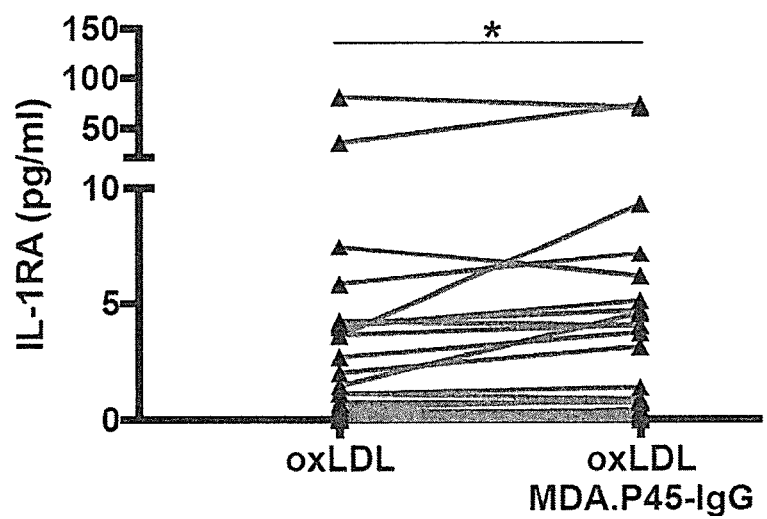

Effect of MDA-p45 IgG on PBMC Isolated from SLE Patients:

Having observed the protective effect of MDA-p45 IgG on atherosclerosis development in B6.lpr.ApoE−/− mice, we next investigated how this antibody affected the interaction of SLE PBMC with oxLDL. We incubated the cells with 10 µg/ml of fluorescently labelled oxLDL for 24 hours with and without addition of 10 µg/ml MDA-p45 IgG. Addition of the antibody resulted in an increased cellular uptake of oxLDL (FIGS. 68A and 68B). A tSNY plot of flow cytometry data revealed that oxLDL primarily was taken up by CD14+ APC (CD3-/HLA-DR+ cells) and that the antibody increased both the expression of CD14 as well as the uptake of oxLDL in CD14+ APC (FIGS. 69-72). Addition of the antibody had small effects on the cytokine release from SLE PBMC with only a modest increase in the anti-inflammatory cytokine IL-1RA reaching statistical significance (FIGS. 73A-73D).

Discussion

Accumulation and oxidation of LDL is considered a key pathogenic driver of the development of atherosclerotic plaques. LDL oxidation promotes inflammation through activation of both innate and adaptive immune responses. Since SLE is characterized by a dysfunctional control of autoimmune responses, it is conceivable that an impaired ability to control immune responses against oxLDL is of particular importance for the development of cardiovascular complications in SLE. Moreover, it is has been shown that LDL from patients with SLE is more susceptible to oxidation. Collectively, these findings suggest that targeting immune responses against oxLDL represents possible approach for prevention of CVD in SLE. There is a significant unmet clinical need for such therapies since traditional preventive cardiovascular medication is less effective in SLE. In the present study, we found no difference in plasma levels of oxLDL between patients with SLE and healthy controls and that PBMC from SLE patients and from healthy controls reacted similarly with an increased release of INF-γ when exposed to oxLDL. However, plasma IL-6 levels correlated more strongly with circulating levels of oxLDL in SLE patients than in controls, indicating that LDL oxidation may be more stressful to SLE patients when occurring in the body. Therefore, an embodiment of the invention provides selecting a subject having a positive correlation between plasma IL-6 level and circulating oxLDL level and exhibiting symptoms or having been diagnosed with SLE, and administering to this subject an anti-P45 antibody, so as to treat, reduce the severity or likelihood of atherosclerosis in the subject.

We used mucosal immunization with the ApoB100-derived peptide P45 genetically fused with CTB to stimulate regulatory responses against LDL in hypercholesterolemic mice with an SLE-like phenotype. This was associated with an expansion of Tregs in mesenteric lymph nodes, reduced plaque formation in the aorta and reduced presence of macrophages in subvalvular plaques. Our findings indicate the possibility that mucosal tolerance induction against LDL antigens could represent a useful approach to decrease cardiovascular risk in SLE. The mucosa-associated lymphoid tissues play an important role in maintaining tolerance against environmental antigens present in gut microflora and in food. It is an attractive possibility to take advantage of this to develop tolerance immuno-therapies for autoimmune diseases. The athero-protective effects were generally attributed to the generation of antigen-specific Tregs in these studies. Collectively, these observations support the possibility of developing novel therapies for prevention of CVD in SLE based on mucosal immunization with p45-CTB and similar LDL-derived antigens. Prior to Applicant's invention, there were few clinically successful examples of mucosal tolerance vaccines for autoimmune diseases reported.

In an alternative approach to inhibiting the development of atherosclerosis in B6.lpr.ApoE−/− mice, we used injection of a human recombinant antibody specific for the MDA-modified 661-680 amino acids in apo B. This IgG antibody binds only to oxidized LDL and not to native LDL, details seen in A. Schiopu, *Circulation*, 2004; 110:2047-2052. This antibody (orticumab) has previously been shown to inhibit plaque development on both ApoE−/− and human ApoB-transgene mice, as well as to potentiate plaque regression caused by cholesterol-lowering in LDL receptor-deficient mice. In the present study we found a remarkable 50% reduction in subvalvular plaque development in response to three injections of the antibody. Importantly, there was also a marked reduction of inflammatory cells in the remaining plaques. There is rationale why this antibody may have a particularly beneficial effect in SLE. An impaired removal of apoptotic material through macrophage scavenger receptors is considered an important cause of activation of autoimmunity in SLE. Since oxLDL binds to the same receptors it is likely to further impair that handling of apoptotic material in SLE. It has previously been shown that the MDA-p45 antibody effectively promotes uptake of ox LDL in cultured monocytes isolated from healthy blood donors. In the present study, we found that this is true also for CD14+ monocytes isolated from patients with SLE. Accordingly, by rerouting uptake of oxLDL from scavenger to Fc receptors the antibody may help to increase the capacity for removal of apoptotic material by scavenger receptors. The mechanisms through which this antibody protects against atherosclerosis are only partly known. One likely mechanism involves the facilitation of removal of toxic oxLDL particles from the extracellular space which at the same time would make the cholesterol available for reverse cholesterol through adenosine triphosphate-binding cassette transporter A1-mediated transfer to HDL. When complexed with oxLDL the antibody has also been shown to suppressive the activity of monocytes by binding to inhibitory FcγIIb receptor. One advantage of the MDA-p45 antibody is that it already has been proven to be safe in clinical studies. In this study, however, the antibody failed to reduce carotid plaque inflammation as assessed by 18F-fluorodeoxyglucose positron emission tomography imaging in stable cardiovascular patients. The reason for the lack of effect of antibody-treatment in this study remains a matter of controversy as the patients may have been in a too stable state of disease to allow identification of a response to treatment. It could also seem counter-intuitive to treat SLE patients with an antibody against a self-antigen since such antibodies are considered a hallmark of the disease. Although there are experimental evidence that some of these antibodies are pathogenic, it remains to be fully elucidated if they are a cause or a consequence of the disease. In conclusion, the present study provides experimental and clinical support for targeting oxLDL autoimmunity as a possible target for prevention of cardiovascular complications in SLE.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for treating systemic lupus erythematosus (SLE) in a subject in need thereof by passive immunization, comprising administering a therapeutically or prophylactically effective amount of an antibody that binds at least one oxidized fragment of apolipoprotein B100 (ApoB100), so as to treat SLE, wherein the antibody comprises a variable heavy region ($V_H$) and a variable light region ($V_L$), wherein the $V_H$ region comprises the sequence set forth in SEQ ID NO: 324 and the variable light region ($V_L$) comprises the sequence set forth in SEQ ID NO: 325.

2. The method of claim 1, wherein the antibody is a human antibody.

3. The method of claim 1, wherein the $V_H$ region consists of the sequence set forth in SEQ ID NO: 324 and the variable light region ($V_L$) consists of the sequence set forth in SEQ ID NO: 325.

4. A method for treating, reducing the severity of, slowing progression of or inhibiting systemic lupus erythematosus (SLE) in a subject in need thereof, comprising:
   administering to the subject an effective amount of an antibody or antibody fragment,
   wherein the antibody or antibody fragment comprises heavy chain complementarity determining region (HCDR) 1 (HCDR1), HCDR 2 (HCDR2) and HCDR 3 (HCDR3) whose sequences comprise SEQ ID NOs: 318, 319 and 320, respectively, and light chain complementarity determining region (LCDR) 1 (LCDR1), LCDR 2 (LCDR2) and LCDR 3 (LCDR3) whose sequences comprises SEQ ID NOs: 321, 322 and 323, respectively.

5. The method of claim 4, wherein the antibody or antibody fragment is capable of binding to a fragment of apolipoprotein B100 (ApoB100), and the fragment of ApoB100 comprises an amino acid sequence of SEQ ID NO:45 and is an aldehyde derivative.

6. The method of claim 4, wherein the antibody or antibody fragment comprises a variable heavy region ($V_H$) of SEQ ID NO: 324, a variable light region ($V_L$) of SEQ ID NO: 325, or both.

7. The method of claim 6, wherein the antibody or antibody fragment comprises a heavy chain of SEQ ID NO: 316, a light chain of SEQ ID NO: 317, or both.

8. The method of claim 4, wherein the antibody is orticumab and is administered intravenously at an initial dose of at least 5 mg/kg, followed by a plurality of subsequent doses, each at least 2 mg/kg/week, at least 2.5 mg/kg/two weeks, or at least 6 mg/kg/month.

9. The method of claim 8, wherein the subsequent doses are administered over at least 2 weeks, 3 weeks, or 1 month.

10. The method of claim 4, wherein the subject is a human, the antibody is orticumab, and the orticumab is administered subcutaneously at a dose of about 330 mg/month for about 3, 4, 5, 6, 7, 8, 9, 10, 11 or 12 months.

11. The method of claim 4, wherein the antibody or antibody fragment is administered at 10-150 µg/kg, 150-750 µg/kg, 1-5 mg/kg, 5-10 mg/kg, 10-15 mg/kg, 15-20 mg/kg, 20-25 mg/kg, 25-50 mg/kg or 50-75 mg/kg.

12. The method of claim 4, further comprising selecting a subject exhibiting symptoms of SLE or a subject who has been diagnosed with SLE.

13. The method of claim 4, comprising administering an anti-malarial therapeutic, a corticosteroid, mycophenolate mofetil, azathioprine, cyclophosphamide, cyclosporine, leflunomide, or methotrexate in combination with the antibody or antibody fragment to the subject.

14. A method for treating, reducing the severity of, slowing progression of or inhibiting atherosclerosis in a subject exhibiting symptoms of or having been diagnosed with systemic lupus erythematosus (SLE), comprising:
   administering to the subject an effective amount of an antibody or antibody fragment capable of binding to a fragment of apolipoprotein B100 (ApoB100),
   wherein the fragment of ApoB100 comprises an amino acid sequence of SEQ ID NO: 45 or an active site thereof, and wherein the antibody or antibody fragment comprises heavy chain complementarity determining region (HCDR) 1 (HCDR1), HCDR 2 (HCDR2) and HCDR 3 (HCDR3) whose sequences comprise SEQ ID NOs: 318, 319 and 320, respectively, and one, two or three light chain complementarity determining region (LCDR) 1 (LCDR1), LCDR 2 (LCDR2) and LCDR 3 (LCDR3) whose sequences comprise SEQ ID NOs: 321, 322 and 323, respectively.

15. The method of claim 14, wherein the antibody or antibody fragment comprises a variable heavy region ($V_H$) of SEQ ID NO: 324, a variable light region ($V_L$) of SEQ ID NO: 325, or both.

16. The method of claim 14, wherein the antibody or antibody fragment comprises a heavy chain of SEQ ID NO: 316, a light chain of SEQ ID NO: 317, or both.

17. The method of claim 14, wherein the subject exhibits symptoms of atherosclerosis and SLE before the administration, and after the administration the subject has reduced plaque volume in artery.

18. The method of claim 14, wherein the antibody is orticumab and is administered intravenously at an initial dose of at least 5 mg/kg, followed by a plurality of subsequent doses, each at least 2 mg/kg/week, at least 2.5 mg/kg/two weeks, or at least 6 mg/kg/month.

19. The method of claim 14, wherein the subject is a human, the antibody is orticumab, and the orticumab is administered subcutaneously at a dose of about 330 mg/month for about 3, 4, 5, 6, 7, 8, 9, 10, 11 or 12 months.

20. The method of claim 14, wherein the atherosclerosis is accelerated atherosclerosis.

\* \* \* \* \*

UNITED STATES PATENT AND TRADEMARK OFFICE
CERTIFICATE OF CORRECTION

PATENT NO. : 10,858,422 B2
APPLICATION NO. : 16/428631
DATED : December 8, 2020
INVENTOR(S) : Jan Nilsson et al.

It is certified that error appears in the above-identified patent and that said Letters Patent is hereby corrected as shown below:

In the Claims

Column 270, Lines 63-64, replace "and one, two or three light chain" with --and light chain--.

Signed and Sealed this
Nineteenth Day of July, 2022

Katherine Kelly Vidal
*Director of the United States Patent and Trademark Office*